US005935818A

United States Patent [19]
Israeli et al.

[11] Patent Number: 5,935,818
[45] Date of Patent: Aug. 10, 1999

[54] ISOLATED NUCLEIC ACID MOLECULE ENCODING ALTERNATIVELY SPLICED PROSTATE-SPECIFIC MEMBRANE ANTIGEN AND USES THEREOF

[75] Inventors: Ron S. Israeli, Staten Island; Warren D. W. Heston; William R. Fair, both of New York, all of N.Y.

[73] Assignee: Sloan-Kettering Institute for Cancer Research, New York, N.Y.

[21] Appl. No.: 08/394,152

[22] Filed: Feb. 24, 1995

[51] Int. Cl.⁶ ................................................... C12P 21/06
[52] U.S. Cl. .................. 435/69.3; 435/325; 435/362; 435/365; 435/252.3; 435/320.1; 435/69.3; 435/348; 536/23.5; 536/24.1
[58] Field of Search .............................. 435/69.3, 320.1, 435/252.3, 325, 362, 365, 348; 536/23.5, 24.1

[56] References Cited

U.S. PATENT DOCUMENTS

| | | |
|---|---|---|
| 4,554,101 | 11/1985 | Hopp . |
| 5,162,504 | 11/1992 | Horoszewicz . |
| 5,538,866 | 7/1996 | Israeli et al. . |

FOREIGN PATENT DOCUMENTS

| | | |
|---|---|---|
| WO 9409820 | 5/1994 | WIPO . |

OTHER PUBLICATIONS

Abdel–Nabi, H., et al. (1992) "Monoclonal Antibodies and Radioimmunoconjugates in the Diagnosis and Treatment of Prostate Cancer", *Seminars on Urology* 127: 45–54.
Axelrod, H. R., et al. (1968) "Preclinical Results and Human Immunohitochemical Studies With 90Y–CYT–356: A New Prostate Cancer Therapeutic Agent" AUA 87th Annual Meeting, May 10–14, 1992.
Carter, B.H. And Coffey, D.S. (1990) "The Prostate: An Increasing Medical Problem" *The Prostate* 16:39–48.
Feng, Q., et al. (1991) "Purification and Biochemical Characterization of the 7E11–C5 Prostate Carcinoma–Associated Antigen", *Proceedings of the American Association for Cancer Research* 32:239.
Chang, Chawnshang, et al. (1988) "Structural Analysis of Complementary DNA and Amino Acid Sequences of Human and Rat Androgen Receptors", *Proc. Natl Acad. Sci USA* 85:7211–7215.
Culver, K.W., et al. (1992) "In Vivo Gene Transfer with Retoviral Vector–Producer Cells for Treatment of Experimental Brain Tumors", *Science* 256:1150–1552.
Decensi, A., et al. (1991) "Phase II Study of the Pure Non–steroidal Antiandrogen Nilutamide in Prostatic Cancer", *Eur J Cancer* 27:1100–1104.
Faber, P.W., et al. (1991) "Characterization of the Human Androgen Transciption Unit" *The Journal of Biological Chemistry* 266:10743–10749.
Fey, Martin F., et al. (1991) "The Polymerase Chain Reaction: A New Tool for the Detection of Minimal Residual Disease in Haematological Malignancies" *Eur J Cancer* 27:89–94.

Henttu, Pirkko and Vihko, Pirkko (1989) "cDNA Coding for the Entire Human Prostate Specific Antigen Shows High Homologies to the Human Tissue Kallikrien Genes" *Biochemical and Biophysical Research Communications* 160:903–910.
Horoszewicz, Julius S., et al. (1987) "Monoclonal Antibodies to a New Antigen Marker in Epithelial Prostatic Cells and Serum of Prostatic Cancer Patients" *AntiCancer Research* 7:927–936.
Huber, Brian E., et al (1991) "Retroviral–medicated Gene Therapy for the Treatment of Hepatocellular Carcinoma: An Innovative Approach for Cancer Therapy" *Proc. Natl. Acad. Sci. USA* 88:8039–8043.
Israeli, Ron S., et al. (1994) "Expression of the Prostate Specific Membrane Antigen" *Cancer Research* 54:1807–1811.
Israeli, Ron S., et al. (1994) "Sensitive Nested Reverse Transrciption Polymerase Chain Reaction Detection of Circulation Prostatic Tumor Cells: Comparison of Prostate–specific Membrane Antigen and Prostate–specific Antigen–based Assays" *Cancer Research* 5:6306–6310.
Keer, Harold N., et al. (1990) "Elevated Transferrin Receptor Content in Human Prostate Cancer Cell Lines Assessed In Vitro In and Vivo" *The Journal of Urology* 143:381–385.
Lopes, A. Dwight., et al (1993) "Immonohistochemical and Pharmacokinetic Characterization of the Site–specific Immunocnjugate CYT–356 Derived from Antiprostate Monoclonal Antibody" *Cancer Research* 50: 6423–6429.
Lubahn, Dennis B., et al. (1989) "Sequence of the Intron/exon junctions of the Coding Region of the Human Adrogen Receptor Gene and Indentification of a Point Mutation in a family with Complete Androgen Insensitivity" *Proc. Natl. Acad. Sci. USA* 86:9534–9538.
Lundwall, Ake and Lilja, Hans., (1987) "Molecular Cloning of Human Prostate Specific Antigen cDNA" 214, No. 2:317–322.
Mukhopadhyay, Tapas., et al. (1991)"Sepecific Inhibitionof K–ras Expression and Tumorigenicity of Lung Cancer Cells by Antisense RNA[1]" *Cancer Research* 51:1744–1748.
Riegman. P.H.J., et al. (1989) "The Prostate–Specific Antigen Gene and the Human Glandular Kallikrein–1 Gene are Tandemly Located on Chromosone 19" vol. 247:123–126.
Sharief, Farida S., et al. "Human Prostatic Acid Phosphatase: cDNA Cloning, Gene Mapping and Protein Sequence Homology With Lysosomal Acid Phoshatase" *Biochemical and Biophysical Research Communications* 160:79–86.

(List continued on next page.)

*Primary Examiner*—Anthony C. Caputa
*Attorney, Agent, or Firm*—John P. White; Cooper & Dunham LLP

[57] ABSTRACT

This invention provides an isolated mammalian nucleic acid molecule encoding an alternatively spliced prostate-specific membrane (PSM') antigen. This invention provides an isolated nucleic acid molecule encoding a prostate-specific membrane antigen promoter. This invention provides a method of detecting hematogenous micrometastic tumor cells of a subject, and determining prostate cancer progression in a subject.

10 Claims, 89 Drawing Sheets

OTHER PUBLICATIONS

Solin, Timo., (1990) "Gene Expression and Prostate Specificity of Human Prostatic Acid Phosphatase (PAP): Evaluation By RNA Blot Analuses" *Biochemica et Biophysica Acta* 1048:72–77.

Troyer, Conference of the American Association for Cancer Research. See Abstract C38, Dec. 1994.

Su, S.L., et al. (1994) "Sensitive Detection of Prostatic Hematogenous Micrometastases Using Prostate Specific Antigen (PSA) and Prostate Specific Membrane Antigen (PSM) Derived parimeters in the Polymerase Chain Reaction" *Proceedings of the American Association for Cancer Research* 35:271.

Vihko, Pirkko., et al (1988) "Molecular Cloning and Sequence Analysis of cDNA Encoding Human Prostatic Acid Phosphatase" 236:275–281.

Vile, Richard G. And Ian R. Hart., (1993) "In Vitro and In Vivo Targeting of Gene Expression to Melanoma Cells" *Cancer Research* 53:962–967.

Israeli, Ron S., et al. (1994) "Expression of the Prostate Specific Membrane Antigen" *Cancer Research* 54:1807–1811.

Waibel, R., et al. (1990) "Therapy of Small Cell Lung Cancer Xenografts in a Nude Mouse model: Evaluation of Radioimmunotherapy and Immonotoxin Therapyogy" 34:54.

Watt, Kenneth W.K., et al (1986) "Human Prostate–Specific Antigen: Structural and Functional Similarity With Serine Proteases" *Proc. Natl. Acad. Sci. USA* 83:3166–3170.

Wright, Jr., et al "Characterization of a New Prostate Carcinoma–Associated Marker" *Antibody Immunoconjugates, and Radiopharmaceuticals* 3:89.

Young, Richard A. and Davis, Ronald W., "Efficient Isolation of Genes by Using Antibody Probes" *Proc. Natl. Acad. Sci. USA* 80:1194–1198.

Israeli, R.S. et al., (1994) "Sensitive Detection of Prostatic Hematogenous Micro–Metastases Using Prostate Specific Antigen (PSA) And Prostate specific Membrane Antigen (PSM) Derived Primers in the Polymerase Chain Reaction (PCR)" J Urol 151:373A.

Israeli, R.S. et al., (1994) "Localization of the Prostate Specific Membrane Antigen (PSM) to the Putative Metastasis–Suppressor Region on Human Chromosome 11" J Urol 151:252A.

Corr, J.G. et al., (1994) "Prostate Specific Membrane Antigen (PSM) Expression in Orthotopically Implanted Human Prostate Cancer Cells in Nude Mice Slows Tumor Growth and Metastatic Potential" J Urol 151:492A.

Israeli, R.S. et al., (1994) "Localization of Prostate Specific Membrane Antigen (PSM) to the Putative Metastasis–Suppressor Region on Human Chromosome 11" Proceedings of the American Association for Cancer Research 35:271.

Israeli, R.S. et al., (1993) "Characterization of the Prostate–Specific Membrane Antigen (PSM)" Cancer Research 34:255.

Israeli, R.S. et al., (1993) "Molecular Cloning and Characterization of a Prostate–Specific Membrane Antigen" J Urol 149:471A.

Israeli, R.S. et al., (1992) "Purification and Molecular Cloning of a New Prostate–Specific Antigen" Cancer Research 33:356.

1 - anti-EGFr PoAB RK-2
2 - Cyt-356 MoAB/RAM
3 - RAM

FIG. 14A

Done on sequence PMSANTIGEN.
Total number of residues is: 750.
Analysis done on the complete sequence.

```
In Helical  (H) conformation [DC = -75 CNAT ] :  264 AA => 35.2%
In Extended (E) conformation [DC = -88 CNAT ] :  309 AA => 41.2%
In Turn     (T) conformation [DC =   0 CNAT ] :   76 AA => 10.1%
In Coil     (C) conformation [DC =   0 CNAT ] :  101 AA => 13.4%
```

Sequence shown with conformation codes.
========================================

Consecutive stretch of 5 or more residues in a given conformation are overlined.

Semi-graphical output.
=====================

Symbols used in the semi-graphical representation:

Helical conformation: X          Extended conformation: -
Turn conformation: >                     Coil conformation: *

```
          10        20        30        40        50
          —         —         —         —         —
MWNLLHETDSAVATARRPRWLCAGAGALVLAGGFFLLGFLFGWFIKSSNEAT
XXXXXXXXXXXXXX---->>----------------XXXXXX*****>X
XXXXXXXXXXXXX----->>-----------------XXXXX*****>X 60        70        80        90       100
          —         —         —         —         —
NITPKHNMKAFLDELKAENIKKFLYNFTQIPHLAGTEQNFQLAKQIQSQW
```

FIG. 14E

```
->>-XXXXXXXXX---->>-----**XXXXXXXX-X---
->>-XXXXXXXXX---->>-----**XXXXXXXX-X---
   110        120        130        140       150
KEFGLDSVELAHYDVLLSYPNKTHPNYISIINEDGNEIFNTSLFEPPPG
->>-XXXXXXXX---->>>-X----*>***X----->>>
->>-XXXXXXXX---->>>-X----*>***X----->>>
   160        170        180        190       200
YENVSDIVPPFSAFSPQGMPEGDLVYVNYARTEDFFKLERDMKINCSGKI
```

FIG. 14F

```
         210          220          230          240          250
          |            |            |            |            |
>-------------->-**>-***-|--------|-----------XXXXXXXXXXXXXX>>>-|--
>-------------->-*-*>-***-|--------|-----------XXXXXXXXXXXXXX>>>-|--
         VIARYGKVFRGNKVKNAQLAGAKGVILYSDPADYFAPGVKSYPDGWNLPG 260          270          280          290          300
          |            |            |            |            |
-------->>>-***XXXXXXXX-|-------->-|--->---->-|-->>->-**>-|-->
-------->>>-***XXXXXXXX-|-------->-|--->---->-|-->>->-**>-|-->
         GGVQRGNILNLNGAGDPLTPGYPANEYAYRRGIAEAVGLPSIPVHPIGYY 310          320          330          340          350
          |            |            |            |            |
>-*----|-->>>-****->-->>->-|---------|-----------XX-|---**-|---
>-*----|-->>>>-****->-->>->-|---------|-----------XX-|---**-|---
         DAQKLLEKMGGSAPPDSSWRGSLKVPYNVGPFTGNFSTQKVKMHIHSTN 360          370          380          390          400
          |            |            |            |            |
XXXXXXX->>>-****>-->>->-|---------|-----------|--*XXXXXX---****
XXXXXXX->>>>-****>-->>->-|---------|-----------|--*XXXXXX---****
         EVTRIYNVIGTLRGAVEPDRYVILGGHRDSWVFGGIDPQSGAAVVHEIVR
```

FIG. 14G

```
                                     ---->***>-!---->>*****>**XXX-!---XX
                                     ---->***>-!---->>*****>**XXX-!---XX
              |         |         |         |
             410       420       430       440       450
            SFGTLKKEGWRPRRTILFASWDAEEFGLLGSTEWAAENSRLLQERGVAYI

XXX****>>>****>-!-------*XXXXXX****XXXXXXXXXX-!------
XXX****>>>****>-!-------*XXXXXX****XXXXXXXXXX-!------
              |         |         |         |
             460       470       480       490       500
            NADSSIEGNYTLRVDCTPLMYSLVHNLTKELKSPDEGFEGKSLYESWTKK

----->>-!--           XXXXXXXXXX****XXXXXXXXXXXXXX>>>*
----->>-!--           XXXXXXXXXX****XXXXXXXXXXXXXX>>>*
              |         |         |         |
             510       520       530       540       550
            SPSPEFSGMPRISKLGSGNDFEVFFQRLGIASGRARYTKNWETNKFSGYP

****>-!----XXXXX>****-!--->>-!*>>-!>>>>>>>*-!--
****>-!----XXXXX>****-!--->>-!*>>-!>>>>>>>*-!--
              |         |         |         |
             560       570       580       590       600
```

FIG. 14H

```
         LYHSVYETYELVEKFYDPMFKYHLTVAQVRGGMVFELANSIVLPFDCRDY
         ------xxxxxxxxxxxxxxxxx-x---------xxxxx------->xxx
         ------xxxxxxxxxxxxxxxxxxxxx-------xxxxx------->xxx
                |        |        |        |        |
               610      620      630      640      650

AVVLRKYADKIYSISMKHPQEMKTYSVSFDSLFSAVKNFTEIASKFSERL
         xxxxxxxxx-----x**xxxxx---------xxxxxxxxxxxxxxxxxx
         xxxxxxxxx-----x**xxxxx---------xxxxxxxxxxxxxxxxxx
                |        |        |        |        |
               660      670      680      690      700

QDFDKSNPIVLRMNDQLMCLERAFIDPLGLPDRPFYRHVIYAPSSHNKY
         xx>>>>-------xxxxxxxxxx--->>**>------------->
         xx>>>>-------xxxxxxxxxx--->>**>------------->
                |        |        |        |        |
               710      720      730      740      750

AGESFPGIYDALFDIESKVDPSKAWGEVKRQIYVAAFTVQAAAETLSEVA
         ----->--xxxxxxxxx***xxxxxxxxx-------xxxxxxxxxxxxx
         ----->--xxxxxxxxx***xxxxxxxxx-------xxxxxxxxxxxxx
```

FIG. 15B

```
****************************************
* PREDICTION OF ANTIGENIC DETERMINANTS *
****************************************

Done on sequence PMSANTIGEN.
Total number of residues is: 750.
Analysis done on the complete sequence.

The method used is that of Hopp and Woods.
The averaging group length is: 6 amino acids.
-> This is the value recommended by the authors <-
```

The three highest points of hydrophilicity are:

```
( 1)  Ah= 1.62 : From   63 to   68 : Asp-Glu-Leu-Lys-Ala-Glu
( 2)  Ah= 1.57 : From  132 to  137 : Asn-Glu-Asp-Gly-Asn-Glu
( 3)  Ah= 1.55 : From  482 to  487 : Lys-Ser-Pro-Asp-Glu-Gly
```

Ah stands for: Average hydrophilicity.

Note that, on a group of control proteins, only the highest point was in 100% of the cases assigned to a known antigenic group. The second and third points gave a proportion of 33% of incorrect predictions.

FIG. 16A

The best scores are:
```
                                                            initn init1  opt
CHKTFER  G.gallus mRNA for transferrin receptor              203   120   321
RATTRFR  Rat transferrin receptor mRNA, 3' end.              164   164   311
HUMTFRR  Human transferrin receptor mRNA, complete cd        145   145   266
```

CHKTFER   G.gallus mRNA for transferrin receptor     203   120   321
51.9% identity in 717 nt overlap

```
           1020       1030       1040       1050       1060       1070
pmsgen TGTCCAGGTGGAAATATCCTAAATCTGAATGGTGCAGGAGACCCTCTCACACCAGGTTA
       :::    :  ::::::::     :   :::::::::  :   ::: :::::  :
CHKTFE TACACTTATCCCATTCGGACATGCCCACCTTGGAACTGGAGACCCTTACACCCCCAGGCTT
           990        1000       1010       1020       1030       1040

1080       1090       1100       1110       1120       1130
pmsgen CCCAGCAAATGAATATGCTTATAGGCGTGAATTGCAGAGGCTGTGTTGGTCTTCCAAGTAT
       :::  :      :  : :: :  :   :: :   ::  :  ::  ::   ::
CHKTFE CCCTTCGTTCAACCACCACCCA---GTTTCCACCAGTTGAATCTTCAGGACTACCCCACAT
           1050       1060       1070       1080       1090       1100

1140       1150       1160       1170       1180       1190
pmsgen TCCTGTTCATCCAATTGGATACTATGATGCACAGAAGCTCCTAGAAAAAATGGGTGGCTC
       :: ::::::: :::::: ::     :::  :   :: :::::::::::  :::
CHKTFE TGCTGTTCAGACCATCTCTAGCAGTGCAGCCCAGGCTGTTCAGCAAATGGATGGAGA
           1110       1120       1130       1140       1150       1160
```

FIG. 16B

```
         1200       1210       1220       1230       1240       1250
pmsgen   AGCCACCACCAGATAGCAGCTGGAGAGGAAGTCTCAAAGTGCCCTACAATGTTGGACCTGG
         ::  : ::  :  : :::::  :::        :: :: :::      ::     :: :::
CHKTFE   CACATGCTCTGA-AG--GTTGGAAAGGTGCGATCCA---TTCCTGTAAGGT--GAC--AA
              1170          1180      1190       1200             1210

1260       1270       1280       1290       1300       1310
pmsgen   CTTTACTGGAAACTTTTCTACACAAAAGTCAAGATGCACATCCACTCTACCAATGAAGT
         ..  : :::  :        :  :: ::   :: :: ::: : : ::: ::
CHKTFE   CAAAGCAGGAGA-----GCCAGA-TAATGGTGAAACTAGATGTGAACAATTCCATGAAAGA
                    1220             1230        1240       1250       1260

1320       1330       1340       1350       1360       1370
pmsgen   GACAAGAATTTACAATGTGATAGGTACTCTCAGAGGAGCAGTGGAACCAGACAGATATGT
         :  :  ::: : : ::  :: : ::: :: :::: :  :  ::::: :  :  ::: ::
CHKTFE   CAGGAAGATTCTGAACATCTTCGGTGCTATCCAGGGATTGAAGAACCTGATCGGTATGT
              1270       1280       1290       1300       1310       1320

1380       1390       1400       1410       1420       1430
pmsgen   CATTCTGGGAGGTCACCGGGACTCATGGGTGTTTTGGTGTATTGACCCTCAGAGTGGAGC
         ::  : ::::::      :: :  : :::: ::::          ::   :: ::: ::
CHKTFE   TGTGATTGGAGCCCCAGAGACTCCTGGGCCCAGGAGTGGCTAAAGCTGGCACTGGGAAC
              1330       1340       1350       1360       1370       1380
```

FIG. 16C

```
              1440      1450      1460      1470      1480      1490
pmsgen   AGCTGTGTTGTTCATGAAATTGTGAG---GAGCTTTGGAACACTGAAAAGGAAGGGTGGAG
         : :: :   :    ::: ::: :    :: ::: ::     :::::: :: ::: : ::
CHKTFE   TGCTATATTGTTGGAACTTGCCCGTGTGATCTCAGACATAGTGAAAACGAGGGCTACAA
              1390      1400      1410      1420      1430      1440

1500      1510      1520      1530      1540      1550
pmsgen   ACCTAGAAGAACAATTTTGTTGCAAGCTGGGATGCAGAAGAATTTGGTCTTCTTGGTTC
         ::: ::   ::   : :: : X::: ::::::   :::: :  :: :::: :::::
CHKTFE   ACCGAGGCGAAGCATCATCTTTGCTAGCTGGAGTGCAGGAGACTACGGAGCTGTGGGTGC
              1450      1460      1470      1480      1490      1500

1560      1570      1580      1590      1600      1610
pmsgen   TACTGAGTGGGCAGAGGAGAATTCAAGACTCCTTCAAGACGTTGGCGTGGCTTATATTAA
         : :::::: :::     ::: :::: :::  :X    :    :  :  :::: : ::
CHKTFE   TACTGAATGGCTGGAGGGTACTCTGCCATGCTGCCAAAGCTTTCACTTACATCA-
              1510      1520      1530      1540      1550      1560

1620      1630      1640      1650      1660      1670
pmsgen   TGC-TGACTCATCATCTATAGAAGGAAACTA-CACTCTGAGAGTTGATTGTACACCGCTGATG
         :  :: :: :: :::  :: :: : ::: ::  :    : :  :  :    : :: ::
CHKTFE   -GCTTGGATGCTCCAGTCCTGGGAGCAAGCCATGTCAAGATTTCTGCCAGCCCCTTGCTG
              1570      1580      1590      1600      1610      1620
```

FIG. 16D

```
             1680       1690       1700       1710       1720       1730
pmsgen TACAGCTTGGTACACAACCTAACACAAAGAGCTGAAAAGCCCTGATGAAGGCTTTGAAGGC
       :: :  :: :  :      :: :  :: :::: :: :: :: ::  :: :
CHKTFE TATATGCTGCTGGGAGTATTATGAAGGGGTGAAGAATCCAGCAGCAGTCTCAGAGAGC
             1630       1640       1650       1660       1670       1680

1740       1750       1760       1770       1780       1790
pmsgen AAATCTCTTTATGAAAGTTGGACTAAAAAAGTCCTTCCCCAGAGTTCAGTGGCATGCCC
       :::: ::  :: :::: : :
CHKTFE ----CTCTATAACAGACTTGGCCCAGACTGGGTAAAAAGCAGTGTTCCTCTTGGCCTGGA
             1690       1700       1710       1720       1730
```

FIG. 16E

RATTRFR   Rat transferrin receptor mRNA, 3' end.           164   164   311
55.5% identity in 560 nt overlap 1210      1220      1230      1240      1250
pmsgen CCACCAGATAGCAGCTGGAGAGGAAGTCTCAAAGTGCCCTACAATGTTGGACCTGGCTT-
       ::: ::   ::: :    :  : :   :: :  ::
RATTRF TGCAGAAAAGCTATTCAAAAACATGGAAGGAAACTGTCCTCCTAGTTGGAATATAGATTC
           610       620       630       640       650       660

1260      1270      1280      1290      1300      1310
pmsgen -TACTGGAAACTTTTCTACACACAAAAGTCAAGATGCACACATC-CACTCT-ACCAATG----
        :  :: ::          :: :  :::  :::      :  :: :::::
RATTRF CTCATGTAAGCTGGAACTTTCACAGAATCAAAATGTGAAGCTCACTGTGAACAATGTACT
           670       680       690       700       710       720

FIG. 16F

```
             1320       1330       1340       1350       1360       1370
pmsgen   --AAGTGACAAGAATTTACAATGTGATAGGTACTCTCAGAGGAGCAGTGGAACCAGACAG
           ::: ::::::::      ::  :  ::   :::    : ::::::::::::::::::
RATTRF   GAAAGAAACAAGAATACTTAACATCTTTGGCGTTATTAAAGGCTATGAGGAACCAGACCG
             730        740        750        760        770        780

1380       1390       1400       1410       1420       1430
pmsgen   ATATGTCATTCTGGGAGGTCACCGGGACTCATGGGTGTTTGGTGTATTGACCCTCAGAG
          ::  :   : ::::  :: ::::    ::  ::::    :: ::: :: :  :: ::: :
RATTRF   CTACATTGTAGTAGGAGCCCAGAGACGCTTGGGCCCTGGT-GTTGCGAAGTCCAGTG
             790        800        810        820        830        840

1440       1450       1460       1470       1480
pmsgen   T-GGAGCAGCTGTGTTCATGAAATTGTGAGGAGCTTTGGAACA-CTGA---AAAAGGAA
          : :::  :: ::  :  :::::::     ::   :: ::   ::   ::     ::  ::
RATTRF   TGGGAACAGGTCTT-CTGTTGAAACTGCCCAAGTATTCTCAGATATGATTTCAAAAGAT
             850        860        870        880        890        900

1490       1500       1510       1520       1530       1540
pmsgen   GGGTGGGAGACCTAGAGAAGAACAATTTTGTTTGCAAGCTGGATGCAGAAGAATTTGGTCTT
          ::  :  X::: ::  :: ::::: :::::: :::::   ::: ::: :: ::: ::: ::
RATTRF   GGATTTAGACCCAGCAGGAGTATTATCTTTGCCAGCTGGACTGCAGGAGACTATGGAGCT
             910        920        930        940        950        960
```

FIG. 16G

```
          1550      1560      1570      1580      1590      1600
pmsgen CTGGGTCTACTGAGTGGGCAGAGGAGAA---TTCAAGACTCCTTCAAGAGCGTGGCGTG
       :::: : :::::::::     :::: : X  :: ::: : :: :: :       ::
RATTRF GTTGGTCCGACTGAGTGGCTGGAGGGGTACCTTTCATCTTTGCATCTAAAG---GCTTTC
         970       980       990      1000      1010      1020

1610      1620      1630      1640      1650      1660
pmsgen GCTTATATTAATGCTGACTCATCTATAGAAGGAAACTA-CACTCTGAGAGTTGATTGTAC
       :::: :::::: ::: :     :: ::: :: :: :    ::: ::: :  :    ::
RATTRF ACTTACATTAAT-CTGGATAAAGTCGTCCTGGGTACTAGCAACTTCAAGGTTTCTGCCAG
        1030       1040      1050      1060      1070      1080

1670      1680      1690      1700      1710      1720
pmsgen ACCGCTGATGTACAGCTTGGTACACAACCTAACAAAGAGCTGAAAAGC-CCTGATGAAG
       :: : ::: : :::: ::     : :: :: :: :::  :: :::: :::: :
RATTRF CCCCCTATTATATACACTTATGGGAAGATAATGCAGGA--CGTAAAGCATCCGA----
        1090       1100      1110      1120      1130
```

FIG. 16H

```
           1730         1740         1750         1760         1770
pmsgen GCTTGAAGGCAAATCTCTTTAT-GAA-----AGTTGGACTAAAAAAGTCCTCCCCAG
       :::: :: :::: ::: :::  :  : ::::: :: ::::: :
RATTRF ---TTGATGGAAAATATCTATATCGAAACAGTAATTGGATTAGCAAATTGAGGAACTTT
           1140         1150         1160         1170         1180         1190

1780         1790         1800         1810         1820         1830
pmsgen AGTTCAGTGGCCATGCCCCAGGATAAGCCAAATTGGGATCTGGAAATGATTTTGAGGTGTTCT RATTRF CCTTGGACAATGCTGCATTCCCTTTCTTGCATATTCAGGAATCCCAGCAGTTTCTTTCT
           1200         1210         1220         1230         1240         1250
```

FIG. 16I

```
HUMTFRR   Human transferrin receptor mRNA, complete cd   145   145   266
          54.3% identity in 464 nt overlap 1230      1240      1250      1260      1270
pmsgen    AGGAAGTCTCAAAGTGCCCTACAATGTGGACCTGGCTTTAC-TGGAAACTTTCTACAC
                :  : ::: :  ::  :: :    : :
HUMTFR    TATGGAAGGAGACTGTGTCCCCTCTGACTGGAAAACAGACTCTACATGTAGGATGGTAACCTC
          1140      1150      1160      1170      1180      1190

1280      1290      1300      1310      1320      1330
pmsgen    AAAAAGTCAAGATGCACATC-CACTCT-ACCAATG-----AAGTGACAAGAATTTACAA
            : :::    :  :::   :  : ::::  : :::::       ::  ::  ::::  ::
HUMTFR    AGAAAGCAAGAATGTGAAGCTCACTGTGAGCAATGTGCTGAAAGAGATAAAAATTCTTAA
          1200      1210      1220      1230      1240      1250

1340      1350      1360      1370      1380      1390
pmsgen    TGTGATAGGTACTCTCAGAGGAGCAGTGGAACCAGAGACAGATATGTCATTCTGGGAGGTCA
             :  : :: : :::      :  : :::::::      :  : : : :  ::
HUMTFR    CATCTTTGGAGTTATTAAAGGCTTTGTAGAACCAGATCACTATGTTGTAGTTGGGGCCCA
          1260      1270      1280      1290      1300      1310

1400      1410      1420      1430      1440      1450
pmsgen    CCGGGACTCATGGGTGTTTGGTGTATTGACCCTCAGAGT-GGAGCAGCTGTTGTTCATG
              : :: ::::::       : ::::: :       : :::: :
HUMTFR    GAGAGATGCATGGGCCCCTGGAGCTGCAAAATC-CGGTGTAGGCACACAGCTCTCCTATTGA
          1320      1330      1340      1350      1360      1370
```

FIG. 16J

```
                 1460      1470      1480      1490      1500
pmsgen  AAATTG---TGAGGAGCTTTGGAACACTGAAAAAGGAAGGGTGGAGACCTAGAAGAACAA
        ::  :::          ::  ::     ::  :: X:::  :: :::  :::::  ::
HUMTFR  AACTTGCCCAGATGTTCTCAGATATGGTCTTAAAAGATGGGTTTCAGCCCAGCAGAAGCA
                 1380      1390      1400      1410      1420      1430

1510      1520      1530      1540      1550      1560
pmsgen  TTTGTTTGCAAGCTGGGATGCAGAAGAATTTGGTCTCTTCTTGGTTCTTCTACTGAGTGGGCAG
        ::  :  :::::  ::   :::  ::::::                ::::: :  :::::: ::
HUMTFR  TTATCTTGCCAGTGCTGGAGTGCTGGAGACTTTGGATCGTTGGTGCCACTGAATGGCTAG
                 1440      1450      1460      1470      1480      1490

1570      1580      1590      1600      1610      1620
pmsgen  A-GGAGAATTCAAGACTCCTTCAAGAGCGTGGCGTGGCTTATATTAATGCTGACTCATCT
         :  ::: :  :  :  :: :::  ::            :::::::::X  ::   ::
HUMTFR  AGGGATACCCTTTCGTC-CCTGCATTTAAAGGCTTTCACTTATATTAATCTGGATAAAGCG
                 1500      1510      1520      1530      1540      1550

1630      1640      1650      1660      1670      1680
pmsgen  ATAGAAGGAAACTACACTCTGAGAGTTGATTGTACACCGCTGATGTACA-GCTTGGT-AC
            ::  :::  ::   :  :  :::   :  :      :::  ::::  :::::   ::
HUMTFR  GTTCTTGGTACCAGCAACTTCAAGGTTTCTGCCAGCCCACTGTTGTATACGCTTATTGAG
                 1560      1570      1580      1590      1600      1610
```

FIG. 16K

```
            1690       1700       1710       1720       1730       1740
pmsgen  ACAACCTAACAACAAAGAGCTGAAAGCCCTGATGAAGGCTTTGAAGGCAAATCTCTTTATG
        :  :::        :::::
HUMTFR  AAACAATGCAAAATGTGAAGCATCCGGTTACTGGGCAATTTCTATATCAGGACAGCAAC
            1620       1630       1640       1650       1660       1670
```

FIG. 23

| CELL LINE/TYPE | 11p11.2-13 REGION | METASTATIC | PSM RNA DETECTED | PSM DNA DETECTED |
|---|---|---|---|---|
| LNCap | | | ++ | ND |
| HUMAN PROSTATE | | | ++ | ND |
| A9 (FIBROSARCOMA) | NO | NO | - | - |
| A9(11) (A9+HUM. 11) | YES | NO | - | REPEAT |
| AT6.1 (RAT PROSTATE) | NO | YES | - | - |
| AT6.1-11-c11 | YES | NO | + | ++ |
| AT6.1-11-c12 | NO | YES | - | - |
| R1564 (RAT MAMMARY) | NO | YES | - | - |
| R1564-11-c14 | YES | YES | - | + |
| R1564-11-c15 | YES | YES | - | REPEAT |
| R1564-11-c16 | YES | YES | - | ND |
| R1564-11-c12 | YES | YES | ND | + |

FIG. 30

| Patient | Stage | Treatment | PSA | PAP | PSA-PCR | PSM-PCR |
|---|---|---|---|---|---|---|
| 1 | T2NxMo | None | 8.9 | 0.7 | − | + |
| 2 | T2NoMo | RRP 7/93 | 6.1 | − | − | + |
| 3 | T2CNoMo | PLND 5/93 | 4.5 | 0.1 | − | + |
| 4 | T2BNoMo | RRP 3/92 | NMA | 0.4 | − | + |
| 5 | T3NxMo | Proscar + Flutamide | 51.3 | 1.0 | − | + |
| 6 | Recur T3 | I-125 1986 | 54.7 | 1.4 | − | + |
| 7 | T3ANoMo | RRP 10/92 | NMA | 0.3 | − | + |
| 8 | T3NxMo | XRT 1987 | 7.5 | 0.1 | − | − |
| 9 | T3NxMo | Proscar + Flutamide | 35.4 | 0.7 | − | − |
| 10 | D2 | S/P XRT Flutamide +Emcyt | 311 | 4.5 | − | + |
| 11 | D2 | RRP 4/91 Lupron 10/92 Velban + Emcyt 12/92 | 1534 | 1.4 | + | + |
| 12 | T2NoMo | RRP 8/91 | NMA | 0.5 | − | + |
| 13 | T3NoMo | RRP 1/88 Lupron + Flutamide 5/92 | 0.1 | 0.3 | − | − |
| 14 | D1 | PLND 1989 XRT 1989 | 1.6 | 0.4 | − | − |
| 15 | D1 | Proscar + Flutamide | 20.8 | 0.5 | − | − |
| 16 | T2CNoMo | RRP 4/92 | 0.1 | 0.3 | − | − |

FIG. 31A

```
              10         20         30         40         50         60
               |          |          |          |          |          |
   1 AAGGGTGCTC CTTAGGCTGA ATGCTTGCAG ACAGGATGCT TGGTTACAGA TGGGCTGTGA
     TTCCCACGAG GAATCCGACT TACGAACGTC TGTCCTACGA ACCAATGTCT ACCCGACACT

61 CTCGAGTGGA GTTTTATAAG GGTGCTCCTT AGGCTGAATG CTTGCAGACA GGATGCTTGG
     GAGCTCACCT CAAAATATTC CCACGAGGAA TCCGACTTAC GAACGTCTGT CCTACGAACC

121 TTACAGATGG GCTGTGAGCT GGGTGCTTGT AAGAGGATGC TTGGGTGCTA AGTGAGCCAT
     AATGTCTACC CGACACTCGA CCCACGAACA TTCTCCTACG AACCCACGAT TCACTCGGTA

181 TTGCAGTTGA CCCTATTCTT GGAACATTCA TTCCCCTCTA CCCTGTTTC TGTTCCTGCC
     AACGTCAACT GGGATAAGAA CCTTGTAAGT AAGGGGAGAT GGGACAAAG ACAAGGACGG

241 AGCTAAGCCC ATTTTTCATT TTTCTTTTAA CTCCTTAGCG CTCCGCAAAA CTTAATCAAT
     TCGATTCGGG TAAAAAGTAA AAAGAAAATT GAGGAATCGC GAGGCGTTTT GAATTAGTTA

301 TTCTTTAAAC CTCAGTTTTC TTATCTGTAA AAGGTAAATA ATAATACAGG GTGCAACAGA
     AAGAAATTTG GAGTCAAAAG AATAGACATT TTCCATTTAT TATTATGTCC CACGTTGTCT

361 AAAATCTAGT GTGGTTTACA TAATCACCTG TTAGAGATTT TAAATTATTT CAGGATAAGT
     TTTTAGATCA CACCAAATGT ATTAGTGGAC AATCTCTAAA ATTTAATAAA GTCCTATTCA

421 CATGATAATT AAATGAAATA ATGCACATAA AGCACATAGT GTGGTGTCCT CCATATAGAA
     GTACTATTAA TTTACTTTAT TACGTGTATT TCGTGTATCA CACCACAGGA GGTATATCTT

481 AATGCTCAGT ATATTGGTTA TTAACTACTT GTTGAAGGTT TATCTTCTCC ACTAAACTGT
     TTACGAGTCA TATAACCAAT AATTGATGAA CAACTTCCAA ATAGAAGAGG TGATTTGACA

541 AAGTTCCACA AGCCTTACAA TATGTGACAG ATATTCATTC ATTGTCTGAA TTCTTCAAAT
     TTCAAGGTGT TCGGAATGTT ATACACTGTC TATAAGTAAG TAACAGACTT AAGAAGTTTA

601 ACATCCTCTT CACCATAGCG TCTTATTAAT TGAATTATTA ATTGAATAAA TTCTATTGTT
     TGTAGGAGAA GTGGTATCGC AGAATAATTA ACTTAATAAT TAACTTATTT AAGATAACAA

661 CAAAAATCAC TTTTATATTT AACTGAAATT TGCTTACTTA TAATCACATC TAACCTTCAA
     GTTTTTAGTG AAAATATAAA TTGACTTTAA ACGAATGAAT ATTAGTGTAG ATTGGAAGTT

721 AGAAAACACA TTAACCAACT GTACTGGGTA ATGTTACTGG GTGATCCCAC GTTTTACAAA
     TCTTTTGTGT AATTGGTTGA CATGACCCAT TACAATGACC CACTAGGGTG CAAAATGTTT
```

FIG. 31B

```
 781 TGAGAAGATA TATTCTGGTA AGTTGAATAC TTAGCACCCA GGGGTAATCA GCTTGGACAG
     ACTCTTCTAT ATAAGACCAT TCAACTTATG AATCGTGGGT CCCCATTAGT CGAACCTGTC

841 GACCAGGTCC AAAGACTGTT AAGAGTCTTC TGACTCCAAA CTCAGTGCTC CCTCCAGTGC
     CTGGTCCAGG TTTCTGACAA TTCTCAGAAG ACTGAGGTTT GAGTCACGAG GGAGGTCACG

901 CACAAGCAAA CTCCATAAAG GTATCCTGTG CTGAATAGAG ACTGTAGAGT GGTACAAAGT
     GTGTTCGTTT GAGGTATTTC CATAGGACAC GACTTATCTC TGACATCTCA CCATGTTTCA

961 AAGACAGACA TTATATTAAG TCTTAGCTTT GTGACTTCGA ATGACTTACC TAATCTAGCT
     TTCTGTCTGT AATATAATTC AGAATCGAAA CACTGAAGCT TACTGAATGG ATTAGATCGA

1021 AAATTTCAGT TTTACCATGT GTAAATCAGG AAGAGTAATA GAACAAACCT TGAAGGGTCC
     TTTAAAGTCA AAATGGTACA CATTTAGTCC TTCTCATTAT CTTGTTTGGA ACTTCCCAGG

1081 CAATGGTGAT TAAATGAGGT GATGTACATA ACATGCATCA CTCATAATAA GTGCTCTTTA
     GTTACCACTA ATTTACTCCA CTACATGTAT TGTACGTAGT GAGTATTATT CACGAGAAAT

1141 AATATTAGTC ACTATTATTA GCCATCTCTG ATTAGATTTG ACAATAGGAA CATTAGGAAA
     TTATAATCAG TGATAATAAT CGGTAGAGAC TAATCTAAAC TGTTATCCTT GTAATCCTTT

1201 GATATAGTAC ATTCAGGATT TTGTTAGAAA GAGATGAAGA AATTCCCTTC CTTCCTGCCC
     CTATATCATG TAAGTCCTAA AACAATCTTT CTCTACTTCT TTAAGGGAAG GAAGGACGGG

1261 TAGGTCATCT AGGAGTTGTC ATGGTTCATT GTTGACAAAT TAATTTTCCC AAATTTTTCA
     ATCCAGTAGA TCCTCAACAG TACCAAGTAA CAACTGTTTA ATTAAAAGGG TTTAAAAAGT

1321 CTTTGCTCAG AAAGTCTACA TCGAAGCACC CAAGACTGTA CAATCTAGTC CATCTTTTTC
     GAAACGAGTC TTTCAGATGT AGCTTCGTGG GTTCTGACAT GTTAGATCAG GTAGAAAAAG

1381 CACTTAACTC ATACTGTGCT CTCCCTTTCT CAAAGCAAAC TGTTTGCTAT TCCTTGAATA
     GTGAATTGAG TATGACACGA GAGGGAAAGA GTTTCGTTTG ACAAACGATA AGGAACTTAT

1441 CACTCTGAGT TTTCTGCCTT TGCCTACTCA GCTGGCCCAT GGCCCCTAAT GTTTCTTCTC
     GTGAGACTCA AAAGACGGAA ACGGATGAGT CGACCGGGTA CCGGGGATTA CAAAGAAGAG

1501 ATCTCCACTG GGTCAAATCC TACCTGTACC TTATGGTTCT GTTAAAAGCA GTGCTTCCAT
     TAGAGGTGAC CCAGTTTAGG ATGGACATGG AATACCAAGA CAATTTTCGT CACGAAGGTA

1561 AAAGTACTCC TAGCAAATGC ACGGCCTCTC TCACGGATTA TAAGAACACA GTTTATTTTA
```

FIG. 31C

```
     TTTCATGAGG ATCGTTTACG TGCCGGAGAG AGTGCCTAAT ATTCTTGTGT CAAATAAAAT

1621 TAAAGCATGT AGCTATTCTC TCCCTCGAAA TACGATTATT ATTATTAAGA ATTTATAGCA
     ATTTCGTACA TCGATAAGAG AGGGAGCTTT ATGCTAATAA TAATAATTCT TAAATATCGT

1681 GGGATATAAT TTTGTATGAT GATTCTTCTG GTTAATCCAA CCAAGATTGA TTTTATATCT
     CCCTATATTA AAACATACTA CTAAGAAGAC CAATTAGGTT GGTTCTAACT AAAATATAGA

1741 ATTACGTAAG ACAGTAGCCA GACATAGCCG GGATATGAAA ATAAAGTCTC TGCCTTCAAC
     TAATGCATTC TGTCATCGGT CTGTATCGGC CCTATACTTT TATTTCAGAG ACGGAAGTTG

1801 AAGTTCCAGT ATTCTTTTCT TTCCTCCCCT CCCTCCCCT CCCTTCCCCT CCCCTTCCTT
     TTCAAGGTCA TAAGAAAAGA AAGGAGGGGA GGGGAGGGGA GGGAAGGGGA GGGGAAGGAA

1861 CCCTTTCCCT TCCCTTCCTT TCTTTCTTGA GGGAGTCTCA CTCTGTCACC AGGCTCCAGT
     GGGAAAGGGA AGGGAAGGAA AGAAAGAACT CCCTCAGAGT GAGACAGTGG TCCGAGGTCA

1921 GCAGTGGCGC TATCTTGGCT GACTGCAACC TCCGCCTCCC CGGTTCAAGC GATTCTCCTG
     CGTCACCGCG ATAGAACCGA CTGACGTTGG AGGCGGAGGG GCCAAGTTCG CTAAGAGGAC

1981 CCTCAGCCTC CTGAGTAGCT GGGACTACAG GAGCCCGCCA CCACGCCCAG CTAATTTTTG
     GGAGTCGGAG GACTCATCGA CCCTGATGTC CTCGGGCGGT GGTGCGGGTC GATTAAAAAC

2041 TATTTTTAGT AGAGATGGGG TTTCACCATG TTGGCCAGGA TGGTCTCGAT TTCTCGACTT
     ATAAAAATCA TCTCTACCCC AAAGTGGTAC AACCGGTCCT ACCAGAGCTA AAGAGCTGAA

2101 CGTGATCCGC CTGTCTGGGC CTCCCAAAGT GCTGGGATTA CAGGCGTGAG CCACCACGCC
     GCACTAGGCG GACAGACCCG GAGGGTTTCA CGACCCTAAT GTCCGCACTC GGTGGTGCGG

2161 CGGCTTTAAA AAATGGTTTT GTAATGTAAG TGGAGGATAA TACCCTACAT GTTTATTAAT
     GCCGAAATTT TTTACCAAAA CATTACATTC ACCTCCTATT ATGGGATGTA CAAATAATTA

2221 AACAATAATA TTCTTTAGGA AAAAGGGCGC GGTGGTGATT TACACTGATG ACAAGCATTC
     TTGTTATTAT AAGAAATCCT TTTTCCCGCG CCACCACTAA ATGTGACTAC TGTTCGTAAG

2281 CCGACTATGG AAAAAAAGCG CAGCTTTTTC TGCTCTGCTT TTATTCAGTA GAGTATTGTA
     GGCTGATACC TTTTTTTCGC GTCGAAAAAG ACGAGACGAA AATAAGTCAT CTCATAACAT

2341 GAGATTGTAT AGAATTTCAG AGTTGAATAA AAGTTCCTCA TAATTATAGG AGTGGAGAGA
     CTCTAACATA TCTTAAAGTC TCAACTTATT TTCAAGGAGT ATTAATATCC TCACCTCTCT
```

FIG. 31D

```
2401 GGAGAGTCTC TTTCTTCCTT TCATTTTTAT ATTTAAGCAA GAGCTGGACA TTTTCCAAGA
     CCTCTCAGAG AAAGAAGGAA AGTAAAAATA TAAATTCGTT CTCGACCTGT AAAAGGTTCT

2461 AAGTTTTTTT TTTTTAAGGC GCCTCTCAAA AGGGGCCGGA TTTCCTTCTC CTGGAGGCAG
     TTCAAAAAAA AAAAATTCCG CGGAGAGTTT TCCCCGGCCT AAAGGAAGAG GACCTCCGTC

2521 ATGTTGCCTC TCTCTCTCGC TCGGATTGGT TCAGTGCACT CTAGAAACAC TGCTGTGGTG
     TACAACGGAG AGAGAGAGCG AGCCTAACCA AGTCACGTGA GATCTTTGTG ACGACACCAC

2581 GAGAAACTGG ACCCCAGGTC TGGAGCGAAT TCCAGCCTGC AGGGCTGATA AGCGAGGCAT
     CTCTTTGACC TGGGGTCCAG ACCTCGCTTA AGGTCGGACG TCCCGACTAT TCGCTCCGTA

2641 TAGTGAGATT GAGAGAGACT TTACCCCGCC GTGGTGGTTG GAGGGCGCGC AGTAGAGCAG
     ATCACTCTAA CTCTCTCTGA AATGGGGCGG CACCACCAAC CTCCCGCGCG TCATCTCGTC

2701 CAGCACAGGC GCGGGTCCCG GGAGGCCGGC TCTGCTCGCG CCGAGATGTG GAATCTCCTT
     GTCGTGTCCG CGCCCAGGGC CCTCCGGCCG AGACGAGCGC GGCTCTACAC CTTAGAGGAA

2761 CACGAAACCG ACTCGGCTGT GGCCACCGCG CGCCGCCCGC GCTGGCTGTG CGCTGGGGCG
     GTGCTTTGGC TGAGCCGACA CCGGTGGCGC GCGGCGGGCG CGACCGACAC GCGACCCCGC

2821 CTGGTGCTGG CGGGTGGCTT CTTTCTCCTC GGCTTCCTCT TCGGTAGGGG GGCGCCTCGC
     GACCACGACC GCCCACCGAA GAAAGAGGAG CCGAAGGAGA AGCCATCCCC CCGCGGAGCG

2881 GGAGCAAACC TCGGAGTCTT CCCCGTGGTG CCGCGGTGCT GGGACTCGCG GGTCAGCTGC
     CCTCGTTTGG AGCCTCAGAA GGGGCACCAC GGCGCCACGA CCCTGAGCGC CCAGTCGACG

2941 CGAGTGGGAT CCTGTTGCTG GTCTTCCCCA GGGGCGGCGA TTAGGGTCGG GGTAATGTGG
     GCTCACCCTA GGACAACGAC CAGAAGGGGT CCCCGCCGCT AATCCCAGCC CCATTACACC

3001 GGTGAGCACC CCTCGAG
     CCACTCGTGG GGAGCTC
```

FIG. 32

Potential binding sites on the PSM promoter*

| Site | Seq | **Location | #nt matched | |
|---|---|---|---|---|
| AP1 | TKAGTCA | 1145 | 7/7 | |
| E2-RS | ACCNNNNNNGGT | 1940 | 12/12 | |
| | | 1951 | 12/12 | |
| GHF | NNNTAAATNNN | 580 | 11/11 | |
| | | 753 | 11/11 | |
| | | 1340 | 11/11 | |
| | | 1882 | 11/11 | |
| | | 1930 | 11/11 | |
| | | 1979 | 11/11 | |
| | | 2001 | 11/11 | |
| | | 2334 | 11/11 | |
| | | 2374 | 11/11 | |
| | | 2591 | 11/11 | |
| | | 2620 | 11/11 | |
| | | 2686 | 11/11 | |
| JVC repeat | GGGNGGRR | 1165 | 8/8 | |
| | | 1175 | 8/8 | |
| | | 1180 | 8/8 | |
| | | 1185 | 8/8 | |
| | | 1190 | 8/8 | |
| NFkB | GGGRHTYYHC | 961 | 10/10 | |
| uteroglobi | RYYWSGTG | 250 | 8/8 | |
| | | 921 | 8/8 | |
| | | 1104 | 8/8 | |
| IFN | AAWAANGAAAGGR | 590 | 13/13 | Cell 41:509 (1985) |

* the PSM promoter sequence 683XFRVS (Fig. 1) starts from the 5' end of the promoter fragment. The 3' region overlapps the previously published PSM cDNA at nt#2485, i.e. the putatative transcription start site is at nt#2485 on sequence 683XFRVS. **The number refered to in this table is in reference to sequence 683XF107 which is the complement and inverse of 683XFRVS.

FIG. 34

```
                                                                              CTCAAAAGGGGCCGGATTTCCT
TCT TGGAGGCAGATGTTGCCTCTCTCTCGCTCGGATTGGTTCAGTGCACTCTAGAAACACTGCTGTGGTGGAGAAACT
GGACCCCAGG TCTGGAGCGAATTCCA GCCTGCAGGGCTGATAAGCGAGGCATTAGTGAGATTGAGAGAGACTTTACCC
CGCGGTGGTTGGAGGGCGCGCAGT AGAGCAGCAGCACAGGCGCGGGGTCCCGGAGGCCGGCTCTGCTCGCGCCGAG
```

ATG TGG AAT CTC CTT CAC GAA ACC GAC TCG GCT GTG GCC ACC GCG CGC CCG CGC TGG CTG
Met Trp Asn Leu Leu His Glu Thr Asp Ser Ala Val Ala Ala Arg Arg Pro Arg Trp Leu

TGC GCT GGG GCG CTG GTG CTG GCG GGT GGC TTC TTT CTC CTC TTC GGC TTC TTT CTC CTC GGC TTC TTT CTC CTC TTC GGA TGG TTT
Cys Ala Gly Ala Leu Val Leu Ala Gly Gly Phe Phe Leu Leu Phe Leu Gly Phe Phe Leu Leu Phe Gly Trp Phe

ATA AAA TCC TCC AAT GAA GCT ACT AAC ATT ACT CCA AAG CAT AAT ATG AAA GCA TTT TTG GAT GAA
Ile Lys Ser Ser Asn Glu Ala Thr Asn Ile Thr Pro Lys His Asn Met Lys Ala Phe Leu Asp Glu
                                                              *

TGG AAA GCT GAG AAC ATC AAG AAG TTC TTA TAT AAT TTT ACA CAG ATA CCA CAT TTA GCA GGA ACA
Leu Lys Ala Glu Asn Ile Lys Lys Phe Leu Tyr Asn Phe Thr Gln Ile Pro His Leu Ala Gly Thr

FIG. 39

```
              10         20         30         40         50         60
              |          |          |          |          |          |
  1 TTTGCAGACT TGACCAACTT TCTAAGAAAA GCAGAACCAC ACAGGCAAGC TCAGACTCTT
    AAACGTCTGA ACTGGTTGAA AGATTCTTTT CGTCTTGGTG TGTCCGTTCG AGTCTGAGAA

61 TTATTAAATT CCAGTTTTGA CTTTGCCACT TCTTAGTGGC CTTGAACAAG TTACCGAGTC
    AATAATTTAA GGTCAAAACT GAAACGGTGA AGAATCACCG GAACTTGTTC AATGGCTCAG

121 CTCTCAGCGT TAGTTACCCT ATTTTAATGA TGAGGATAAT ATTATCTGCC CAAATTATTG
    GAGAGTCGCA ATCAATGGGA TAAAATTACT ACTCCTATTA TAATAGACGG GTTTAATAAC

181 GTATAGTAAA TATATAGCAT GTAAATCTCC TAGCAGAGTA CTGGGATTTC GCCACTTTAT
    CATATCATTT ATATATCGTA CATTTAGAGG ATCGTCTCAT GACCCTAAAG CGGTGAAATA

241 TTCTTCTTTA CCAAGATACT CCTATTGGAC TTAATACACA GGACTAGTCT AAGGTATCAC
    AAGAAGAAAT GGTTCTATGA GGATAACCTG AATTATGTGT CCTGATCAGA TTCCATAGTG

301 CAGGTAGTCC ACTCCTGCTC GGAATCTGAC CCGGGATTAG AGTAGGGCAT GGACCAGATG
    GTCCATCAGG TGAGGACGAG CCTTAGACTG GGCCCTAATC TCATCCCGTA CCTGGTCTAC

361 GGTTTAAACA AATTCAATAT CTTCCACTAG CTTCACCTTG GGGTTGTAAA AGTTTTTGAA
    CCAAATTTGT TTAAGTTATA GAAGGTGATC GAAGTGGAAC CCCAACATTT TCAAAAACTT

421 CCACACACTG TGCTCATAAC AATCTTCATC TCTTAAAAGG ATTTTATTCT TCCTGGTATC
    GGTGTGTGAC ACGAGTATTG TTAGAAGTAG AGAATTTTCC TAAAATAAGA AGGACCATAG

481 CTCACTCTCA TCCCTTGTAT TCCGTGCTCA GTGGCTGACA CAGAAGAGTT CTTTATNNNN
    GAGTGAGAGT AGGGAACATA AGGCACGAGT CACCGACTGT GTCTTCTCAA GAAATANNNN

541 NNNNNNNNNN CATCCTGTTC ATTTTTCAGA TCTCAGTTCA AGCATCTCGT CCTCAGTGTG
    NNNNNNNNNN GTAGGACAAG TAAAAAGTCT AGAGTCAAGT TCGTAGAGCA GGAGTCACAC

601 GTGTTNNCTG ATCCCTCACT CTAATCCAAG TCTTTCTGTT TTATGCACAG GTTGGAATCT
    CACAANNGAC TAGGGAGTGA GATTAGGTTC AGAAAGACAA AATACGTGTC CAACCTTAGA

661 TATTTCCGTT TGCGNNCCAA TCNAATNGTA TTTAATATGC ATGTATATAT GTATGTGCAT
    ATAAAGGCAA ACGCNNGGTT AGNTTANCAT AAATTATACG TACATATATA CATACACGTA

721 TTGTATGCTA NGCGATTAAG AACTAGAATA ATTAATAATT GGAAGTCTAG AAGTGG
    AACATACGAT NCGCTAATTC TTGATCTTAT TAATTATTAA CCTTCAGATC TTCACC
```

FIG. 40A

```
              10         20         30         40         50         60
              |          |          |          |          |          |
  1  TGAAAAATAC ATCAAAAATA GGCATGAGAT ACGAGCCTAT AGATAGGACT TATTTTTTAT
     ACTTTTTATG TAGTTTTTAT CCGTACTCTA TGCTCGGATA TCTATCCTGA ATAAAAAATA

61  TATTGTTGTA TGTATTATTT GTAAAACACA AATTATCAAT ATTACCTCTG ACATTAGGTG
     ATAACAACAT ACATAATAAA CATTTTGTGT TTAATAGTTA TAATGGAGAC TGTAATCCAC

121  AGATATTCTG AATTTTAATT TCTCTTGCCT ACTTTCACTG AAAAAGAGTC ATGCAAACAG
     TCTATAAGAC TTAAAATTAA AGAGAACGGA TGAAAGTGAC TTTTTCTCAG TACGTTTGTC

181  ATTTTTAAGT TGCAAACCAA TTGCAAAATA TTTTTTTATC CAACTTCAAT GATAGGTATT
     TAAAAATTCA ACGTTTGGTT AACGTTTTAT AAAAAAATAG GTTGAAGTTA CTATCCATAA

241  GCTGTTAATT CTAAGATATG CATTAATTGT TTCAACTAAT GGGTGTCAAA CGAGATGTTC
     CGACAATTAA GATTCTATAC GTAATTAACA AAGTTGATTA CCCACAGTTT GCTCTACAAG

301  TGAAAATGAA GGCAAAAAGG AGATCCACCT TCTACTTTCA TAAAGTTTCT ATCTTCCTCT
     ACTTTTACTT CCGTTTTTCC TCTAGGTGGA AGATGAAAGT ATTTCAAAGA TAGAAGGAGA

361  GCTGACTCAA ATAAGCATTT AATACATTTT ATAACGAATT AATTATGAAT ATATTTCAAA
     CGACTGAGTT TATTCGTAAA TTATGTAAAA TATTGCTTAA TTAATACTTA TATAAAGTTT

421  TAAATAAATT ATTTCCAAGT GTTGAAGGAA ATTCAGACTT CTAATTTGCT CTGATTCTGA
     ATTTATTTAA TAAAGGTTCA CAACTTCCTT TAAGTCTGAA GATTAAACGA GACTAAGACT

481  AACTAAAACA AATGCTCTGT GAGAGTTTGC GTTTCCAGTG AAGTAGCGTG AGAAATCCAA
     TTGATTTTGT TTACGAGACA CTCTCAAACG CAAAGGTCAC TTCATCGCAC TCTTTAGGTT

541  GTCAGACAGC TACATGAAAC TACATTTACC AGCTCTCTGC CAGACACCAG TGCACGATAG
     CAGTCTGTCG ATGTACTTTG ATGTAAATGG TCGAGAGACG GTCTGTGGTC ACGTGCTATC

601  CGCAGAACAT GTAGCTAGAT CTCAGTCATA GCTNNNNNNN NNNNNNNNNN AGACCTTGCA
     GCGTCTTGTA CATCGATCTA GAGTCAGTAT CGANNNNNNN NNNNNNNNNN TCTGGAACGT

661  GTTGGCTTTT AACCTGAAGG AGATAAGGCA AGATTCCAGG GTTTATTTAG AGAAATTACA
     CAACCGAAAA TTGGACTTCC TCTATTCCGT TCTAAGGTCC CAAATAAATC TCTTTAATGT

721  GGATCTGGGA ATAAAGTAGT TACAAAATTA GTCCCCAACC AGCTTTCATG GAGCTTTCAA
     CCTAGACCCT TATTTCATCA ATGTTTTAAT CAGGGGTTGG TCGAAAGTAC CTCGAAAGTT
```

FIG. 40B

```
 781 TTATTAATTA TTCTAGTTCT TAATCGCATG CATACAATGC ACATACATAT ATACATGCAT
     AATAATTAAT AAGATCAAGA ATTAGCGTAC GTATGTTACG TGTATGTATA TATGTACGTA

841 ATTAAAATAC ATGATTGGAC GCAAACGGAA ATAAGATTCC ACCTGTGCAT AAAACAGAAA
     TAATTTTATG TACTAACCTG CGTTTGCCTT TATTCTAAGG TGGACACGTA TTTTGTCTTT

901 GACTTGGTTA GAGTGAGGGA TCAGGAAACA CCACACTGAG GACGAGATGN NNNNNNNNNN
     CTGAACCAAT CTCACTCCCT AGTCCTTTGT GGTGTGACTC CTGCTCTACN NNNNNNNNNN

961 NTAGTGGGTG GGGGGCGGAC ATCAATAAAG AACTCTTCTG TGTCAGCCAC TGAGCACGGA
     NATCACCCAC CCCCCGCCTG TAGTTATTTC TTGAGAAGAC ACAGTCGGTG ACTCGTGCCT

1021 ATAAAGGGAT GAGAGTGAGG GCAANTACCA GAAGAATAAA ATCCTTTTAA GAGATGAAGA
     TATTTCCCTA CTCTCACTCC CGTTNATGGT CTTCTTATTT TAGGAAAATT CTCTACTTCT

1081 TTGTTATGAG CACAGTGTGT GGNTTCAAAA ATCTTTTAAC AACCCCAAGG TGAAGCTAGT
     AACAATACTC GTGTCACACA CCNAAGTTTT TAGAAAATTG TTGGGGTTCC ACTTCGATCA

1141 TGGAAGATAT TTGAATTTGT TTAAACCCAT CTGGTCCTAG CCCTATTCTT TGAATCCGAA
     ACCTTCTATA AACTTAAACA AATTTGGGTA GACCAGGATC GGGATAAGAA ACTTAGGCTT

1201 GAGGTCAAGA ATTCCGAGCA GAGTGGACTA CCTGTGATAC CTTAGACTAG TCCTGTGTAT
     CTCCAGTTCT TAAGGCTCGT CTCACCTGAT GGACACTATG GAATCTGATC AGGACACATA

1261 TCAAGTCCAA TGAGAGTATC TGTAAGAGAA TAAGTGCGAA ATCCAGATCT
     AGTTCAGGTT ACTCTCATAG ACATTCTCTT ATTCACGCTT TAGGTCTAGA
```

FIG. 41

```
              10         20         30         40         50         60
              |          |          |          |          |          |
  1  GGATTCTGTT GAGCCCTAGC TCATTATGAT GTCCTGTTGT CCTACCCAAA TAAGACTCAT
     CCTAAGACAA CTCGGGATCG AGTAATACTA CAGGACAACA GGATGGGTTT ATTCTGAGTA

61  CCCAACTACA TCTCAATAAT TAATGAAGAT GGAAATGAGG TAAAAAATAA ATAAATAAAT
     GGGTTGATGT AGAGTTATTA ATTACTTCTA CCTTTACTCC ATTTTTTATT TATTTATTTA

121  AAAAGAAACA TTCCCCCCCA TTTATTATTT TTTCAAATAC CTTCTATGAA ATAATGTTCT
     TTTTCTTTGT AAGGGGGGGT AAATAATAAA AAAGTTTATG GAAGATACTT TATTACAAGA

181  ATCCCTCTCT AAATATTAAT AGAAATCAAT ATTATTGGAA CTGTGAATAC CTTTAATATC
     TAGGGAGAGA TTTATAATTA TCTTTAGTTA TAATAACCTT GACACTTATG GAAATTATAG

241  TCATTATCCG GTGTCAACTA CTTTCCTATG ATGTTGAGTT ACTGGGTTTA GAAGTCGGGA
     AGTAATAGGC CACAGTTGAT GAAAGGATAC TACAACTCAA TGACCCAAAT CTTCAGCCCT

301  AATAATGCTG TAAANNNNNN AGTTAGTCTA CACACCAATA TCAAATATGA TATACTTGTA
     TTATTACGAC ATTTNNNNNN TCAATCAGAT GTGTGGTTAT AGTTTATACT ATATGAACAT

361  AACCTCCAAG CATAAAAAGA GATACTTTAT AAAAGAGGTT CTTTTTTTCT TTTTTTTTTT
     TTGGAGGTTC GTATTTTTCT CTATGAAATA TTTTCTCCAA GAAAAAAAGA AAAAAAAAAA

421  TCCAGATGGA GTTTCACTCC TGTCAGGCAG GCNGAGTGCA GTGGTGCCAT CTCGGCTCAC
     AGGTCTACCT CAAAGTGAGG ACAGTCCGTC CGNCTCACGT CACCACGGTA GAGCCGAGTG

481  TGCAACCTCC ACCTCCCATG TTCAAGGGAT TCTCCTTCCT CAGTCTCCTG AGTAGCTGGG
     ACGTTGGAGG TGGAGGGTAC AAGTTCCCTA AGAGGAAGGA GTCAGAGGAC TCATCGACCC

541  ATTACAGGTG TGCACCACCA CACCCAGCTA ATTTTTGTAT TTTTAATAGA GACAGGGTTT
     TAATGTCCAC ACGTGGTGGT GTGGGTCGAT TAAAAACATA AAAATTATCT CTGTCCCAAA

601  CGATCGATGT TGGCCAGGCT AGTCTCGAAC TCCTGACCTC TAGGTGATCC ACCCGCTCAG
     GCTAGCTACA ACCGGTCCGA TCAGAGCTTG AGGACTGGAG ATCCACTAGG TGGGCGAGTC

661  CTCCCAAAGT TGTAGAATTA CACGTGTGAG GCACTGCGCC TTGCCAGGAG ATACATTTTT
     GAGGGTTTCA ACATCTTAAT GTGCACACTC CGTGACGCGG AACGGTCCTC TATGTAAAAA

721  GATAGGTTTA ATTTATAAAG ACACTGCACA GATTTGAGTT GCTGGGAAAT GCACGGATTC
     CTATCCAAAT TAAATATTTC TGTGACGTGT CTAAACTCAA CGACCCTTTA CGTGCCTAAG

781  CAGTATGCA
     GTCATACGT
```

FIG. 42

```
             10         20         30         40         50         60
             |          |          |          |          |          |
  1  AATCAAAATA AAACAGTTAA AGTTTGATTA CTATAAATCAA ACACAAAAAA AATGAATATT
     TTAGTTTTAT TTTGTCAATT TCAAACTAAT GATATTAGTT TGTGTTTTTT TTACTTATAA

61  ATCTTTTATG TCAGTAGAGG GTGAATGAAT CCTTCAGGAT TTTGATGATA GTATCAGATA
     TAGAAAATAC AGTCATCTCC CACTTACTTA GGAAGTCCTA AAACTACTAT CATAGTCTAT

121  CCCAGCACTA TGCTAGAAGT TGTGAAGAAT TCACGAGATG AATAAATCAC AGATTCTGTC
     GGGTCGTGAT ACGATCTTCA ACACTTCTTA AGTGCTCTAC TTATTTAGTG TCTAAGACAG

181  CTCAAAATGG TTAGATCTAT TCAGGAAACA AAGCTAAAAA AACCCCACCA ATAACTAAAA
     GAGTTTTACC AATCTAGATA AGTCCTTTGT TTCGATTTTT TTGGGGTGGT TATTGATTTT

241  ATCAACCAAA TGAAAAACAA CAATCATAAA ATAAGTAAGT ACCTATAGAA AGAAAAGCTC
     TAGTTGGTTT ACTTTTTGTT GTTAGTATTT TATTCATTCA TGGATATCTT TCTTTTCGAG

301  AGAGGAGGTA AAAAGAATCT CCTTAAAAGG AATACTATAT ACTGTAAAAC TGTGACTGAT
     TCTCCTCCAT TTTTCTTAGA GGAATTTTCC TTATGATATA TGACATTTTG ACACTGACTA

361  AGAAGGAA
     TCTTCCTT
```

FIG. 43A

```
            10         20         30         40         50         60
             |          |          |          |          |          |
  1 TATGGGAAAG TTTTCAGAGG AAATAAGGTA AGGGAAAAGT TATCTCTTTT TTTCTCTCCC
    ATACCCTTTC AAAAGTCTCC TTTATTCCAT TCCCTTTTCA ATAGAGAAAA AAAGAGAGGG

61 CCAATGTAAA AAGTTATAGT GGGTTTTACA TGTGTAGAAT CATTTTCTTA AAACTTTATG
    GGTTACATTT TTCAATATCA CCCAAAATGT ACACATCTTA GTAAAAGAAT TTTGAAATAC

121 AATACCATTA TTTTCTTGTA TTCTGTGACA TGCCACCTTA CAGAGAGGAC ACATTTACTA
    TTATGGTAAT AAAAGAACAT AAGACACTGT ACGGTGGAAT GTCTCTCCTG TGTAAATGAT

181 GGTTATATCC CGGGGTTAAA TTCGAGCATT GGAATTTGGC CAGTGTAGAT GTTTAGAGTG
    CCAATATAGG GCCCCAATTT AAGCTCGTAA CCTTAAACCG GTCACATCTA CAAATCTCAC

241 AACAGAACAA TTTTTCTGTG CTTACAGGTT ATGGCTGTGG CGTACAAGAA GCATGCACTG
    TTGTCTTGTT AAAAAGACAC GAATGTCCAA TACCGACACC GCATGTTCTT CGTACGTGAC

301 GGTTTATTAT TAACTTTCAG TATCTTTGTT TTAAATATTT TCTACAAAAA TGTTTACTAA
    CCAAATAATA ATTGAAAGTC ATAGAAACAA AATTTATAAA AGATGTTTTT ACAAATGATT

361 ATTAAATTGT AGTATGAATT GTTATAAATA ATGAGGGAAA CATTTACACA TAGCAAATTT
    TAATTTAACA TCATACTTAA CAATATTTAT TACTCCCTTT GTAAATGTGT ATCGTTTAAA

421 AAAAATTACT GTCATTTGAT TTGTTAATAT ATTTTTCTCT TTAGTGGGAA ATTAAATTAA
    TTTTTAATGA CAGTAAACTA AACAATTATA TAAAAAGAGA AATCACCCTT TAATTTAATT

481 AAAATTCCTT TCGACTGTCA GACAATAGGA TTGCTGTGGT CTACTTGCTT ATTATATTTG
    TTTTAAGGAA AGCTGACAGT CTGTTATCCT AACGACACCA GATGAACGAA TAATATAAAC

541 TAGAGTCTAG AATGCAATCT CACTACACTA TAGACATCTC ANNCTAACGT AGGACAATTC
    ATCTCAGATC TTACGTTAGA GTGATGTGAT ATCTGTAGAG TNNGATTGCA TCCTGTTAAG

601 TGAGAAACTA TTCCAGACCT CCTTATGGGC TTAGCCAAGG NTATCCTTCA GCTGGCATTG
    ACTCTTTGAT AAGGTCTGGA GGAATACCCG AATCGGTTCC NATAGGAAGT CGACCGTAAC

661 CAGGGTGACT TCTNCCTCNN AATCCAGCTC TCTNTCACAG ATGTGATCCA AGAGACACTC
    GTCCCACTGA AGANGGAGNN TTAGGTCGAG AGANAGTGTC TACACTAGGT TCTCTGTGAG

721 ACAATTAATC AACTAGCATT CTAAATTTCA ATTCCAGATC TATTACCTTA ATATGGTAGC
    TGTTAATTAG TTGATCGTAA GATTTAAAGT TAAGGTCTAG ATAATGGAAT TATACCATCG
```

FIG. 43B

```
781 TGAAGCTTTN NTCACTGTCA ATTCTGATCA GATATATGAC AATTTTAAAT TATTTGCAGT
    ACTTCGAAAN NAGTGACAGT TAAGACTAGT CTATATACTG TTAAAATTTA ATAAACGTCA

841 GTGTAAGAAA CGCTTCAGGT AGTTTAAATT TAAGGCT
    CACATTCTTT GCGAAGTCCA TCAAATTTAA ATTCCGA
```

FIG. 44A

```
              10         20         30         40         50         60
              |          |          |          |          |          |
  1  CTCCTTTGGC CCCTGCCAGC TGGGCATTTT TAACCTAGTT TACACAGTGT CTTTTTTTCC
     GAGGAAACCG GGGACGGTCG ACCCGTAAAA ATTGGATCAA ATGTGTCACA GAAAAAAAGG

61  TTATTTTAAA TTGGTTGTTC CAGATTCGGT AATATCAATT TTTAATATTA CACTTAAATG
     AATAAAATTT AACCAACAAG GTCTAAGCCA TTATAGTTAA AAATTATAAT GTGAATTTAC

121  AGTACCAGAA CTTTATCTTC AACCTTTTTC TCATTAGGCC TACAACATAG GACATCTCGG
     TCATGGTCTT GAAATAGAAG TTGGAAAAAG AGTAATCCGG ATGTTGTATC CTGTAGAGCC

181  ATAGAATTTC CTTTTCTTTT TGCTACTATA AGCTGCTAAA ATCCTCAGAA CATCAGATTT
     TATCTTAAAG GAAAAGAAAA ACGATGATAT TCGACGATTT TAGGAGTCTT GTAGTCTAAA

241  AGAAATGTTC TTATTAGTGG TAGTGAGCAT TTGCTATTTC CTACCACTAG CTTACAAATA
     TCTTTACAAG AATAATCACC ATCACTCGTA AACGATAAAG GATGGTGATC GAATGTTTAT

301  TAATAAGCAA GTAGACCCCA CAGGCCAAAT TCCTATTTGT TCTACAGTCG AAAGGGAATT
     ATTATTCGTT CATCTGGGGT GTCCGGTTTA AGGATAAACA AGATGTCAGC TTTCCCTTAA

361  TTTTAAAATT TAATTTCCAC TAAAGAGAAA AATATATTAA CAATCAAATT GACAGTCGAT
     AAAATTTTAA ATTAAGGTG ATTTCTCTTT TTATATAATT GTTAGTTTAA CTGTCAGCTA

421  TTTAATTGCT ATGTGTAATT GTTTTCCCTC ATTATTTATA ACAATTCATA CTACAATTTA
     AAATTAACGA TACACATTAA CAAAAGGGAG TAATAAATAT TGTTAAGTAT GATGTTAAAT

481  ATTTAGTAAA CATTTTTGTA GACCATATTT AAAACAAAGA TACTGAAAGT TAATATAAAC
     TAAATCATTT GTAAAAACAT CTGGTATAAA TTTTGTTTCT ATGACTTTCA ATTATATTTG

541  CCAGTGCATG CTCTCTGTAG GCCACAGCCA TAACCTGTAA GCACAGAAAA ATTTGTTCTG
     GGTCACGTAC GAGAGACATC CGGTGTCGGT ATTGGACATT CGTGTCTTTT TAAACAAGAC

601  TTACTCTAAA CATCTACACT GGCCAAATTC CAATGCTCGA ATTTAACCCC GGGATATAAC
     AATGAGATTT GTAGATGTGA CCGGTTTAAG GTTACGAGCT TAAATTGGGG CCCTATATTG

661  CTAGTAAATG TGTCCTCTCT GTCAAGGTGG GCATGTCACA GAATACAGAA CAATCAATGG
     GATCATTTAC ACAGGAGAGA CAGTTCCACC CGTACAGTGT CTTATGTCTT GTTAGTTACC

721  TATTCATAAA GTTTTAAGAA AATGATTCTA CACATGTAAA ACCCACTATA ACTTTTTACA
     ATAAGTATTT CAAAATTCTT TTACTAAGAT GTGTACATTT TGGGTGATAT TGAAAAATGT
```

FIG. 44B

```
781 TTGGGGGAGA GAAAAAAAGA GATAATTTTT ACCTTACCTT ATTTCCTCTG AAAACTTTCC
    AACCCCCTCT CTTTTTTTCT CTATTAAAAA TGGAATGGAA TAAAGGAGAC TTTTGAAAGG

841 CATATCTGGC AATTACAATT TTCCCAGAGC AATTGATTTT CATGTCCCGT TCC
    GTATAGACCG TTAATGTTAA AAGGGTCTCG TTAACTAAAA GTACAGGGCA AGG
```

FIG. 45A

```
              10         20         30         40         50         60
               |          |          |          |          |          |
   1  GATGCTATTT GGGCAATTTC TTATTGACAG TTTTGAAATG TTAGGCTTTT ATCTCCATTT
      CTACGATAAA CCCGTTAAAG AATAACTGTC AAAACTTTAC AATCCGAAAA TAGAGGTAAA

61  TTTAGTACTT AAATTTTCCA ACATGGGTGT TGCTTGTTAT TTTATCAGTA TAAAATAGAA
      AAATCATGAA TTTAAAAGGT TGTACCCACA ACGAACAATA AAATAGTCAT ATTTTATCTT

121  GAGTGGTTCT GTTCTGGAAT TTAGTATATA CATGAGTATC TAGTGTATGT CAGCCATGAA
      CTCACCAAGA CAAGACCTTA AATCATATAT GTACTCATAG ATCACATACA GTCGGTACTT

181  AATGAACCTT TCAGATGTTT AACTTCAGGG AACCTAATTG AGTCATTGCT CCAGACATTG
      TTACTTGGAA AGTCTACAAA TTGAAGTCCC TTGGATTAAC TCAGTAACGA GGTCTGTAAC

241  TTGCTTTGAA CCCACTATAT TNNNNNNNCT CGGGCAATGA CTCAGTGTGG CAAGGATACT
      AACGAAACTT GGGTGATATA ANNNNNNNGA GCCCGTTACT GAGTCACACC GTTCCTATGA

301  ACTGCAGGCC TGTTTCTGGA AGGCACTGGA CTCCTCTGAT GCAAACTTTG GCCAGGGACT
      TGACGTCCGG ACAAAGACCT TCCGTGACCT GAGGAGACTA CGTTTGAAAC CGGTCCCTGA

361  CCTTGATAGC TCTTAAATAG ATGCTGCACC AACACTCTCT TTCTTTTCTC TCTTTTTCTT
      GGAACTATCG AGAATTTATC TACGACGTGG TTGTGAGAGA AAGAAAAGAG AGAAAAAGAA

421  TATTCAATAT TAGACTACAA GCAGTCTAAG GACTTCTCAG GGTTTCTAGC TCTCTCTCAT
      ATAAGTTATA ATCTGATGTT CGTCAGATTC CTGAAGAGTC CCAAAGATCG AGAGAGAGTA

481  TTCACACATG CTTTCCTAGT AATCTCTACT CATATATCTT ACTGCTACGC TGGGGCCAGA
      AAGTGTGTAC GAAAGGATCA TTAGAGATGA GTATATAGAA TGACGATGCG ACCCCGGTCT

541  TAACNNNNNN CTTCCATTTT GTTTTTATCT CTATTCTTCT TCCCCTTCTG CTTTCATTAT
      ATTGNNNNNN GAAGGTAAAA CAAAATAGA GATAAGAAGA AGGGAAGAC GAAAGTAATA

601  TGAAACTTTC TGCTTTCATT ATTGAAACTT TCCCAGATTT GTTCTGCTTA ACCTGGCATT
      ACTTTGAAAG ACGAAAGTAA TAACTTTGAA AGGGTCTAAA CAAGACGAAT TGGACCGTAA

661  GGAACTGTTT CCTCTTCCCT GTGCTGCTTT CTCCCATTGC CATGTCCTTT TTTTTTTTTT
      CCTTGACAAA GGAGAAGGGA CACGACGAAA GAGGGTAACG GTACAGGAAA AAAAAAAAAA

721  TTTTTTTTTT TGAGACAGTG TCACTCTGTT GCCCAGGCTG GAGTGCAATG GTGCAATCTT
      AAAAAAAAAA ACTCTGTCAC AGTGAGACAA CGGGTCCGAC CTCACGTTAC CACGTTAGAA
```

FIG. 45B

```
 781 GGCCACTGCA ACCCCGACTC CGGGTTCAAG TGATTCTCTA CCTGCCTCAG CCTCCTGAGT
     CCGGTGACGT TGGGGCTGAG GCCCAAGTTC ACTAAGAGAT GGACGGAGTC GGAGGACTCA

841 AGCTGGGATT ACAGGTGCCA CCACTATGCC GGCTGATTTT GTATTTTAGT AGAGATGGGT
     TCGACCCTAA TGTCCACGGT GGTGATACGG CCGACTAAAA CATAAAATCA TCTCTACCCA

901 TCACATGCAG ATCAGCTGTT CCGACTCTGA CCAGNNNNNN NNNNNNNNNN ATCAAAGTCA
     AGTGTACGTC TAGTCGACAA GGCTGAGACT GGTCNNNNNN NNNNNNNNNN TAGTTTCAGT

961 GCCAAAGTGC TAGGCTTAGA GTAATTGTGT AATTTCCACA CAAGTGCAAC CTAGTGTAAT
     CGGTTTCACG ATCCGAATCT CATTAACACA TTAAAGGTGT GTTCACGTTG GATCACATTA

1021 GCCTCAAGAA TGTNNNTATG AATGTCTCGA ACGTTAGTAA CTAATAACAA GTAGTTAGTT
     CGGAGTTCTT ACANNNATAC TTACAGAGCT TGCAATCATT GATTATTGTT CATCAATCAA

1081 TATAGATGTA TCCTAGTATG TAGCA
     ATATCTACAT AGGATCATAC ATCGT
```

FIG. 46A

```
              10         20         30         40         50         60
               |          |          |          |          |          |
    1 CACAAAAAAA GATTATTAGC CACAAAAAAA CCTTGAAGTA ACGCATTAAA ATGTTAATGG
      GTGTTTTTTT CTAATAATCG GTGTTTTTTT GGAACTTCAT TGCGTAATTT TACAATTACC

61 ATTCACTTTA TTGAGCATCT GCTCATAATA CTTTAATGAG TGCAAAGTGC TTTGAATATA
      TAAGTGAAAT AACTCGTAGA CGAGTATTAT GAAATTACTC ACGTTTCACG AAACTTATAT

121 ATACGTCATT TAAACCTTAC CATAATTCTG AGGAATTGCT ACCTCCACTT CACAGATGGG
      TATGCAGTAA ATTTGGAATG GTATTAAGAC TCCTTAACGA TGGAGGTGAA GTGTCTACCC

181 GCACAGGAGG CTTAGATAAC ATGCCCAAAG TCATGCTTCT AGTAAATGGA TATAATTAAG
      CGTGTCCTCC GAATCTATTG TACGGGTTTC AGTACGAAGA TCATTTACCT ATATTAATTC

241 ATTCAAATTA TTGATAAGAA TTTGATCTGC CTTACCAGTA TCTAGTAGTA AATCTAAAAG
      TAAGTTTAAT AACTATTCTT AAACTAGACG GAATGGTCAT AGATCATCAT TTAGATTTTC

301 CGCTTTCCAG AGCATGTGCT GTTGATAGAG CTTGATGTCT AACTCTCTGA AATTTTCCAT
      GCGAAAGGTC TCGTACACGA CAACTATCTC GAACTACAGA TTGAGAGACT TTAAAAGGTA

361 TCTTATTTGT CTCACTGGTA TATAGTTATT TTTTACTACT TTCATACACC TACTAAGAAG
      AGAATAAACA GAGTGACCAT ATATCAATAA AAAATGATGA AAGTATGTGG ATGATTCTTC

421 ACAGGAGGAT CAAAGATAGG ATTTCATTTA GAATGCCTAA AGCTTCACGT ATTTTAATTC
      TGTCCTCCTA GTTTCTATCC TAAAGTAAAT CTTACGGATT TCGAAGTGCA TAAAATTAAG

481 AGAATAAGAT TCAGGCAGAC CACCAGTATA TGCCATGGTC CCTGGTTATC TTTCAGCAGG
      TCTTATTCTA AGTCCGTCTG GTGGTCATAT ACGGTACCAG GGACCAATAG AAAGTCGTCC

541 TGACCGAGAA AGAAAACATG GTAATGTTTA TGAAATGGTG GGTTCTTGTA GTTTCACTTC
      ACTGGCTCTT TCTTTTGTAC CATTACAAAT ACTTTACCAC CCAAGAACAT CAAAGTGAAG

601 AACATATCTG CCTTTACTGT ATTAAGATGA TGGATTAACT TATTCTTGAT ATGGGCATGT
      TTGTATAGAC GGAAATGACA TAATTCTACT ACCTAATTGA ATAAGAACTA TACCCGTACA

661 AAAACAATAT ACTTTTACTA AACAGCTACA GAGAGACAAA TGTGTTTCCA GACAAACTTA
      TTTTGTTATA TGAAAATGAT TTGTCGATGT CTCTCTGTTT ACACAAAGGT CTGTTTGAAT

721 AGAGACTGAG TGTTCAAACT GAATAATCTC GACCTTAATT GTAACTATAT TTTATGAAAT
      TCTCTGACTC ACAAGTTTGA CTTATTAGAG CTGGAATTAA CATTGATATA AAATACTTTA
```

FIG. 46B

```
781 CCAGCTGTAA GGCAAAACAG ACTCTTGGCT ACACGGCATT TGTCTGTTAA TGATACTCAA
    GGTCGACATT CCGTTTTGTC TGAGAACCGA TGTGCCGTAA ACAGACAATT ACTATGAGTT

841 CCTTAACCGT CACTTAATAA TGCTGAATAA TGTCATTAAT CTGAGATGTT AGTATGATCA
    GGAATTGGCA GTGAATTATT ACGACTTATT ACAGTAATTA GACTCTACAA TCATACTAGT

901 ATGGGAATCA CTGCTGAGCT CTCGAAGCCC
    TACCCTTAGT GACGACTCGA GAGCTTCGGG
```

FIG. 47A

```
CTCAAAAGGG GCCGGATTTC CTTCTCCTGG AGGCAGATGT TGCCTCTCTC TCTCGCTCGG   60

ATTGGTTCAG TGCACTCTAG AAACACTGCT GTGGTGGAGA AACTGGACCC CAGGTCTGGA  120

GCGAATTCCA GCCTGCAGGG CTGATAAGCG AGGCATTAGT GAGATTGAGA GAGACTTTAC  180

CCCGCCGTGG TGGTTGGAGG GCGCGCAGTA GAGCAGCAGC ACAGGCGCGG GTCCCGGGAG  240

GCCGGCTCTG CTCGCGCCGA G ATG TGG AAT CTC CTT CAC GAA ACC GAC TCG    291
                        Met Trp Asn Leu Leu His Glu Thr Asp Ser
                         1               5                  10
GCT GTG GCC ACC GCG CGC CGC CCG CGC TGG CTG TGC GCT GGG GCG CTG    339
Ala Val Ala Thr Ala Arg Arg Pro Arg Trp Leu Cys Ala Gly Ala Leu
                 15                  20                  25
                                                          Intron
GTG CTG GCG GGT GGC TTC TTT CTC CTC GGC TTC CTC TTC GGG TGG|TTT    387
Val Leu Ala Gly Gly Phe Phe Leu Leu Gly Phe Leu Phe Gly Trp|Phe
             30                  35                  40

ATA AAA TCC TCC AAT GAA GCT ACT AAC ATT ACT CCA AAG CAT AAT ATG    435
Ile Lys Ser Ser Asn Glu Ala Thr Asn Ile Thr Pro Lys His Asn Met
         45                  50                  55

AAA GCA TTT TTG GAT GAA TTG AAA GCT GAG AAC ATC AAG AAG TTC TTA    483
Lys Ala Phe Leu Asp Glu Leu Lys Ala Glu Asn Ile Lys Lys Phe Leu
     60                  65                  70

TAT AAT TTT ACA CAG ATA CCA CAT TTA GCA GGA ACA GAA CAA AAC TTT    531
Tyr Asn Phe Thr Gln Ile Pro His Leu Ala Gly Thr Glu Gln Asn Phe
 75   *              80                  85                  90

CAG CTT GCA AAG CAA ATT CAA TCC CAG TGG AAA GAA TTT GGC CTG GAT    579
Gln Leu Ala Lys Gln Ile Gln Ser Gln Trp Lys Glu Phe Gly Leu Asp
                 95                 100                 105

TCT GTT GAG CTA GCA CAT TAT GAT GTC CTG TTG TCC TAC CCA AAT AAG    627
Ser Val Glu Leu Ala His Tyr Asp Val Leu Leu Ser Tyr Pro Asn Lys
            110                 115                 120  *
                                                          Intron
ACT CAT CCC AAC TAC ATC TCA ATA ATT AAT GAA GAT GGA AAT GAG|ATT    675
Thr His Pro Asn Tyr Ile Ser Ile Ile Asn Glu Asp Gly Asn Glu|Ile
        125                 130                 135

TTC AAC ACA TCA TTA TTT GAA CCA CCT CCT CCA GGA TAT GAA AAT GTT    723
Phe Asn Thr Ser Leu Phe Glu Pro Pro Pro Pro Gly Tyr Glu Asn Val
    140                 145                 150              *
     *

TCG GAT ATT GTA CCA CCT TTC AGT GCT TTC TCT CCT CAA GGA ATG CCA    771
Ser Asp Ile Val Pro Pro Phe Ser Ala Phe Ser Pro Gln Gly Met Pro
155                 160                 165                 170

GAG GGC GAT CTA GTG TAT GTT AAC TAT GCA CGA ACT GAA GAC TTC TTT    819
Glu Gly Asp Leu Val Tyr Val Asn Tyr Ala Arg Thr Glu Asp Phe Phe
                175                 180                 185
```

FIG. 47B

```
AAA TTG GAA CGG GAC ATG AAA ATC AAT TGC TCT GGG AAA ATT GTA ATT    867
Lys Leu Glu Arg Asp Met Lys Ile Asn Cys Ser Gly Lys Ile Val Ile
            190                 195                 200
                                  *
                                            Intron
GCC AGA TAT GGG AAA GTT TTC AGA GGA AAT AAG GTT A|AA AAT GCC CAG    915
Ala Arg Tyr Gly Lys Val Phe Arg Gly Asn Lys Val L|ys Asn Ala Gln
            205                 210              215

CTG GCA GGG GCC AAA GGA GTC ATT CTC TAC TCC GAC CCT GCT GAC TAC    963
Leu Ala Gly Ala Lys Gly Val Ile Leu Tyr Ser Asp Pro Ala Asp Tyr
        220                 225                 230

TTT GCT CCT GGG GTG AAG TCC TAT CCA GAT GGT TGG AAT CTT CCT GGA   1011
Phe Ala Pro Gly Val Lys Ser Tyr Pro Asp Gly Trp Asn Leu Pro Gly
235             240                 245                     250

GGT GGT GTC CAG CGT GGA AAT ATC CTA AAT CTG AAT GGT GCA GGA GAC   1059
Gly Gly Val Gln Arg Gly Asn Ile Leu Asn Leu Asn Gly Ala Gly Asp
                    255                 260                 265

CCT CTC ACA CCA GGT TAC CCA GCA AAT GAA TAT GCT TAT AGG CGT GGA   1107
Pro Leu Thr Pro Gly Tyr Pro Ala Asn Glu Tyr Ala Tyr Arg Arg Gly
            270                 275                 280

ATT GCA GAG GCT GTT GGT CTT CCA AGT ATT CCT GTT CAT CCA ATT GGA   1155
Ile Ala Glu Ala Val Gly Leu Pro Ser Ile Pro Val His Pro Ile Gly
            285                 290                 295
                                          Intron
TAC TAT GAT GCA CAG AAG CTC CTA GAA AAA ATG GGT|GGC TCA GCA CCA   1203
Tyr Tyr Asp Ala Gln Lys Leu Leu Glu Lys Met Gly|Gly Ser Ala Pro
        300                 305                 310

CCA GAT AGC AGC TGG AGA GGA AGT CTC AAA GTG CCC TAC AAT GTT GGA   1251
Pro Asp Ser Ser Trp Arg Gly Ser Leu Lys Val Pro Tyr Asn Val Gly
315                 320                 325                 330

CCT GGC TTT ACT GGA AAC TTT TCT ACA CAA AAA GTC AAG ATG CAC ATC   1299
Pro Gly Phe Thr Gly Asn Phe Ser Thr Gln Lys Val Lys Met His Ile
                335   *             340                 345

CAC TCT ACC AAT GAA GTG ACA AGA ATT TAC AAT GTG ATA GGT ACT CTC   1347
His Ser Thr Asn Glu Val Thr Arg Ile Tyr Asn Val Ile Gly Thr Leu
            350                 355                 360

AGA GGA GCA GTG GAA CCA GAC AGA TAT GTC ATT CTG GGA GGT CAC CGG   1395
Arg Gly Ala Val Glu Pro Asp Arg Tyr Val Ile Leu Gly Gly His Arg
            365                 370                 375

GAC TCA TGG GTG TTT GGT GGT ATT GAC CCT CAG AGT GGA GCA GCT GTT   1443
Asp Ser Trp Val Phe Gly Gly Ile Asp Pro Gln Ser Gly Ala Ala Val
    380                 385                 390

GTT CAT GAA ATT GTG AGG AGC TTT GGA ACA CTG AAA AAG GAA GGG TGG   1491
Val His Glu Ile Val Arg Ser Phe Gly Thr Leu Lys Lys Glu Gly Trp
395                 400                 405                 410

AGA CCT AGA AGA ACA ATT TTG|TTT GCA AGC TGG GAT GCA GAA GAA TTT   1539
Arg Pro Arg Arg Thr Ile Leu|Phe Ala Ser Trp Asp Ala Glu Glu Phe
                        415     420                 425
```

FIG. 47C

```
GGT CTT CTT GGT TCT ACT GAG TGG GCA GAG GAG AAT TCA AGA CTC CTT    1587
Gly Leu Leu Gly Ser Thr Glu Trp Ala Glu Glu Asn Ser Arg Leu Leu
            430             435                 440

CAA GAG CGT GGC GTG GCT TAT ATT AAT GCT GAC TCA TCT ATA GAA GGA    1635
Gln Glu Arg Gly Val Ala Tyr Ile Asn Ala Asp Ser Ser Ile Glu Gly
        445             450                 455

AAC TAC ACT CTG AGA GTT GAT TGT ACA CCG CTG ATG TAC AGC TTG GTA    1683
Asn Tyr Thr Leu Arg Val Asp Cys Thr Pro Leu Met Tyr Ser Leu Val
 *  460             465                 470

CAC AAC CTA ACA AAA GAG CTG AAA AGC CCT GAT GAA GGC TTT GAA GGC    1731
His Asn Leu Thr Lys Glu Leu Lys Ser Pro Asp Glu Gly Phe Glu Gly
475  *          480                 485                     490

AAA TCT CTT TAT GAA AGT TGG ACT AAA AAA AGT CCT TCC CCA GAG TTC    1779
Lys Ser Leu Tyr Glu Ser Trp Thr Lys Lys Ser Pro Ser Pro Glu Phe
            495                 500                 505

AGT GGC ATG CCC AGG ATA AGC AAA TTG GGA TCT GGA AAT GAT TTT GAG    1827
Ser Gly Met Pro Arg Ile Ser Lys Leu Gly Ser Gly Asn Asp Phe Glu
            510                 515                 520

GTG TTC TTC CAA CGA CTT GGA ATT GCT TCA GGC AGA GCA CGG TAT ACT    1875
Val Phe Phe Gln Arg Leu Gly Ile Ala Ser Gly Arg Ala Arg Tyr Thr
        525                 530                 535

AAA AAT TGG GAA ACA AAC AAA TTC AGC GGC TAT CCA CTG TAT CAC AGT    1923
Lys Asn Trp Glu Thr Asn Lys Phe Ser Gly Tyr Pro Leu Tyr His Ser
540                 545                 550

GTC TAT GAA ACA TAT GAG TTG GTG GAA AAG TTT TAT GAT CCA ATG TTT    1971
Val Tyr Glu Thr Tyr Glu Leu Val Glu Lys Phe Tyr Asp Pro Met Phe
555                 560                 565                 570

AAA TAT CAC CTC ACT GTG GCC CAG GTT CGA GGA GGG ATG GTG TTT GAG    2019
Lys Tyr His Leu Thr Val Ala Gln Val Arg Gly Gly Met Val Phe Glu
                575                 580                 585

CTA GCC AAT TCC ATA GTG CTC CCT TTT GAT TGT CGA GAT TAT GCT GTA    2067
Leu Ala Asn Ser Ile Val Leu Pro Phe Asp Cys Arg Asp Tyr Ala Val
            590                 595                 600

GTT TTA AGA AAG TAT GCT GAC AAA ATC TAC AGT ATT TCT ATG AAA CAT    2115
Val Leu Arg Lys Tyr Ala Asp Lys Ile Tyr Ser Ile Ser Met Lys His
        605                 610                 615

CCA CAG GAA ATG AAG ACA TAC AGT GTA TCA TTT GAT TCA CTT TTT TCT    2163
Pro Gln Glu Met Lys Thr Tyr Ser Val Ser Phe Asp Ser Leu Phe Ser
    620                 625                 630

GCA GTA AAG AAT TTT ACA GAA ATT GCT TCC AAG TTC AGT GAG AGA CTC    2211
Ala Val Lys Asn Phe Thr Glu Ile Ala Ser Lys Phe Ser Glu Arg Leu
635          *      640                 645                 650

CAG GAC TTT GAC AAA AGC AAC CCA ATA GTA TTA AGA ATG ATG AAT GAT    2259
Gln Asp Phe Asp Lys Ser Asn Pro Ile Val Leu Arg Met Met Asn Asp
                655                 660                 665
```

FIG. 47D

```
CAA CTC ATG TTT CTG GAA AGA GCA TTT ATT GAT CCA TTA GGG TTA CCA    2307
Gln Leu Met Phe Leu Glu Arg Ala Phe Ile Asp Pro Leu Gly Leu Pro
        670                 675                 680

GAC AGG CCT TTT TAT AGG CAT GTC ATC TAT GCT CCA AGC AGC CAC AAC    2355
Asp Arg Pro Phe Tyr Arg His Val Ile Tyr Ala Pro Ser Ser His Asn
        685                 690                 695

AAG TAT GCA GGG GAG TCA TTC CCA GGA ATT TAT GAT GCT CTG TTT GAT    2403
Lys Tyr Ala Gly Glu Ser Phe Pro Gly Ile Tyr Asp Ala Leu Phe Asp
        700                 705                 710

ATT GAA AGC AAA GTG GAC CCT TCC AAG GCC TGG GGA GAA GTG AAG AGA    2451
Ile Glu Ser Lys Val Asp Pro Ser Lys Ala Trp Gly Glu Val Lys Arg
715                 720                 725                 730

CAG ATT TAT GTT GCA GCC TTC ACA GTG CAG GCA GCT GCA GAG ACT TTG    2499
Gln Ile Tyr Val Ala Ala Phe Thr Val Gln Ala Ala Ala Glu Thr Leu
                    735                 740                 745

AGT GAA GTA GCC TAAGAGGATT CTTTAGAGAA TCCGTATTGA ATTTGTGTGG        2551
Ser Glu Val Ala
            750

TATGTCACTC AGAAAGAATC GTAATGGGTA TATTGATAAA TTTTAAAATT GGTATATTTG  2611

AAATAAAGTT GAATATTATA TATAAAAAAA AAAAAAAAAA AA                    2653
```

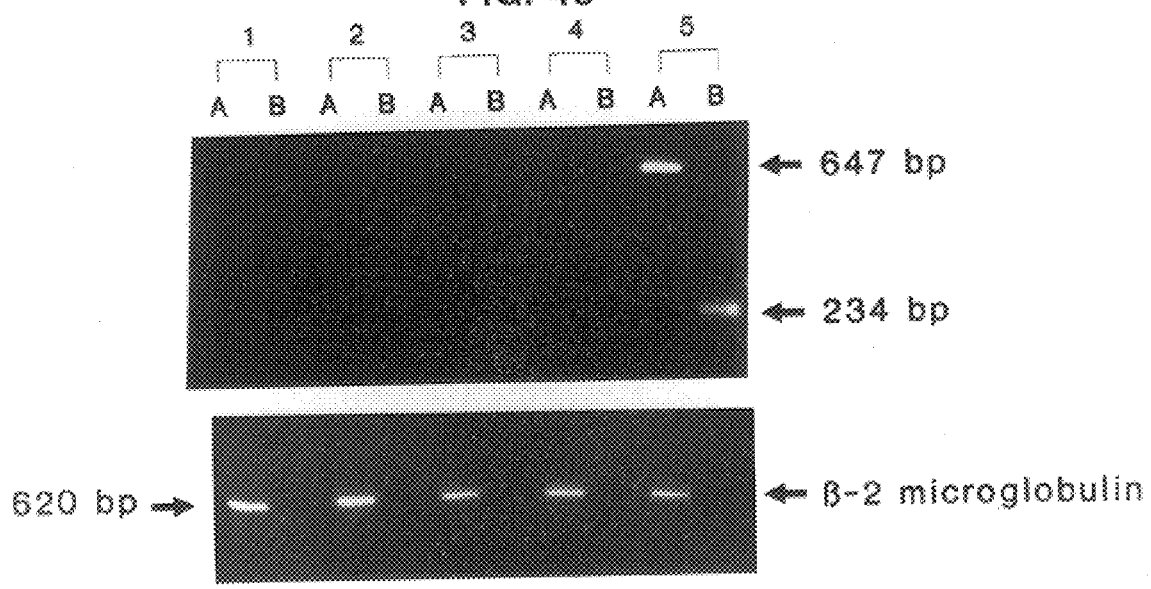

FIG. 53

| TISSUE/CELL LINE | CANCER CELL TYPE | ¹PSM DNA | ²PSM RNA |
|---|---|---|---|
| HUMAN PROSTATE | N.A. | + | + |
| HUMAN MAMMARY | N.A. | + | - |
| AT6.1 | RAT PROSTATIC ADENOCARCINOMA | - | - |
| AT6.1-11-CL1 | " | + | + |
| AT6.1-11-CL2 | " | - | - |
| R1564 | RAT MAMMARY ADENOCARCINOMA | + | - |
| R1564-11-CL2 | " | + | - |
| R1564-11-CL4 | " | + | - |
| R1564-11-CL5 | " | + | - |
| R1564-11-CL6 | " | - | - |
| A9 | MOUSE FIBROSARCOMA | + | - |
| A9(11) | " | | |

FIG. 58A

```
           10         20         30         40         50         60
  1 GCGCCTTAAA AAAAAAAAAC TTTCTTGGAA AATGTCCAGC TCTTGCTTAA ATATAAAAAT
    CGCGGAATTT TTTTTTTTTG AAAGAACCTT TTACAGGTCG AGAACGAATT TATATTTTTA

61 GAAAGGAAGA AAGAGACTCT CCTCTCTCCA CTCCTATAAT TATGAGGAAC TTTTATTCAA
    CTTTCCTTCT TTCTCTGAGA GGAGAGAGGT GAGGATATTA ATACTCCTTG AAAATAAGTT

121 CTCTGAAATT CTATACAATC TCTACAATAC TCTACTGAAT AAAAGCAGAG CAGAAAAAGC
    GAGACTTTAA GATATGTTAG AGATGTTATG AGATGACTTA TTTTCGTCTC GTCTTTTTCG

181 TGCGCTTTTT TTCCATAGTC GGGAATGCTT GTCATCAGTG TAAATCACCA CCGCGCCCTT
    ACGCGAAAAA AAGGTATCAG CCCTTACGAA CAGTAGTCAC ATTTAGTGGT GGCGCGGGAA

241 TTTCCTAAAG AATATTATTG TTATTAATAA ACATGTAGGG TATTATCCTC CACTTACATT
    AAAGGATTTC TTATAATAAC AATAATTATT TGTACATCCC ATAATAGGAG GTGAATGTAA

301 ACAAAACCAT TTTTTAAAGC CGGGCGTGGT GGCTCACGCC TGTAATCCCA GCACTTTGGG
    TGTTTTGGTA AAAAATTTCG GCCCGCACCA CCGAGTGCGG ACATTAGGGT CGTGAAACCC

361 AGGCCCAGAC AGGCGGATCA CGAAGTCGAG AAATCGAGAC CATCCTGGCC AACATGGTGA
    TCCGGGTCTG TCCGCCTAGT GCTTCAGCTC TTTAGCTCTG GTAGGACCGG TTGTACCACT

421 AACCCCATCT CTACTAAAAA TACAAAAATT AGCTGGGCGT GGTGGCGGGC TCCTGTAGTC
    TTGGGGTAGA GATGATTTTT ATGTTTTTAA TCGACCCGCA CCACCGCCCG AGGACATCAG

481 CCAGCTACTC AGGAGGCTGA GGCAGGAGAA TCGCTTGAAC CGGGGAGGCG GAGGTTGCAG
    GGTCGATGAG TCCTCCGACT CCGTCCTCTT AGCGAACTTG GCCCCTCCGC CTCCAACGTC

541 TCAGCCAAGA TAGCGCCACT GCACTGGAGC CTGGTGACAG AGTGAGACTC CCTCAAGAAA
    AGTCGGTTCT ATCGCGGTGA CGTGACCTCG GACCACTGTC TCACTCTGAG GGAGTTCTTT

601 GAAAGGAAGG GAAGGGAAAG GGAAGGAAGG GGAGGGGAAG GGAGGGGAGG GGAGGGGAGG
    CTTTCCTTCC CTTCCCTTTC CCTTCCTTCC CCTCCCCTTC CCTCCCCTCC CCTCCCCTCC

661 AAAGAAAAGA ATACTGGAAC TTGTTGAAGG CAGAGACTTT ATTTTCATAT CCCGGCTATG
    TTTCTTTTCT TATGACCTTG AACAACTTCC GTCTCTGAAA TAAAAGTATA GGGCCGATAC

721 TCTGGCTACT GTCTTACGTA ATAGATATAA AATCAATCTT GGTTGGATTA ACCAGAAGAA
    AGACCGATGA CAGAATGCAT TATCTATATT TTAGTTAGAA CCAACCTAAT TGGTCTTCTT

781 TGAGAAGATA TATTCTGGTA AGTTGAATAC TTAGCACCCA GGGGTAATCA GCTTGGACAG
    ACTCTTCTAT ATAAGACCAT TCAACTTATG AATCGTGGGT CCCCATTAGT CGAACCTGTC

841 GACCAGGTCC AAAGACTGTT AAGAGTCTTC TGACTCCAAA CTCAGTGCTC CCTCCAGTGC
    CTGGTCCAGG TTTCTGACAA TTCTCAGAAG ACTGAGGTTT GAGTCACGAG GGAGGTCACG

901 CACAAGCAAA CTCCATAAAG GTATCCTGTG CTGAATAGAG ACTGTAGAGT GGTACAAAGT
    GTGTTCGTTT GAGGTATTTC CATAGGACAC GACTTATCTC TGACATCTCA CCATGTTTCA

961 AAGACAGACA TTATATTAAG TCTTAGCTTT GTGACTTCGA ATGACTTACC TAATCTAGCT
    TTCTGTCTGT AATATAATTC AGAATCGAAA CACTGAAGCT TACTGAATGG ATTAGATCGA
```

FIG. 58B

```
1021 AAATTTCAGT TTTACCATGT GTAAATCAGG AAGAGTAATA GAACAAACCT TGAAGGGTCC
     TTTAAAGTCA AAATGGTACA CATTTAGTCC TTCTCATTAT CTTGTTTGGA ACTTCCCAGG

1081 CAATGGTGAT TAAATGAGGT GATGTACATA ACATGCATCA CTCATAATAA GTGCTCTTTA
     GTTACCACTA ATTTACTCCA CTACATGTAT TGTACGTAGT GAGTATTATT CACGAGAAAT

1141 AATATTAGTC ACTATTATTA GCCATCTCTG ATTAGATTTG ACAATAGGAA CATTAGGAAA
     TTATAATCAG TGATAATAAT CGGTAGAGAC TAATCTAAAC TGTTATCCTT GTAATCCTTT

1201 GATATAGTAC ATTCAGGATT TTGTTAGAAA GAGATGAAGA AATTCCCTTC CTTCCTGCCC
     CTATATCATG TAAGTCCTAA AACAATCTTT CTCTACTTCT TTAAGGGAAG GAAGGACGGG

1261 TAGGTCATCT AGGAGTTGTC ATGGTTCATT GTTGACAAAT TAATTTTCCC AAATTTTTCA
     ATCCAGTAGA TCCTCAACAG TACCAAGTAA CAACTGTTTA ATTAAAAGGG TTTAAAAAGT

1321 CTTTGCTCAG AAAGTCTACA TCGAAGCACC CAAGACTGTA CAATCTAGTC CATCTTTTTC
     GAAACGAGTC TTTCAGATGT AGCTTCGTGG GTTCTGACAT GTTAGATCAG GTAGAAAAAG

1381 CACTTAACTC ATACTGTGCT CTCCCTTTCT CAAAGCAAAC TGTTTGCTAT TCCTTGAATA
     GTGAATTGAG TATGACACGA GAGGGAAAGA GTTTCGTTTG ACAAACGATA AGGAACTTAT

1441 CACTCTGAGT TTTCTGCCTT TGCCTACTCA GCTGGCCCAT GGCCCCTAAT GTTTCTTCTC
     GTGAGACTCA AAAGACGGAA ACGGATGAGT CGACCGGGTA CCGGGGATTA CAAAGAAGAG

1501 ATCTCCACTG GGTCAAATCC TACCTGTACC TTATGGTTCT GTTAAAAGCA GTGCTTCCAT
     TAGAGGTGAC CCAGTTTAGG ATGGACATGG AATACCAAGA CAATTTTCGT CACGAAGGTA

1561 AAAGTACTCC TAGCAAATGC ACGGCCTCTC TCACGGATTA TAAGAACACA GTTTATTTTA
     TTTCATGAGG ATCGTTTACG TGCCGGAGAG AGTGCCTAAT ATTCTTGTGT CAAATAAAAT

1621 TAAAGCATGT AGCTATTCTC TCCCTCGAAA TACGATTATT ATTATTAAGA ATTTATAGCA
     ATTTCGTACA TCGATAAGAG AGGGAGCTTT ATGCTAATAA TAATAATTCT TAAATATCGT

1681 GGGATATAAT TTTGTATGAT GATTCTTCTG GTTAATCCAA CCAAGATTGA TTTTATATCT
     CCCTATATTA AAACATACTA CTAAGAAGAC CAATTAGGTT GGTTCTAACT AAAATATAGA

1741 ATTACGTAAG ACAGTAGCCA GACATAGCCG GGATATGAAA ATAAAGTCTC TGCCTTCAAC
     TAATGCATTC TGTCATCGGT CTGTATCGGC CCTATACTTT TATTTCAGAG ACGGAAGTTG

1801 AAGTTCCAGT ATTCTTTTCT TTCCTCCCCT CCCCTCCCCT CCCTTCCCCT CCCCTTCCTT
     TTCAAGGTCA TAAGAAAAGA AAGGAGGGGA GGGGAGGGGA GGGAAGGGGA GGGGAAGGAA

1861 CCCTTTCCCT TCCCTTCCTT TCTTTCTTGA GGGAGTCTCA CTCTGTCACC AGGCTCCAGT
     GGGAAAGGGA AGGGAAGGAA AGAAAGAACT CCCTCAGAGT GAGACAGTGG TCCGAGGTCA

1921 GCAGTGGCGC TATCTTGGCT GACTGCAACC TCCGCCTCCC CGGTTCAAGC GATTCTCCTG
     CGTCACCGCG ATAGAACCGA CTGACGTTGG AGGCGGAGGG GCCAAGTTCG CTAAGAGGAC

1981 CCTCAGCCTC CTGAGTAGCT GGGACTACAG GAGCCCGCCA CCACGCCCAG CTAATTTTTG
     GGAGTCGGAG GACTCATCGA CCCTGATGTC CTCGGGCGGT GGTGCGGGTC GATTAAAAAC
```

FIG. 58C

```
2041 TATTTTTAGT AGAGATGGGG TTTCACCATG TTGGCCAGGA TGGTCTCGAT TTCTCGACTT
     ATAAAAATCA TCTCTACCCC AAAGTGGTAC AACCGGTCCT ACCAGAGCTA AAGAGCTGAA

2101 CGTGATCCGC CTGTCTGGGC CTCCCAAAGT GCTGGGATTA CAGGCGTGAG CCACCACGCC
     GCACTAGGCG GACAGACCCG GAGGGTTTCA CGACCCTAAT GTCCGCACTC GGTGGTGCGG

2161 CGGCTTTAAA AAATGGTTTT GTAATGTAAG TGGAGGATAA TACCCTACAT GTTTATTAAT
     GCCGAAATTT TTTACCAAAA CATTACATTC ACCTCCTATT ATGGGATGTA CAAATAATTA

2221 AACAATAATA TTCTTTAGGA AAAGGGCGC GGTGGTGATT TACACTGATG ACAAGCATTC
     TTGTTATTAT AAGAAATCCT TTTTCCCGCG CCACCACTAA ATGTGACTAC TGTTCGTAAG

2281 CCGACTATGG AAAAAAAGCG CAGCTTTTTC TGCTCTGCTT TTATTCAGTA GAGTATTGTA
     GGCTGATACC TTTTTTTCGC GTCGAAAAAG ACGAGACGAA AATAAGTCAT CTCATAACAT

2341 GAGATTGTAT AGAATTTCAG AGTTGAATAA AAGTTCCTCA TAATTATAGG AGTGGAGAGA
     CTCTAACATA TCTTAAAGTC TCAACTTATT TTCAAGGAGT ATTAATATCC TCACCTCTCT

2401 GGAGAGTCTC TTTCTTCCTT TCATTTTTAT ATTTAAGCAA GAGCTGGACA TTTTCCAAGA
     CCTCTCAGAG AAAGAAGGAA AGTAAAAATA TAAATTCGTT CTCGACCTGT AAAAGGTTCT

2461 AAGTTTTTTT TTTTTAAGGC GCCTCTCAAA AGGGGCCGGA TTTCCTTCTC CTGGAGGCAG
     TTCAAAAAAA AAAAATTCCG CGGAGAGTTT TCCCCGGCCT AAAGGAAGAG GACCTCCGTC

2521 ATGTTGCCTC TCTCTCTCGC TCGGATTGGT TCAGTGCACT CTAGAAACAC TGCTGTGGTG
     TACAACGGAG AGAGAGAGCG AGCCTAACCA AGTCACGTGA GATCTTTGTG ACGACACCAC

2581 GAGAAACTGG ACCCCAGGTC TGGAGCGAAT TCCAGCCTGC AGGGCTGATA AGCGAGGCAT
     CTCTTTGACC TGGGGTCCAG ACCTCGCTTA AGGTCGGACG TCCCGACTAT TCGCTCCGTA

2641 TAGTGAGATT GAGAGAGACT TTACCCCGCC GTGGTGGTTG GAGGGCGCGC AGTAGAGCAG
     ATCACTCTAA CTCTCTCTGA AATGGGGCGG CACCACCAAC CTCCCGCGCG TCATCTCGTC

2701 CAGCACAGGC GCGGGTCCCG GGAGGCCGGC TCTGCTCGCG CCGAGATGTG GAATCTCCTT
     GTCGTGTCCG CGCCCAGGGC CCTCCGGCCG AGACGAGCGC GGCTCTACAC CTTAGAGGAA

2761 CACGAAACCG ACTCGGCTGT GGCCACCGCG CGCCGCCCGC GCTGGCTGTG CGCTGGGGCG
     GTGCTTTGGC TGAGCCGACA CCGGTGGCGC GCGGCGGGCG CGACCGACAC GCGACCCCGC

2821 CTGGTGCTGG CGGGTGGCTT CTTTCTCCTC GGCTTCCTCT TCGGTAGGGG GGCGCCTCGC
     GACCACGACC GCCCACCGAA GAAAGAGGAG CCGAAGGAGA AGCCATCCCC CCGCGGAGCG

2881 GGAGCAAACC TCGGAGTCTT CCCCGTGGTG CCGCGGTGCT GGGACTCGCG GGTCAGCTGC
     CCTCGTTTGG AGCCTCAGAA GGGGCACCAC GGCGCCACGA CCCTGAGCGC CCAGTCGACG

2941 CGAGTGGGAT CCTGTTGCTG GTCTTCCCCA GGGGCGGCGA TTAGGGTCGG GGTAATGTGG
     GCTCACCCTA GGACAACGAC CAGAAGGGGT CCCCGCCGCT AATCCCAGCC CCATTACACC

3001 GGTGAGCACC CCTCGAG
     CCACTCGTGG GGAGCTC
```

ISOLATED NUCLEIC ACID MOLECULE ENCODING ALTERNATIVELY SPLICED PROSTATE-SPECIFIC MEMBRANE ANTIGEN AND USES THEREOF

This invention disclosed herein was made in part with Government support under NIH Grants No. DK-CA47650 and CA58192 from the Department of Health and Human Services. Accordingly, the U.S. Government has certain rights in this invention.

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citation for these references may be found at the end of each set of Examples in the Experimental Details section.

Prostate cancer is among the most significant medical problems in the United States, as the disease is now the most common malignancy diagnosed in American males. In 1992 there were over 132,000 new cases of prostate cancer detected with over 36,000 deaths attributable to the disease, representing a 17.3% increase over 4 years (2). Five year survival rates for patients with prostate cancer range from 88% for those with localized disease to 29% for those with metastatic disease. The rapid increase in the number of cases appears to result in part from an increase in disease awareness as well as the widespread use of clinical markers such as the secreted proteins prostate-specific antigen (PSA) and prostatic acid phosphatase (PAP) (37).

The prostate gland is a site of significant pathology affected by conditions such as benign growth (BPH), neoplasia (prostatic cancer) and infection (prostatitis). Prostate cancer represents the second leading cause of death from cancer in man (1). However prostatic cancer is the leading site for cancer development in men. The difference between these two facts relates to prostatic cancer occurring with increasing frequency as men age, especially in the ages beyond 60 at a time when death from other factors often intervenes. Also, the spectrum of biologic aggressiveness of prostatic cancer is great, so that in some men following detection the tumor remains a latent histologic tumor and does not become clinically significant, whereas in other it progresses rapidly, metastasizes and kills the man in a relatively short 2–5 year period (1, 3).

In prostate cancer cells, two specific proteins that are made in very high concentrations are prostatic acid phosphatase (PAP) and prostate specific antigen (PSA) (4, 5, 6). These proteins have been characterized and have been used to follow response to therapy. With the development of cancer, the normal architecture of the gland becomes altered, including loss of the normal duct structure for the removal of secretions and thus the secretions reach the serum. Indeed measurement of serum PSA is suggested as a potential screening method for prostatic cancer. Indeed, the relative amount of PSA and/or PAP in the cancer reduces as compared to normal or benign tissue.

PAP was one of the earliest serum markers for detecting metastatic spread (4). PAP hydrolyses tyrosine phosphate and has a broad substrate specificity. Tyrosine phosphorylation is often increased with oncogenic transformation. It has been hypothesized that during neoplastic transformation there is less phosphatase activity available to inactivate proteins that are activated by phosphorylation on tyrosine residues. In some instances, insertion of phosphatases that have tyrosine phosphatase activity has reversed the malignant phenotype.

PSA is a protease and it is not readily appreciated how loss of its activity correlates with cancer development (5, 6). The proteolytic activity of PSA is inhibited by zinc. Zinc concentrations are high in the normal prostate and reduced in prostatic cancer. Possibly the loss of zinc allows for increased proteolytic activity by PSA. As proteases are involved in metastasis and some proteases stimulate mitotic activity, the potentially increased activity of PSA could be hypothesized to play a role in the tumors metastases and spread (7).

Both PSA and PAP are found in prostatic secretions. Both appear to be dependent on the presence of androgens for their production and are substantially reduced following androgen deprivation.

Prostate-specific membrane antigen (PSM) which appears to be localized to the prostatic membrane has been identified. This antigen was identified as the result of generating monoclonal antibodies to a prostatic cancer cell, LNCaP (8).

Dr. Horoszewicz established a cell line designated LNCaP from the lymph node of a hormone refractory, heavily pretreated patient (9). This line was found to have an aneuploid human male karyotype. It maintained prostatic differentiation functionality in that it produced both PSA and PAP. It possessed an androgen receptor of high affinity and specificity. Mice were immunized with LNCaP cells and hybridomas were derived from sensitized animals. A monoclonal antibody was derived and was designated 7E11-C5 (8). The antibody staining was consistent with a membrane location and isolated fractions of LNCaP cell membranes exhibited a strongly positive reaction with immunoblotting and ELISA techniques. This antibody did not inhibit or enhance the growth of LNCaP cells in vitro or in vivo. The antibody to this antigen was remarkably specific to prostatic epithelial cells, as no reactivity was observed in any other component. Immunohistochemical staining of cancerous epithelial cells was more intense than that of normal or benign epithelial cells.

Dr. Horoszewicz also reported detection of immunoreactive material using 7E11-C5 in serum of prostatic cancer patients (8). The immunoreactivity was detectable in nearly 60% of patients with stage D-2 disease and in a slightly lower percentage of patients with earlier stage disease, but the numbers of patients in the latter group are small. Patients with benign prostatic hyperplasia (BPH) were negative. Patients with no apparent disease were negative, but 50–60% of patients in remission yet with active stable disease or with progression demonstrated positive serum reactivity. Patients with non prostatic tumors did not show immunoreactivity with 7E11-C5.

The 7E11-C5 monoclonal antibody is currently in clinical trials. The aldehyde groups of the antibody were oxidized and the linker-chelator glycol-tyrosyl-(n, $\epsilon$-diethylenetriamine-pentacetic acid)-lysine (GYK-DTPA) was coupled to the reactive aldehydes of the heavy chain (10). The resulting antibody was designated CYT-356. Immunohistochemical staining patterns were similar except that the CYT-356 modified antibody stained skeletal muscle. The comparison of CYT-356 with 7E11-C5 monoclonal antibody suggested both had binding to type 2 muscle fibers. The reason for the discrepancy with the earlier study, which reported skeletal muscle to be negative, was suggested to be due to differences in tissue fixation techniques. Still, the most intense and definite reaction was observed with prostatic epithelial cells, especially cancerous cells. Reactivity with mouse skeletal muscle was detected with immunohistochemistry but not in imaging studies. The Indium[111]-labeled antibody localized to LNCaP tumors grown in nude mice with an uptake of nearly 30% of the injected dose per gram tumor at four days. In-vivo, no selective retention of the antibody was observed in antigen negative tumors such as PC-3 and DU-145, or by skeletal muscle.

Very little was known about the PSM antigen. An effort at purification and characterization has been described at meetings by Dr. George Wright and colleagues (11, 12). These investigators have shown that following electrophoresis on acrylamide gels and Western blotting, the PSM antigen maintains a molecular weight of 100 kilodaltons (kd). Chemical and enzymatic treatment showed that both the peptide and carbohydrate moieties of the PSM antigen are required for recognition by the 7E11-C5 monoclonal antibody. Competitive binding studies with specific lectins suggested that galNAc is the dominant carbohydrate of the antigenic epitope.

The 100 kd glycoprotein unique to prostate cells and tissues was purified and characterized. The protein was digested proteolytically with trypsin and nine peptide fragments were sequenced. Using the technique of degenerate PCR (polymerase chain reaction), the full-length 2.65 kilobase (kb) cDNA coding for this antigen was cloned. Preliminary results have revealed that this antigen is highly expressed in prostate cancer tissues, including bone and lymph node metastases (13). The entire DNA sequence for the cDNA as well as the predicted amino acid sequence for the antigen was determined.

BRIEF DESCRIPTION OF THE FIGURES

Figure 14A:
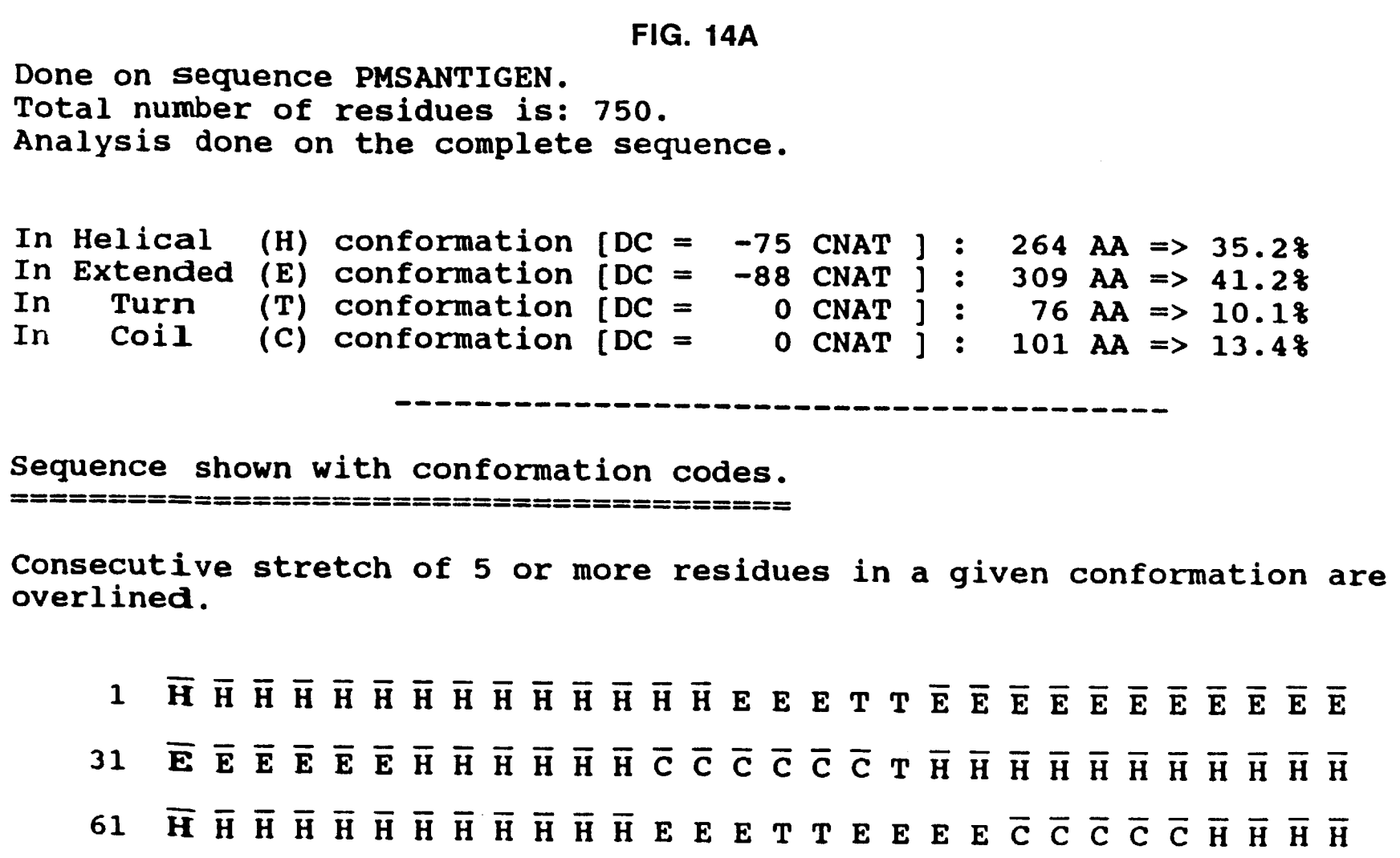
Figure 14B:
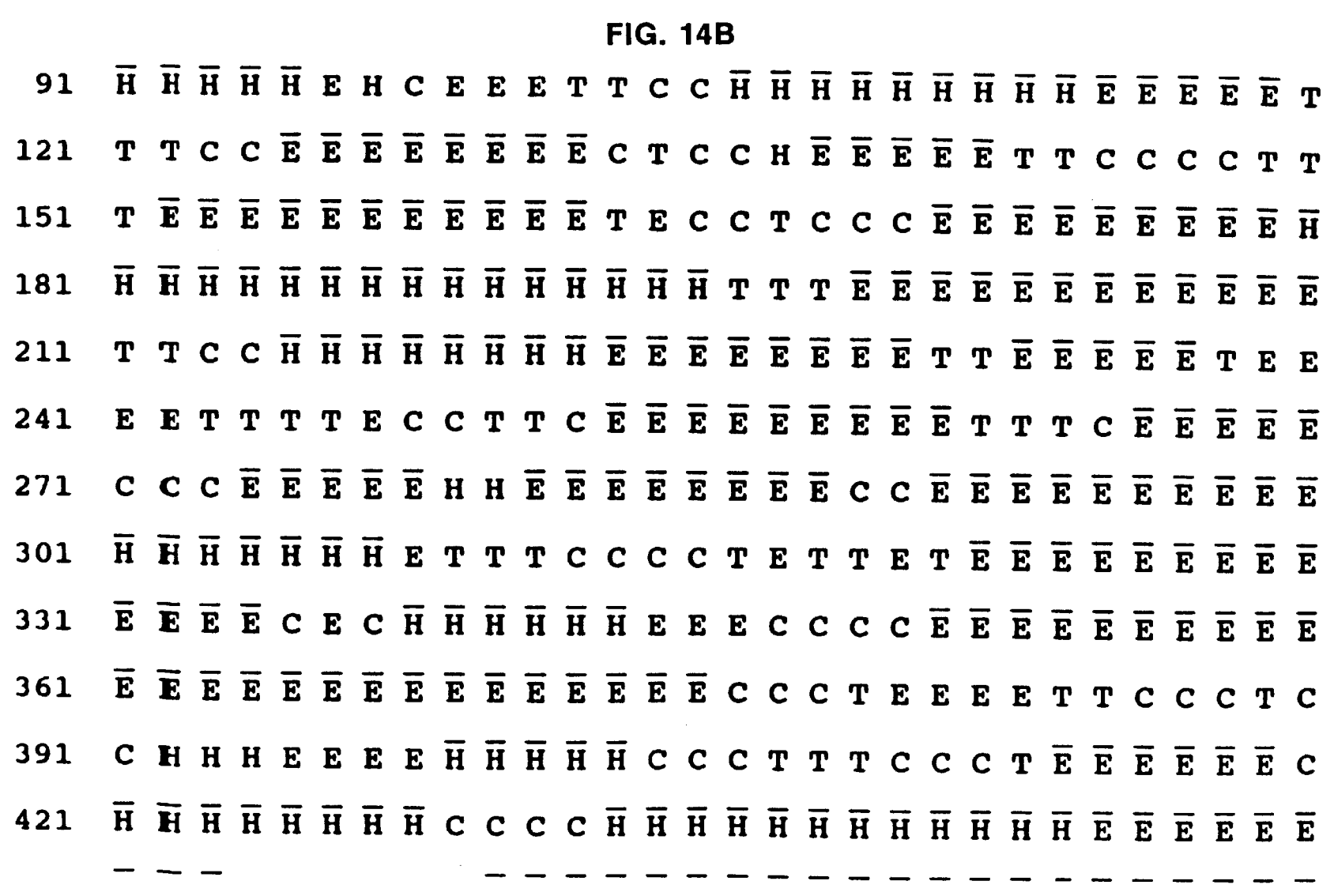
Figure 14C:
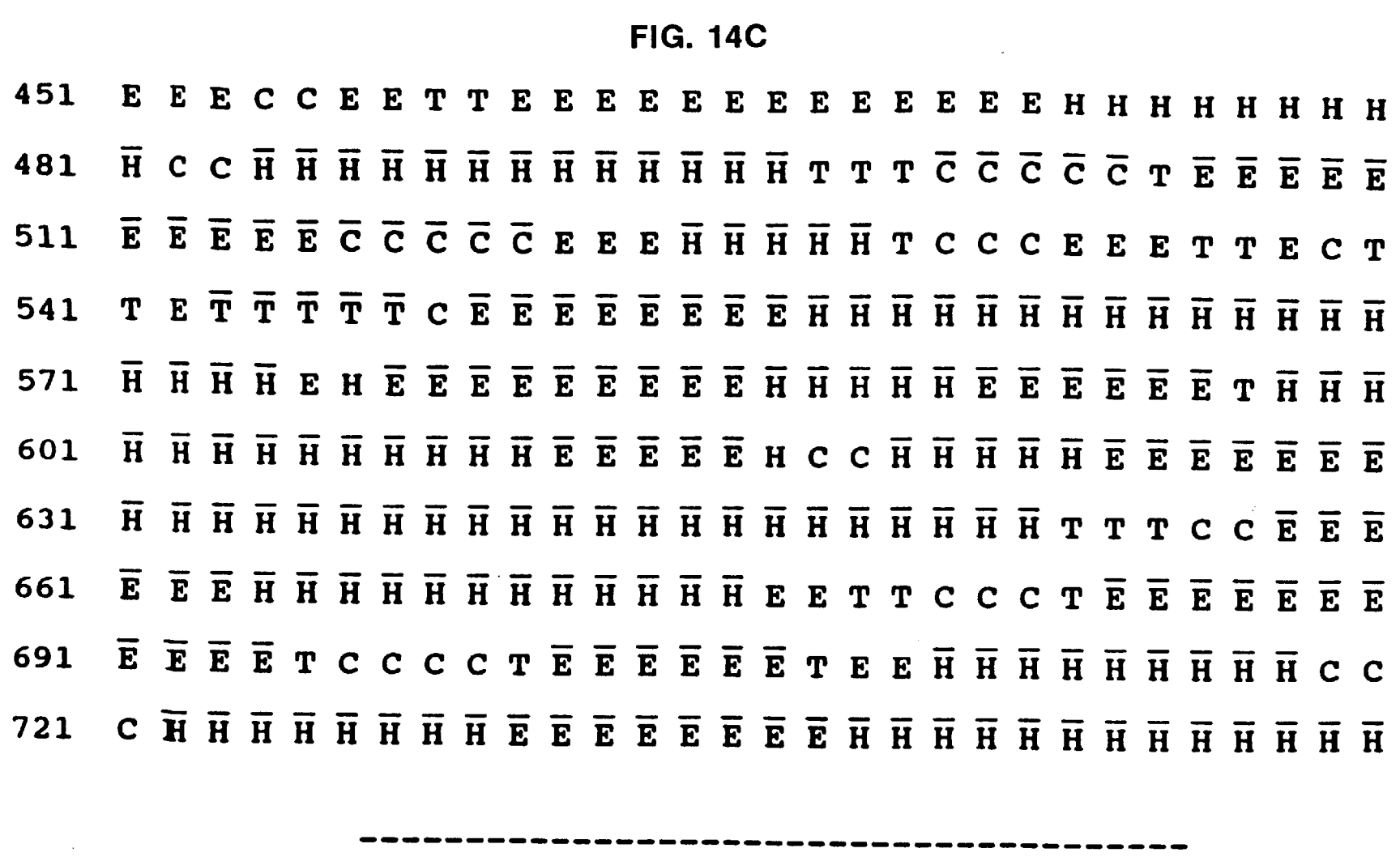

FIGS. 14A–14H Secondary structure of PSM antigen (see SEQ ID NO: 2)

FIGS. 15A–15B: A. Hydrophilicity plot of PSM antigen B. Prediction of membrane spanning segments (see SEQ ID NOS: 35–37)

FIGS. 16A–16K Homology with chicken, rat and human transferrin receptor sequence (see SEQ ID NOS.: 27–29).

FIG. 23: Data illustrating results of PSM DNA and RNA presence in transfect Dunning cell lines employing Southern and Northern blotting techniques

FIG. B indicates actual potency at a particular site. The tumor was implanted in prostate cells and treated with immune cells at two different sites.

Figure 25A:
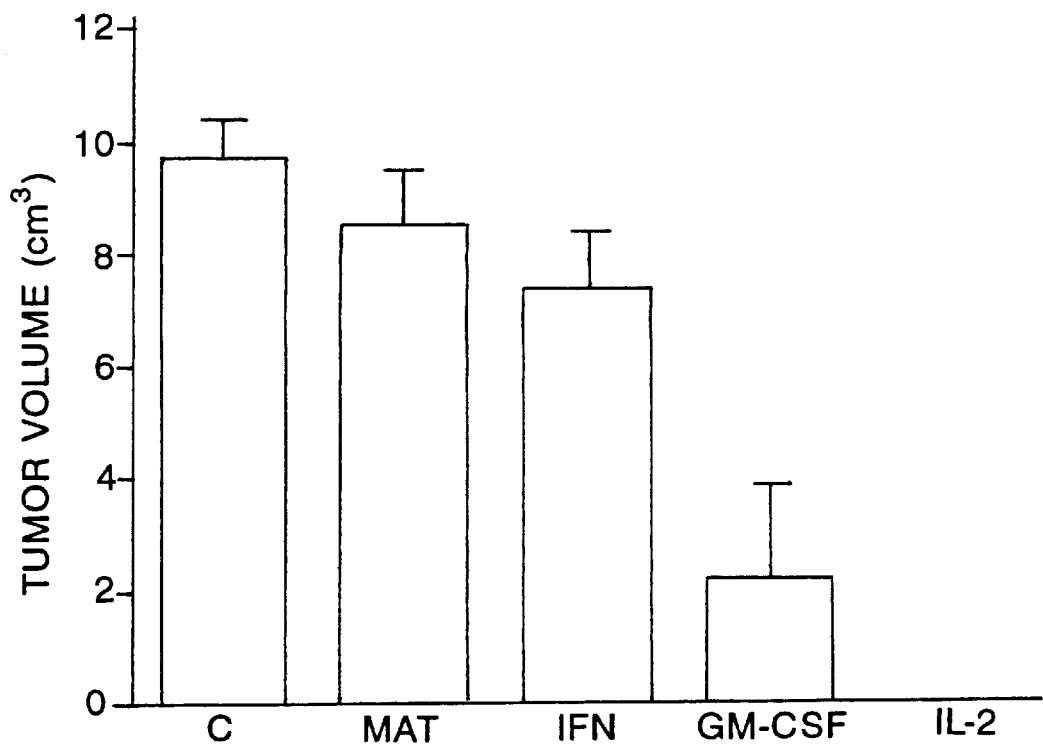
Figure 25B:
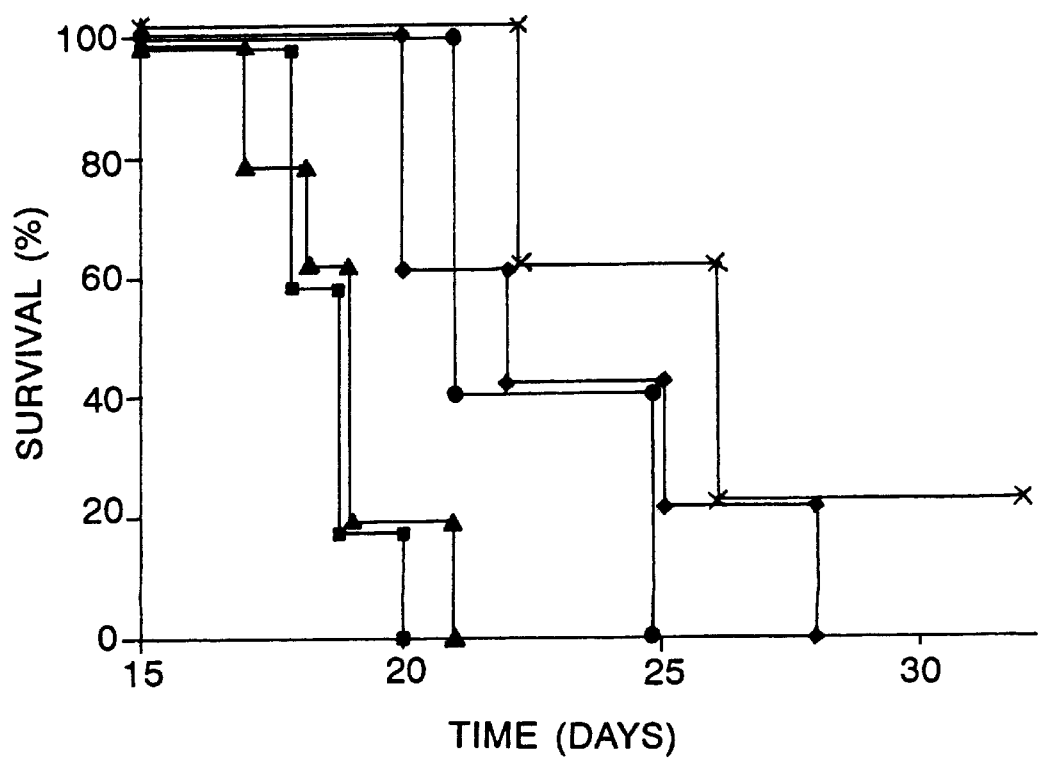

FIGS. 25A–25B: Relates potency of cytokines in inhibiting growth of primary tumors. Animals administered un-modified parental tumor cells and administered as a vaccine transfected cells. Following prostatectomy of rodent tumor results in survival increase.

Figure 26:
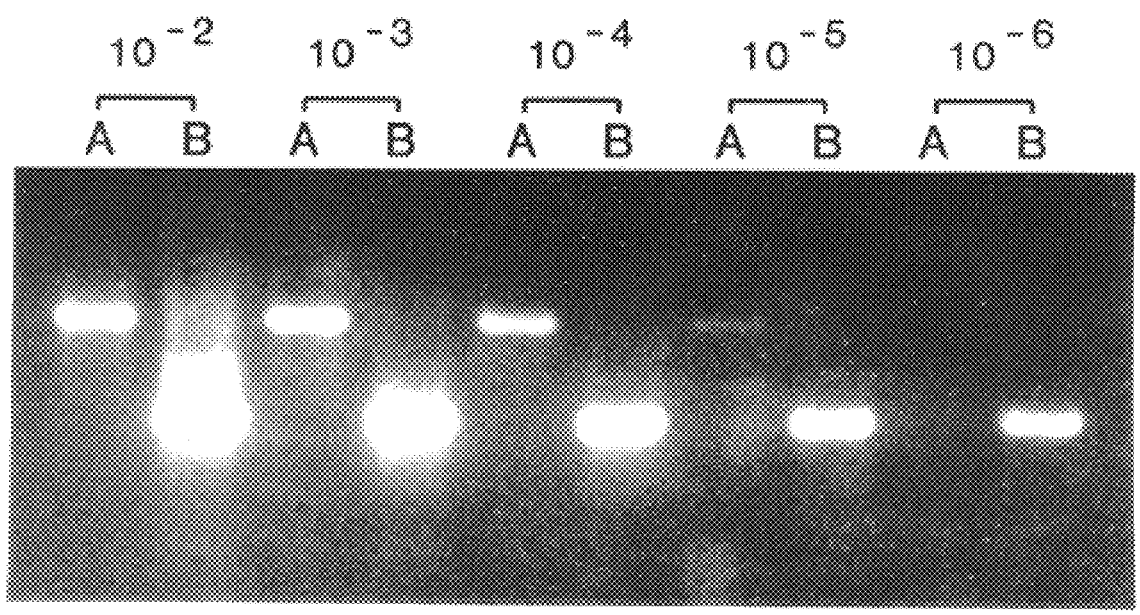

FIG. 26: PCR amplification with nested primers improved the level of detection of prostatic cells from approximately one prostatic cell per 10,000 MCF-7 cells to better than one cell per million MCF-7 cells, using either PSA.

Figure 27:
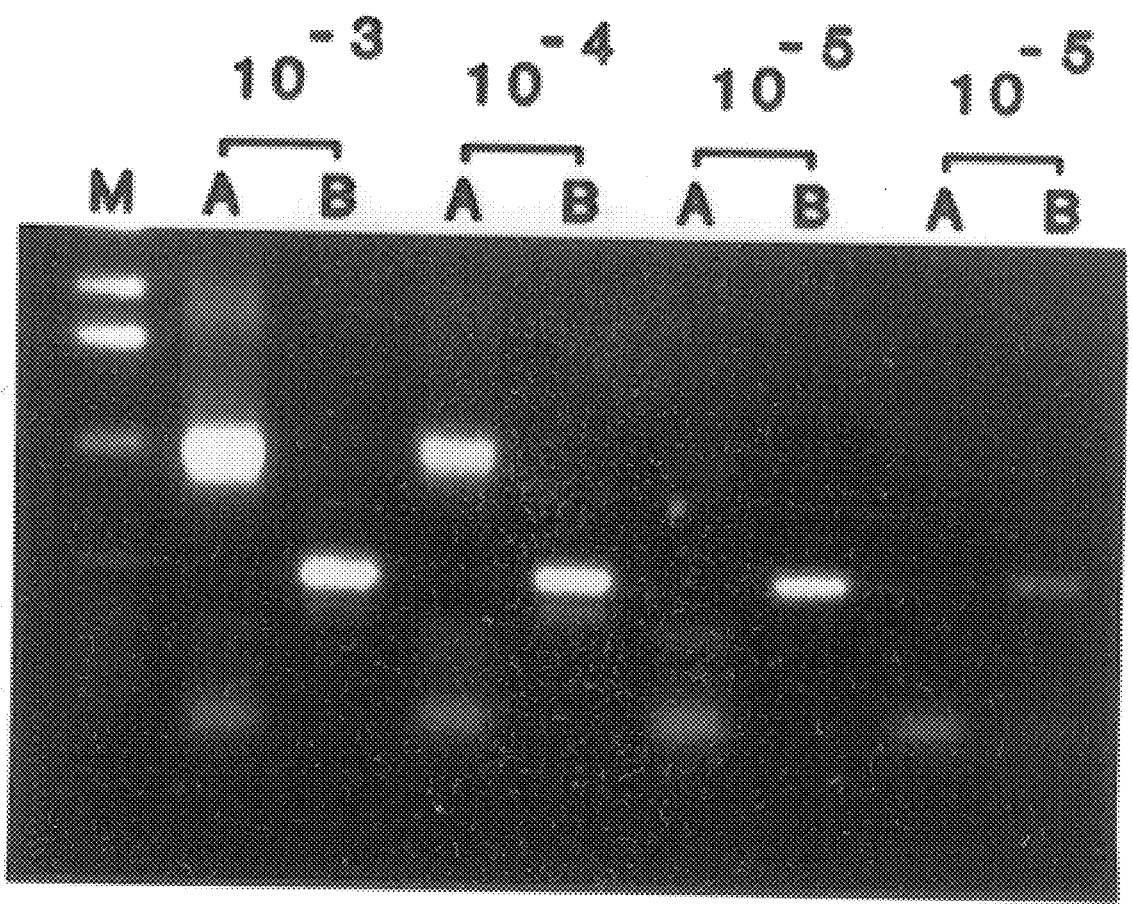

FIG. 27: PCR amplification with nested primers improved the level of detection of prostatic cells from approximately one prostatic cell per 10,000 MCF-7 cells to better than one cell per million MCF-7 cells, using PSM-derived primers.

Figure 28:
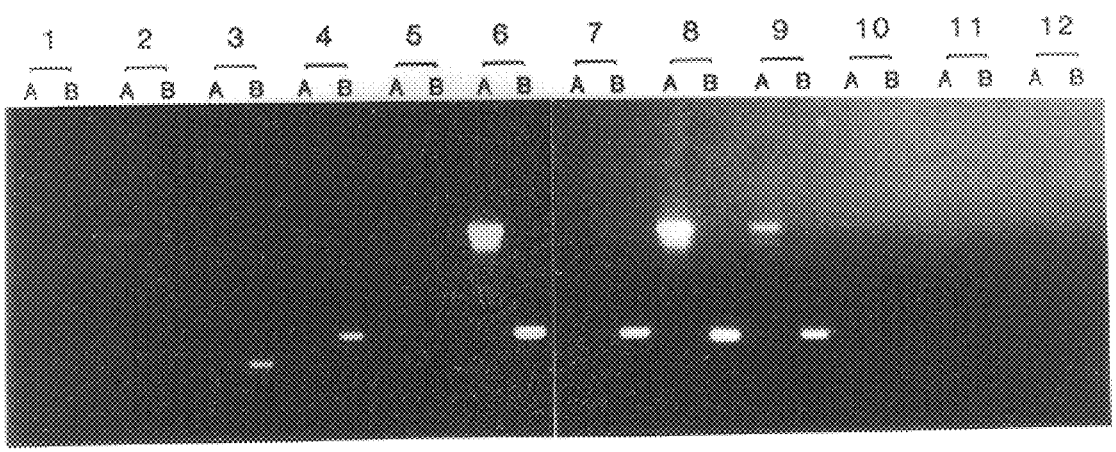

FIG. 28: A representative ethidium stained gel photograph for PSM-PCR. Samples run in lane A represent PCR products generated from the outer primers and samples in lanes labeled B are products of inner primer pairs.

Figure 4:
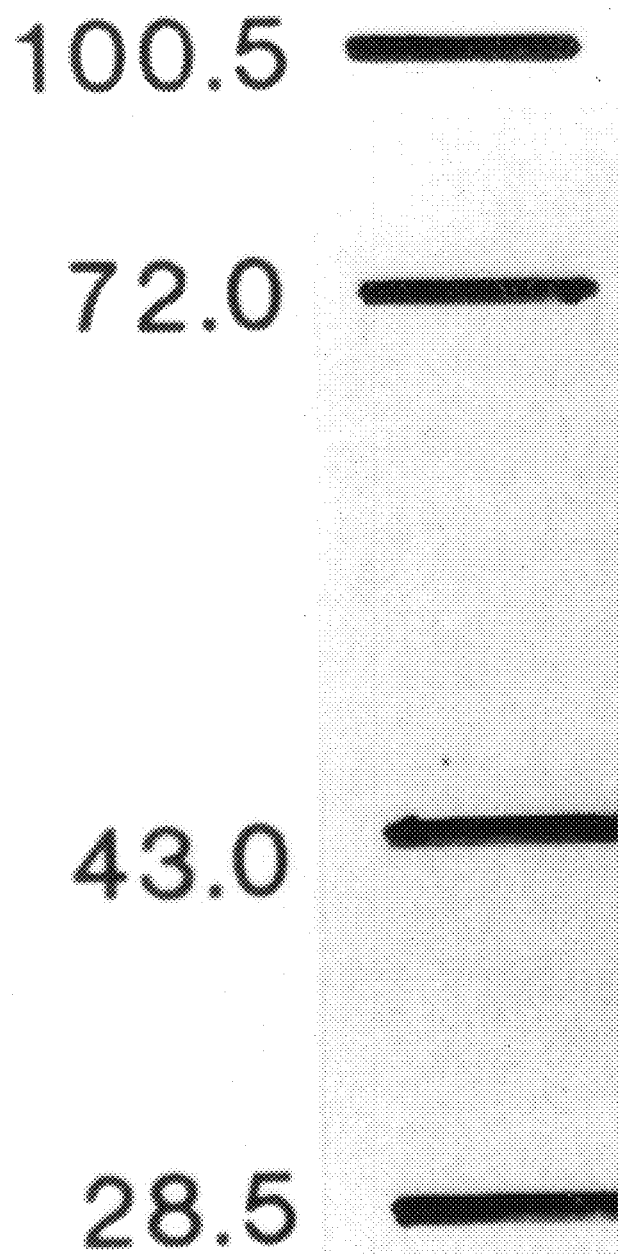
FIG. 4: 100 kD PSM antigen following immunoprecipitation of $^{35}$S-Methionine labelled LNCaP cells with Cyt-356 antibody.
Figure 29:
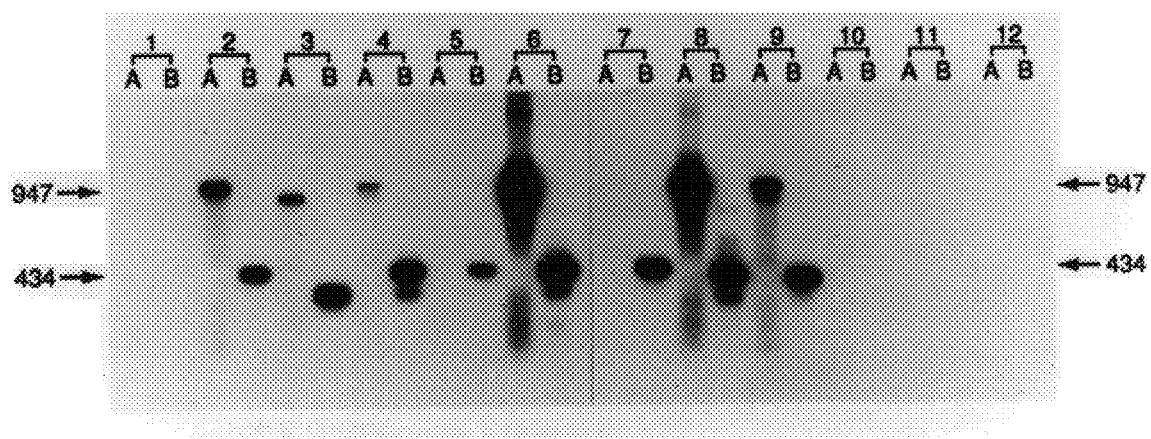

FIG. 29: PSM Southern blot autoradiograph. The sensitivity of the Southern blot analysis exceeded that of ethidium staining, as can be seen in several samples where the outer product is not visible on FIG. 3, but is detectable by Southern blotting as shown in FIG. 4.

FIG. 30: Characteristics of the 16 patients analyzed with respect to their clinical stage, treatment, serum PSA and PAP values, and results of assay.

FIGS. 31A–31D: The DNA sequence of the 3 kb XhoI fragment of p683 which includes 500 bp of DNA from the RNA start site was determined Sequence 683XFRVS starts from the 5' distal end of PSM promoter.

FIG. 32: Potential binding sites on the PSM promoter (see SEQ ID NO: 39).

Figure 33:
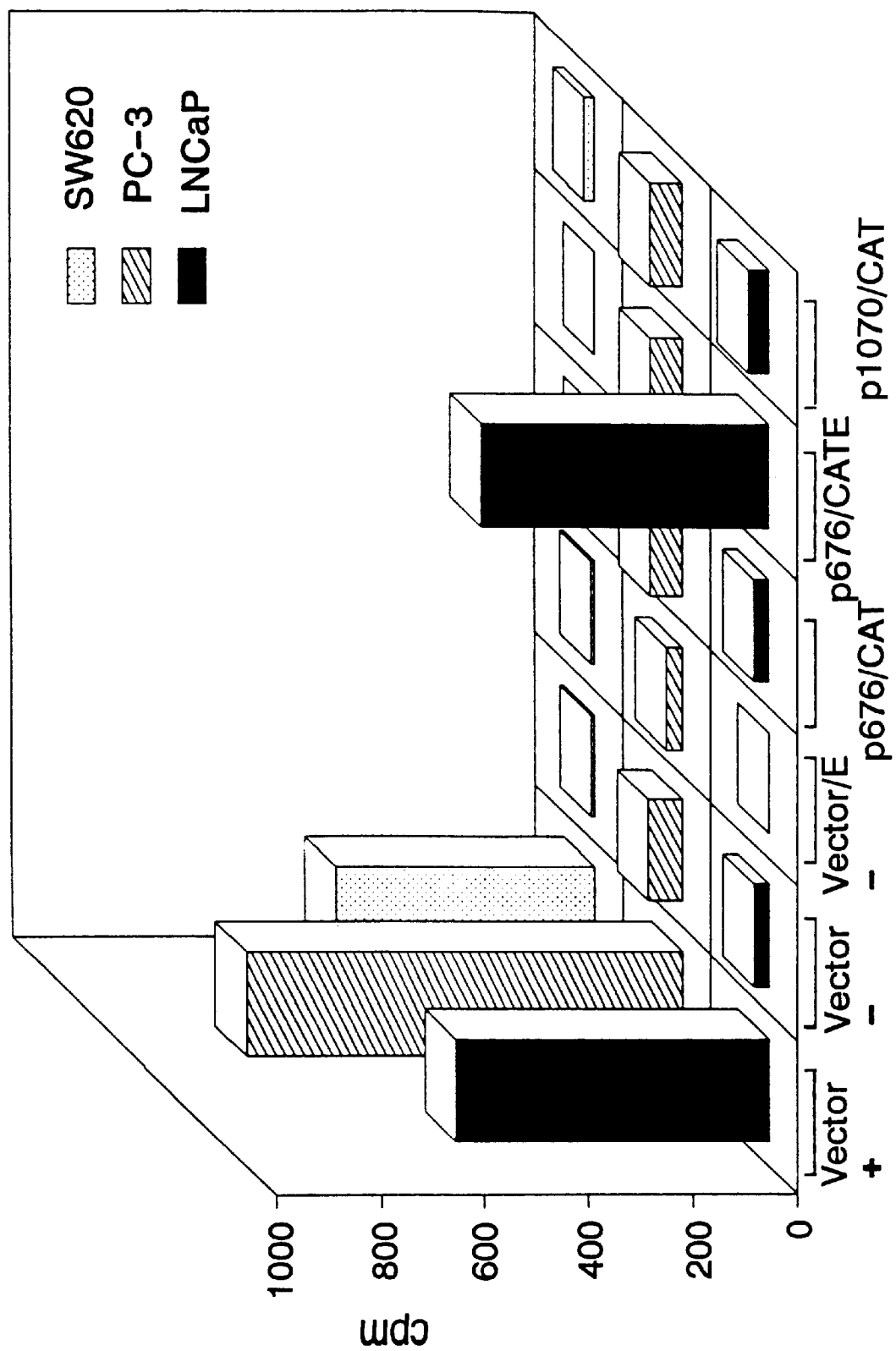

FIG. 33: Promoter activity of PSM up-stream fragment/ CAT gene chimera.

FIG. 34: Comparision between PSM and PSM' cDNA. Sequence of the 5' end of PSM cDNA (5) is shown (see nucleotides 1 to 519 of SEQ ID NO: 1). Underlined region denotes nucleotides which are present in PSM cDNA sequence but absent in PSM' cDNA. Boxed region represents the putative transmembrane domain of PSM antigen. * Asterisk denotes the putative translation initiation site for PSM'.

Figure 35:
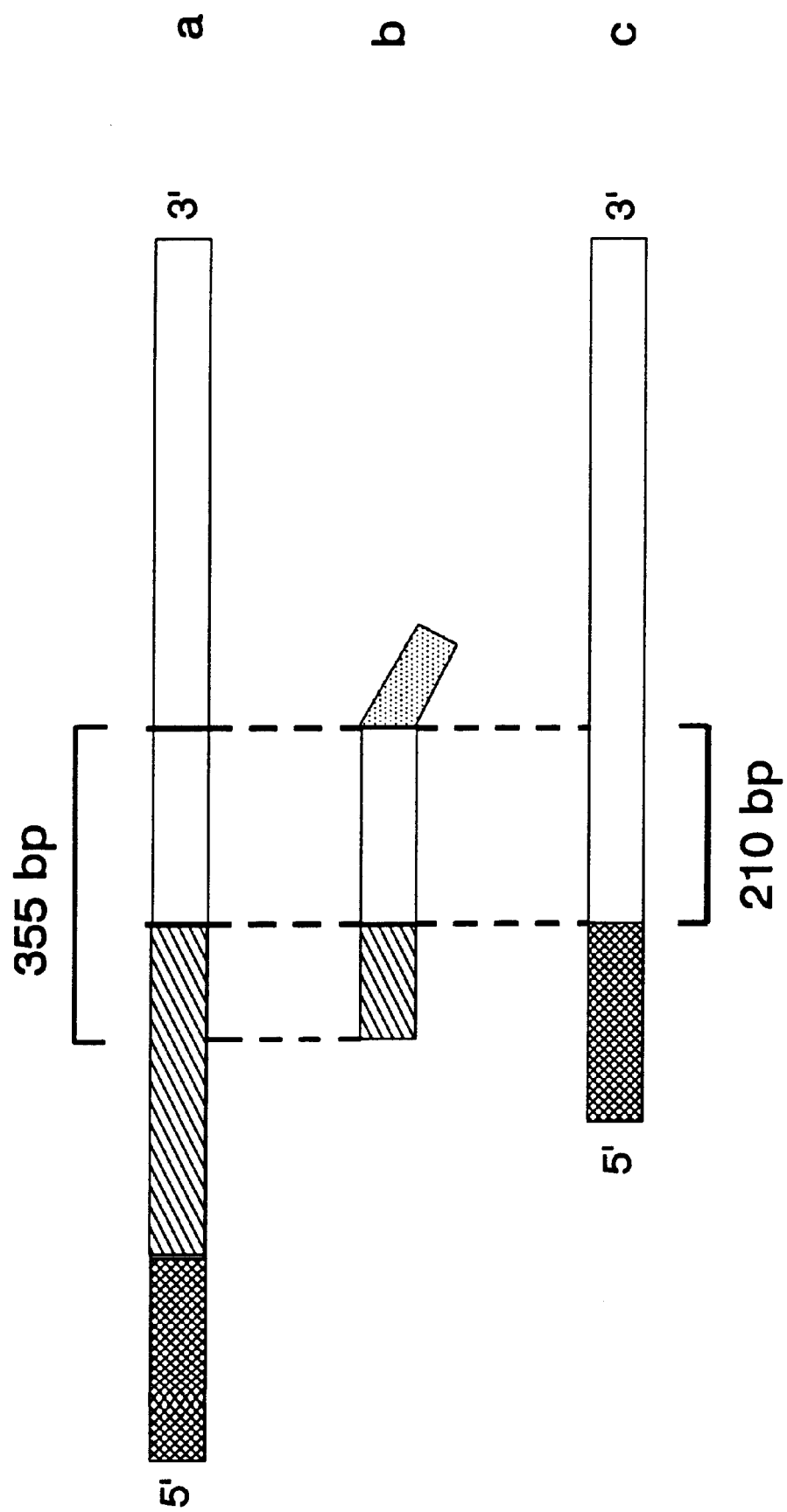

FIG. 35: Graphical representation of PSM and PSM' cDNA sequences and antisense PSM RNA probe (b). PSM cDNA sequence with complete coding region (5). (a) PSM' cDNA sequence from this study. (c) Cross hatched and open boxes denote sequences identity in PSM and PSM'. Hatched box indicates sequence absent from PSM'. Regions of cDNA sequence complementary to the antisense probe are indicated by dashed lines between the sequences.

Figure 36:
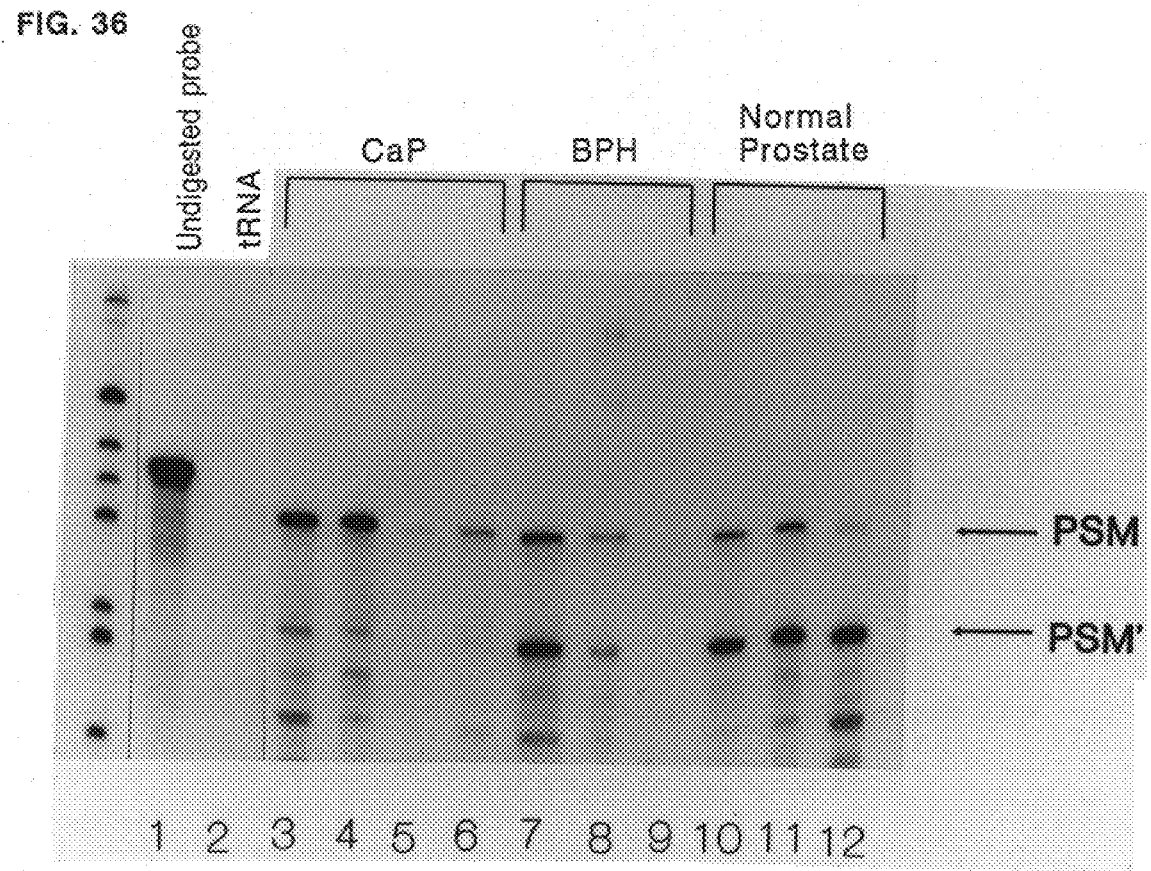

FIG. 36: RNase protection assay with PSM specific probe in primary prostatic tissues. Total cellular RNA was isolated from human prostatic samples: normal prostate, BPH, and CaP. PSM and PSM' spliced variants are indicated with arrows at right. The left lane is a DNA ladder. Samples from different patients are classified as: lanes 3–6, CaP, carcinoma of prostate; BPH, benign prostatic hypertrophy, lanes 7–9; normal, normal prostatic tissue, lanes 10–12. Autoradiograph was exposed for longer period to read lanes 5 and 9.

Figure 37:
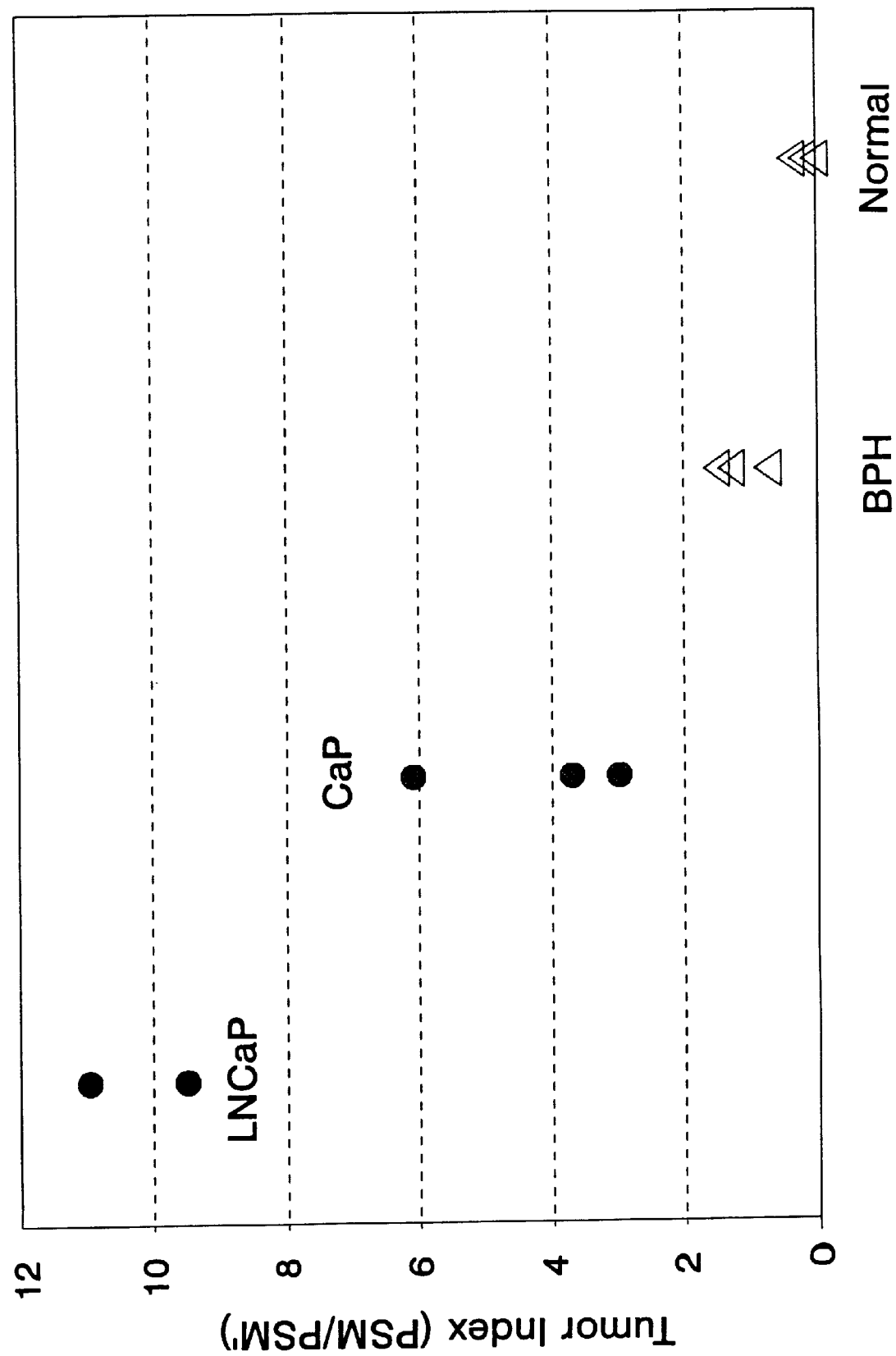

FIG. 37: Tumor Index, a quantification of the expression of PSM and PSM'. Expression of PSM and PSM' (FIG. 3) was quantified by densitometry and expressed as a ratio of PSM/PSM' on the Y-axis. Three samples each were quantitated for primary CaP, BPH and normal prostate tissues. Two samples were quantitated for LNCaP. Normal, normal prostate tissue.

Figure 38:
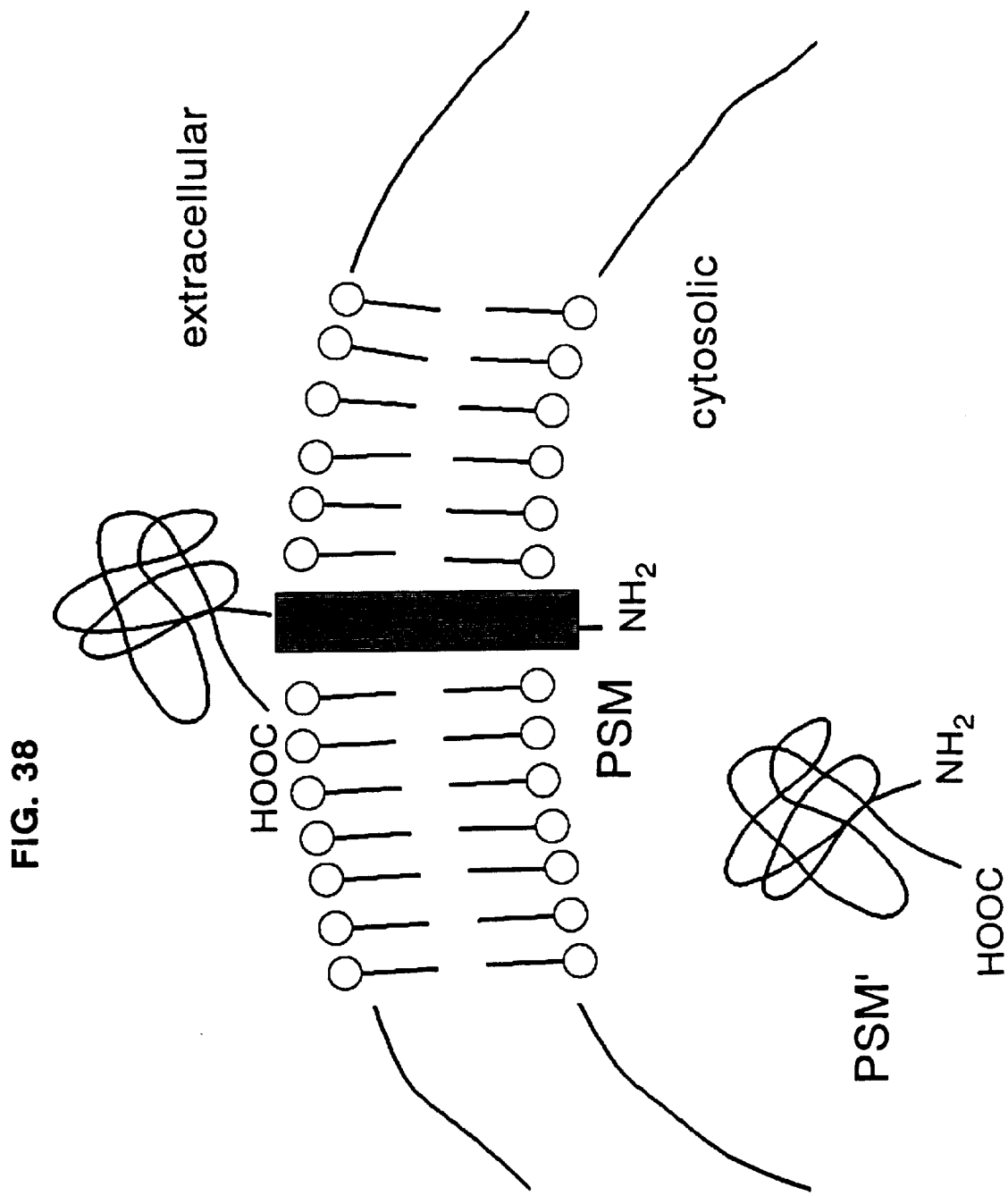

FIG. 38: Characterization of PSM membrane bound and PSM' in the cytosol.

FIG. 39: Intron 1F: Forward Sequence. Intron 1 contains a number of trinucleotide repeats which can be area associated with chromosomal instability in tumor cells. LNCaP cells and primary prostate tissue are identical, however in the PC-3 and Du-145 tumors they have substantially altered levels of these trinucleotide repeats which may relate to their lack of expression of PSM (see SEQ ID NO: 40).

FIGS. 40A–40B: Intron 1R: Reverse Sequence (see SEQ ID NO: 41)

FIG. 41: Intron 2F: Forward Sequence (see SEQ ID NO: 42)

FIG. 42: Intron 2R: Reverse Sequence (see SEQ ID NO: 43)

FIGS. 43A–43B: Intron 3F: Forward Sequence (see SEQ ID NO: 44)

FIGS. 44A–44B: Intron 3R: Reverse Sequence (see SEQ ID NO: 45)

FIGS. 45A–45B: Intron 4F: Forward Sequence (see SEQ ID NO: 46)

FIGS. 46A–46B: Intron 4R: Reverse Sequence (see SEQ ID NO: 47)

FIGS. 47A–47D: Sequence of the genomic region upstream of the 5' transcription start site of PSM (see SEQ ID NO: 1).

FIG. 48: Photograph of ethidium bromide stained gel depicting representative negative and positive controls used in the study. Samples 1–5 were from, respectively: male with prostatis, a healthy female volunteer, a male with BPH, a control 1:1,000,000 dilution of LNCaP cells, and a patient with renal cell carcinoma. Below each reaction is the corresponding control reaction performed with beta-2-microglobulin primers to assure RNA integrity. No PCR products were detected for any of these negative controls.

Figure 49:
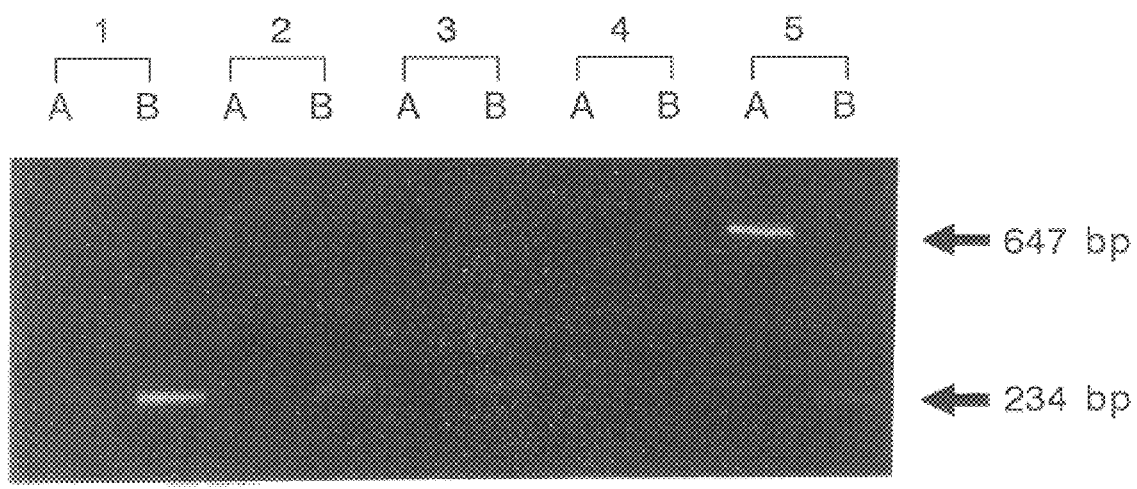

FIG. 49: Photograph of gel displaying representative positive PCR results using PSM primers in selected patients with either localized or disseminated prostate cancer. Sample 1–5 were from. respectively: a patient with clinically localized stage $T1_c$ disease, a radical prostatectomy patient with organ confined disease and a negative serum PSA, a radical prostatectomy patient with locally advanced disease and a negative serum PSA, a patient with treated stage D2 disease, and a patient with treated hormone refractory disease.

Figure 50:
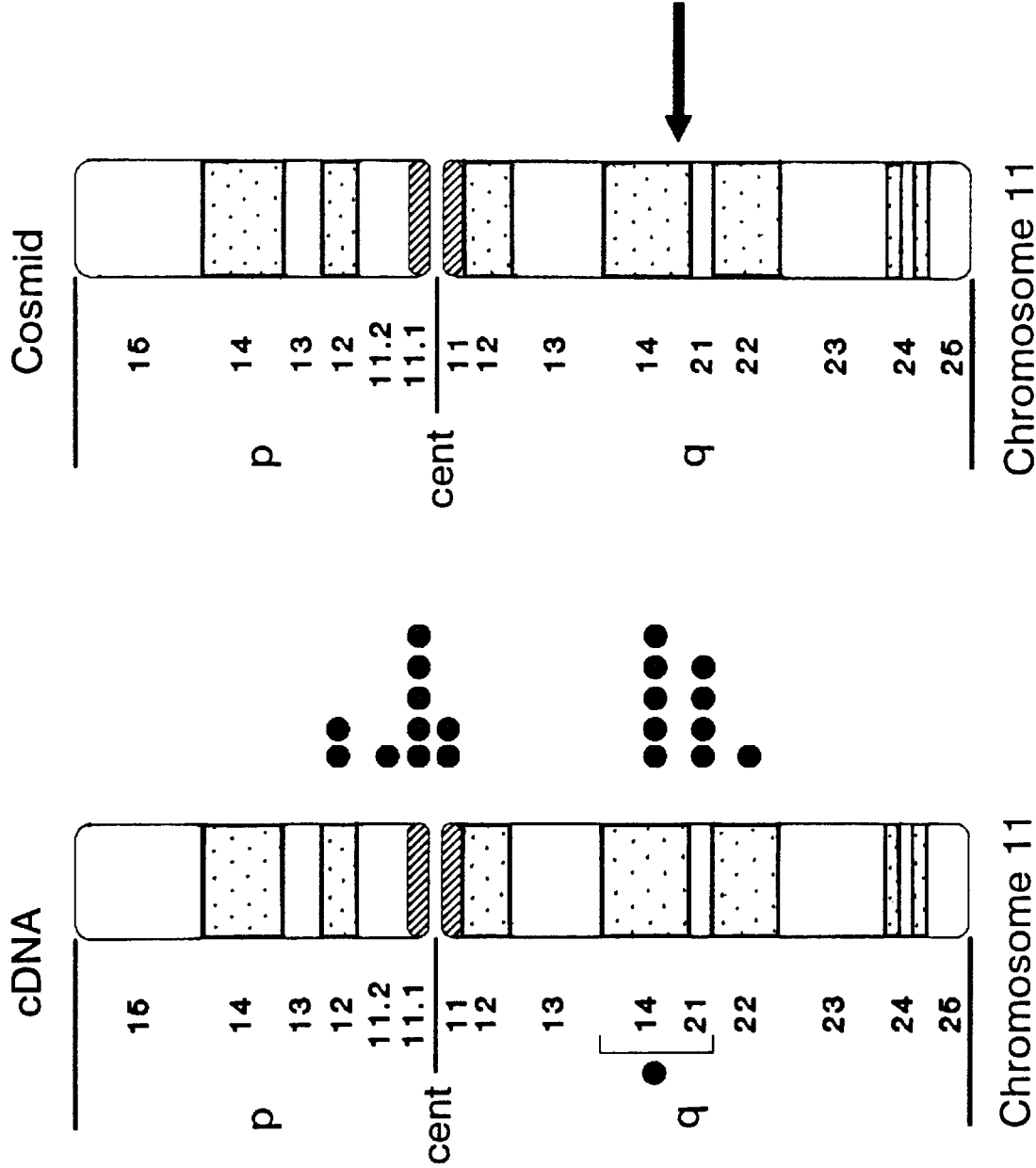

FIG. 50: Chromosomal location of PSM based on cosmid construction.

Figure 51:
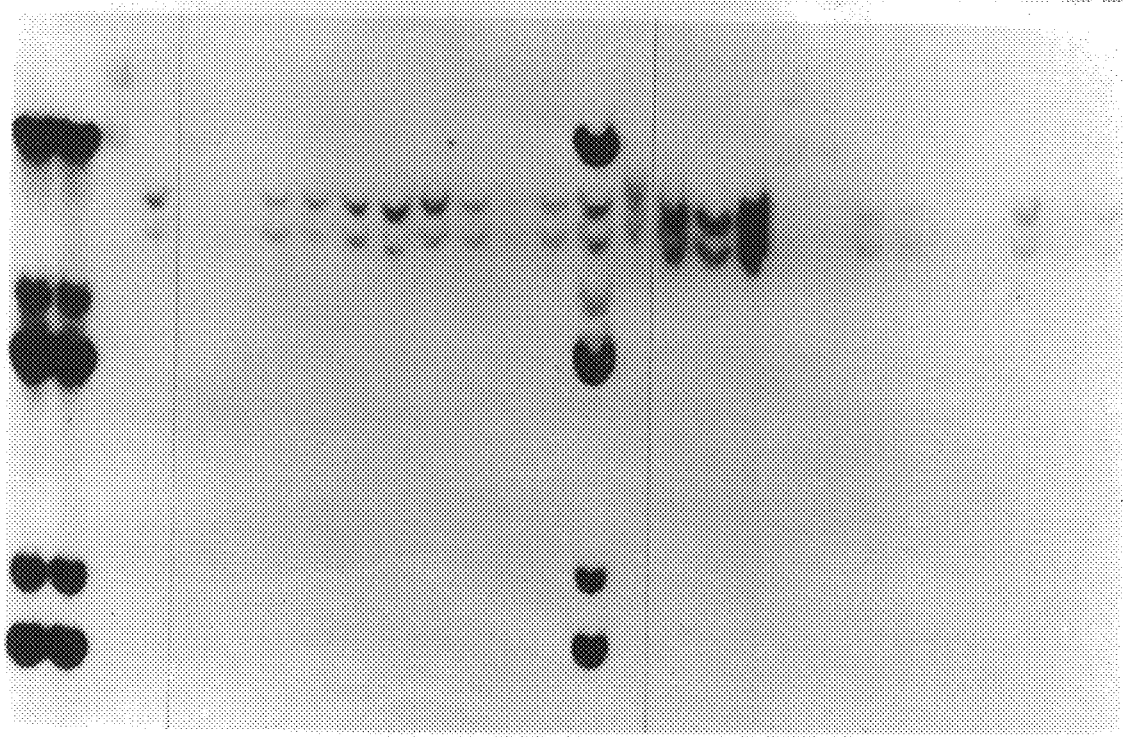

FIG. 51: Human monochromosomal somatic cell hybrid blot showing that chromosome 11 contained the PSM genetic sequence by Southern analysis. DNA panel digested with PstI restriction enzyme and probed with PSM cDNA. Lanes M and H refer to mouse and hamster DNAs. The numbers correspond to the human chromosomal DNA in that hybrid.

Figure 52:
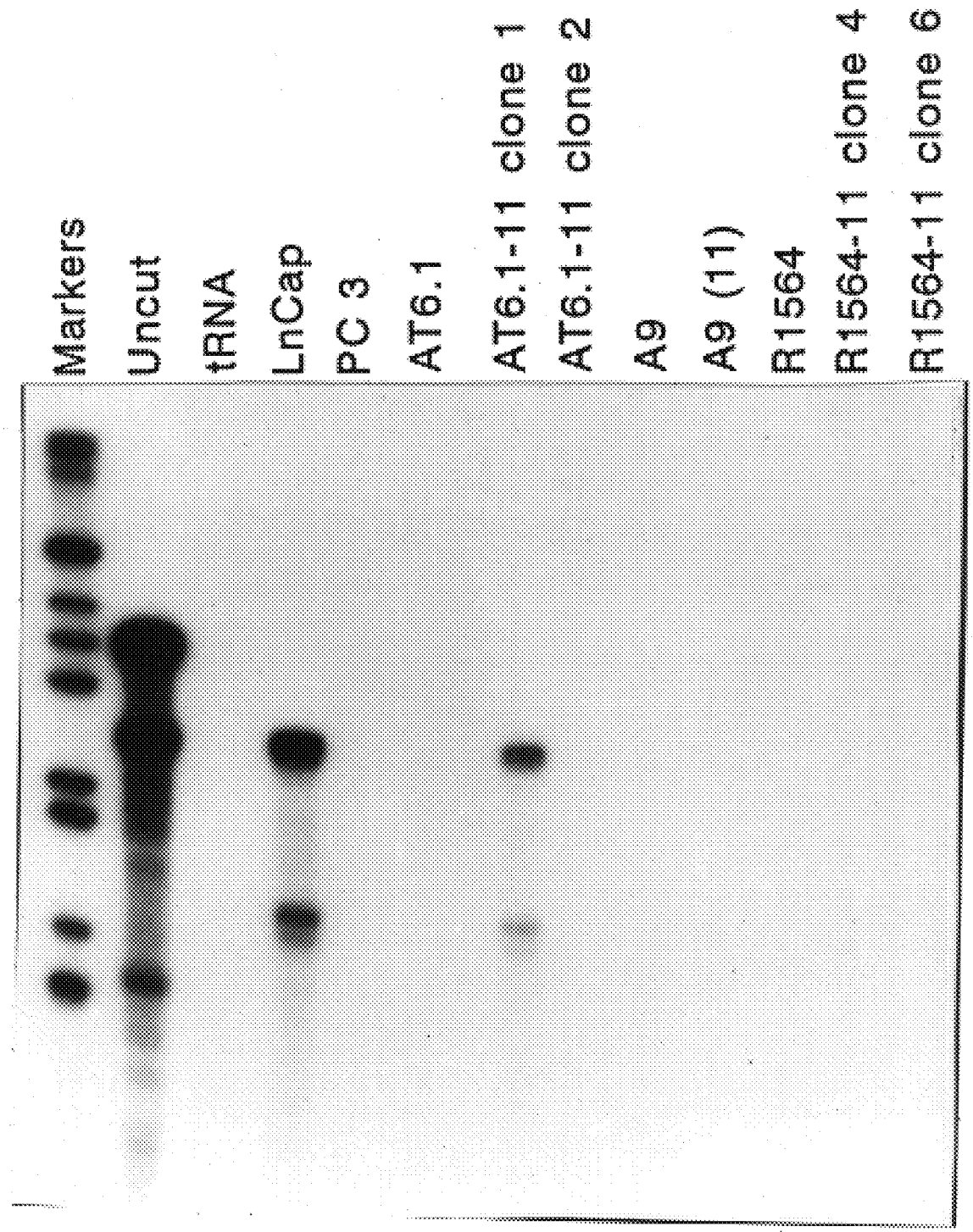

FIG. 52: Ribonuclease protection assay using PSM radio-labeled RNA probe revels an abundant PSM mRNA expression in AT6.1- 11 clone 1, but not in AT6.1-11 clone 2, thereby mapping PSM to 11p11.2-13 region.

FIG. 53: Tissue specific expression of PSM RNA by Northern blotting and RNAse protection assay.

Figure 54:
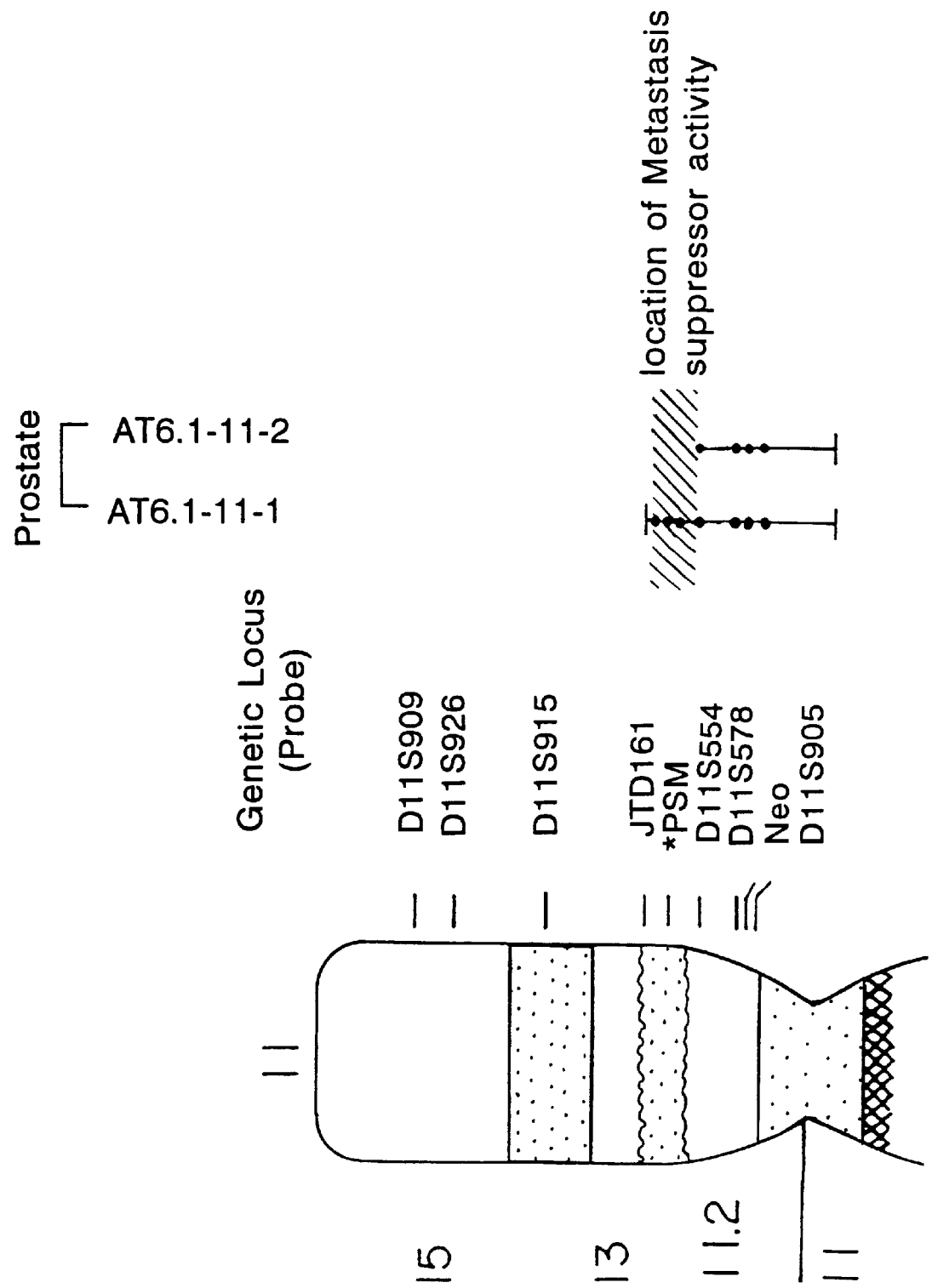

FIG. 54: Mapping of the PSM gene to the 11p11.2-p13 region of human chromosome 11 by southern blotting and in-situ hybridization.

Figure 55:
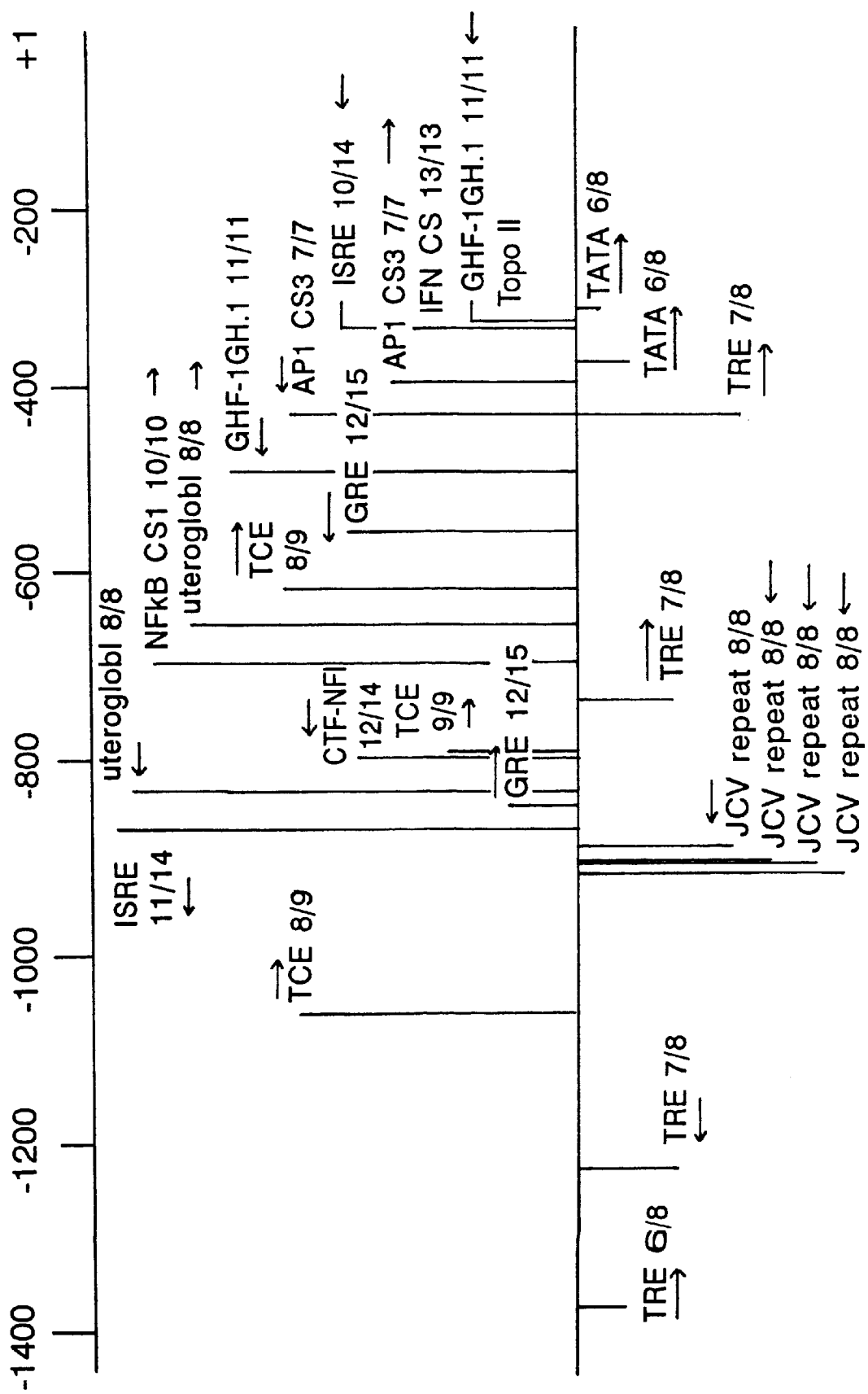

FIG. 55: Schematic of potential response elements.

Figure 56:
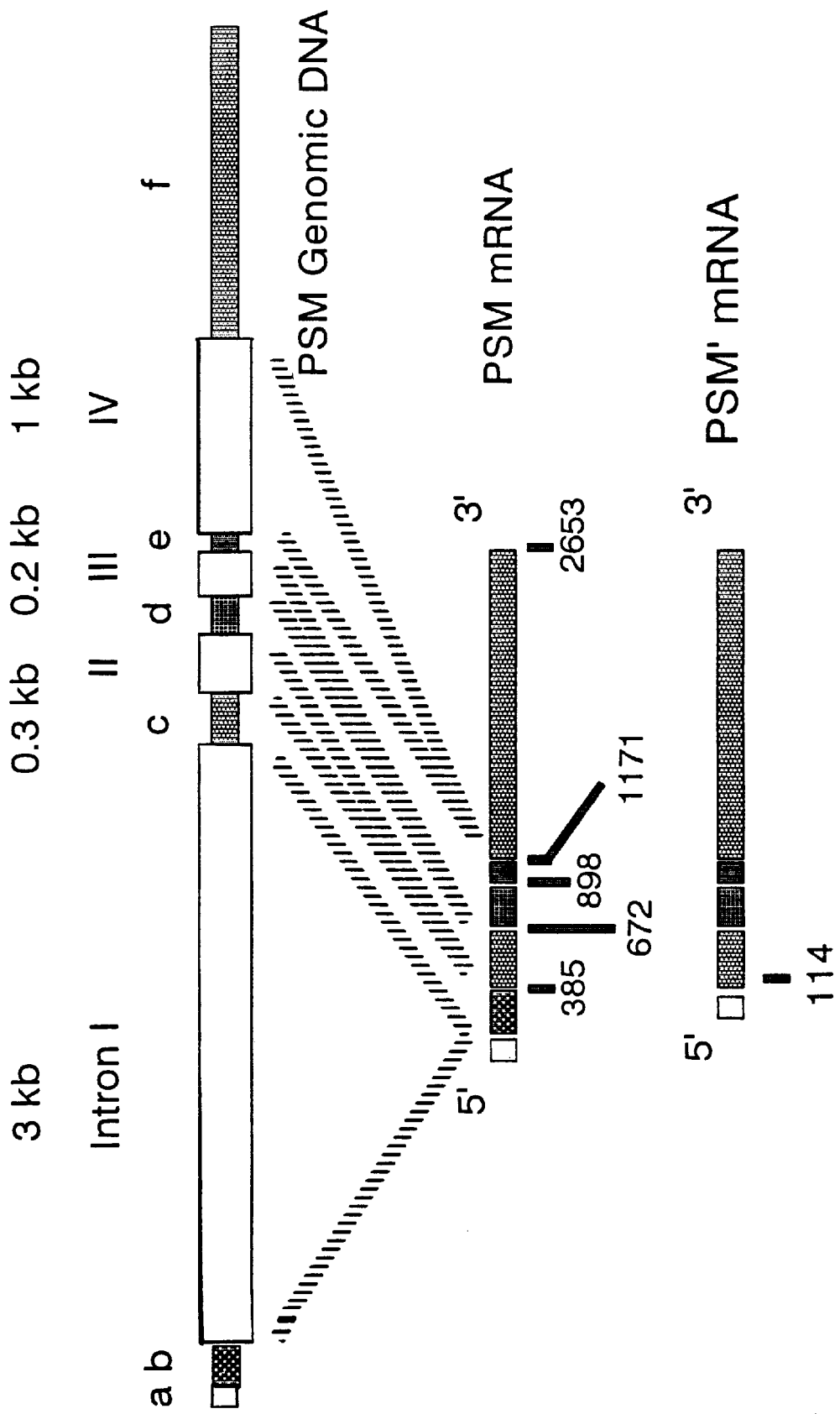

FIG. 56: Genomic organization of PSM gene.

Figure 57:
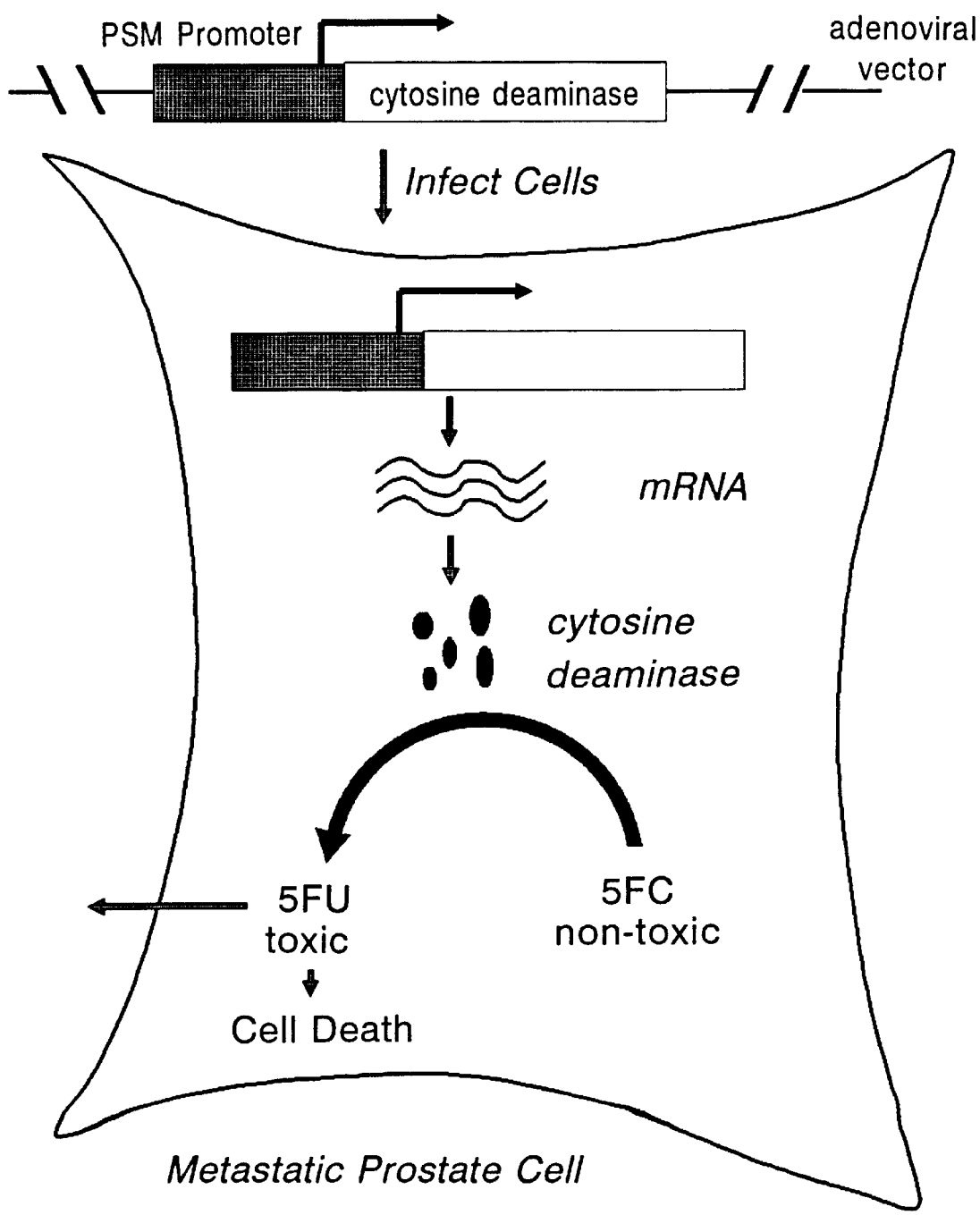

FIG. 57: Schematic of metastatic prostate cell

FIG. 58A–58C: Nucleic acid of PSM genomic DNA is read 5 prime away from the transcription start site: number on the sequences indicates nucleotide upstream from the start site. Therefore, nucleotide #121 is actually −121 using conventional numbering system. cell

SUMMARY OF THE INVENTION

This invention provides an isolated mammalian nucleic acid molecule encoding an alternatively spliced prostate-specific membrane (PSM') antigen.

This invention provides an isolated nucleic acid molecule encoding a prostate-specific membrane antigen promoter. This invention provides a method of detecting hematogenous micrometastic tumor cells of a subject, and determining prostate cancer progression in a subject.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

| C = cytosine | A = adenosine |
| T = thymidine | G = guanosine |

A "gene" means a nucleic acid molecule, the sequence of which includes all the information required for the normal regulated production of a particular protein, including the structural coding sequence, promoters and enhancers.

This invention provides an isolated mammalian nucleic acid encoding an alternatively spliced prostate-specific membrane (PSM') antigen.

This invention provides an isolated mammalian nucleic acid encoding a mammalian prostate-specific membrane (PSM) antigen.

This invention further provides an isolated mammalian DNA molecule of an isolated mammalian nucleic acid molecule encoding an alternatively spliced prostate-specific membrane antigen. This invention also provides an isolated mammalian cDNA molecule encoding a mammalian alternatively spliced prostate-specific membrane antigen. This invention provides an isolated mammalian RNA molecule encoding a mammalian alternatively spliced prostate-specific cytosolic antigen.

This invention further provides an isolated mammalian DNA molecule of an isolated mammalian nucleic acid molecule encoding a mammalian prostate-specific membrane antigen. This invention also provides an isolated mammalian cDNA molecule encoding a mammalian prostate-specific membrane antigen. This invention provides an isolated mammalian RNA molecule encoding a mammalian prostate-specific membrane antigen.

In the preferred embodiment of this invention, the isolated nucleic sequence is cDNA from human as shown in FIGS. 47A–47D. This human sequence was submitted to GenBank (Los Alamos National Laboratory, Los Alamos, New Mexico) with Accession Number, M99487 and the description as PSM, *Homo sapiens,* 2653 base-pairs.

This invention also encompasses DNAs and cDNAs which encode amino acid sequences which differ from those of PSM or PSM' antigen, but which should not produce phenotypic changes. Alternatively, this invention also encompasses DNAs and cDNAs which hybridize to the DNA and cDNA of the subject invention. Hybridization methods are well known to those of skill in the art.

For example, high stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6×SSC solution, washing at room temperature with 6×SSC solution, followed by washing at about 68° C. in a 6×SSC in a 0.6×SSX solution.

Hybridization with moderate stringency may be attained for example by: 1) filter pre-hybridizing and hybridizing with a solution of 3×sodium chloride, sodium citrate (SSC), 50% formamide, 0.1 M Tris buffer at Ph 7.5, 5×Denhardt's solution; 2) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4× for 1 minute each at room temperature at 4× at 60° C. for 30 minutes each; and 6) dry and expose to film.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated mammalian nucleic acid molecules encoding a mammalian prostate-specific membrane antigen and the alternatively spliced PSM' are useful for the development of probes to study the tumorigenesis of prostate cancer.

This invention also provides an isolated nucleic acid molecule of at least 15 nucleotides capable of specifically hybridizing with a sequence of a nucleic acid molecule encoding the prostate-specific membrane antigen or the alternatively spliced prostate specific membrane antigen.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a nucleic acid molecule encoding the prostate-specific membrane antigen can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes PSM antigen into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the PSM antigen molecule downstream of a bacteriophage promoter such as T3, T7 or SP6. Large amounts of RNA probe may be produced by incubating the labeled nucleotides with the linearized PSM antigen fragment where it contains an upstream promoter in the presence of the appropriate RNA polymerase.

This invention also provides a nucleic acid molecule of at least 15 nucleotides capable of specifically hybridizing with a sequence of a nucleic acid molecule which is complementary to the mammalian nucleic acid molecule encoding a mammalian prostate-specific membrane antigen. This molecule may either be a DNA or RNA molecule.

The current invention further provides a method of detecting the expression of a mammalian PSM or PSM' antigen expression in a cell which comprises obtaining total mRNA from the cell, contacting the mRNA so obtained with a labelled nucleic acid molecule of at least 15 nucleotides capable of specifically hybridizing with a sequence of the nucleic acid molecule encoding a mammalian PSM or PSM' antigen under hybridizing conditions, determining the presence of mRNA hybridized to the molecule and thereby detecting the expression of the mammalian prostate-specific membrane antigen in the cell. The nucleic acid molecules synthesized above may be used to detect expression of a PSM or PSM' antigen by detecting the presence of mRNA coding for the PSM antigen. Total mRNA from the cell may be isolated by many procedures well known to a person of ordinary skill in the art. The hybridizing conditions of the labelled nucleic acid molecules may be determined by routine experimentation well known in the art. The presence of mRNA hybridized to the probe may be determined by gel electrophoresis or other methods known in the art. By measuring the amount of the hybrid made, the expression of the PSM antigen by the cell can be determined. The labelling may be radioactive. For an example, one or more radioactive nucleotides can be incorporated in the nucleic acid when it is made.

In one embodiment of this invention, nucleic acids are extracted by precipitation from lysed cells and the mRNA is isolated from the extract using an oligo-dT column which binds the poly-A tails of the mRNA molecules (13). The mRNA is then exposed to radioactively labelled probe on a nitrocellulose membrane, and the probe hybridizes to and thereby labels complementary mRNA sequences. Binding may be detected by luminescence autoradiography or scintillation counting. However, other methods for performing these steps are well known to those skilled in the art, and the discussion above is merely an example.

This invention further provides another method to detect expression of a PSM or PSM' antigen in tissue sections which comprises contacting the tissue sections with a labelled nucleic acid molecule of at least 15 nucleotides capable of specifically hybridizing with a sequence of nucleic acid molecules encoding a mammalian PSM antigen under hybridizing conditions, determining the presence of mRNA hybridized to the molecule and thereby detecting the expression of the mammalian PSM or PSM' antigen in tissue sections. The probes are also useful for in-situ hybridization or in order to locate tissues which express this gene, or for other hybridization assays for the presence of this gene or its mRNA in various biological tissues. The in-situ hybridization using a labelled nucleic acid molecule is well known in the art. Essentially, tissue sections are incubated with the labelled nucleic acid molecule to allow the hybridization to occur. The molecule will carry a marker for the detection because it is "labelled", the amount of the hybrid will be determined based on the detection of the amount of the marker and so will the expression of PSM antigen.

This invention further provides isolated PSM or PSM' antigen nucleic acid molecule operatively linked to a promoter of RNA transcription. The isolated PSM or PSM' antigen sequence can be linked to vector systems. Various vectors including plasmid vectors, cosmid vectors, bacteriophage vectors and other viruses are well known to ordinary skilled practitioners. This invention further provides a vector which comprises the isolated nucleic acid molecule encoding for the PSM or PSM' antigen.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the PSM sequence is cloned in the Not I/Sal I site of pSPORT/vector (Gibco®-BRL). This plasmid, p55A-PSM, was deposited on Aug. 14, 1992 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, p55A-PSM, was accorded ATCC Accession Number 75294.

This invention further provides a host vector system for the production of a polypeptide having the biological activity of the prostate-specific membrane antigen. These vectors may be transformed into a suitable host cell to form a host cell vector system for the production of a polypeptide having the biological activity of PSM antigen.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (14). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the PSM antigen.

This invention further provides an isolated DNA or cDNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention further provides a method of producing a polypeptide having the biological activity of the prostate-specific membrane antigen which comprising growing host cells of a vector system containing the PSM antigen sequence under suitable conditions permitting production of the polypeptide and recovering the polypeptide so produced.

This invention provides a mammalian cell comprising a DNA molecule encoding a mammalian PSM or PSM' antigen, such as a mammalian cell comprising a plasmid adapted for expression in a mammalian cell, which comprises a DNA molecule encoding a mammalian PSM antigen and the regulatory elements necessary for expression of the DNA in the mammalian cell so located relative to the DNA encoding the mammalian PSM or PSM' antigen as to permit expression thereof.

Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the mammalian PSM antigen may be otherwise introduced into mammalian cells, e.g., by microinjection, to obtain mammalian cells which comprise DNA, e.g., cDNA or a plasmid, encoding a mammalian PSM antigen.

This invention provides a method for determining whether a ligand can bind to a mammalian prostate-specific membrane antigen which comprises contacting a mammalian cell comprising an isolated DNA molecule encoding a mammalian prostate-specific membrane antigen with the ligand under conditions permitting binding of ligands to the mammalian prostate-specific membrane antigen, and thereby determining whether the ligand binds to a mammalian prostate-specific membrane antigen. This invention further provides ligands bound to the mammalian PSM or PSM' antigen.

This invention also provides a therapeutic agent comprising a ligand identified by the above-described method and a cytotoxic agent conjugated thereto. The cytotoxic agent may either be a radioisotope or a toxin. Examples of radioisotopes or toxins are well known to one of ordinary skill in the art.

This invention also provides a method of imaging prostate cancer in human patients which comprises administering to the patients at least one ligand identified by the above-described method, capable of binding to the cell surface of the prostate cancer cell and labelled with an imaging agent under conditions permitting formation of a complex between the ligand and the cell surface PSM or PSM' antigen. This invention further provides a composition comprising an effective imaging agent of the PSM OR PSM' antigen ligand and a pharmaceutically acceptable carrier. Pharmaceutically acceptable carriers are well known to one of ordinary skill in the art. For an example, such a pharmaceutically acceptable carrier can be physiological saline.

Also provided by this invention is a purified mammalian PSM and PSM' antigen. As used herein, the term "purified prostate-specific membrane antigen" shall mean isolated naturally-occurring prostate-specific membrane antigen or protein (purified from nature or manufactured such that the primary, secondary and tertiary conformation, and posttranslational modifications are identical to naturally-occurring material) as well as non-naturally occurring polypeptides having a primary structural conformation (i.e. continuous sequence of amino acid residues). Such polypeptides include derivatives and analogs.

This invention provides an isolated nucleic acid molecule encoding a prostate-specific membrane antigen promoter. In one embodiment the PSM promoter has at least the sequence as in FIGS. 58A–58C.

This invention provides an isolated nucleic acid molecule encoding an alternatively spliced prostate-specific membrane antigen promoter.

This invention further provides a polypeptide encoded by the isolated mammalian nucleic acid sequence of PSM and PSM' antigen.

It is believed that there may be natural ligand interacting with the PSM or PSM' antigen. This invention provides a method to identify such natural ligand or other ligand which can bind to the PSM or PSM' antigen. A method to identify the ligand comprises a) coupling the purified mammalian PSM or PSM' antigen to a solid matrix, b) incubating the coupled purified mammalian PSM or PSM' protein with the potential ligands under the conditions permitting binding of ligands and the purified PSM or PSM' antigen; c) washing the ligand and coupled purified mammalian PSM or PSM' antigen complex formed in b) to eliminate the nonspecific binding and impurities and finally d) eluting the ligand from the bound purified mammalian PSM or PSM' antigen. The techniques of coupling proteins to a solid matrix are well known in the art. Potential ligands may either be deduced from the structure of mammalian PSM or PSM' by other empirical experiments known by ordinary skilled practitioners. The conditions for binding may also easily be determined and protocols for carrying such experimentation have long been well documented (15).

The ligand-PSM antigen complex will be washed. Finally, the bound ligand will be eluted and characterized. Standard ligands characterization techniques are well known in the art.

The above method may also be used to purify ligands from any biological source. For purification of natural ligands in the cell, cell lysates, serum or other biological samples will be used to incubate with the mammalian PSM or PSM' antigen bound on a matrix. Specific natural ligand will then be identified and purified as above described.

With the protein sequence information, antigenic areas may be identified and antibodies directed against these areas may be generated and targeted to the prostate cancer for imaging the cancer or therapies.

This invention provides an antibody directed against the amino acid sequence of a mammalian PSM or PSM' antigen.

This invention provides a method to select specific regions on the PSM or PSM' antigen to generate antibodies. The protein sequence may be determined from the PSM or PSM' DNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to mammalian PSM antigen. For an example, hydrophilic sequences of the human PSM antigen shown in hydrophilicity plot of FIGS. 16:1–11 may be easily selected. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian PSM antigen in living animals, in humans, or in biological tissues or fluids isolated from animals or humans.

In one embodiment, peptides Asp-Glu-Leu-Lys-Ala-Glu (SEQ ID No. 35), Asn-Glu-Asp-Gly-Asn-Glu (SEQ ID No. 36) and Lys-Ser-Pro-Asp-Glu-Gly (SEQ ID No. 37) of human PSM antigen are selected.

This invention further provides polyclonal and monoclonal antibody(ies) against peptides Asp-Glu-Leu-Lys-Ala-Glu (SEQ ID No. 35), Asn-Glu-Asp-Gly-Asn-Glu (SEQ ID No. 36) and Lys-Ser-Pro-Asp-Glu-Gly (SEQ ID No. 37).

This invention provides a therapeutic agent comprising antibodies or ligand(s) directed against PSM antigen and a cytotoxic agent conjugated thereto or antibodies linked enzymes which activate prodrug to kill the tumor. The cytotoxic agent may either be a radioisotope or toxin.

This invention provides a method of imaging prostate cancer in human patients which comprises administering to the patient the monoclonal antibody directed against the peptide of the mammalian PSM or PSM' antigen capable of binding to the cell surface of the prostate cancer cell and labeled with an imaging agent under conditions permitting formation of a complex between the monoclonal antibody and the cell surface prostate-specific membrane antigen. The imaging agent is a radioisotope such as Indium$^{111}$.

This invention further provides a prostate cancer specific imaging agent comprising the antibody directed against PSM or PSM' antigen and a radioisotope conjugated thereto.

This invention also provides a composition comprising an effective imaging amount of the antibody directed against the PSM or PSM' antigen and a pharmaceutically acceptable carrier. The methods to determine effective imaging amounts are well known to a skilled practitioner. One method is by titration using different amounts of the antibody.

This invention further provides an immunoassay for measuring the amount of the prostate-specific membrane antigen in a biological sample comprising steps of a) contacting the biological sample with at least one antibody directed against the PSM or PSM' antigen to form a complex with said antibody and the prostate-specific membrane antigen, and b) measuring the amount of the prostate-specific membrane antigen in said biological sample by measuring the amount of said complex. One example of the biological sample is a serum sample.

This invention provides a method to purify mammalian prostate-specific membrane antigen comprising steps of a) coupling the antibody directed against the PSM or PSM' antigen to a solid matrix; b) incubating the coupled antibody of a) with lysate containing prostate-specific membrane antigen under the condition which the antibody and prostate membrane specific can bind; c) washing the solid matrix to eliminate impurities and d) eluting the prostate-specific membrane antigen from the coupled antibody.

This invention also provides a transgenic nonhuman mammal which comprises the isolated nucleic acid molecule encoding a mammalian PSM or PSM' antigen. This invention further provides a transgenic nonhuman mammal whose genome comprises antisense DNA complementary to DNA encoding a mammalian prostate-specific membrane antigen so placed as to be transcribed into antisense mRNA complementary to mRNA encoding the prostate-specific membrane antigen and which hybridizes to mRNA encoding the prostate specific antigen thereby reducing its translation.

Animal model systems which elucidate the physiological and behavioral roles of mammalian PSM or PSM' antigen are produced by creating transgenic animals in which the expression of the PSM or PSM' antigen is either increased or decreased, or the amino acid sequence of the expressed PSM antigen is altered, by a variety of techniques. Examples of these techniques include, but are not limited to: 1) Insertion of normal or mutant versions of DNA encoding a mammalian PSM or PSM' antigen, by microinjection, electroporation, retroviral transfection or other means well known to those skilled in the art, into appropriate fertilized embryos in order to produce a transgenic animal (16) or 2) Homologous recombination (17) of mutant or normal, human or animal versions of these genes with the native gene locus in transgenic animals to alter the regulation of expression or the structure of these PSM or PSM' antigen sequences. The technique of homologous recombination is well known in the art. It replaces the native gene with the inserted gene and so is useful for producing an animal that cannot express native PSM antigen but does express, for example, an inserted mutant PSM antigen, which has replaced the native PSM antigen in the animal's genome by recombination, resulting in underexpression of the transporter. Microinjection adds genes to the genome, but does not remove them, and so is useful for producing an animal which expresses its own and added PSM antigens, resulting in overexpression of the PSM antigens.

One means available for producing a transgenic animal, with a mouse as an example, is as follows: Female mice are mated, and the resulting fertilized eggs are dissected out of their oviducts. The eggs are stored in an appropriate medium such as M2 medium (16). DNA or cDNA encoding a mammalian PSM antigen is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Another use of the PSM antigen sequence is to isolate homologous gene or genes in different mammals. The gene or genes can be isolated by low stringency screening of either cDNA or genomic libraries of different mammals using probes from PSM sequence. The positive clones identified will be further analyzed by DNA sequencing techniques which are well known to an ordinary person skilled in the art. For example, the detection of members of the protein serine kinase family by homology probing.

This invention provides a method of suppressing or modulating metastatic ability of prostate tumor cells, prostate tumor growth or elimination of prostate tumor cells comprising introducing a DNA molecule encoding a prostate specific membrane antigen operatively linked to a 5' regulatory element into a tumor cell of a subject, in a way that expression of the prostate specific membrane antigen is under the control of the regulatory element, thereby suppressing or modulating metastatic ability of prostate tumor cells, prostate tumor growth or elimination of prostate tumor cells. The subject may be a mammal or more specifically a human.

In one embodiment, the DNA molecule encoding prostate specific membrane antigen operatively linked to a 5' regulatory element forms part of a transfer vector which is inserted into a cell or organism. In addition the vector is capable or replication and expression of prostate specific membrane antigen. The DNA molecule encoding prostate specific membrane antigen can be integrated into a genome of a eukaryotic or prokaryotic cell or in a host cell containing and/or expressing a prostate specific membrane antigen.

Further, the DNA molecule encoding prostate specific membrane antigen may be introduced by a bacterial, viral, fungal, animal, or liposomal delivery vehicle. Other means are also available and known to an ordinary skilled practitioner.

Further, the DNA molecule encoding a prostate specific membrane antigen operatively linked to a promoter or enhancer. A number of viral vectors have been described including those made from various promoters and other regulatory elements derived from virus sources. Promoters consist of short arrays of nucleic acid sequences that interact specifically with cellular proteins involved in transcription. The combination of different recognition sequences and the cellular concentration of the cognate transcription factors determines the efficiency with which a gene is transcribed in a particular cell type.

Examples of suitable promoters include a viral promoter. Viral promoters include: adenovirus promoter, an simian virus 40 (SV40) promoter, a cytomegalovirus (CMV) promoter, a mouse mammary tumor virus (MMTV) promoter, a Malony murine leukemia virus promoter, a murine sarcoma virus promoter, and a Rous sarcoma virus promoter.

Further, another suitable promoter is a heat shock promoter. Additionally, a suitable promoter is a bacteriophage promoter. Examples of suitable bacteriophage promoters include but not limited to, a T7 promoter, a T3 promoter, an SP6 promoter, a lambda promoter, a baculovirus promoter.

Also suitable as a promoter is an animal cell promoter such as an interferon promoter, a metallothionein promoter, an immunoglobulin promoter. A fungal promoter is also a suitable promoter. Examples of fungal promoters include but are not limited to, an ADC1 promoter, an ARG promoter, an ADH promoter, a CYC1 promoter, a CUP promoter, an ENO1 promoter, a GAL promoter, a PHO promoter, a PGK promoter, a GAPDH promoter, a mating type factor promoter. Further, plant cell promoters and insect cell promoters are also suitable for the methods described herein.

This invention provides a method of suppressing or modulating metastatic ability of prostate tumor cells, prostate tumor growth or elimination of prostate tumor cells, comprising introducing a DNA molecule encoding a prostate specific membrane antigen operatively linked to a 5' regulatory element coupled with a therapeutic DNA into a tumor cell of a subject, thereby suppressing or modulating metastatic ability of prostate tumor cells, prostate tumor growth or elimination of prostate tumor cells. The subject may be a mammal or more specifically a human.

Further, the therapeutic DNA which is coupled to the DNA molecule encoding a prostate specific membrane antigen operatively linked to a 5' regulatory element into a tumor cell may code for a cytokine, viral antigen, or a pro-drug activating enzyme. Other means are also available and known to an ordinary skilled practitioner.

In addition, this invention provides a prostate tumor cell, comprising a DNA molecule isolated from mammalian nucleic acid encoding a mammalian prostate-specific membrane antigen under the control of a prostate specific membrane antigen operatively linked to a 5' regulatory element.

As used herein, DNA molecules include complementary DNA (cDNA), synthetic DNA, and genomic DNA.

This invention provides a therapeutic vaccine for preventing human prostate tumor growth or stimulation of prostate tumor cells in a subject, comprising administering an effective amount to the prostate cell, and a pharmaceutical acceptable carrier, thereby preventing the tumor growth or stimulation of tumor cells in the subject. Other means are also available and known to an ordinary skilled practitioner.

This invention provides a method of detecting hematogenous micrometastic tumor cells of a subject, comprising (A) performing nested polymerase chain reaction (PCR) on blood, bone marrow or lymph node samples of the subject using the prostate specific membrane antigen primers or alternatively spliced prostate specific antigen primers, and (B) verifying micrometastases by DNA sequencing and Southern analysis, thereby detecting hematogenous micrometastic tumor cells of the subject. The subject may be a mammal or more specifically a human.

The micrometastatic tumor cell may be a prostatic cancer and the DNA primers may be derived from prostate specific antigen. Further, the subject may be administered with simultaneously an effective amount of hormones, so as to increase expression of prostate specific membrane antigen. Further, growth factors or cytokine may be administered in separately or in conjunction with hormones. Cytokines include, but are not limited to: transforming growth factor beta, epidermal growth factor (EGF) family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, adhesion molecule, and soluble tumor necrosis factor (TNF) receptors.

This invention provides a method of abrogating the mitogenic response due to transferrin, comprising introducing a DNA molecule encoding prostate specific membrane antigen operatively linked to a 5' regulatory element into a tumor cell, the expression of which gene is directly associated with a defined pathological effect within a multicellular organism, thereby abrogating mitogen response due to transferrin. The tumor cell may be a prostate cell.

This invention provides a method of determining prostate cancer progression in a subject which comprises: a) obtaining a suitable prostate tissue sample; b) extracting RNA from the prostate tissue sample; c) performing a RNAse protection assay on the RNA thereby forming a duplex RNA-RNA hybrid; d) detecting PSM and PSM' amounts in the tissue sample; e) calculating a PSM/PSM' tumor index, thereby determining prostate cancer progression in the subject. In-situ hyribridization may be performed in conjunction with the above detection method.

This invention provides a method of detecting prostate cancer in a subject which comprises: (a) obtaining from a subject a prostate tissue sample; (b) treating the tissue sample so as to separately recover nucleic acid molecules present in the prostate tissue sample; (c) contacting the resulting nucleic acid molecules with multiple pairs of single-stranded labeled oligonucleotide primers, each such pair being capable of specifically hybridizing to the tissue sample, under hybridizing conditions; (d) amplifying any nucleic acid molecules to which a pair of primers hybridizes so as to obtain a double-stranded amplification product; (e) treating any such double-stranded amplification product so as to obtain single-stranded nucleic acid molecules therefrom; (f) contacting any resulting single-stranded nucleic acid molecules with multiple single-stranded labeled oligonucleotide probes, each such probe containing the same label and being capable of specifically hybridizing with such tissue sample, under hybridizing conditions; (g) contacting any resulting hybrids with an antibody to which a marker is attached and which is capable of specifically forming a complex with the labeled-probe, when the probe is present in such a complex, under complexing conditions; and (h) detecting the presence of any resulting complexes, the presence thereof being indicative of prostate cancer in a subject.

This invention provides a method of enhancing antibody based targeting of PSM or PSM' in prostate tissue for diagnosis or therapy of prostate cancer comprising administering to a patient b-FGF in sufficient amount to cause upregulation of PSM or PSM' expression.

This invention provides a method of enhancing antibody based targeting of PSM or PSM' in prostate tissue for diagnosis or therapy of prostate cancer comprising administering to a patient TGF in sufficient amount to cause upregulation of PSM expression or PSM'.

This invention provides a method of enhancing antibody based targeting of PSM or PSM' in prostate tissue for diagnosis or therapy of prostate cancer comprising administering to a patient EGF in sufficient amount to cause upregulation of PSM or PSM' expression.

This invention provides a method for obtaining prostate specific expression of a gene comprising administering a vector containing a gene operatively linked to the PSM or PSM' promoter.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

Materials and Methods: The approach for cloning the gene involved purification of the antigen by immunoprecipitation, and microsequencing of several internal peptides for use in synthesizing degenerate oligonucleotide primers for subsequent use in the polymerase chain reaction (19, 20). A partial cDNA was amplified as a PCR product and this was used as a homologous probe to clone the full-length cDNA molecule from a LNCaP (Lymph Node Carcinoma of Prostate) cell line cDNA plasmid library (8).

Figure 1:
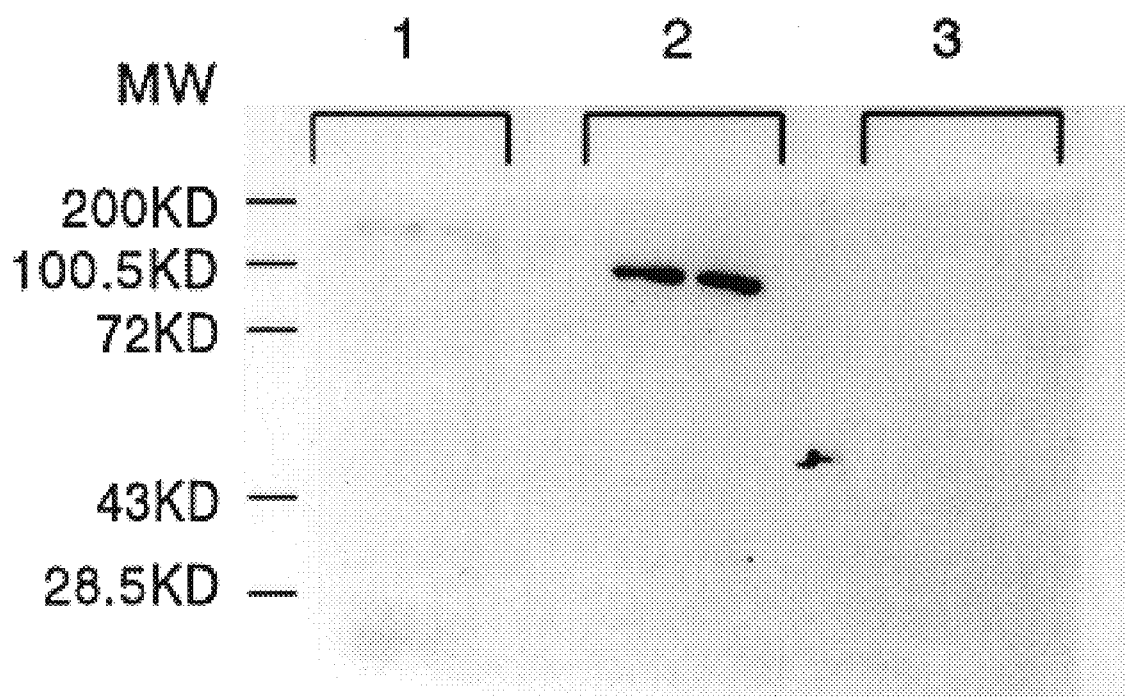
FIG. 1: Signal in lane 2 represent the 100 kD PSM antigen. The EGFr was used as the positive control and is shown in lane 1. Incubation with rabbit antimouse (RAM) antibody alone served as negative control and is shown in lane 3.
Figures 2A, 2B, 2C, 2D:
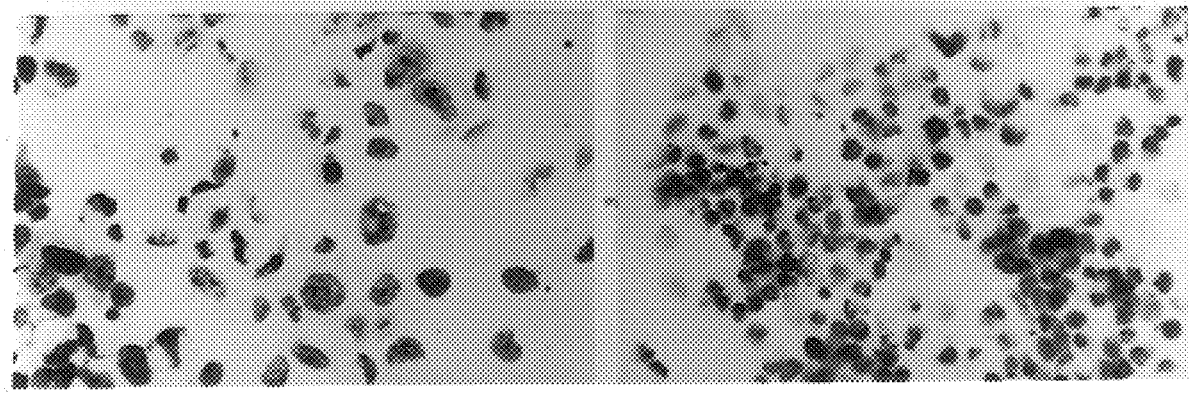
FIGS. 2A–2D: Upper two photos show LNCaP cytospins staining positively for PSM antigen. Lower left in DU-145 and lower right is PC-3 cytospin, both negative for PSM antigen expression.
Figure 3A:
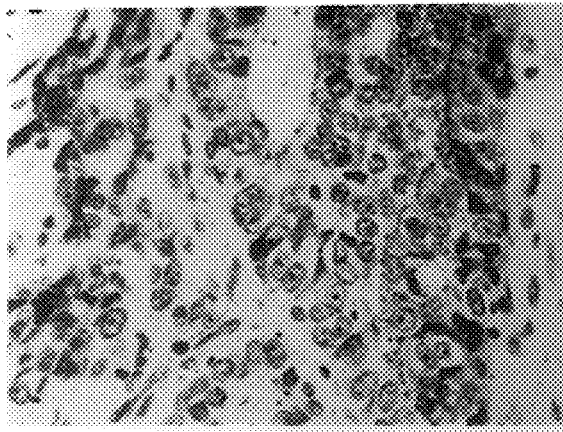
FIGS. 3A–3D: Upper two panels are human prostate sections (BPH) staining positively for PSM antigen. The lower two panels show invasive prostate carcinoma human sections staining positively for expression of the PSM antigen.
Figure 3B:
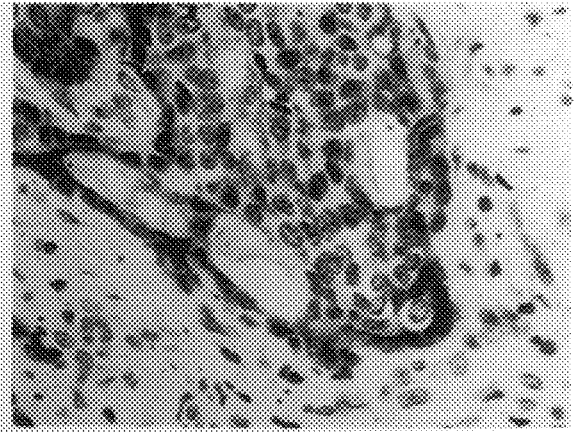
Figure 3C:
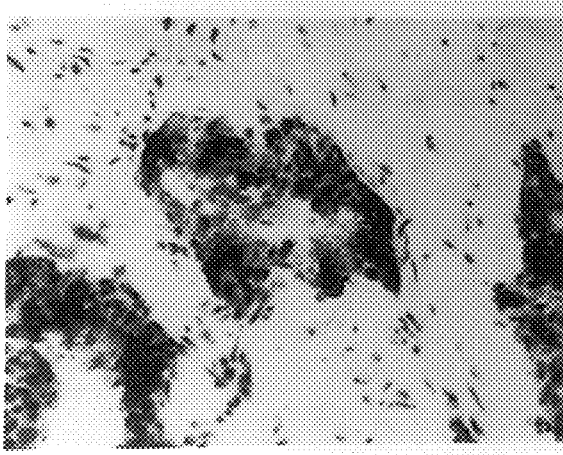
Figure 3D:
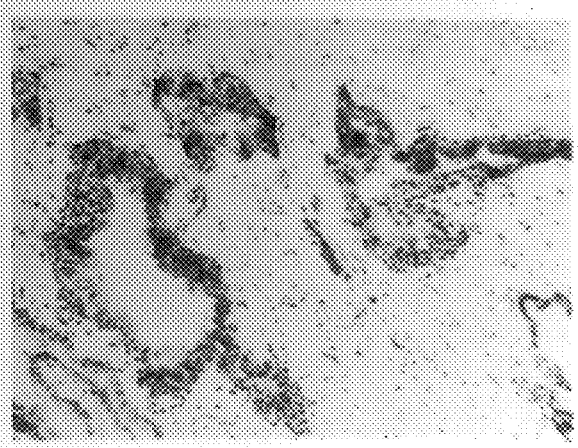

Western Analysis of the PSM Antigen: Membrane proteins were isolated from cells by hypotonic lysis followed by centrifugation over a sucrose density gradient (21). 10–20 μg of LNCaP, DU-145, and PC-3 membrane proteins were electrophoresed through a 10% SDS-PAGE resolving gel with a 4% stacking gel at 9–10 milliamps for 16–18 hours. Proteins were electroblotted onto polyvinylidene difluoride (PDVF) membranes (Millipore Corp.) in transfer buffer (48 mM Tris base, 39 mM Glycine, 20% Methanol) at 25 volts overnight at 4° C. Membranes were blocked in TSB (0.15 M NaCl, 0.01 M Tris base, 5% BSA) for 30 minutes at room temperature followed by incubation with 10–15 μg/ml of CYT-356 monoclonal antibody (Cytogen Corp.) for 2 hours. Membranes were then incubated with 10–15 μg/ml of rabbit anti-mouse immunoglobulin (Accurate Scientific) for 1 hour at room temperature followed by incubation with $^{125}$I-Protein A (Amersham®) at 1×10$^6$ cpm/ml at room temperature. Membranes were then washed and autoradiographed for 12–24 hours at −70° C. (FIG. 1).

Immunohistochemical Analysis of PSM Antigen Expression: The avidin-biotin method of immunohistochemical detection was employed to analyze both human tissue sections and cell lines for PSM Antigen expression (22). Cryostat-cut prostate tissue sections (4–6 μm thick) were fixed in methanol/acetone for 10 minutes. Cell cytospins were made on glass slides using 50,000 cells/100 μl/slide. Samples were treated with 1% hydrogen peroxide in PBS for 10–15 minutes in order to remove any endogenous peroxidase activity. Tissue sections were washed several times in PBS, and then incubated with the appropriate suppressor serum for 20 minutes. The suppressor serum was drained off and the sections or cells were then incubated with the diluted CYT-356 monoclonal antibody for 1 hour. Samples were then washed with PBS and sequentially incubated with secondary antibodies (horse or goat immunoglobulins, 1:200 dilution for 30 minutes), and with avidin-biotin complexes (1:25 dilution for 30 minutes). DAB was used as a chromogen, followed by hematoxylin counterstaining and mounting. Frozen sections of prostate samples and duplicate cell cytospins were used as controls for each experiment. As a positive control, the anti-cytokeratin monoclonal antibody CAM 5.2 was used following the same procedure described above. Tissue sections are considered by us to express the PSM antigen if at least 5% of the cells demonstrate immunoreactivity. The scoring system is as follows: 1=<5%; 2=5–19%; 3=20–75%; and 4=>75% positive cells. Homogeneity versus heterogeneity was accounted for by evaluating positive and negative cells in 3–5 high power light microscopic fields (400×), recording the percentage of positive cells among 100–500 cells. The intensity of immunostaining is graded on a 1+ to 4+ scale, where 1+ represents mild, 2–3+ represents moderate, and 4+ represents intense immunostaining as compared to positive controls.

Immunoprecipitation of the PSM Antigen: 80%-confluent LNCaP cells in 100 mm petri dishes were starved in RPMI media without methionine for 2 hours, after which $^{35}$S-Methionine was added at 100 µCi/ml and the cells were grown for another 16–18 hours. Cells were then washed and lysed by the addition of 1 ml of lysis buffer (1% Triton X-100, 50 mM Hepes pH 7.5, 10% glycerol, 150 mM MgCl$_2$, 1 mM PMSF, and 1 mM EGTA) with incubation for 20 minutes at 4° C. Lysates were pre-cleared by mixing with PANSORBIN CELLS which are killed, hardened cells of staphylococcus aureus, Cowan I strain, coated with immuno-globin-binding protein A on the cell surface (Calbiochem®) for 90 minutes at 4° C. Cell lysates were then mixed with Protein A Sepharose® CL-4B beads (Pharmacia®) previously bound with CYT-356 antibody (Cytogen Corp.) and RAM antibody (Accurate Scientific) for 3–4 hours at 4° C. 12 µg of antibody was used per 3 mg of beads per petri dish. Beads were then washed with HNTG buffer (20 mM Hepes pH 7.5, 150 mM NaCl, 0.1% Triton X-100, 10% glycerol, and 2 mM Sodium Orthovanadate), resuspended in sample loading buffer containing β-mercaptoethanol, denatured at 95° C. for 5–10 minutes and run on a 10% SDS-PAGE gel with a 4° stacking gel at 10 milliamps overnight. Gels were stained with Coomassie Blue, destained with acetic acid/methanol, and dried down in a vacuum dryer at 60° C. Gels were then autoradiographed for 16–24 hours at −70° C. (FIGS. 2A–2D).

Immunoprecipitation and Peptide Sequencing: The procedure described above for immunoprecipitation was repeated with 8 confluent petri dishes containing approximately 6×10$^7$ LNCaP cells. The immunoprecipitation product was pooled and loaded into two lanes of a 10% SDS-PAGE gel and electrophoresed at 9–10 milliamps for 16 hours. Proteins were electroblotted onto nitrocellulose filters (BA-85) 0.45 micron pores, Shleicher & Schuell, Keene, N.H. for 2 hours at 75 volts at 4° C. in transfer buffer. Membranes were stained with Ponceau Red to visualize the proteins and the 100 kD protein band was excised, solubilized, and digested proteolytically with trypsin. HPLC was then performed on the digested sample on an Applied Biosystems Model 171C and clear dominant peptide peaks were selected and sequenced by modified Edman degradation on a modified post liquid Applied Biosystems Model 477A Protein/Peptide Microsequencer (23). Sequencing data on all of the peptides is included within this document. We attempted to sequence the amino-terminus of the PSM antigen by a similar method which involved purifying the antigen by immunoprecipitation and transfer via electroblotting to a PVDF membrane (Millipore®). Protein was analyzed on an Applied Biosystems Model 477A Protein/Peptide Sequencer and the amino terminus was found to be blocked, and therefore no sequence data could be obtained by this technique.

PSM Antigen Peptide Sequences:

| | |
|---|---|
| 2T17 #5 | SLYES (W) TK (SEQ ID No. 3) |
| 2T22 #9 | (S) YPDGXNLPGG (g) VQR (SEQ ID No. 4) |
| 2T26 #3 | FYDPMFK (SEQ ID No. 5) |
| 2T27 #4 | IYNVIGTL (K) (SEQ ID No. 6) |
| 2T34 #6 | FLYXXTQIPHLAGTEQNFQLAK (SEQ ID No. 7) |
| 2T35 #2 | G/PVILYSDPADYFAPD/GVK (SEQ ID No. 8, 9) |
| 2T38 #1 | AFIDPLGLPDRPFYR (SEQ ID No. 10) |
| 2T46 #8 | YAGESFPGIYDALFDIESK (SEQ ID No. 11) |
| 2T47 #7 | TILFAS (W) DAEEFGXX (q) STE (e) A (E) . . . (SEQ ID No. 12) |

Notes: X means that no residue could be identified at this position. Capital denotes identification but with a lower degree of confidence. (lower case) means residue present but at very low levels. . . . indicates sequence continues but has dropped below detection limit.

All of these peptide sequences were verified to be unique after a complete homology search of the translated Genbank computer database.

Degenerate PCR: Sense and anti-sense 5'-unphosphorylated degenerate oligonucleotide primers 17 to 20 nucleotides in length corresponding to portions of the above peptides were synthesized on an Applied Biosystems Model 394A DNA Synthesizer. These primers have degeneracies from 32 to 144. The primers used are shown below. The underlined amino acids in the peptides represent the residues used in primer design.

Peptide 3: <u>FYDPMFK</u> (SEQ ID No. 5)
PSM Primer "A" TT(C or T)-TA(C or T)-GA(C or T)CCX-ATG-TT (SEQ ID No. 13)
PSM Primer "B" AAC-ATX-GG(A or G)-TC(A or G)-TA(A or G)-AA (SEQ ID No. 14)
Primer A is sense primer and B is anti-sense. Degeneracy is 32-fold.

Peptide 4: <u>IYNVIGTL</u>(K) (SEQ ID No. 6)
PSM Primer "C" AT(T or C or A)-TA(T or C)-AA(T or C)-GTX-AT(T or C or A)-GG (SEQ ID No. 15)
PSM Primer "D" CC(A or T or G)-ATX-AC(G or A)-TT(A or G)-TA(A or G or T)-AT (SEQ ID No. 16)
Primer C is sense primer and D is anti-sense. Degeneracy is 144-fold.

Peptide 2: G/PVILYSD<u>PADYFA</u>PD/GVK (SEQ ID No. 8,9)
PSM Primer "E" CCX-GCX-GA(T or C)-TA(T or C)-TT(T or C)-GC (SEQ ID No. 17)
PSM Primer "F" GC(G or A)-AA(A or G)-TA(A or G)-TXC-GCX-GG (SEQ ID No. 18)
Primer E is sense primer and F is antisense primer. Degeneracy is 128-fold.

Peptide 6: FLYXXTQIPHLAG<u>TEQNFQ</u>LAK (SEQ ID No. 7)
PSM Primer "I" ACX-GA(A or G)-CA(A or G)-AA(T or C)-TT(T or C)-CA(A or G)-CT (SEQ ID No. 19)
PSM Primer "J" AG-(T or C)TG-(A or G)AA-(A or G)TT-(T or C)TG-(T or C)TC-XGT (SEQ ID No 20)
PSM Primer "K" GA(A or G)-CA(A or G)-AA(T or C)-TT(T or C) CA(A or G)-CT (SEQ ID No. 21)
PSM Primer "L" AG-(T or C)TG-(A or G)AA-(A or G)TT-(T or C)TG-(T or C)TC (SEQ ID No. 22)
Primers I and K are sense primers and J and L are anti-sense. I and J have degeneracies of 128-fold and K and L have 32-fold degeneracy.

Peptide 7: TILFAS(W)DAEEFGXX(q)STE(e)A(E) . . . (SEQ ID No. 12)
PSM Primer "M" TGG-GA(T or C)-GCX-GA(A or G)-GA(A or G)-TT(C or T)-GG (SEQ ID No. 23)
PSM Primer "N" CC-(G or A)AA-(T or C)TC-(T or C)TC-XGC-(A or G)TC-CCA (SEQ ID No. 24)
PSM Primer "O" TGG-GA(T or C)-GCX-GA(A or G)-GA(A or G)-TT (SEQ ID No. 25)
PSM Primer "P" AA-(T or C)TC-(T or C)TC-XGC-(A or G)TC-CCA (SEQ ID No. 26)
Primers M and O are sense primers and N and P are anti-sense. M and N have degeneracy of 64-fold and O and P are 32-fold degenerate.

Degenerate PCR was performed using a automatic thermal cycler (DNA Thermal Cycler, Perkin Elmer Model 490). cDNA template for the PCR was prepared from LNCaP mRNA which had been isolated by standard methods of oligo dT chromatography (Collaborative Research). The cDNA synthesis was carried out as follows:

| | |
|---|---|
| 4.5 µl | LNCaP poly A+ RNA (2 µg) |
| 1.0 µl | Oligo dT primers (0.5 µg) |
| 4.5 µl | dH₂O |
| 10 µl | |

Incubate at 68° C.×10 minutes.
Quick chill on ice×5 minutes.
Add:

| | |
|---|---|
| 4 µl | 5 × RT Buffer |
| 2 µl | 0.1 M DTT |
| 1 µl | 10 mM dNTPs |
| 0.5 µl | RNasin (Promega) |
| 1.5 µl | dH₂O |
| 19 µl | |

Incubate for 2 minutes at 37° C.
Add 1 µl SUPERSCRIPT RNase H[31] REVERSE TRANSCRIPTASE containing a pol gene, reverse transcriptase, murine leukemia virus with RNAase H deleted and purified as a recombinant protein from E. coli. (Gibco®-BRL)
Incubate for 1 hour at 37° C.
Add 30 µl dH₂O.
Use 2 µl per PCR reaction.

Degenerate PCR reactions were optimized by varying the annealing temperatures, Mg++ concentrations, primer concentrations, buffer composition, extension times and number of cycles. Our optimal thermal cycler profile was: Denaturation at 94° C. ×30 seconds, Annealing at 45–55° C. for 1 minute (depending on the mean $T_m$ of the primers used), and Extension at 72° C. for 2 minutes.

| | |
|---|---|
| 5 µl | 10 × PCR Buffer* |
| 5 µl | 2.5 mM dNTP Mix |
| 5 µl | Primer Mix (containing 0.5–1.0 µg each of sense and anti-sense primers) |
| 5 µl | 100 mM β-mercaptoethanol |
| 2 µl | LNCaP cDNA template |
| 5 µl | 25 mM MgCl₂ (2.5 mM final) |
| 21 µl | dH₂O |
| 2 µl | diluted Taq Polymerase a purified thermostable DNA polymerase from T. Aquaticus (0.5 U/µl) |
| 50 µl | total volume |

Tubes were overlaid with 60 µl of light mineral oil and amplified for 30 cycles. PCR products were analyzed by electrophoresing 5 µl of each sample on a 2–3% agarose gel followed by staining with Ethidium bromide and photography.

*10× PCR Buffer
166 mM NH₄SO₄
670 mM Tris, pH 8.8
2 mg/ml BSA

Figure 5:
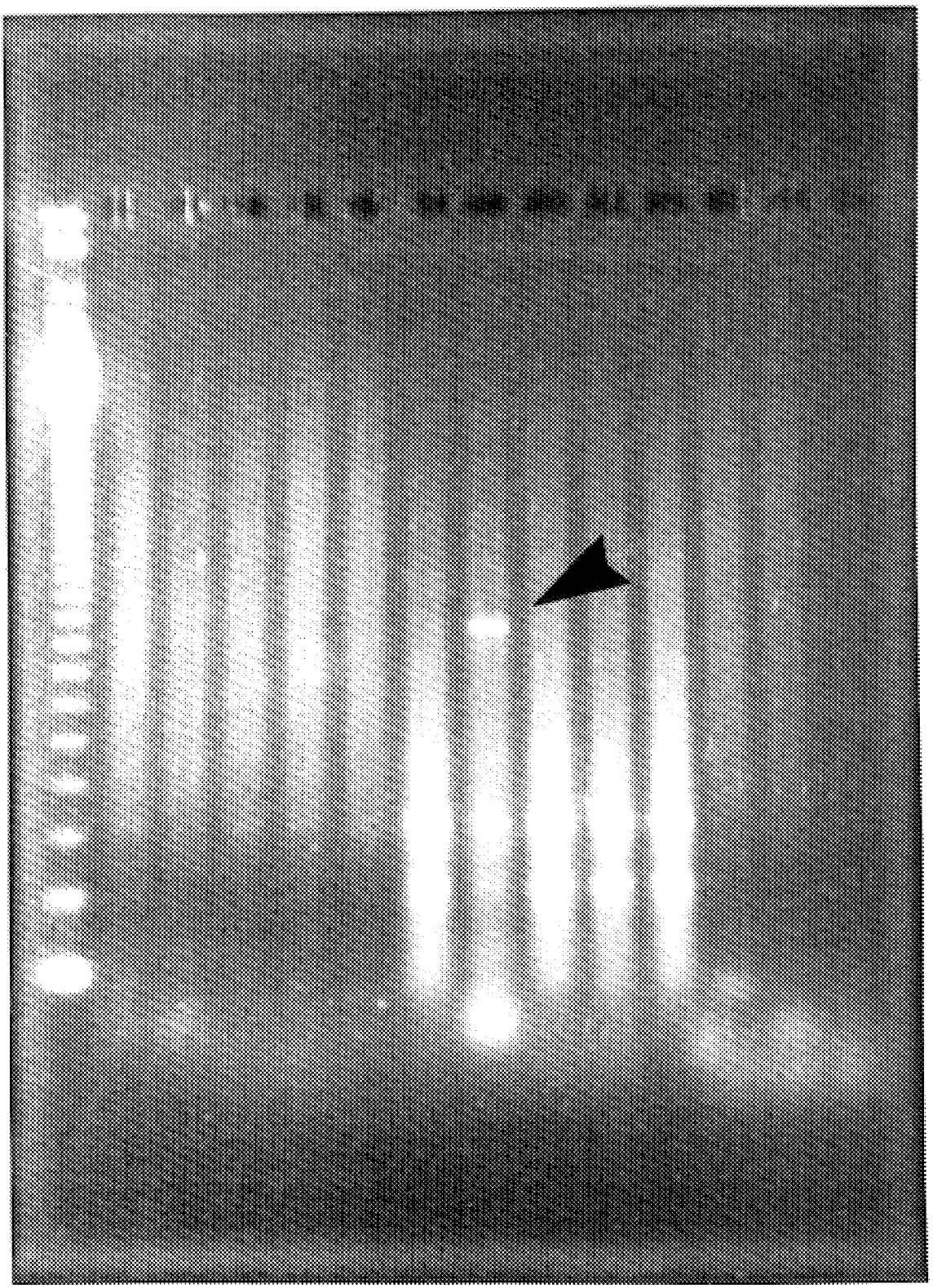
FIG. 5: 3% agarose gels stained with Ethidium bromide revealing PCR products obtained using the degenerate PSM antigen primers. The arrow points to sample IN-20, which is a 1.1 kb PCR product which was later confirmed to be a partial cDNA coding for the PSM gene.

Representative photographs displaying PCR products are shown in FIG. 5.

Figures 6A, 6B:
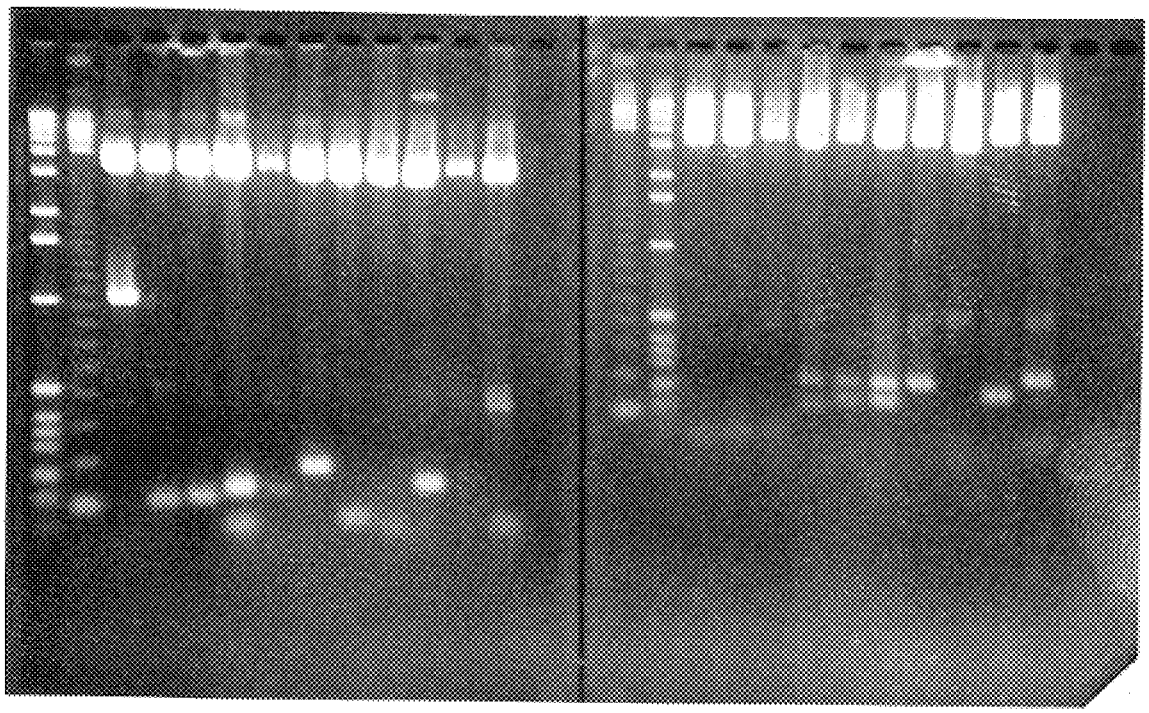
FIGS. 6A–6B: 2% agarose gels of plasmid DNA resulting from TA cloning of PCR products. Inserts are excised from the PCR II vector (Invitrogen Corp.) by digestion with EcoRI. 1.1 kb PSM gene partial cDNA product is shown in lane 3 of gel 1.

Cloning of PCR Products: In order to further analyze these PCR products, these products were cloned into a suitable plasmid vector using "TA Cloning" (Invitrogen® Corp.). The cloning strategy employed here is to directly ligate PCR products into a plasmid vector possessing overhanging T residues at the insertion site, exploiting the fact that Taq polymerase leaves overhanging A residues at the ends of the PCR products. The ligation mixes are transformed into competent E. coli cells and resulting colonies are grown up, plasmid DNA is isolated by the alkaline lysis method (24), and screened by restriction analysis (FIGS. 6A–6B).

DNA Sequencing of PCR Products: TA Clones of PCR products were then sequenced by the dideoxy method (25) using Sequenase a modified bacteriophage T7 DNA polymerase (United States Biochemicals, Cleveland, Ohio) (U.S. Biochemical). 3–4 µg of each plasmid DNA was denatured with NaOH and ethanol precipitated. Labeling reactions were carried out as per the manufacturers recommendations using $^{35}$S-ATP, and the reactions were terminated as per the same protocol. Sequencing products were then analyzed on 6% polyacrylamide/7 M Urea gels using an IBI sequencing apparatus. Gels were run at 120 watts for 2 hours. Following electrophoresis, the gels were fixed for 15–20 minutes in 10% methanol/10% acetic acid, transferred onto Whatman 3MM paper filter paper, and dried down in a Biorad® vacuum dryer at 80° C. for 2 hours. Gels were then autoradiographed at room temperature for 16–24 hours. In order to determine whether the PCR products were the correct clones, we analyzed the sequences obtained at the 5' and 3' ends of the molecules looking for the correct primer sequences, as well as adjacent sequences which corresponded to portions of the peptides not used in the design of the primers.

IN-20 was confirmed to be correct and represent a partial cDNA for the PSM gene. In this PCR reaction, I and N primers were used. The DNA sequence we obtained when reading from the I primer was:

ACG GAG CAA AAC TTT CAG CTT GCA AAG
(SEQ ID No. 30)
<u>T   E   Q   N   F   Q</u>   L   A   K
(SEQ ID No. 31)

The underlined amino acids were the portion of peptide 6 that was used to design this sense primer and the remaining amino acids which agree with those present within the peptide confirm that this end of the molecule represents the correct protein (PSM antigen).

When analyzed the other end of the molecule by reading from the N primer the anti-sense sequence was:

CTC TTC GGC ATC CCA GCT TGC AAA CAA AAT TGT TCT
(SEQ ID No. 32)

Sense (complementary) Sequence:

AGA ACA ATT TTG TTT GCA AGC TGG GAT GCC AAG GAG
(SEQ ID No. 33)

R   T   I   L   F   A   S   <u>W   D   A   E   E</u>
(SEQ ID No. 34)

The underlined amino acids here represent the portion of peptide 7 used to create primer N. All of the amino acids upstream of this primer are correct in the IN-20 clone, agreeing with the amino acids found in peptide 7. Further DNA sequencing has enabled us to identify the presence of other PSM peptides within the DNA sequence of the positive clone.

Figure 7:
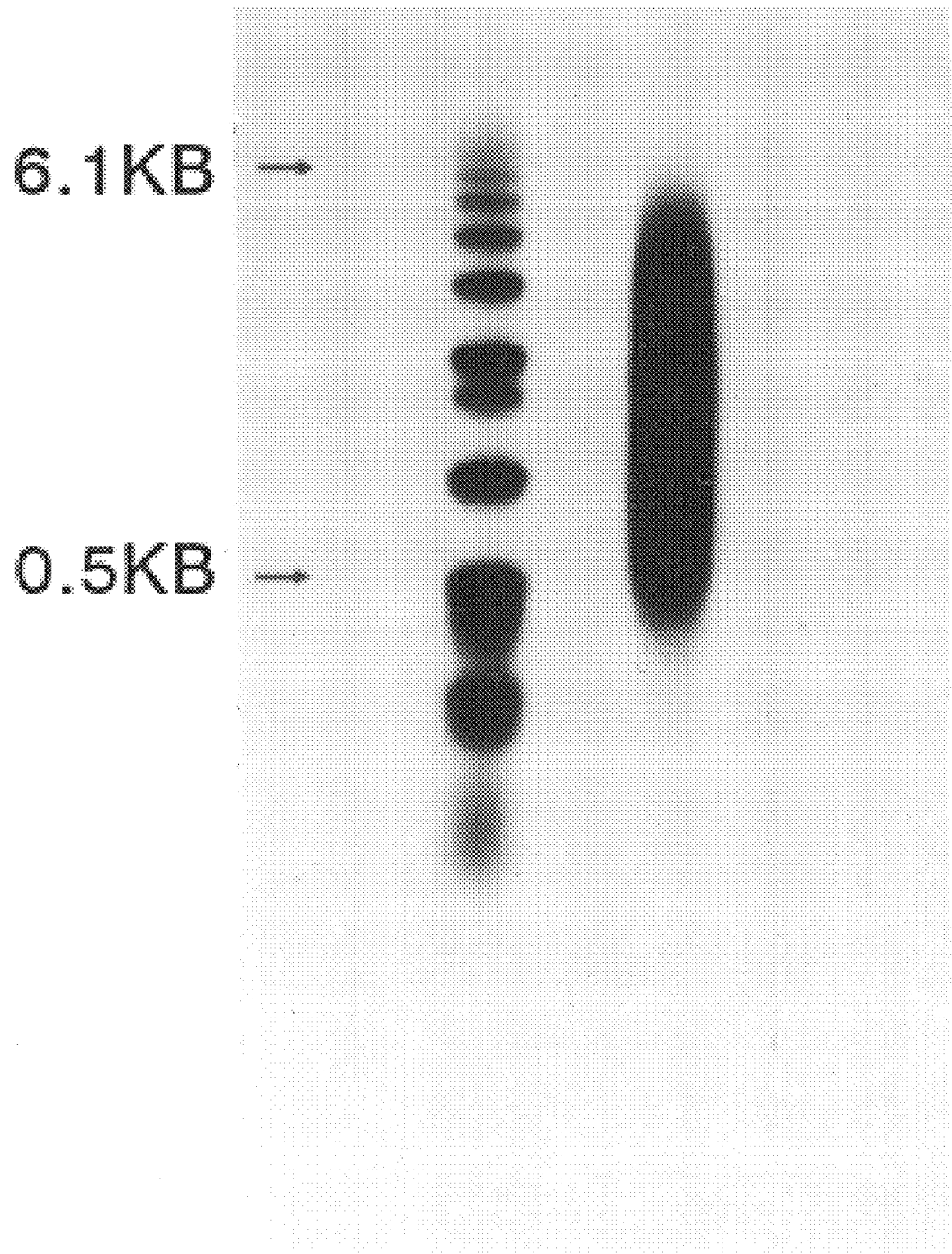
FIG. 7: Autoradiogram showing size of cDNA represented in applicants' LNCaP library using M-MLV reverse transcriptase.
Figure 8:
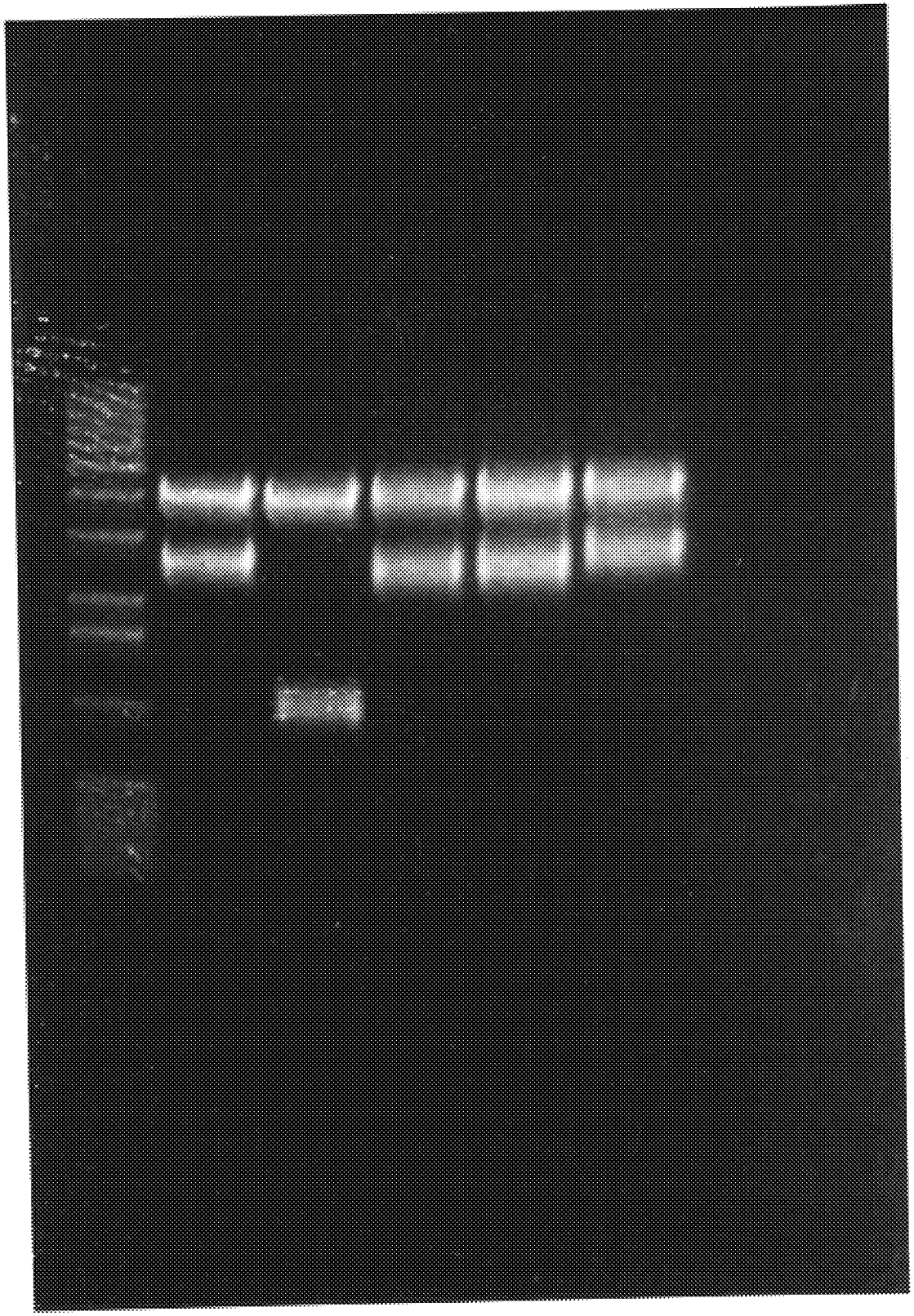
FIG. 8: Restriction analysis of full-length clones of PSM gene obtained after screening cDNA library. Samples have been cut with Not I and Sal I restriction enzymes to liberate the insert.
Figure 9:
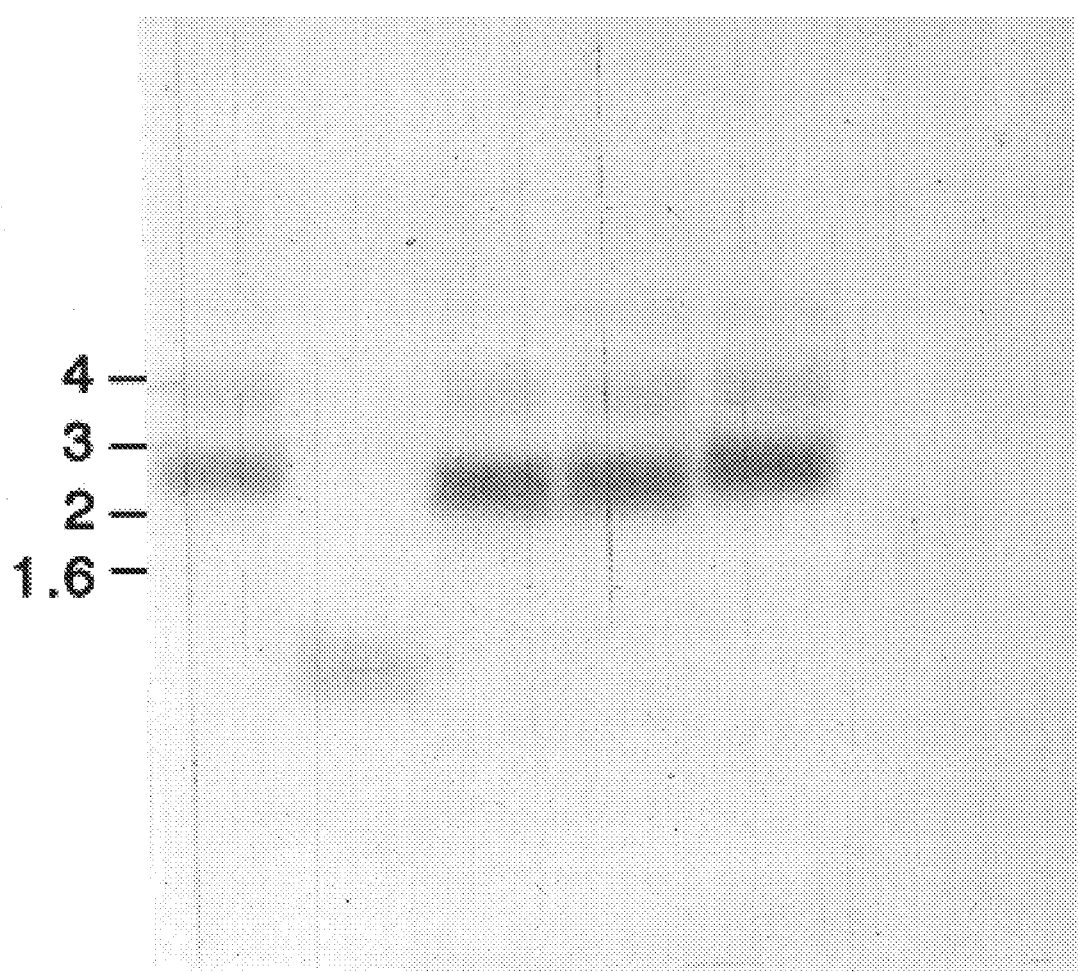
FIG. 9: Plasmid Southern autoradiogram of full length PSM gene clones. Size is approximately 2.7 kb.
Figure 10:
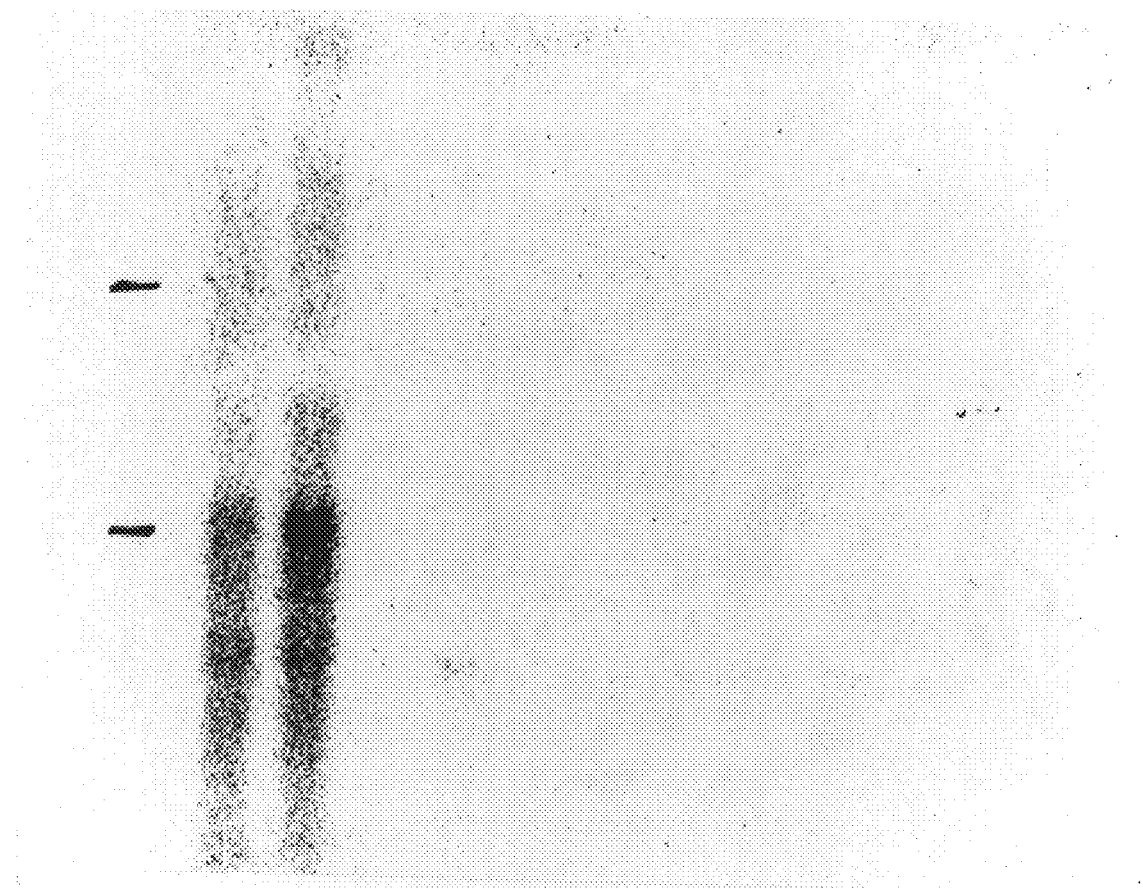
FIG. 10: Northern blot revealing PSM expression limited to LNCaP prostate cancer line and H26 Ras-transfected LNCaP cell line. PC-3, DU-145, T-24, SKRC-27, HELA, MCF-7, HL-60, and others were are all negative.
Figure 11:
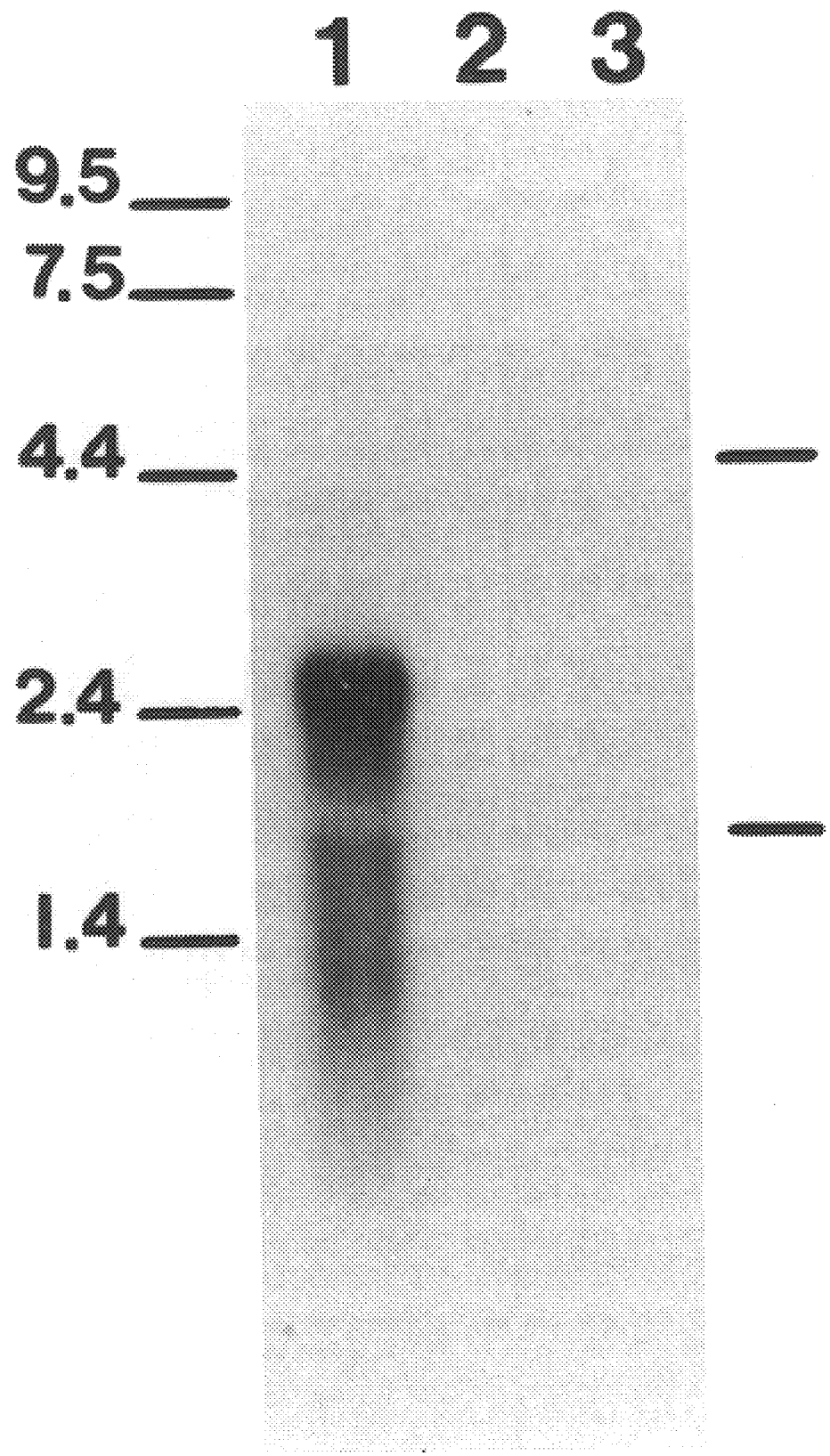
FIG. 11: Autoradiogram of Northern analysis revealing expression of 2.8 kb PSM message unique to the LNCaP cell line (lane 1), and absent from the DU-145 (lane 2) and PC-3 cell lines (lane 3). RNA size ladder is shown on the left (kb), and 28S and 18S ribosomal RNA bands are indicated on the right.
Figure 12A:
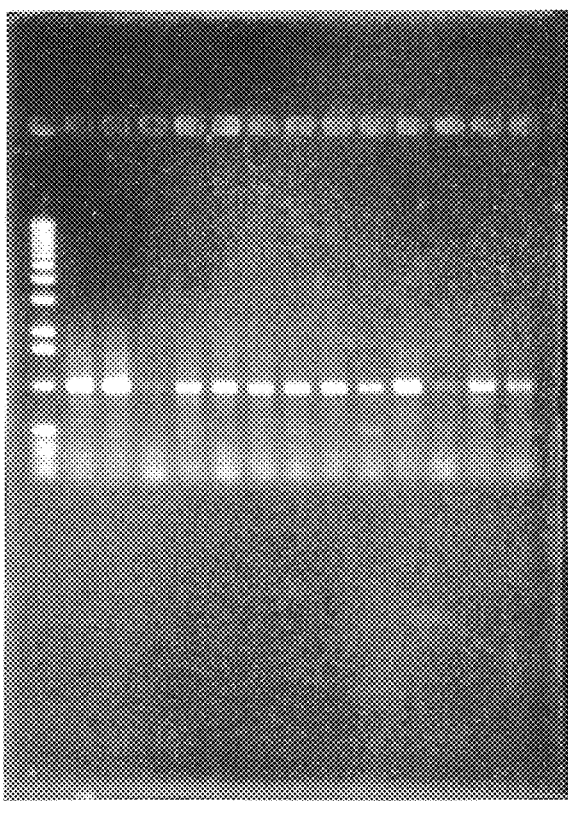
FIGS. 12A–12B: Results of PCR of human prostate tissues using PSM gene primers. Lanes are numbered from left to right. Lane 1, LNCaP; Lane 2, H26; Lane 3, DU-145; Lane 4, Normal Prostate; Lane 5, BPH; Lane 6, Prostate Cancer; Lane 7, BPH; Lane 8, Normal; Lane 9, BPH; Lane 10, BPH; Lane 11, BPH; Lane 12, Normal; Lane 13, Normal; Lane 14, Cancer; Lane 15, Cancer; Lane 16, Cancer; Lane 17, Normal; Lane 18, Cancer; Lane 19, IN-20 Control; Lane 20, PSM cDNA
Figure 12B:
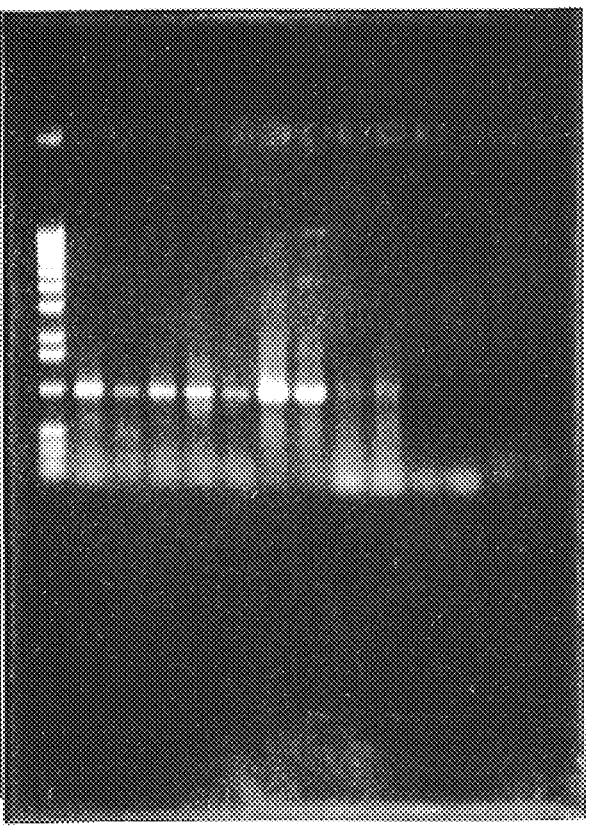
Figure 13:
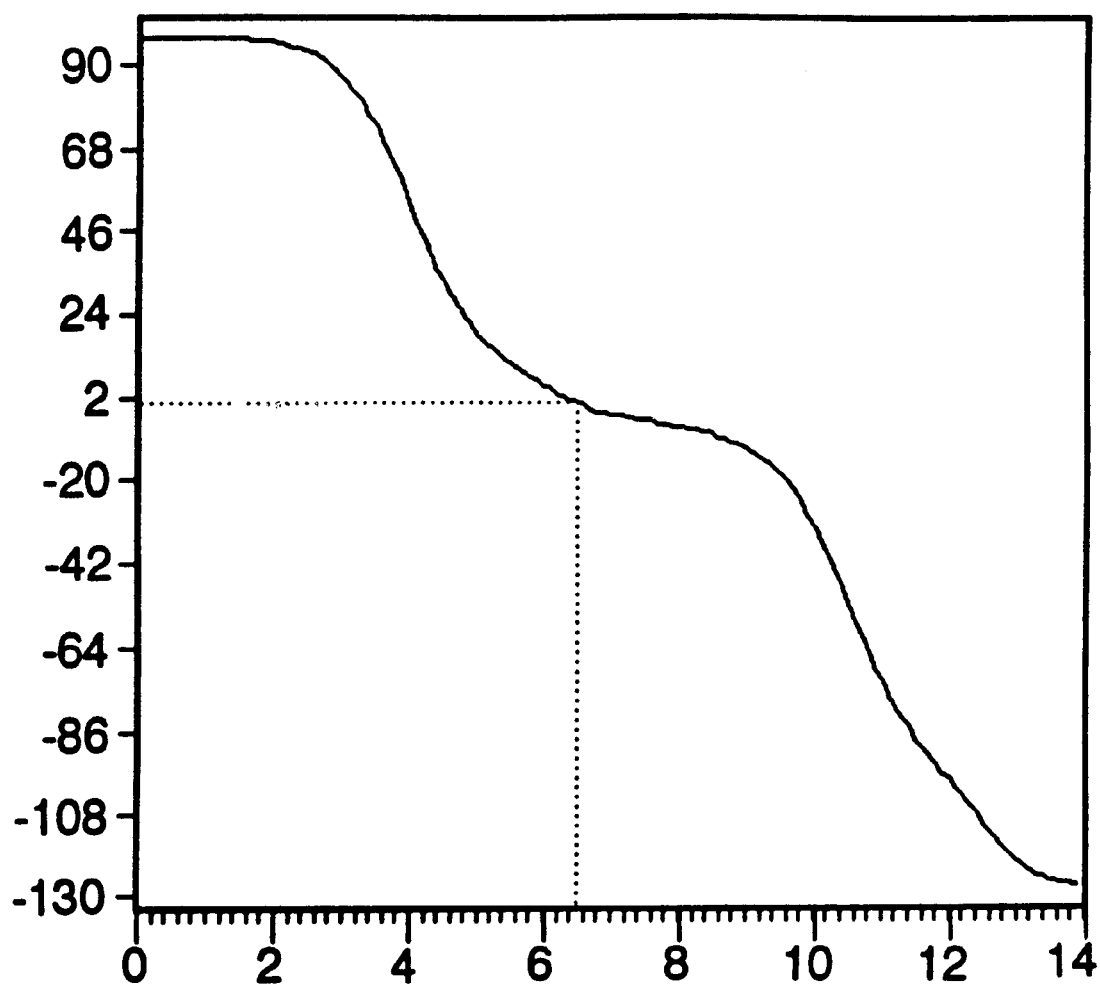
FIG. 13: Isoelectric point of PSM antigen (non-glycosylated)
Figure 15A:
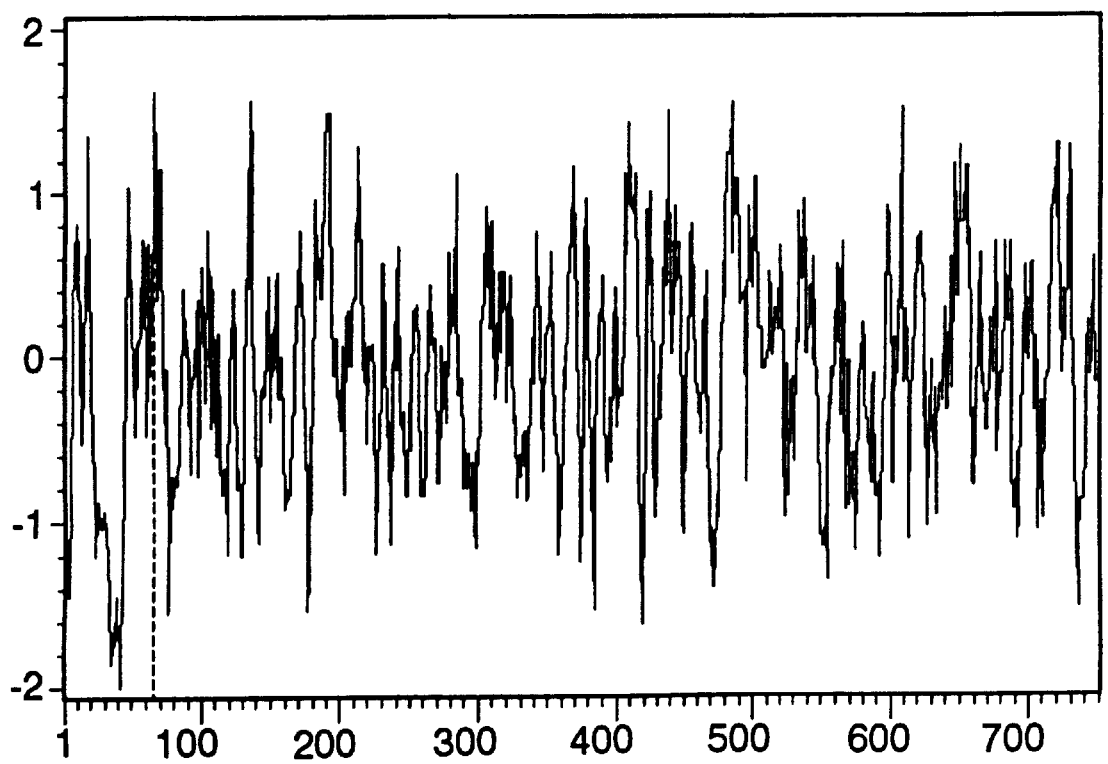

The DNA sequence of this partial cDNA was found to be unique when screened on the Genbank computer database.

cDNA Library Construction and Cloning of Full-Length PSM cDNA: A cDNA library from LNCaP mRNA was constructed using the Superscript® plasmid system (BRL®-Gibco). The library was transformed using competent DH5-α cells and plated onto 100 mm plates containing LB plus 100 μg/ml of Carbenicillin. Plates were grown overnight at 37° C. and colonies were transferred to nitrocellulose filters. Filters were processed and screened as per Grunstein and Hogness (26), using the 1.1 kb partial cDNA homologous probe which was radiolabelled with $^{32}$P-dCTP by random priming (27). Eight positive colonies were obtained which upon DNA restriction and sequencing analysis proved to represent full-length cDNA molecules coding for the PSM antigen. Shown in FIG. 7 is an autoradiogram showing the size of the cDNA molecules represented in the library and in FIG. 8 restriction analysis of several full-length clones is shown. FIG. 9 is a plasmid Southern analysis of the samples in FIG. 8, showing that they all hybridize to the 1.1 kb partial cDNA probe.

Both the cDNA as well as the antigen have been screened through the Genbank Computer database (Human Genome Project) and have been found to be unique.

Northern Analysis of PSM Gene Expression: Northern analysis (28) of the PSM gene has revealed that expression is limited to the prostate and to prostate carcinoma.

RNA samples (either 10 μg of total RNA or 2 μg of poly A+ RNA) were denatured and electrophoresed through 1.1% agarose/formaldehyde gels at 60 milliamps for 6–8 hours. RNA was then transferred to nylon membrane (Nytran, Schleicher & Schuell, Keene, N.H.) by pressure blotting in 10×SSC with a Posi-blotter (Stratagene®) RNA was cross-linked to the membranes using a Stratalinker (Stratagene®) and subsequently baked in a vacuum oven at 80° C. for 2 hours. Blots were prehybridized at 65° C. for 2 hours in prehybridization solution (BRL®) and subsequently hybridized for 16 hours in hybridization buffer (BRL®) containing 1–2×10$^6$ cpm/ml of $^{32}$P-labelled random-primed cDNA probe. Membranes were washed twice in 1×SSPE/1% SDS and twice in 0.1×SSPE/1% SDS at 42° C. Membranes were then air-dried and autoradiographed for 12–36 hours at −70° C.

PCR Analysis of PSM Gene Expression in Human Prostate Tissues: PCR was performed on 15 human prostate samples to determine PSM gene expression. Five samples each from normal prostate tissue, benign prostatic hyperplasia, and prostate cancer were used (histology confirmed by MSKCC Pathology Department).

10 μg of total RNA from each sample was reverse transcribed to made cDNA template as previously described in section IV. The primers used corresponded to the 5' and 3' ends of the 1.1 kb partial cDNA, IN-20, and therefore the expected size of the amplified band is 1.1 kb. Since the $T_m$ of the primers is 64° C. PCR primers were annealed at 60° C. PCR was carried out for 35 cycles using the same conditions previously described in section IV.

LNCaP and H26-Ras transfected LNCaP (29) were included as a positive control and DU-145 as a negative control. 14/15 samples clearly amplified the 1.1 kb band and therefore express the gene.

Experimental Results

Figure 17A:
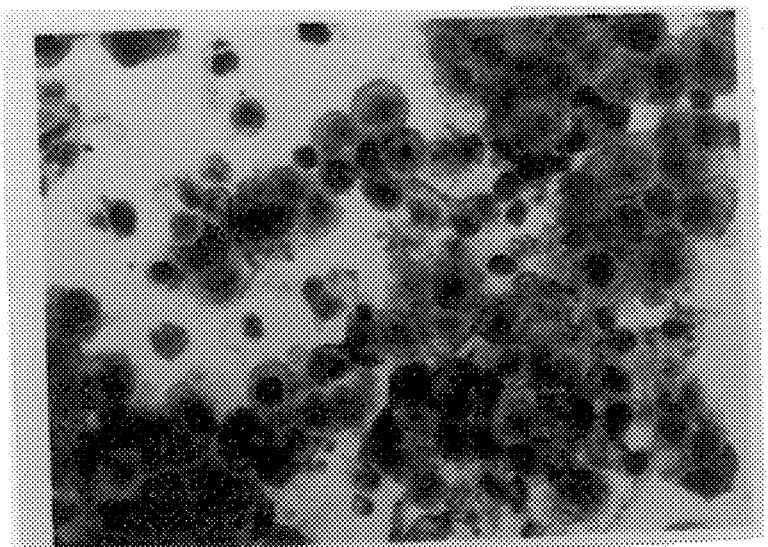
FIGS. 17A–17C: Immunohistochemical detection of PSM antigen expression in prostate cell lines. Top panel reveals uniformly high level of expression in LNCaP cells; middle panel and lower panel are DU-145 and PC-3 cells respectively, both negative.
Figure 17B:
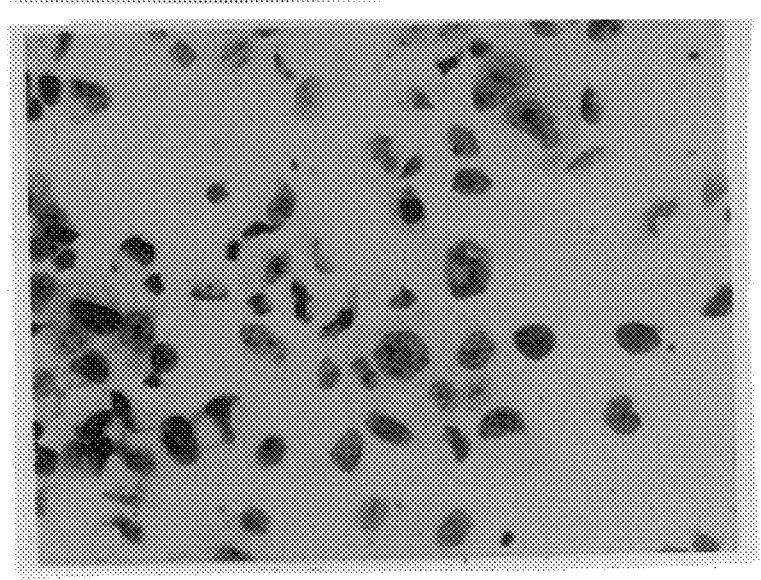
Figure 17C:
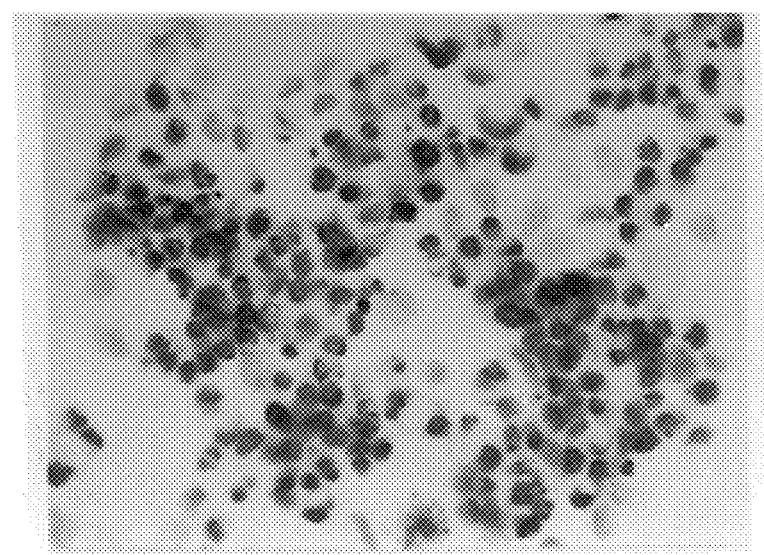

The gene which encodes the 100 kD PSM antigen has been identified. The complete cDNA sequence is shown in Sequence ID #1. Underneath that nucleic acid sequence is the predicted translated amino acid sequence. The total number of the amino acids is 750, ID #2. The hydrophilicity of the predicted protein sequence is shown in FIGS. 16:1–11. Shown in FIGS. 17A–17C are three peptides with the highest point of hydrophilicity. They are: Asp-Glu-Leu-Lys-Ala-Glu (SEQ ID No. 35); Asn-Glu-Asp-Gly-Asn-Glu (SEQ ID No. 36); and Lys-Ser-Pro-Asp-Glu-Gly (SEQ ID No. 37).

By the method of Klein, Kanehisa and DeLisi, a specific membrane-spanning domain is identified. The sequence is from the amino acid #19 to amino acid #44: Ala-Gly-Ala-Leu-Val-Leu-Aal-Gly-Gly-Phe-Phe-Leu-Leu-Gly-Phe-Leu-Phe (SEQ ID No. 38).

This predicted membrane-spanning domain was computed on PC Gene (computer software program). This data enables prediction of inner and outer membrane domains of the PSM antigen which aids in designing antibodies for uses in targeting and imaging prostate cancer.

Figure 18:
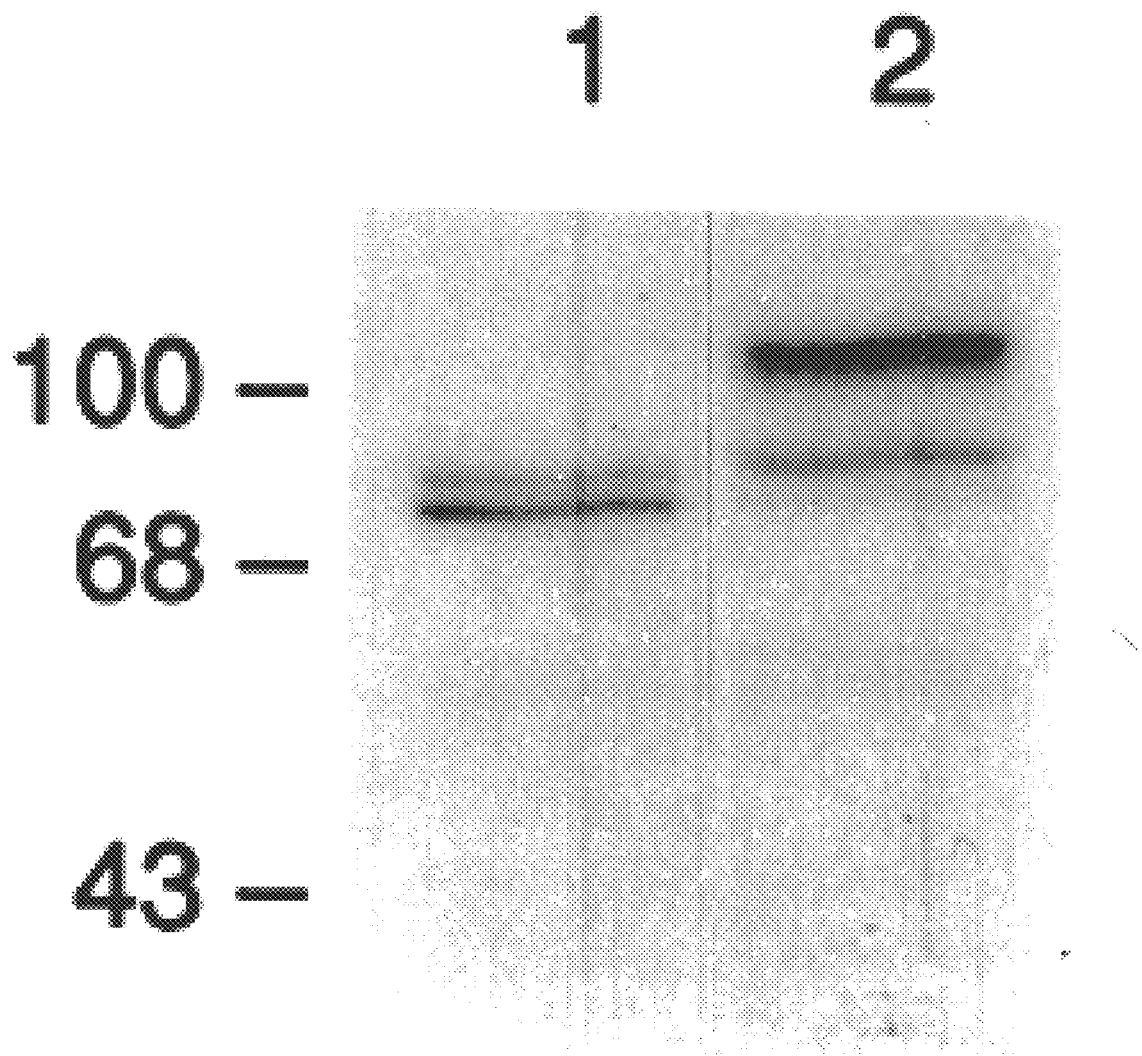
FIG. 18: Autoradiogram of protein gel revealing products of PSM coupled in-vitro transcription/translation. Non-glycosylated PSM polypeptide is seen at 84 kDa (lane 1) and PSM glycoprotein synthesized following the addition of microsomes is seen at 100 kDa (lane 2).

When the PSM antigen sequence with other known sequences of the GeneBank were compared, homology between the PSM antigen sequence and the transferrin receptor sequence were found. The data are shown in FIG. 18.

Experimental Discussions

Potential Uses for PSM Antigen

1. Tumor detection

Microscopic

Unambiguous tumor designation can be accomplished by use of probes for different antigens. For prostatic cancer, the PSM antigen probe may prove beneficial. Thus PSM could be used for diagnostic purposes and this could be accomplished at the microscopic level using in-situ hybridization using sense (control) and antisense probes derived from the coding region of the cDNA cloned by the applicants. This could be used in assessment of local extraprostatic extension, involvement of lymph node, bone or other metastatic sites. As bone metastasis presents a major problem in prostatic cancer, early detection of metastatic spread is required especially for staging. In some tumors detection of tumor cells in bone marrow portends a grim prognosis and suggests that interventions aimed at metastasis be tried. Detection of PSM antigen expression in bone marrow aspirates or sections may provide such early information. PCR amplification or in-situ hybridization may be used. Using RT-PCR cells in the circulating can be detected by hematogenous metastasis.

2. Antigenic Site Identification

The knowledge of the cDNA for the antigen also provides for the identification of areas that would serve as good antigens for the development of antibodies for use against specific amino acid sequences of the antigen. Such sequences may be at different regions such as outside, membrane or inside of the PSM antigen. The development of these specific antibodies would provide for immunohistochemical identification of the antigen. These derived antibodies could then be developed for use, especially ones that work in paraffin fixed sections as well as frozen section as they have the greatest utility for immunodiagnosis.

3. Restriction Fragment Length Polymorphism and Genomic DNA

Restriction fragment length polymorphisms (RFLPS) have proven to be useful in documenting the progression of genetic damage that occurs during tumor initiation and promotion. It may be that RFLP analysis will demonstrate that changes in PSM sequence restriction mapping may provide evidence of predisposition to risk or malignant potential or progression of the prostatic tumor.

Depending on the chromosomal location of the PSM antigen, the PSM antigen gene may serve as a useful chromosome location marker for chromosome analysis.

4. Serum

With the development of antigen specific antibodies, if the antigen or selected antigen fragments appear in the serum they may provide for a serum marker for the presence of metastatic disease and be useful individually or in combination with other prostate specific markers.

5. Imaging

As the cDNA sequence implies that the antigen has the characteristics of a membrane spanning protein with the majority of the protein on the exofacial surface, antibodies, especially monoclonal antibodies to the peptide fragments exposed and specific to the tumor may provide for tumor imaging local extension of metastatic tumor or residual tumor following prostatectomy or irradiation. The knowledge of the coding region permits the generation of monoclonal antibodies and these can be used in combination to provide for maximal imaging purposes. Because the antigen shares a similarity with the transferrin receptor based on cDNA analysis (approximately 54%), it may be that there is a specific normal ligand for this antigen and that identification of the ligand(s) would provide another means of imaging.

6. Isolation of Ligands

The PSM antigen can be used to isolate the normal ligand(s) that bind to it. These ligand(s) depending on specificity may be used for targeting, or their serum levels may be predictive of disease status. If it is found that the normal ligand for PSM is a carrier molecule then it may be that PSM could be used to bind to that ligand for therapy purposes (like an iron chelating substance) to help remove the ligand from the circulation. If the ligand promotes tumor growth or metastasis then providing soluble PSM antigen would remove the ligand from binding the prostate. Knowledge of PSM antigen structure could lend to generation of small fragment that binds ligand which could serve the same purpose.

7. Therapeutic Uses a) Ligands. The knowledge that the cDNA structure of PSM antigen shares structural homology with the transferrin receptor (54% on the nucleic acid level) implies that there may be an endogenous ligand for the receptor that may or may not be transferrin-like. Transferrin is thought to be a ligand that transports iron into the cell after binding to the transferrin receptor. However, apotransferrin is being reported to be a growth factor for some cells which express the transferrin receptor (30). Whether transferrin is a ligand for this antigen or some other ligand binds to this ligand remains to be determined. If a ligand is identified it may carry a specific substance such as a metal ion (iron or zinc or other) into the tumor and thus serve as a means to deliver toxic substances (radioactive or cytotoxic chemical i.e. toxin like ricin or cytotoxic alkylating agent or cytotoxic prodrug) to the tumor.

The main metastatic site for prostatic tumor is the bone. The bone and bone stroma are rich in transferrin. Recent studies suggest that this microenvironment is what provides the right "soil" for prostatic metastasis in the bone (31). It may be that this also promotes attachment as well, these factors which reduce this ability may diminish prostatic metastasis to the bone and prostatic metastatic growth in the bone.

It was found that the ligand for the new antigen (thought to be an oncogene and marker of malignant phenotype in breast carcinoma) served to induce differentiation of breast cancer cells and thus could serve as a treatment for rather than promotor of the disease. It may be that ligand binding to the right region of PSM whether with natural ligand or with an antibody may serve a similar function.

Antibodies against PSM antigen coupled with a cytotoxic agent will be useful to eliminate prostate cancer cells. Transferrin receptor antibodies with toxin conjugates are cytotoxic to a number of tumor cells as tumor cells tend to express increased levels of transferrin receptor (32). Transferrin receptors take up molecules into the cell by endocytosis. Antibody drug combinations can be toxic. Transferrin linked toxin can be toxic.

b) Antibodies against PSM antigen coupled with a cytotoxic agent will be useful to eliminate prostate cancer cells. The cytotoxic agent may be a radioisotope or toxin as known in ordinary skill of the art. The linkage of the antibody and the toxin or radioisotope can be chemical. Examples of direct linked toxins are doxorubicin, chlorambucil, ricin, pseudomonas exotoxin etc., or a hybrid toxin can be generated ½ with specificity for PSM and the other ½ with specificity for the toxin. Such a bivalent molecule can serve to bind to the tumor and the other ½ to deliver a cytotoxic to the tumor or to bind to and activate a cytotoxic lymphocyte such as binding to the $T_1$–$T_3$ receptor complex. Antibodies of required specificity can also be cloned into T cells and by replacing the immunoglobulin domain of the T cell receptor (TcR); cloning in the desired MAb heavy and light chains; splicing the $U_h$ and $U_L$ gene segments with the constant regions of the α and β TCR chains and transfecting these chimeric Ab/TcR genes in the patients' T cells, propagating these hybrid cells and infusing them into the patient (33). Specific knowledge of tissue specific antigens for targets and generation of MAb's specific for such targets will help make this a usable approach. Because the PSM antigen coding region provides knowledge of the entire coding region, it is possible to generate a number of antibodies which could then be used in combination to achieve an additive or synergistic anti-tumor action. The antibodies can be linked to enzymes which can activate non-toxic prodrugs at its site of the tumor such as Ab-carboxypeptidase and 4-(bis(2 chloroethyl)amino) benzoyl-α-glutamic acid and its active parent drug in mice (34).

It is possible to produce a toxic genetic chimera such as TP-40 a genetic recombinant that possesses the cDNA from TGF-alpha and the toxic portion of pseudomonas exotoxin so the TGF and portion of the hybrid binds the epidermal growth factor receptor (EGFR) and the pseudomonas portion gets taken up into the cell enzymatically and inactivates the ribosomes ability to perform protein synthesis resulting in cell death.

In addition, once the ligand for the PSM antigen is identified, toxin can be chemically conjugated to the ligands. Such conjugated ligands can be therapeutically useful. Examples of the toxins are daunomycin, chlorambucil, ricin, pseudomonas exotoxin, etc. Alternatively, chimeric construct can be created linking the cDNA of the ligand with the cDNA of the toxin. An example of such toxin is TGFα and pseudomonas exotoxin (35).

8. Others

The PSM antigen may have other uses. It is well known that the prostate is rich in zinc, if the antigen provides function relative to this or other biologic function the PSM antigen may provide for utility in the treatment of other prostatic pathologies such as benign hyperplastic growth and/or prostatitis.

Because purified PSM antigen can be generated, the purified PSM antigen can be linked to beads and use it like a standard "affinity" purification. Serum, urine or other biological samples can be used to incubate with the PSM antigen bound onto beads. The beads may be washed thoroughly and then eluted with salt or pH gradient. The eluted material is SDS gel purified and used as a sample for microsequencing. The sequences will be compared with other known proteins and if unique, the technique of degenerated PCR can be employed for obtaining the ligand. Once known, the affinity of the ligand will be determined by standard protocols (15).

References of Example 1

1. Chiaroda, A. (1991) National roundtable of prostate cancer: research directions. Cancer Res. 51:2498–2505.
2. Coffey, D. S. Prostate Cancer—An overview of an increasing dilemma. Cancer Supplement, 71,3:880–886, 1993.
3. Warner, J. A., et al., (1991) Future developments of non-hormonal systemic therapy for prostatic carcinoma. Urologic Clin. North Amer. 18:25–33.
4. Nguyen, L., et al., (1990) Prostatic acid phosphatase in the serum of cancer patients with prostatic cancer is a specific phosphotyrosine acid phosphatase. Clin. Chem. 35:1450–1455.
5. Henttu, P., et al., (1989) cDNA coding for the entire human prostate specific antigen show high homologies to the human tissue kallikrein genes. Bioch. Biophys. Res. Comm. 160:903–908.
6. Yong, CY- F., et al., (1991) Hormonal regulation of prostate-specific antigen messenger RNA in human prostatic adenocarcinoma cell line LNCaP. Cancer Res. 51:3748–3752.
7. Liotta, L. A. (1986) Tumor invasion and metastases: role of the extracellular matrix. Cancer Res. 46:1–7.
8. Horoszewicz, J. S., et al. (1987) Monoclonal antibodies to a new antigenic marker in epithelial prostatic cells and serum of prostatic cancer patients. Anticancer Res. 7:927–936.
9. Horoszewicz, J. S., et al. (1983) LNCaP model of human prostatic carcinoma. Cancer Res., 43:1809–1818.
10. Lopes, D., et al. (1990) Immunohistochemical and pharmacokinetic characterization of the site-specific immunoconjugate CYT-356, derived from anti-prostate monoclonal antibody 7E11-C5. Cancer Res., 50:6423–6429.
11. Wright, Jr., et al., (1990) Characterization of a new carcinoma associated marker:7E11-C5. Antibod. Immunoconj. Radiopharm.3:(abst#193).
12. Feng, Q., et al., (1991) Purification and biochemical characterization of the 7E11-C5 prostate carcinoma associated antigen. Proc. Amer. Assoc. Cancer Res. 32:239.
13. Axelrod, H. R., et al., Preclinical results and human immunohistochemical studies with $^{90}$Y-CYT356. A New prostate cancer agent. Abstract 596. AUA 87th Annual Meeting, May 10–14, 1992. Washington, D.C.
14. Maniatis, T., et al., (1982) Molecular Cloning; Cold Spring Harbor Laboratory, pp.197–98 (1982).
15. Maniatis, et al., (1982) Molecular Cloning, Cold Spring Harbor Laboratory.
16. Methods in Enzymology vol. 34: 1–810, 1974 (E) B. Jacoby and M. Wilchek Academic Press, New York 1974.
17. Hogan B. et al. (1986) Manipulating the Mouse Embryo, A Laboratory Manual, Cold Spring Harbor Laboratory.
18. Capecchi M. R. Science (1989) 244:1288–1292; Zimmer, A. and Gruss, P. (1989) Nature 338:150–153.
19. Trowbridge, I. S., (1982) Prospects for the clinical use of cytotoxic monoclonal antibodies conjugates in the treatment of cancer. Cancer Surveys 1:543–556.
20. Hank, S. K. (1987) Homology probing: Identification of cDNA clones encoding members of the protein-serine kinase family. Proc. Natl. Acad. Sci. 84:388–392.
21. Lee, C. C., et al., (1988) Generation of cDNA probes directed by amino acid sequences: cloning of urate oxidase. Science, 239, 1288.
22. Girgis, S. I., et al. (1988) Generation of DNA probes for peptides with highly degenerate codons using mixed primer PCR. Nucleic Acids Res. 16:10932.
23. Kartner, N., et al. (1977) Isolation of plasma membranes from human skin fibroblasts. J. Membrane Biology, 36:191–211.
24. Hsu, S. M., et al. (1981) Comparative study of the immunoperoxidase, anti-peroxidase, and avidin-biotin complex method for studying polypeptide hormones with radioimmunoassay antibodies. Am. J. Pathology, 75:734.
25. Tempst, P., et al. (1989) Examination of automated polypeptide sequencing using standard phenylisothiocyanate reagent and subpicomole high performance liquid chromatography analysis. Analytical Biochem. 183:290–300.
26. Birnboim, H. C. (1983) A rapid alkaline extraction method for the isolation of plasmid DNA. Meth. Enzymol, 100:243–255.
27. Sanger, F., et al. (1977) DNA sequencing with chain-terminating inhibitors. Proc. Natl. Acad. Sci. USA, 74:5463–5467.
28. Grunstein, M., et al. (1975) Colony hybridization as a method for the isolation of cloned DNAs that contain a specific gene. Proc. Natl. Acad. Sci. USA, 72:3961.
29. Feinberg, A. P., et al. (1983) A technique for radiolabeling DNA restriction endonuclease fragments to high specific activity. Anal. Biochem, 132, 6.
30. Rave, N., et al. (1979) Identification of procollagen mRNAs transferred to diazobenzylomethyl paper from formaldehyde gels. Nucleic Acids Research, 6:3559.
31. Voeller, H. J., et al. (1991) v-ras$^H$ expression confers hormone-independent in-vitro growth to LNCaP prostate carcinoma cells. Molec. Endocrinology. Vol. 5. No. 2, 209–216.
32. Sirbasku, D. A. (1991) Purification of an equine apotransferrin variant (thyromedin) essential for thyroid hormone dependent growth of $GH_1$, rat pituitary tumor cells in chemically defined culture. Biochem., 30:295–301.
33. Rossi, M. C. (1992) Selective stimulation of prostatic carcinoma cell proliferation by transferrin. Proc. Natl. Acad. Sci. (USA) 89:6197–6201.
34. Eshhan, Z. (1990) Chimeric T cell receptor which incorporates the anti-tumor specificity of a monoclonal antibody with the cytolytic activity of T cells: a model system for immunotherapeutic approach. B. J. Cancer 62:27–29.
35. Antonie, P. (1990) Disposition of the prodrug 4-(bis(2 chloroethyl) amino) benzoyl-α-glutamic acid and its active parent in mice. B. J. Cancer 62:905–914.
36. Heimbrook, D. C., et al. (1990) Transforming growth factor alpha-pseudomonas exotoxin fusion protein prolongs survival of nude mice bearing tumor xenografts. Proc. Natl. Acad. Sci. (USA) 87:4697–4701.
37. Chiarodo, A. National Cancer Institute roundtable on prostate cancer; future research directions. Cancer Res., 51: 2498–2505, 1991.
38. Abdel-Nabi, H., Wright, G. L., Gulfo, J. V., Petrylak, D. P., Neal, C. E., Texter, J. E., Begun, F. P., Tyson, I., Heal, A., Mitchell, E., Purnell, G., and Harwood, S. J. Monoclonal antibodies and radioimmunoconjugates in the diagnosis and treatment of prostate cancer. Semin. Urol., 10:45–54, 1992.

Example 2

Expression of the Prostate Specific Membrane Antigen

Applicants have cloned a 2.65 kb complementary DNA encoding PSM, the prostate-specific membrane antigen recognized by the 7E11-C5.3 anti-prostate monoclonal antibody. Immunohistochemical analysis of the LNCaP, DU-145, and PC-3 prostate cancer cell lines for PSM expression using the 7E11-C5.3 antibody reveals intense staining in the LNCaP cells, with no detectable expression in both the DU-145 and PC-3 cells. Coupled in-vitro transcription/translation of the 2.65 kb full-length PSM cDNA yields an 84 kDa protein corresponding to the predicted polypeptide molecular weight of PSM. Post-translational modification of this protein with pancreatic canine microsomes yields the expected 100 kDa PSM antigen. Following transfection of PC-3 cells with the full-length PSM cDNA in a eukaryotic expression vector applicant's detect expression of the PSM glycoprotein by Western analysis using the 7E11-C5.3 monoclonal antibody. Ribonuclease protection analysis demonstrates that the expression of PSM mRNA is almost entirely prostate-specific in human tissues. PSM expression appears to be highest in hormone-deprived states and is hormonally modulated by steroids, with DHT downregulating PSM expression in the human prostate cancer cell line LNCaP by 8–10 fold, testosterone downregulating PSM by 3–4 fold, and corticosteroids showing no significant effect. Normal and malignant prostatic tissues consistently show high PSM expression, whereas heterogeneous, and at times absent, from expression of PSM in benign prostatic hyperplasia. LNCaP tumors implanted and grown both orthotopically and subcutaneously in nude mice, abundantly express PSM providing an excellent in-vivo model system to study the regulation and modulation of PSM expression.

Materials and Methods

Cells and Reagents: The LNCaP, DU-145, and PC-3 cell lines were obtained from the American Type Culture Collection. Details regarding the establishment and characteristics of these cell lines have been previously published (5A,7A,8A). Unless specified otherwise, LNCaP cells were grown in RPMI 1640 media supplemented with L-glutamine, nonessential amino acids, and 5% fetal calf serum (Gibco-BRL, Gaithersburg, Md.) in a $CO_2$ incubator at 37 C. DU-145 and PC-3 cells were grown in minimal essential medium supplemented with 10% fetal calf serum. All cell media were obtained from the MSKCC Media Preparation Facility. Restriction and modifying enzymes were purchased from Gibco-BRL unless otherwise specified.

Immunohistochemical Detection of PSM: Avidin-biotin method of detection was employed to analyze prostate cancer cell lines for PSM antigen expression (9A). Cell cytospins were made on glass slides using $5 \times 10^4$ cells/100 ul per slide. Slides were washed twice with PBS and then incubated with the appropriate suppressor serum for 20 minutes. The suppressor serum was drained off and the cells were incubated with diluted 7E11-C5.3 (5 g/ml) monoclonal antibody for 1 hour. Samples were then washed with PBS and sequentially incubated with secondary antibodies for 30 minutes and with avidin-biotin complexes for 30 minutes. Diaminobenzidine served as the chromogen and color development followed by hematoxylin counterstaining and mounting. Duplicate cell cytospins were used as controls for each experiment. As a positive control, the anti-cytokeratin monoclonal antibody CAM 5.2 was used following the same procedure described above. Human EJ bladder carcinoma cells served as a negative control.

In-Vitro Transcription/Translation of PSM Antigen: Plasmid 55A containing the full length 2.65 kb PSM cDNA in the plasmid pSPORT 1 (Gibco-BRL) was transcribed in-vitro using the Promega TNT system (Promega Corp. Madison, Wis.). T7 RNA polymerase was added to the cDNA in a reaction mixture containing rabbit reticulocyte lysate, an amino acid mixture lacking methionine, buffer, and $^{35}$S-Methionine (Amersham) and incubated at 30 C. for 90 minutes. Post-translational modification of the resulting protein was accomplished by the addition of pancreatic canine microsomes into the reaction mixture (Promega Corp. Madison, Wis.). Protein products were analyzed by electrophoresis on 10% SDS-PAGE gels which were subsequently treated with Amplify autoradiography enhancer (Amersham, Arlington Heights, Ill.) according to the manufacturers instructions and dried at 80 C. in a vacuum dryer. Gels were autoradiographed overnight at −70 C. using Hyperfilm MP (Amersham).

Transfection of PSM into PC-3 Cells: The full length PSM cDNA was subcloned into the pREP7 eukaryotic expression vector (Invitrogen, San Diego, Calif.). Plasmid DNA was purified from transformed DH5-alpha bacteria (Gibco-BRL) using Qiagen maxi-prep plasmid isolation columns (Qiagen Inc., Chatsworth, Calif.). Purified plasmid DNA (6–10 g) was diluted with 900 ul of Optimem media (Gibco-BRL) and mixed with 30 ul of Lipofectin reagent (Gibco-BRL) which had been previously diluted with 900 l of Optimem media. This mixture was added to T-75 flasks of 40–50% confluent PC-3 cells in Optimem media. After 24–36 hours, cells were trypsinized and split into 100 mm dishes containing RPMI 1640 media supplemented with 10% fetal calf serum and 1 mg/ml of Hygromycin B (Calbiochem, La Jolla, Calif.). The dose of Hygromycin B used was previously determined by a time course/dose response cytotoxicity assay. Cells were maintained in this media for 2–3 weeks with changes of media and Hygromycin B every 4–5 days until discrete colonies appeared. Colonies were isolated using 6 mm cloning cylinders and expanded in the same media. As a control, PC-3 cells were also transfected with the pREP7 plasmid alone. RNA was isolated from the transfected cells and PSM mRNA expression was detected by both RNase Protection analysis (described later) and by Northern analysis.

Western Blot Detection of PSM Expression: Crude protein lysates were isolated from LNCaP, PC-3, and PSM-transfected PC-3 cells as previously described (10A). LNCaP cell membranes were also isolated according to published methods (10A). Protein concentrations were quantitated by the Bradford method using the BioRad protein reagent kit (BioRad, Richmond, Calif.). Following denaturation, 20 µg of protein was electrophoresed on a 10% SDS-PAGE gel at 25 mA for 4 hours. Gels were electroblotted onto Immobilon P membranes (Millipore, Bedford, Mass.) overnight at 4 C. Membranes were blocked in 0.15 M NaCl/0.01 M Tris-HCl (TS) plus 5% BSA followed by a 1 hour incubation with 7E11-C5.3 monoclonal antibody (10 µg/ml). Blots were washed 4 times with 0.15 M NaCl/0/01 M Tris-HCl/0.05% Triton-X 100 (TS-X) and incubated for 1 hour with rabbit anti-mouse IgG (Accurate Scientific, Westbury, N.Y.) at a concentration of 10 µg/ml.

Blots were then washed 4 times with TS-X and labeled with $^{125}$I-Protein A (Amersham, Arlington Heights, Ill.) at a concentration of 1 million cpm/ml. Blots were then washed 4 times with TS-X and dried on Whatman 3MM paper, followed by overnight autoradiography at −70 C. using Hyperfilm MP (Amersham).

Orthotopic and Subcutaneous LNCaP Tumor Growth in Nude Mice: LNCaP cells were harvested from sub-confluent cultures by a one minute exposure to a solution of 0.25% trypsin and 0.02% EDTA. Cells were resuspended in RPMI 1640 media with 5% fetal bovine serum, washed and diluted in either Matrigel (Collaborative Biomedical Products, Bedford, Mass.) or calcium and magnesium-free Hank's balanced salt solution (HBSS). Only single cell suspensions with greater than 90% viability by trypan blue exclusion were used for in vivo injection. Male athymic Swiss (nu/nu) nude mice 4–6 weeks of age were obtained from the Memorial Sloan-Kettering Cancer Center Animal Facility. For subcutaneous tumor cell injection one million LNCaP cells resuspended in 0.2 mls. of Matrigel were injected into the hindlimb of each mouse using a disposable syringe fitted with a 28 gauge needle. For orthotopic injection, mice were first anesthetized with an intraperitoneal injection of Pentobarbital and placed in the supine position. The abdomen was cleansed with Betadine and the prostate was exposed through a midline incision. 2.5 million LNCaP tumor cells in 0.1 ml. were injected directly into either posterior lobe using a 1 ml disposable syringe and a 28 gauge needle. LNCaP cells with and without Matrigel were injected. Abdominal closure was achieved in one layer using Autoclip wound clips (Clay Adams, Parsippany, N.J.). Tumors were harvested in 6–8 weeks, confirmed histologically by faculty of the Memorial Sloan-Kettering Cancer Center Pathology Department, and frozen in liquid nitrogen for subsequent RNA isolation.

RNA Isolation: Total cellular RNA was isolated from cells and tissues by standard techniques (11,12) as well as by using RNAzol B (Cinna/Biotecx, Houston, Tex.). RNA concentrations and quality were assessed by UV spectroscopy on a Beckman DU 640 spectrophotometer and by gel analysis. Human tissue total RNA samples were purchased from Clontech Laboratories, Inc., Palo Alto, Calif.

Ribonuclease Protection Assays: A portion of the PSM cDNA was subcloned into the plasmid vector pSPORT 1 (Gibco-BRL) and the orientation of the cDNA insert relative to the flanking T7 and SP6 RNA polymerase promoters was verified by restriction analysis. Linearization of this plasmid upstream of the PSM insert followed by transcription with SP6 RNA polymerase yields a 400 nucleotide antisense RNA probe, of which 350 nucleotides should be protected from RNase digestion by PSM RNA. This probe was used in FIG. 20. Plasmid IN-20, containing a 1 kb partial PSM cDNA in the plasmid pCR II (Invitrogen) was also used for riboprobe synthesis. IN-20 linearized with Xmn I (Gibco-BRL) yields a 298 nucleotide anti-sense RNA probe when transcribed using SP6 RNA polymerase, of which 260 nucleotides should be protected from RNase digestion by PSM mRNA. This probe was used in FIGS. 21 and 22. Probes were synthesized using SP6 RNA polymerase (Gibco-BRL), rNTPs (Gibco-BRL), RNAsin (Promega), and $^{32}$P-rCTP (NEN, Wilmington, Del.) according to published protocols (13). Probes were purified over NENSORB 20 purification columns (NEN) and approximately 1 million cpm of purified, radiolabeled PSM probe was mixed with 10 μ of each RNA and hybridized overnight at 45 C. using buffers and reagents from the RPA II kit (Ambion, Austin, Tex.). Samples were processed as per manufacturer's instructions and analyzed on 5% polyacrilamide/7M urea denaturing gels using Seq ACRYL reagents (ISS, Natick, Mass.). Gels were pre-heated to 55 C. and run for approximately 1–2 hours at 25 watts. Gels were then fixed for 30 minutes in 10% methanol/10% acetic acid, dried onto Whatman 3MM paper at 80 C. in a BioRad vacuum dryer and autoradiographed overnight with Hyperfilm MP (Amersham). Quantitation of PSM expression was determined by using a scanning laser densitometer (LKB, Piscataway, N.J.).

Steroid Modulation Experiment: LNCaP cells (2 million) were plated onto T-75 flasks in RPMI 1640 media supplemented with 5% fetal calf serum and grown 24 hours until approximately 30–40% confluent. Flasks were then washed several times with phophate-buffered saline and RPMI medium supplemented with 5% charcoal-extracted serum was added. Cells were then grown for another 24 hours, at which time dihydrotesterone, testosterone, estradiol, progesterone, and dexamethasone (Steraloids Inc., Wilton, N.H.) were added at a final concentration of 2 nM. Cells were grown for another 24 hours and RNA was then harvested as previously described and PSM expression analyzed by ribonuclease protection analysis.

Experimental Results

Immunohistochemical Detection of PSM: Using the 7E11-C5.3 anti-PSM monoclonal antibody, PSM expression is clearly detectable in the LNCaP prostate cancer cell line, but not in the PC-3 and DU-145 cell lines (FIGS. 17A–17C). All normal and malignant prostatic tissues analyzed stained positively for PSM expression.

In-Vitro Transcription/Translation of PSM Antigen: As shown in FIG. 18, coupled in-vitro transcription/translation of the 2.65 kb full-length PSM cDNA yields an 84 kDa protein species in agreement with the expected protein product from the 750 amino acid PSM open reading frame. Following post-translational modification using pancreatic canine microsomes were obtained a 100 kDa glycosylated protein species consistent with the mature, native PSM antigen.

Figure 19:
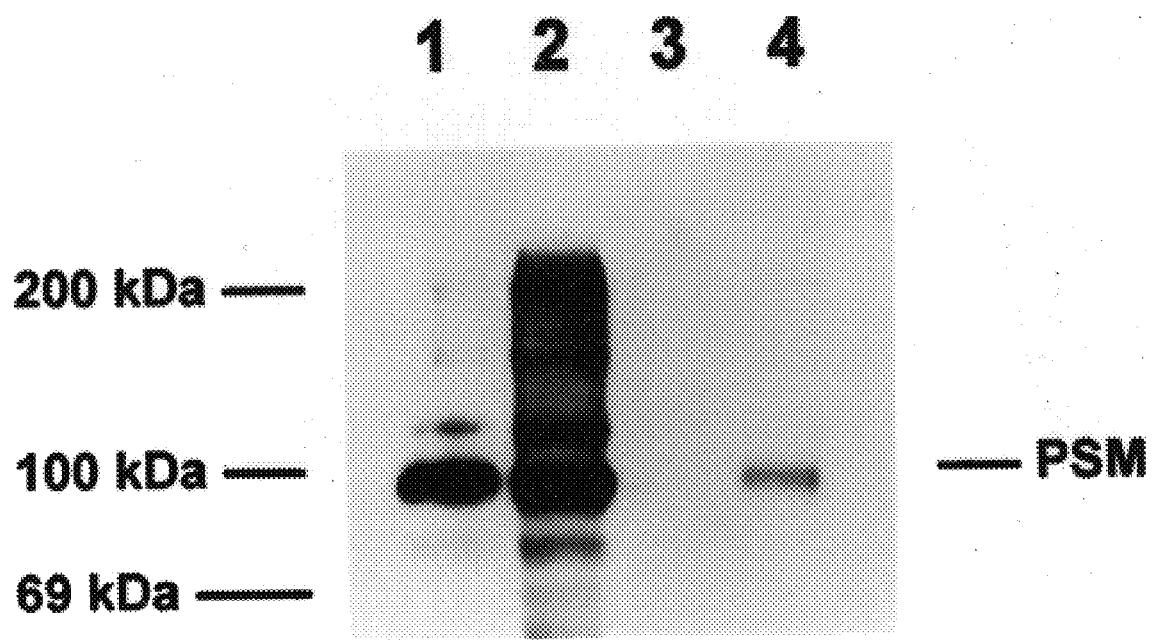
FIG. 19: Western Blot analysis detecting PSM expression in transfected non-PSM expressing PC-3 cells. 100 kDa PSM glycoprotein species is clearly seen in LNCaP membranes (lane 1), LNCaP crude lysate (lane 2), and PSM-transfected PC-3 cells (lane 4), but is undetectable in native PC-3 cells (lane 3).

Detection of PSM Antigen in LNCaP Cell Membranes and Transfected PC-3 Cells: PC-3 cells transfected with the full length PSM cDNA in the pREP7 expression vector were assayed for expression of SM mRNA by Northern analysis. A clone with high PSM mRNA expression was selected for PSM antigen analysis by Western blotting using the 7E11-C5.3 antibody. In FIG. 19, the 100 kDa PSM antigen is well expressed in LNCaP cell lysate and membrane fractions, as well as in PSM-transfected PC-3 cells but not in native PC-3 cells. This detectable expression in the transfected PC-3 cells proves that the previously cloned 2.65 kb PSM cDNA encodes the antigen recognized by the 7E11-C5.3 anti-prostate monoclonal antibody.

Figure 20:
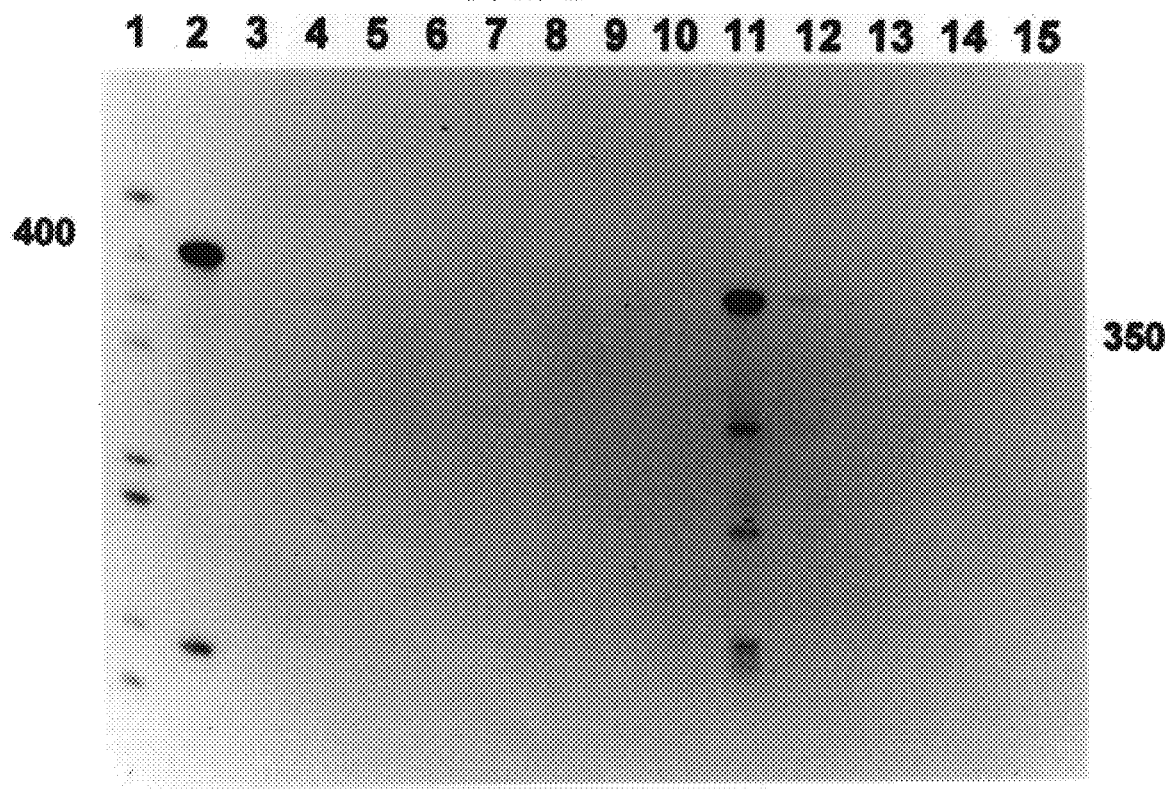
FIG. 20: Autoradiogram of ribonuclease protection gel assaying for PSM mRNA expression in normal human tissues. Radiolabeled 1 kb DNA ladder (Gibco-BRL) is shown in lane 1. Undigested probe is 400 nucleotides (lane 2), expected protected PSM band is 350 nucleotides, and tRNA control is shown (lane 3). A strong signal is seen in human prostate (lane 11), with very faint, but detectable signals seen in human brain (lane 4) and human salivary gland (lane 12).
Figure 21:
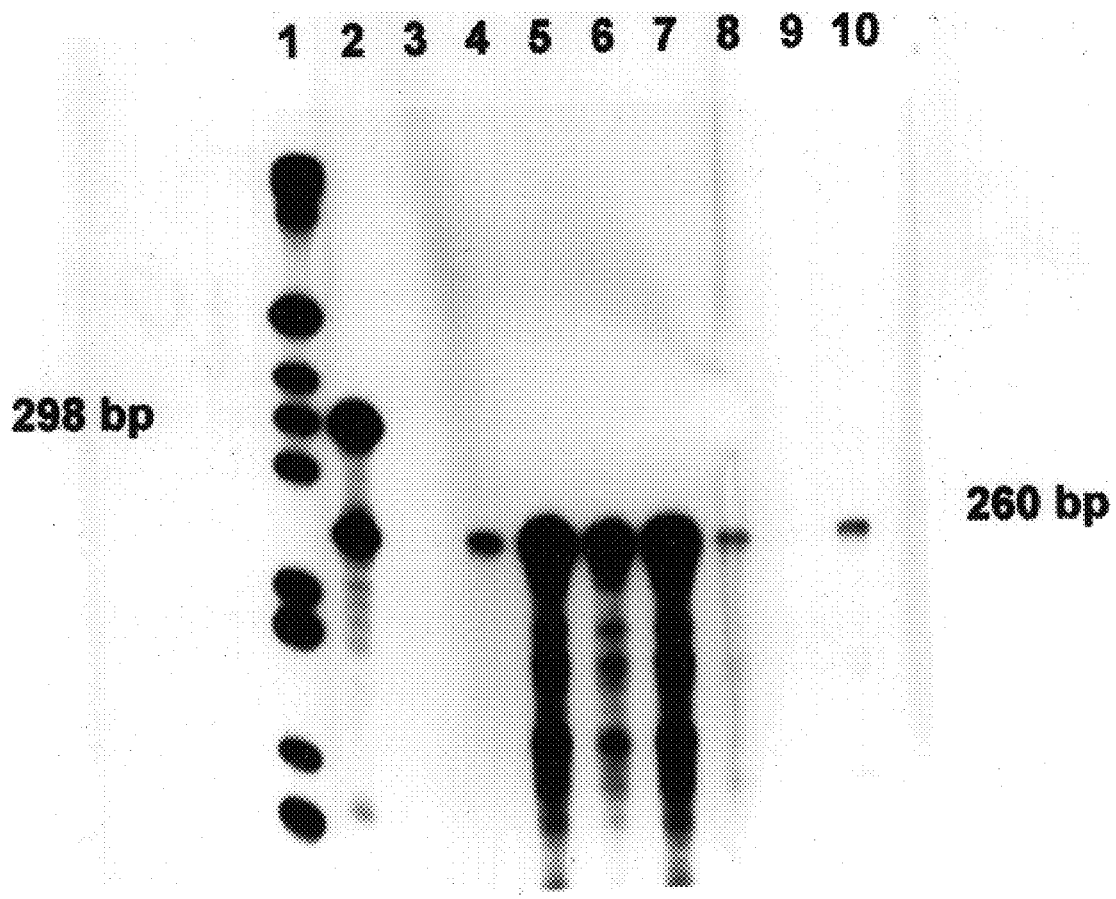
FIG. 21: Autoradiogram of ribonuclease protection gel assaying for PSM mRNA expression in LNCaP tumors grown in nude mice, and in human prostatic tissues. $^{32}$P-labeled 1 kb DNA ladder is shown in lane 1. 298 nucleotide undigested probe is shown (lane 2), and tRNA control is shown (lane 3). PSM mRNA expression is clearly detectable in LNCaP cells (lane 4), orthotopically grown LNCaP tumors in nude mice with and without matrigel (lanes 5 and 6), and subcutaneously implanted and grown LNCaP tumors in nude mice (lane 7). PSM mRNA expression is also seen in normal human prostate (lane 8), and in a moderately differentiated human prostatic adenocarcinoma (lane 10). Very faint expression is seen in a sample of human prostate tissue with benign hyperplasia (lane 9).
Figure 22:
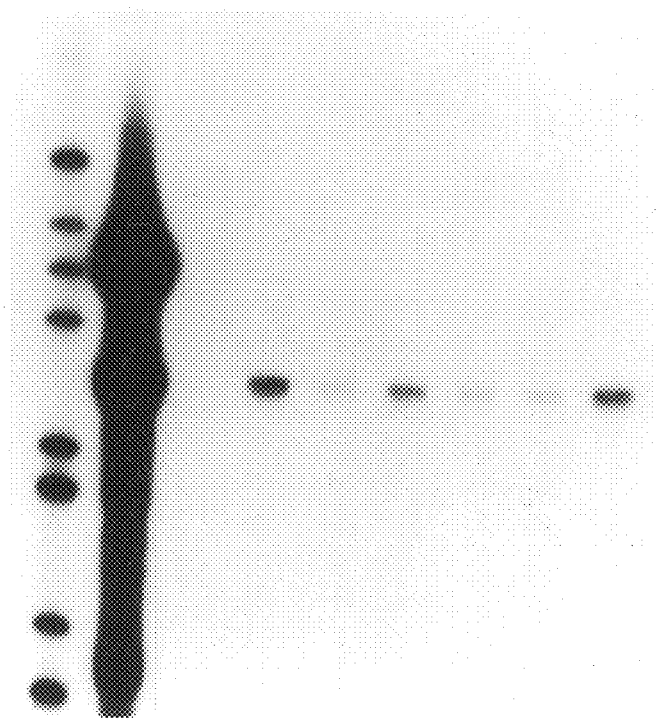
FIG. 22: Ribonuclease protection assay for PSM expression in LNCaP cells treated with physiologic doses of various steroids for 24 hours. $^{32}$P-labeled DNA ladder is shown in lane 1. 298 nucleotide undigested probe is shown (lane 2), and tRNA control is shown (lane 3). PSM mRNA expression is highest in untreated LNCaP cells in charcoal-stripped media (lane 4). Applicant see significantly diminished PSM expression in LNCaP cells treated with DHT (lane 5), Testosterone (lane 6), Estradiol (lane 7), and Progesterone (lane 8), with little response to Dexamethasone (lane 9).
Figure 24A:
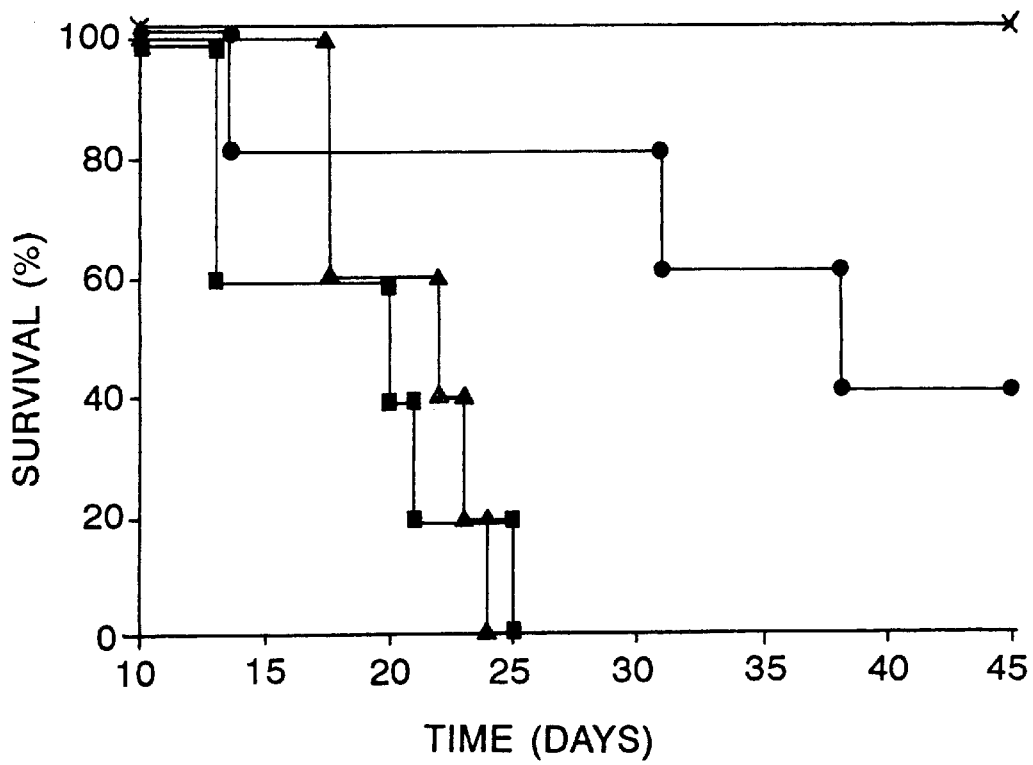
FIGS. 24A–24B: FIG. A indicates the power of cytokine transfected cells to teach unmodified cells. Administration was directed to the parental flank or prostate cells. The results indicate the microenvironment considerations.
Figure 24B:
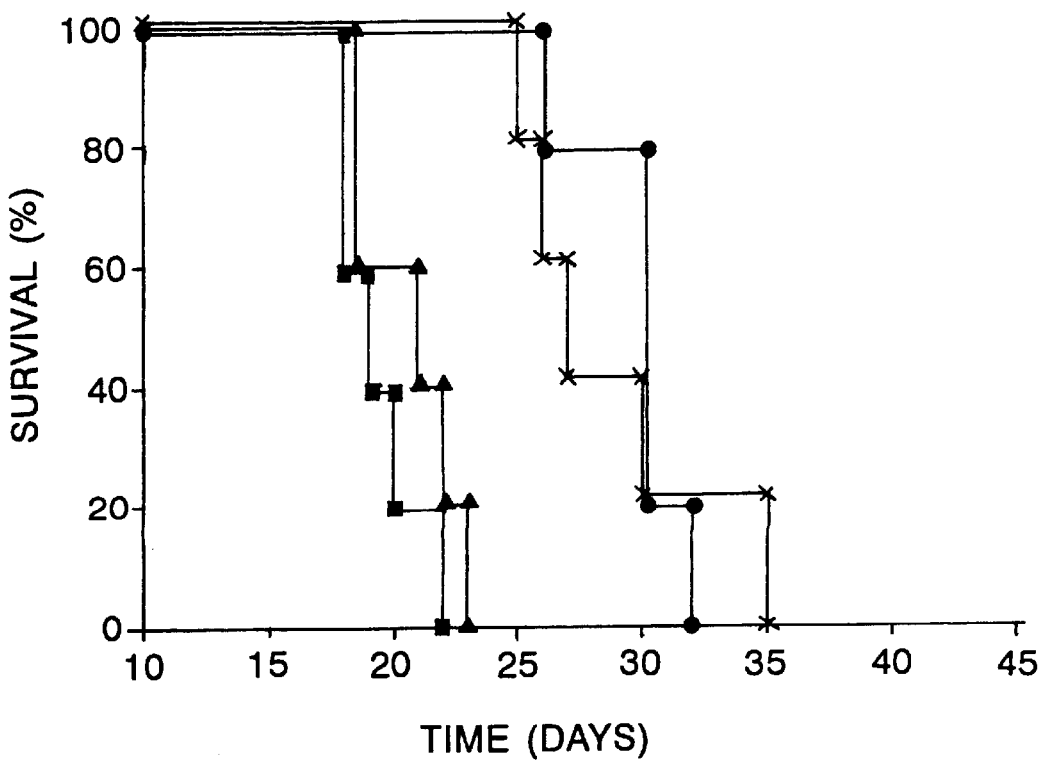

PSM mRNA Expression: Expression of PSM mRNA in normal human tissues was analyzed using ribonuclease protection assays. Tissue expression of PSM appears predominantly within the prostate, with very low levels of expression detectable in human brain and salivary gland (FIG. 20). No detectable PSM mRNA expression was evident in non-prostatic human tissues when analyzed by Northern analysis. On occasion it is noted that detectable PSM expression in normal human small intestine tissue, however this mRNA expression is variable depending upon the specific riboprobe used. All samples of normal human prostate and human prostatic adenocarcinoma assayed have revealed clearly detectable PSM expression, whereas generally decreased or absent expression of PSM in tissues exhibiting benign hyperplasia (FIG. 21). In human LNCaP tumors grown both orthotopically and subcutaneously in nude mice abundant PSM expression with or without the use of matrigel, which is required for the growth of subcutaneously implanted LNCaP cells was detected (FIG. 21). PSM mRNA expression is distinctly modulated by the presence of steroids in physiologic doses (FIG. 22). DHT downregulated expression by 8–10 fold after 24 hours and testosterone diminished PSM expression by 3–4 fold. Estradiol and progesterone also downregulated PSM expression in LNCaP cells, perhaps as a result of binding to the mutated androgen receptor known to exist in the LNCaP cell. Overall, PSM expression is highest in the untreated LNCaP cells grown in steroid-depleted media, a situation that simulates the hormone-deprived (castrate) state in-vivo. This experiment was repeated at steroid dosages ranging from 2–200 nM and at time points from 6 hours to 7 days with similar results; maximal downregulation of PSM mRNA was seen with DHT at 24 hours at doses of 2–20 nM.

Experimental Discussion

Previous research has provided two valuable prostatic bio-markers, PAP and PSA, both of which have had a significant impact on the diagnosis, treatment, and management of prostate malignancies. The present work describing the preliminary characterization of the prostate-specific membrane antigen (PSM) reveals it to be a gene with many interesting features. PSM is almost entirely prostate-specific as are PAP and PSA, and as such may enable further delineation of the unique functions and behavior of the prostate. The predicted sequence of the PSM protein (3) and its presence in the LNCaP cell membrane as determined by Western blotting and immunohistochemistry, indicate that it is an integral membrane protein. Thus, PSM provides an attractive cell surface epitope for antibody-directed diagnostic imaging and cytotoxic targeting modalities (14). The ability to synthesize the PSM antigen in-vitro and to produce tumor xenografts maintaining high levels of PSM expression provides us with a convenient and attractive model system to further study and characterize the regulation and modulation of PSM expression. Also, the high level of PSM expression in the LNCaP cells provides an excellent in-vitro model system. Since PSM expression is hormonally-responsive to steroids and may be highly expressed in hormone-refractory disease (15). The detection of PSM mRNA expression in minute quantities in brain, salivary gland, and small intestine warrants further investigation, although these tissues were negative for expression of PSM antigen by immunohistochemistry using the 7E11-C5.3 antibody (16). In all of these tissues, particularly small intestine, mRNA expression using a probe corresponding to a region of the PSM cDNA near the 3' end, whereas we were unable to detect expression when using a 5' end PSM probe was detected. These results may indicate that the PSM mRNA transcript undergoes alternative splicing in different tissues. Previous protein studies have suggested that the 7E11-C5.3 antibody may actually detect two other slightly larger protein species in addition to the 100 kDa PSM antigen (17). These other protein species can be seen in the LNCaP lysate and membrane samples in FIG. 19. Possible origins of these proteins include alternatively spliced PSM mRNA, other genes distinct from but closely related to PSM, or different post-translational modifications of the PSM protein.

Applicants approach is based on prostate tissue specific promotor: enzyme or cytokine chimeras. Promotor specific activation of prodrugs such as non toxic gancyclovir which is converted to a toxic metabolite by herpes simplex thymidine kinase or the prodrug 4-(bis(2chloroethyl)amino) benzoyl-1-glutamic acid to the benzoic acid mustard alkylating agent by the pseudomonas carboxy peptidase G2 was examined. As these drugs are activated by the enzyme (chimera) specifically in the tumor the active drug is released only locally in the tumor environment, destroying the surrounding tumor cells. Promotor specific activation of cytokines such as IL-12, IL-2 or GM-CSF for activation and specific antitumor vaccination is examined. Lastly the tissue specific promotor activation of cellular death genes may also prove to be useful in this area.

Gene Therapy Chimeras: The establishment of "chimeric DNA" for gene therapy requires the joining of different segments of DNA together to make a new DNA that has characteristics of both precursor DNA species involved in the linkage. In this proposal the two pieces being linked involve different functional aspects of DNA, the promotor region which allows for the reading of the DNA for the formation of mRNA will provide specificity and the DNA sequence coding for the mRNA will provide for therapeutic functional DNA.

DNA-Specified Enzyme or Cytokine mRNA: When effective, antitumor drugs can cause the regression of very large amounts of tumor. The main requirements for antitumor drug activity is the requirement to achieve both a long enough time (t) and high enough concentration (c) (cxt) of exposure of the tumor to the toxic drug to assure sufficient cell damage for cell death to occur. The drug also must be "active" and the toxicity for the tumor greater than for the hosts normal cells (22). The availability of the drug to the tumor depends on tumor blood flow and the drugs diffusion ability. Blood flow to the tumor does not provide for selectivity as blood flow to many normal tissues is often as great or greater than that to the tumor. The majority of chemotherapeutic cytotoxic drugs are often as toxic to normal tissue as to tumor tissue. Dividing cells are often more sensitive than non-dividing normal cells, but in many slow growing solid tumors such as prostatic cancer this does not provide for antitumor specificity (22).

Previously a means to increase tumor specificity of antitumor drugs was to utilize tumor associated enzymes to activate nontoxic prodrugs to cytotoxic agents (19). A problem with this approach was that most of the enzymes found in tumors were not totally specific in their activity and similar substrate active enzymes or the same enzyme at only slightly lower amounts was found in other tissue and thus normal tissues were still at risk for damage.

To provide absolute specificity and unique activity, viral, bacterial and fungal enzymes which have unique specificity for selected prodrugs were found which were not present in human or other animal cells. Attempts to utilize enzymes such as herpes simplex thymidine kinase, bacterial cytosine deaminase and carboxypeptidase G-2 were linked to antibody targeting systems with modest success (19). Unfortunately, antibody targeted enzymes limit the number of enzymes available per cell. Also, most antibodies do not have a high tumor target to normal tissue ratio thus normal tissues are still exposed reducing the specificity of these unique enzymes. Antibodies are large molecules that have poor diffusion properties and the addition of the enzymes molecular weight further reduces the antibodies diffusion.

Gene therapy could produce the best desired result if it could achieve the specific expression of a protein in the tumor and not normal tissue in order that a high local concentration of the enzyme be available for the production in the tumor environment of active drug (21).

Cytokines:

Applicant's research group has demonstrated that Applicant's can specifically and non-toxically "cure" an animal of an established tumor, in models of bladder or prostate cancer. The prostate cancer was the more difficult to cure especially if it was grown orthotopically in the prostate.

Results demonstrated that tumors such as the bladder and prostate were not immunogenic, that is the administration of irradiated tumor cells to the animal prior to subsequent administration of non-irradiated tumor cells did not result in a reduction of either the number of tumor cells to produce a tumor nor did it reduce the growth rate of the tumor. But if the tumor was transfected with a retrovirus and secreted large concentrations of cytokines such as Il-2 then this could act as an antitumor vaccine and could also reduce the growth potential of an already established and growing tumor. IL-2 was the best, GM-CSF also had activity whereas a number of other cytokines were much less active. In clinical studies just using IL-2 for immunostimulation, very large concentrations had to be given which proved to be toxic. The key to the success of the cytokine gene modified tumor cell is that the cytokine is produced at the tumor site locally and is not toxic and that it stimulates immune recognition of the tumor and allows specific and non toxic recognition and destruction of the tumor. The exact mechanisms of how IL-2 production by the tumor cell activates immune recognition is not fully understood, but one explanation is that it bypasses the need for cytokine production by helper T cells and directly stimulates tumor antigen activated cytotoxic CD8 cells. Activation of antigen presenting cells may also occur.

Tissue Promotor-Specific Chimera DNA Activation
  Non-Prostatic Tumor Systems

It has been observed in non-prostatic tumors that the use of promotor specific activation can selectively lead to tissue specific gene expression of the transfected gene. In melanoma the use of the tyrosinase promoter which codes for the enzyme responsible for melanin expression produced over a 50 fold greater expression of the promotor driven reporter gene expression in melanoma cells and not non melanoma cells. Similar specific activation was seen in the melanoma cells transfected when they were growing in mice. In that experiment no non-melanoma or melanocyte cell expressed the tyrosinase drive reporter gene product. The research group at Welcome Laboratories have cloned and sequenced the promoter region of the gene coding for carcinoembryonic antigen (CEA). CEA is expressed on colon and colon carcinoma cells but specifically on metastatic. A gene chimera was generated which cytosine deaminase. Cytosine deaminase which converts 5 flurorocytosine into 5 fluorouracil and observed a large increase in the ability to selectively kill CEA promotor driven colon tumor cells but not normal liver cells. In vivo they observed that bystander tumor cells which were not transfected with the cytosine deaminase gene were also killed, and that there was no toxicity to the host animal as the large tumors were regressing following treatment. Herpes simplex virus, (HSV), thymidine kinase similarly activates the prodrug gancyclovir to be toxic towards dividing cancer cells and HSV thymidine kinase has been shown to be specifically activatable by tissue specific promoters.

Prostatic Tumor Systems: The therapeutic key to effective cancer therapy is to achieve specificity and spare the patient toxicity. Gene therapy may provide a key part to specificity in that non-essential tissues such as the prostate and prostatic tumors produce tissue specific proteins, such as acid phosphatase (PAP), prostate specific antigen (PSA), and a gene which was cloned, prostate-specific membrane antigen (PSM). Tissues such as the prostate contain selected tissue specific transcription factors which are responsible for binding to the promoter region of the DNA of these tissue specific mRNA. The promoter for PSA has been cloned. Usually patients who are being treated for metastatic prostatic cancer have been put on androgen deprivation therapy which dramatically reduces the expression of mRNA for PSA. PSM on the other hand increases in expression with hormone deprivation which-means it would be even more intensely expressed on patients being treated with hormone therapy.

References of Example 2

1. Coffey, D. S. Prostate Cancer—An overview of an increasing dilemma. Cancer Supplement, 71,3:880–886, 1993.

2. Chiarodo, A. National Cancer Institute roundtable on prostate cancer; future research directions. Cancer Res., 51:2498–2505, 1991.

3. Israeli, R. S., Powell, C. T., Fair, W. R., and Heston, W. D. W. Molecular cloning of a complementary DNA encoding a prostate-specific membrane antigen. Cancer Res., 53:227–230, 1993.

4. Horoszewicz, J. S., Kawinski, E., and Murphy, G. P. Monoclonal antibodies to a new antigenic marker in epithelial cells and serum of prostatic cancer patients. Anticancer Res., 7:927–936, 1987.

5. Horoszewicz, J. S., Leong, S. S., Kawinski, E., Karr, J. P., Rosenthal, H., Chu, T. M., Mirand, E. A., and Murphy, G. P. LNCaP model of human prostatic carcinoma. Cancer Res., 43:1809–1818, 1983.

6. Abdel-Nabi, H., Wright, G. L., Gulfo, J. V., Petrylak, D. P., Neal, C. E., Texter, J. E., Begun, F. P., Tyson, I., Heal, A., Mitchell, E., Purnell, G., and Harwood, S. J. Monoclonal antibodies and radioimmunoconjugates in the diagnosis and treatment of prostate cancer. Semin. Urol., 10:45–54, 1992.

7. Stone, K. R., Mickey, D. D., Wunderli, H., Mickey, G. H., and Paulson, D. F. Isolation of a human prostate carcinoma cell line (DU-145). Int. J. Cancer, 21:274–281, 1978.

8. Kaign, M. E., Narayan, K. S., Ohnuki, Y., and Lechner, J. F. Establishment and characterization of a human prostatic carcinoma cell line (PC-3). Invest. Urol., 17:16–23, 1979.

9. Hsu, S. M., Raine, L., and Fanger, H. Review of present methods of immunohistochemical detection. Am. J. Clin. Path. 75:734–738, 1981.

10. Harlow, E., and Lane, D. Antibodies: A Laboratory Manual. New York: Cold Spring Harbor Laboratory, p. 449, 1988.

11. Glisin, V., Crkvenjakov, R., and Byus, C. Ribonucleic acid isolated by cesium chloride centrifugation. Biochemistry, 13:2633–2637, 1974.

12. Aviv, H., and Leder, P. Purification of biologically active globin messenger RNA by chromatography on oligothymidylic acid cellulose. Proc. Natl. Acad. Sci. USA, 69:1408–1412, 1972.

13. Melton, D. A., Krieg, P. A., Rebagliati, M. R., Maniatis, T. A., Zinn, K., and Careen, M. R. Efficient in-vitro synthesis of biologically active RNA and RNA hybridization probes from plasmids containing a bacteriophage SP6 promoter. Nucl. Acids. Res. 12:7035–7056, 1984.

14.

15. Axelrod, H. R., Gilman, S. C., D'Aleo, C. J., Petrylak, D., Reuter, V., Gulfo, J. V., Saad, A., Cordon-Cardo, C., and Scher, H. I. Preclinical results and human immunohistochemical studies with $^{90}$Y-CYT-356; a new prostatic cancer therapeutic agent. AUA Proceedings, Abstract 596, 1992.

16. Lopes, A. D., Davis, W. L., Rosenstraus, M. J., Uveges, A. J., and Gilman, S. C. Immunohistochemical and pharmacokinetic characterization of the site-specific immunoconjugate CYT-356 derived from antiprostate monoclonal antibody 7E11-C5. Cancer Res., 50:6423–6429, 1990.

17. Troyer, J. K., Qi, F., Beckett, M. L., Morningstar, M. M., and Wright, G. L. Molecular characterization of the 7E11-C5 prostate tumor-associated antigen. AUA Proceedings. Abstract 482, 1993.

18. Roemer, K., Friedmann, T. Concepts and strategies for human gene therapy. FEBS. 223:212–225.

19. Antonie, P. Springer, C. J., Bagshawe, F., Searle, F., Melton, R. G., Rogers, G. T., Burke, P. J., Sherwood, R. F. Disposition of the prodrug 4-bis(2chloroethyl) amino) benzoyl-1-glutamic acid and its active parent drug in mice. Br.J.Cancer 62:909–914, 1990.

20. Connor, J. Bannerji, R., Saito, S., Heston, W. D. W., Fair, W. R., Gilboa, E. Regression of bladder tumors in mice treated with interleukin 2 gene-modified tumor cells. J.Exp.Med. 177:1127–1134, 1993. (appendix)

21. Vile R., Hart, I. R. In vitro and in vivo targeting of gene expression to melanoma cells. Cancer Res. 53:962–967, 1993.

22. Warner, J. A., Heston, W. D. W. Future developments of nonhormonal systemic therapy for prostatic carcinoma. Urologic Clinics of North America 18:25–33, 1991.

23. Vile, R. G., Hart, I. R. Use of tissue specific expression of the herpes simplex virus thymidine kinase gene to inhibit growth of established murine melanomas following direct intratumoral injection of DNA. Cancer Res. 53:3860–3864, 1993.

Example 3

Sensitive Detection of Prostatic Hematogenous Micrometastases Using PSA and PSM-Derived Primers in the Polymerase Chain Reaction A PCR-based assay was developed enabling sensitive detection of hematogenous micrometastases in patients with prostate cancer. "Nested PCR", was performed by amplifying mRNA sequences unique to prostate-specific antigen and to the prostate-specific membrane antigen, and have compared their respective results. Micrometastases were detected in 2/30 patients (6.7%) by PCR with PSA-derived primers, while PSM-derived primers detected tumor cells in 19/16 patients (63.3%). All 8 negative controls were negative with both PSA and PSM PCR. Assays were repeated to confirm results, and PCR products were verified by DNA sequencing and Southern analysis. Patients harboring circulating prostatic tumor cells as detected by PSM, and not by PSA-PCR included 4 patients previously treated with radical prostatectomy and with non-measurable serum PSA levels at the time of this assay. The significance of these findings with respect to future disease recurrence and progression will be investigated.

Improvement in the overall survival of patients with prostate cancer will depend upon earlier diagnosis. Localized disease, without evidence of extra-prostatic spread, is successfully treated with either radical prostatectomy or external beam radiation, with excellent long-term results (2, 3). The major problem is that approximately two-thirds of men diagnosed with prostate cancer already have evidence of advanced extra-prostatic spread at the time of diagnosis, for which there is at present no cure (4). The use of clinical serum markers such as prostate-specific antigen (PSA) and prostatic acid phosphatase (PAP) have enabled clinicians to detect prostatic carcinomas earlier and provide useful parameters to follow responses to therapy (5). Yet, despite the advent of sensitive serum PSA assays, radionuclide bone scans, CT scans and other imaging modalities, results have not detected the presence of micrometastatic cells prior to their establishment of solid metastases. Previous work has been done utilizing the polymerase chain reaction to amplify mRNA sequences unique to breast, leukemia, and other malignant cells in the circulation and enable early detection of micrometastases (6, 7). Recently, a PCR-based approach utilizing primers derived from the PSA DNA sequence was published (8). In this study 3/12 patients with advanced, stage D prostate cancer had detectable hematogenous micrometastases.

PSM appears to be an integral membrane glycoprotein which is very highly expressed in prostatic tumors and metastases and is almost entirely prostate-specific (10). Many anaplastic tumors and bone metastases have variable and at times no detectable expression of PSA, whereas these lesions appear to consistently express high levels of PSM. Prostatic tumor cells that escape from the prostate gland and enter the circulation are likely to have the potential to form metastases and are possibly the more aggressive and possibly anaplastic cells, a population of cells that may not express high levels of PSA, but may retain high expression of PSM. DNA primers derived from the sequences of both PSA and PSM in a PCR assay were used to detect micrometastatic cells in the peripheral circulation. Despite the high level of amplification and sensitivity of conventional RNA PCR, "Nested" PCR approach in which we first amplify a target sequence was employed, and subsequently use this PCR product as the template for another round of PCR amplification with a new set of primers totally contained within the sequence of the previous product. This approach has enabled us to increase the level of detection from one prostatic tumor cell per 10,000 cells to better than one cell per ten million cells.

Materials and Methods

Cells and Reagents: LNCaP and MCF-7 cells were obtained from the American Type Culture Collection (Rockville, Md.). Details regarding the establishment and characteristics of these cell lines have been previously published (11, 12). Cells were grown in RPMI 1640 media supplemented with L-glutamine, nonessential amino acids, obtained from the MSKCC Media Preparation Facility, and 5% fetal calf serum (Gibco-BRL, Gaithersburg, Md.) in a $Co_2$ incubator at 37 C. All cell media was obtained from the MSKCC Media Preparation Facility. Routine chemical reagents were of the highest grade possible and were obtained from Sigma Chemical Company, St. Louis, Mo.

Patient Blood Specimens: All blood specimens used in this study were from patients seen in the outpatient offices of urologists on staff at MSKCC. Two anti-coagulated (purple top) tubes per patient were obtained at the time of their regularly scheduled blood draws. Specimen procurement was conducted as per the approval of the MSKCC Institutional Review Board. Samples were promptly brought to the laboratory for immediate processing. Serum PSA and PAP determinations were performed by standard techniques by the MSKCC Clinical Chemistry Laboratory. PSA determinations were performed using the Tandem PSA assay (Hybritech, San Diego, Calif.). The eight blood specimens used as negative controls were from 2 males with normal serum PSA values and biopsy-proven BPH, one healthy female, 3 healthy males, one patient with bladder cancer, and one patient with acute promyelocytic leukemia.

Blood Sample Processing/RNA Extraction: 4 ml of whole anticoagulated venous blood was mixed with 3 ml of ice cold phosphate buffered saline and then carefully layered atop 8 ml of Ficoll (Pharmacia, Uppsala, Sweden) in a 15-ml polystyrene tube. Tubes were centrifuged at 200×g for 30 min. at 4 C. Using a sterile pasteur pipette, the buffy coat layer (approx. 1 ml.) was carefully removed and rediluted up to 50 ml with ice cold phosphate buffered saline in a 50 ml polypropylene tube. This tube was then centrifuged at 2000×g for 30 min at 4 C. The supernatant was carefully decanted and the pellet was allowed to drip dry. One ml of RNazol B was then added to the pellet and total RNA was isolated as per manufacturers directions (Cinna/Biotecx, Houston, Tex.). RNA concentrations and purity were determined by UV spectroscopy on a Beckman DU 640 spectrophotometer and by gel analysis.

Determination of PCR Sensitivity: RNA was isolated from LNCaP cells and from mixtures of LNCaP and MCF-7 cells at fixed ratios (i.e. 1:100, 1:1000, etc.) using RNAzol B. Nested PCR was then performed as described below with both PSA and PSM primers in order to determine the limit of detection for the assay. LNCaP:MCF-7 (1:100,000) cDNA was diluted with distilled water to obtain concentrations of 1:1,000,000 and 1:10,000,000. MCF-7 cells were chosen because they have been previously tested and shown not to express PSM by PCR.

Polymerase Chain Reaction: The PSA outer primers used span portions of exons 4 and 5 to yield a 486 bp PCR product and enable differentiation between cDNA and possible contaminating genomic DNA amplification. The upstream primer sequence beginning at nucleotide 494 in PSA cDNA sequence is 5'-TACCCACTGCATCAGGAACA-3'(SEQ. ID. No. 39) and the downstream primer at nucleotide 960 is 5'-CCTTGAAGCACACCATTACA-3'(SEQ. ID. No. 40). The PSA inner upstream primer (beginning at nucleotide 559) 5'-ACACAGGCCAGGTATTTCAG-3'(SEQ. ID. No. 41) and the downstream primer (at nucleotide 894) 5'-GTCCAGCGTCCAGCACACAG-3'(SEQ. ID. No. 42) yield a 355 bp PCR product. All primers were synthesized by the MSKCC Microchemistry Core Facility. 5 $\mu$g of total RNA was reverse-transcribed into cDNA in a total volume of 20 $\mu$l using Superscript reverse transcriptase (Gibco-BRL) according to the manufacturers recommendations. 1 $\mu$l of this cDNA served as the starting template for the outer primer PCR reaction. The 20 $\mu$l PCR mix included: 0.5 U Taq polymerase (Promega Corp., Madison, Wis.), Promega reaction buffer, 1.5 mM MgCl$_2$, 200 mM dNTPs, and 1.0 $\mu$M of each primer. This mix was then transferred to a Perkin Elmer 9600 DNA thermal cycler and incubated for 25 cycles. The PCR profile was as follows: 94 C.×15 sec., 60 C.×15 sec., and 72 C. for 45 sec. After 25 cycles, samples were placed on ice, and 1 $\mu$l of this reaction mix served as the template for another round of PCR using the inner primers. The first set of tubes were returned to the thermal cycler for 25 additional cycles. PSM-PCR required the selection of primer pairs that also spanned an intron in order to be certain that cDNA and not genomic DNA were being amplified. Since the genomic DNA sequence of PSM has not yet been determined, this involved trying different primer pairs until a pair was found that produced the expected size PCR product when cDNA was amplified, but with no band produced from a genomic DNA template, indicating the presence of a large intron. The intron position was sequenced and results indicated that no introns are located in this area. The PSM outer primers yield a 946 bp product and the inner primers a 434 bp product. The PSM outer upstream primer used was 5'-ATGGGTGTTTGGTGGTATTGACC-3' (SEQ. ID. No. 43) (beginning at nucleotide 1401) and the downstream primer (at nucleotide 2348) was 5'-TGCTTGGAGCATAGATGACATGC-3'(SEQ. ID. No. 44) The PSM inner upstream primer (at nucleotide 1581) was 5'-ACTCCTTCAAGAGCGTGGCG-3'(SEQ. ID. No. 45) and the downstream primer (at nucleotide 2015) was 5'-AACACCATCCCTCCTCGAACC-3'(SEQ. ID. No. 46). cDNA used was the same as for the PSA assay. The 501 PCR mix included: 1 U Taq Polymerase (Promega), 250 M dNTPs, 10 mM-mercaptoethanol, 2 mM MgCl$_2$, and 5 l of a 10 x buffer mix containing: 166 mM NH$_4$SO$_4$, 670 mM Tris pH 8.8, and 2 mg/ml of acetylated BSA. PCR was carried out in a Perkin Elmer 480 DNA thermal cycler with the following parameters: 94 C.×4 minutes for 1 cycle, 94 C.×30 sec., 58 C.×1 minute, and 72 C.×1 minute for 25 cycles, followed by 72 C×10 minutes. Samples were then iced and 2 l of this reaction mix was used as the template for another 25 cycles with a new reaction mix containing the inner PSM primers. cDNA quality was verified by performing control reactions using primers derived from -actin yielding a 446 bp PCR product. The upstream primer used was 5'-AGGCCAACCGCGAGAAGATGA-3'(SEQ. ID. No. 47) (exon 3) and the downstream primer was 5'-ATGTCACACTGGGGAAGC-3'(SEQ. ID. No. 48) (exon 4). The entire PSA mix and 10 l of each PSM reaction mix were run on 1.5–2% agarose gels, stained with ethidium bromide and photographed in an Eagle Eye Video Imaging System (Stratagene, Torrey Pines, Calif.). Assays were repeated at least 3 times to verify results.

Cloning and Sequencing of PCR Products: PCR products were cloned into the pCR II plasmid vector using the TA cloning system (Invitrogen). These plasmids were transformed into competent E. coli cells using standard methods (13) and plasmid DNA was isolated using Magic Minipreps (Promega) and screened by restriction analysis. TA clones were then sequenced by the dideoxy method (14) using Sequenase (U.S. Biochemical). 3–4 g of each plasmid was denatured with NaOH and ethanol precipitated. Labeling reactions were carried out according to the manufacturers recommendations using $^{35}$S-dATP (NEN), and the reactions were terminated as discussed in the same protocol. Sequencing products were then analyzed on 6% polyacrilamide/7 M urea gels run at 120 watts for 2 hours. Gels were fixed for 20 minutes in 10% methanol/10% acetic acid, transferred to Whatman 3MM paper and dried down in a vacuum dryer for 2 hours at 80 C. Gels were then autoradiographed at room temperature for 18 hours.

Southern Analysis: Ethidium-stained agarose gels of PCR products were soaked for 15 minutes in 0.2 N HCl, followed by 30 minutes each in 0.5 N NaOH/1.5 M NaCl and 0.1 M Tris pH 7.5/1.5 M NaCl. Gels were then equilibrated for 10 minutes in 10×SSC (1.5 M NaCl/0.15 M Sodium Citrate. DNA was transferred onto Nytran nylon membranes (Schleicher and Schuell) by pressure blotting in 10×SSC with a Posi-blotter (Stratagene). DNA was cross-linked to the membrane using a UV Stratalinker (Stratagene). Blots were pre-hybridized at 65 C. for 2 hourthes and subsequently hybridized with denatured $^{32}$P-labeled, random-primed cDNA probes (either PSM or PSA) (9, 15). Blots were washed twice in 1×SSPE/0.5% SDS at 42 C. and twice in 0.1×SSPE/0.5% SDS at 50 C. for 20 minutes each. Membranes were air-dried and autoradiographed for 30 minutes to 1 hour at −70 C. with Kodak X-Omat film.

Experimental Results

PCR amplification with nested primers improved the level of detection of prostatic cells from approximately one prostatic cell per 10,000 MCF-7 cells to better than one cell per million MCF-7 cells, using either PSA or PSM-derived primers (FIGS. 26 and 27). This represents a substantial improvement in the ability to detect minimal disease. Characteristics of the 16 patients analyzed with respect to their clinical stage, treatment, serum PSA and PAP values, and results of the assay are shown in table 1. In total, PSA-PCR detected tumor cells in 2/30 patients (6.7%), whereas PSM-PCR detected cells in 19/30 patients (63.3%). There were no patients positive for tumor cells by PSA and not by PSM, while PSM provided 8 positive patients not detected by PSA. Patients 10 and 11 in table 1, both with very advanced hormone-refractory disease were detected by both PSA and PSM. Both of these patients have died since the time these samples were obtained. Patients 4, 7, and 12, all of whom were treated with radical prostatectomies for clinically localized disease, and all of whom have non-measurable serum PSA values 1–2 years postoperatively were positive for circulating prostatic tumor cells by PSM-PCR, but negative by PSA-PCR. A representative ethidium stained gel photograph for PSM-PCR is shown in FIG. 28. Samples run in lane A represent PCR products generated from the outer primers and samples in lanes labeled B are products of inner primer pairs. The corresponding PSM Southern blot autoradiograph is shown in FIG. 29. The sensitivity of the Southern blot analysis exceeded that of ethidium staining, as can be seen in several samples where the outer product is not visible on FIG. 28, but is detectable by Southern blotting as shown in FIG. 29. In addition, sample 3 on FIGS. 28 and 29 (patient 6 in FIG. 30) appears to contain both outer and inner bands that are smaller than the corresponding bands in the other patients. DNA sequencing has confirmed that the nucleotide sequence of these bands matches that of PSM, with the exception of a small deletion. This may represent either an artifact of PCR, alternative splicing of PSM mRNA in this patient, or a PSM mutation. All samples sequenced and analyzed by Southern analysis have been confirmed as true positives for PSA and PSM.

Experimental Details

The ability to accurately stage patients with prostate cancer at the time of diagnosis is clearly of paramount importance in selecting appropriate therapy and in predicting long-term response to treatment, and potential cure. Pre-surgical staging presently consists of physical examination, serum PSA and PAP determinations, and numerous imaging modalities including transrectal ultrasonography, CT scanning, radionuclide bone scans, and even MRI scanning. No present modality, however, addresses the issue of hematogenous micrometastatic disease and the potential negative impact on prognosis that this may produce. Previous work has shown that only a fractional percentage of circulating tumor cells will inevitably go on to form a solid metastasis (16), however, the detection of and potential quantification of circulating tumor cell burden may prove valuable in more accurately staging disease. The long-term impact of hematogenous micrometastatic disease must be studied by comparing the clinical courses of patients found to have these cells in their circulation with patients of similar stage and treatment who test negatively.

The significantly higher level of detection of tumor cells with PSM as compared to PSA is not surprising to us, since more consistent expression of PSM in prostate carcinomas of all stages and grades as compared to variable expression of PSA in more poorly differentiated and anaplastic prostate cancers is noted. The detection of tumor cells in the three patients that had undergone radical prostatectomies with subsequent undetectable amounts of serum PSA was suprising. These patients would be considered to be surgical "cures" by standard criteria, yet they apparently continue to harbor prostatic tumor cells. It will be interesting to follow the clinical course of these patients as compared to others without PCR evidence of residual disease.

References of Example 3

1. Boring, C. C., Squires, T. S., and Tong, T.: Cancer Statistics, 1993. CA Cancer J. Clin., 43:7–26, 1993.

2. Lepor, H., and Walsh, P. C.: Long-term results of radical prostatectomy in clinically localized prostate cancer: Experience at the Johns Hopkins Hospital. NCI Monogr., 7:117–122, 1988.

3. Bagshaw, M. A., Cox, R. S., and Ray, G. R.: Status of radiation treatment of prostate cancer at Stanford University. NCI Monogr., 7:47–60, 1988.

4. Thompson, I. M., Rounder, J. B., Teague, J. L., et al.: Impact of routine screening for adenocarcinoma of the prostate on stage distribution. J. Urol., 137:424–426, 1987.

5. Chiarodo, A.: A National Cancer Institute roundtable on prostate cancer; future research directions. Cancer Res., 51:2498–2505, 1991.

6. Wu, A., Ben-Ezra, J., and Colombero, A.: Detection of micrometastasis in breast cancer by the polymerase chain reaction. Lab. Invest., 62:109A, 1990.

7. Fey, M. F., Kulozik, A. E., and Hansen-Hagge, T. E.: The polymerase chain reaction: A new tool for the detection of minimal residual disease in hematological malignancies. Eur. J. Cancer, 27:89–94, 1991.

8. Moreno, J. G., Croce, C. M., Fischer, R., Monne, M., Vihko, P., Mulholland, S. G., and Gomella, L. G.: Detection of hematogenous micrometastasis in patients with prostate cancer. Cancer Res., 52:6110–6112, 1992.

9. Israeli, R. S., Powell, C. T., Fair, W. R., and Heston, W. D. W.: Molecular cloning of a complementary DNA encoding a prostate-specific membrane antigen. Cancer Res., 53:227–230, 1993.

10. Israeli, R. S., Powell, C. T., Corr, J. G., Fair, W. R., and Heston, W. D. W.: Expression of the prostate-specific membrane antigen (PSM).: Submitted to Cancer Research.

11. Horoszewicz, J. S., Leong, S. S., Kawinski, E., Karr, J. P., Rosenthal, H., Chu, T. M., Mirand, E. A., and Murphy, G. P.: LNCaP model of human prostatic carcinoma. Cancer Res., 43:1809–1818, 1983.

12. Soule, H. D., Vazquez, J., Long, A., Albert, S., and Brennan, M.: A human cell line from a pleural effusion derived from a breast carcinoma. J. Natl. Can. Inst., 51:1409–1416, 1973.

13. Hanahan, D.: Studies on transformation of *Escherichia coli* with plasmids. J. Mol. Biol., 166:557–580, 1983.

14. Sanger, F., Nicklen, S., and Coulson, A. R.: DNA sequencing with chain-terminating inhibitors. Proc. Natl. Acad. Sci. USA, 74:5463–5467, 1977.

15. Lundwall, A., and Lilja, H.: Molecular cloning of a human prostate specific antigen cDNA. FEBS Letters, 214:317, 1987.

16. Liotta, L. A., Kleinerman, J., and Saidel, G. M.: Quantitative relationships of intravascular tumor cells, tumor vessels, and pulmonary metastases following tumor implantation. Cancer Res., 34:997–1003, 1974.

Example 4

Expression of the Prostate Specific Membrane Antigen (PSM) Diminishes the Mitogenic Stimulation of Aggressive Human Prostatic Carcinoma Cells by Transferrin An association between transferrin and human prostate cancer has been suggested by several investigators. It has been shown that the expressed prostatic secretions of patients with prostate cancer are enriched with respect to their content of transferrin and that prostate cancer cells are rich in transferrin receptors (J. Urol. 143, 381, 1990).

Transferrin derived from bone marrow has been shown to selectively stimulate the growth of aggressive prostate cancer cells (PNAS 89, 6197, 1992). DNA sequence analysis has revealed that a portion of the coding region, from nucleotide 1250 to 1700 possesses a 54% homology to the human transferrin receptor. PC-3 cells do not express PSM mRNA or protein and exhibit increased cell growth in response to transferrin, whereas, LNCaP prostate cancer cells which highly express PSM have a very weak response to transferrin. To determine whether PSM expression by prostatic cancer cells impacts upon their mitogenic response to transferrin the full-length PSM cDNA was transfected into the PC-3 prostate cancer cells. Clones highly expressing PSM mRNA were identified by Northern analysis and expression of PSM protein was verified by Western analysis using the anti-PSM monoclonal antibody 7E11-C5.3.

$2 \times 10^4$ PC-3 or PSM-transfected PC-3 cells per well ere plated in RPMI medium supplemented with 10% fetal bovine serum and at 24 hrs. added 1 $\mu$g per ml. of holotransferrin to the cells. Cells were counted at 1 day to be highly mitogenic to the PC-3 cells. Cells were counted at 1 day to determine plating efficiency and at 5 days to determine the effect of the transferrin. Experiments were repeated to verify the results.

PC-3 cells experienced an average increase of 275% over controls, whereas the LNCaP cells were only stimulated 43%. Growth kinetics revealed that the PSM-transfected PC-3 cells grew 30% slower than native PC-3 cells. This data suggests that PSM expression in aggressive, metastatic human prostate cancer cells significantly abrogates their mitogenic response to transferrin.

The use of therapeutic vaccines consisting of cytokine-secreting tumor cell preparations for the treatment of established prostate cancer was investigated in the Dunning R3327-MatLyLu rat prostatic adenocarcinoma model. Only IL-2 secreting, irradiated tumor cell preparations were capable of curing animals from subcutaneously established tumors, and engendered immunological memory that protected the animals from another tumor challenge. Immunotherapy was less effective when tumors were induced orthotopically, but nevertheless led to improved outcome, significantly delaying, and occasionally preventing recurrence of tumors after resection of the cancerous prostate. Induction of a potent immune response in tumor bearing animals against the nonimmunogenic MatLyLu tumor supports the view that active immunotherapy of prostate cancer may have therapeutic benefits.

Example 5

Cloning and Characterization of the Prostate Specific Membrane Antigen (PSM) Promoter The expression and regulation of the PSM gene is complex. By immunostaining, PSM antigen was found to be expressed brilliantly in metastasized tumor, and in organ confined tumor, less so in normal prostatic tissue and more heterogenous in BPH. PSM is strongly expressed in both anaplastic and hormone refractory tumors. PSM mRNA has been shown to be down regulated by androgen. Expression of PSM RNA is also modulated by a host of cytokines and growth factors. Knowledge of the regulation of PSM expression should aid in such diagnostic and therapeutic strategies as imunoscintigraphic imaging of prostate cancer and protate-specific promoter-driven gene therapy.

Sequencing of a 3 kb genomic DNA clone that contained 2.5 kb upstream of the transcription start site revealed that two stretches of about 300 b.p. (−260 to −600; and −1325 to −1625) have substantial homology (79–87%) to known genes. The promoter lacks a GC rich region, nor does it have a consensus TATA box. However, it contains a TA-rich region from position −35 to −65.

Several consensus recognition sites for general transcription factors such as AP1, AP2, NFkB, GRE and E2-RE were identified. Chimeric constructs containing fragments of the upstream region of the PSM gene fused to a promoterless chloramphenicol acetyl transferase gene were transfected into, and transiently expressed in LNCaP, PC-3, and SW620 (a colonic cell line). With an additional SV40 enhancer, sequence from −565 to +76 exhibited promoter activity in LNCaP but not in PC-3 nor in SW620.

Materials and Methods

Cell Lines. LNCaP and PC-3 prostatic carcinoma cell lines (American Type Culture Collection) were cultured in RPMI and MEM respectively, supplemented with 5% fetal calf serum at 37° C. and 5% $CO_2$. SW620, a colonic cell line, is a gift from Melisa.

Polymerase Chain Reaction. The reaction was performed in a 50 $\mu$l volume with a final concentration of the following reagents: 16.6 mM $NH_4SO_4$, 67 mM Tris-HCl pH 8.8, acetylated BSA 0.2 mg/ml, 2 mM $MgCl_2$, 250 $\mu$M dNTPs, 10 mM $\beta$-mercaptoethanol, and 1 U of rth 111 Taq polymerase (Boehringer Mannhiem, California). A total of 25 cycles were completed with the following profile: cycle 1, 94° C. 4 min.; cycle 2 through 25, 94° C. 1 min, 60° C. 1 min, 72° C. 1 min. The final reaction was extended for 10 min at 72° C. Aliquots of the reaction were electrophoresed on 1% agarose gels in 1X Tris-acetate-EDTA buffer.

Cloning of PSM promoter. A bacteriophage P1 library of human fibroblast genomic DNA (Genomic Sysytems, Inc., St. Louis, Mich.), was screened using a PCR method of Pierce et al. Primers located at the 5' end of PSM cDNA were used: 5'-CTCAAAAGGGGCCGGATTTCC-3'(see nucleotides 1–21 of SEQ ID NO: 1) and 5'CTCTCAATCTCACTAATGCCTC-3'(see nucleotides 363–384 of SEQ ID NO: 48). A positive clone, p683, was digested with XhoI restriction enzyme. Southern analysis of the restricted fragments using a DNA probe from the extreme 5' to the Ava-1 site of PSM cDNA confirmed that a 3 Kb fragment contains the 5' regulatory sequence of the PSM gene. The 3 kb XhoI fragment was subcloned into pKSBluescrpt vectors and sequenced using the dideoxy method.

Functional Assay of PSM Promoter. Chloramphenicol Acetyl Transferase, (CAT) gene plasmids were constructed from the Sma1-HindIII fragments or subfragements (using either restriction enzyme subfragments or PCR) by insertion into promoterless pCAT basic or pCAT-enhancer vectors (Promega) . pCAT-constructs were cotransfected with pSV$\beta$gal plasmid (5 $\mu$g of each plasmid) into cell lines in duplicates, using a calcium phosphate method (Gibco-BRL, Gaithersburg, Md.). The transfected cells were harvested 72 hours later and assayed (15 $\mu$g of lysate) for CAT activity using the LSC method and for $\beta$gal activity (Promega). CAT activities were standardized by comparision to that of the $\beta$gal activities.

Results

Sequence of the 5' End of the PSM Gene

The DNA sequence of the 3 kb XhoI fragment of p683 which includes 500 bp of DNA from the RNA start site was determined (FIGS. 31A–31D) Sequence 683XFRVS starts from the 5' distal end of PSM promoter, it overlaps with the published PSM putative promoter at nt 2485, i.e. the putative transcription start site is at nt 2485; sequence 683XF107 is the reverse, complement of 683XFRVS). The sequence from the XhoI fragment displayed a remarkable arrays of elements and motifs which are characteristic of eukaryotic promoters and regulatory regions found in other genes (FIG. 32).

Functional Analysis of Upstream PSM Genomic Elements for Promoter Activity

Various pCAT-PSM promoter constructs were tested for promoter activities in two prostatic cell lines: LNCaP, PC-3 and a colonic SW620 (FIG. 33). Induction of CAT activity was neither observed in p1070-CAT which contained a 1070 bp PSM 5' promoter fragment, nor in p676-CAT which contained a 641 bp PSM 5' promoter fragment. However, with an additional SV-40 enhancer, sequence from −565 to +76 (p676-CATE) exhibited promoter activity in LNCaP but not in PC-3 nor in SW620.

Therefore, a LNCaP specific promoter fragment from −565 to +76 has been isolated which can be used in PSM promoter-driven gene therapy.

Example 6

Alternatively Spliced Variants of Prostate Specific Membrane Antigen RNA: Ratio of Expression as a Potential Measurement of Progression Materials and Methods Cell Lines. LNCaP and PC-3 prostatic carcinoma cell lines were cultured in RPMI and MEM respectively, supplemented with 5% fetal calf serum at 37° C. and 5% $CO_2$.

Primary tissues. Primary prostatic tissues were obtained from MSKCC's in-house tumor procurement service. Gross specimen were pathologically staged by MSKCC's pathology service.

RNA Isolation. Total RNA was isolated by a modified guanidinium thiocynate/phenol/chloroform method using a RNAzol B kit (Tel-Test, Friendswood, Tex.). RNA was stored in diethyl pyrocarbonate-treated water at −80° C. RNA was quantified using spectrophometric absorption at 260 nm.

cDNA synthesis. Two different batches of normal prostate mRNAs obtained from trauma-dead males (Clontech, Palo Alto, Calif.) were denatured at 70° C. for 10 min., then reverse transcribed into cDNA using random hexamers and Superscript II reverse transcriptase (GIBCO-BRL, Gaithersburg, Md. ) at 50° C. for 30 min. followed by a 94° C. incubation for 5 min.

Polymerase Chain Reaction. Oligonucleotide primers (5'-CTCAAAAGGGGCCGGATTTCC-3' and 5'-AGGCTACTTCACTCAAAG-3'), specific for the 5' and 3'ends of PSM cDNA were designed to span the cDNA sequence. The reaction was performed in a 50 μl volume with a final concentration of the following reagents: 16.6 mM $NH_4SO_4$, 67 mM Tris-HCl pH 8.8, acetylated BSA 0.2 mg/ml, 2 mM $MgCl_2$, 250 μM dNTPs, 10 mM β-mercaptoethanol, and 1 U of rTth polymerase (Perkin Elmer, Norwalk, Conn.). A total of 25 cycles were completed with the following profile: cycle 1, 94° C. 4 min.; cycle 2 through 25, 94° C. 1 min, 60° C. 1 min, 72° C. 1 min. The final reaction was extended for 10 min at 72° C. Aliquots of the reaction were electrophoresed on 1% agarose gels in 1X Trisacetate-EDTA buffer.

Cloning of PCR products. PCR products were cloned by the TA cloning method into pCRII vector using a kit from Invitrogen (San Diego, Calif.). Ligation mixture were transformed into competent *Escherichia coli* Inv5α.

Sequencing. Sequencing was done by the dideoxy method using a sequenase kit from US Biochemical (Cleveland, Ohio). Sequencing products were electrophoresed on a 5% polyacrylamide/7 M urea gel at 52° C.

RNase Protection Assays. Full length PSM cDNA clone was digested with NgoM 1 and Nhe1. A 350 b.p. fragment was isolated and subcloned into pSPORT1 vector (GIBCO-BRL, Gaithersburg, Md.). The resultant plasmid, pSP350, was linearized, and the insert was transcribed by SP6 RNA polymerase to yield antisense probe of 395 nucleotide long, of which 355 nucleotides and/or 210 nucleotides should be protected from RNAse digestion by PSM or PSM' RNA respectively (FIG. 2). Total celluar RNA (20 μg) from different tissues were hybridized to the aforementioned antisense RNA probe. Assays were performed as described (7). tRNA was used as negative control. RPAs for LNCaP and PC-3 were repeated.

Results

RT-PCR of mRNA from normal prostatic tissue. Two independent RT-PCR of mRNA from normal prostates were performed as described in Materials and Methods. Subsequent cloning and sequencing of the PCR products revealed the presence of an alternatively spliced variant, PSM'. PSM' has a shorter cDNA (2387 nucleotides) than PSM (2653 nucleotides). The results of the sequence analysis are shown in FIG. 34. The cDNAs are identical except for a 266 nucleotide region near the 5' end of PSM cDNA (nucleotide 114 to 380) that is absent in PSM' cDNA. Two independent repetitions of RT-PCR of different mRNA samples yielded identical results.

RNase Protection Assays. An RNA probe complementary to PSM RNA and spanning the 3'splice junction of PSM' RNA was used to measure relative expression of PSM and PSM' mRNAs (FIG. 35). With this probe, both PSM and PSM' RNAs in LNCaP cells was detected and the predominant form was PSM. Neither PSM nor PSM' RNA was detected in PC-3 cells, in agreement with previous Northern and Western blot data (5, 6). FIG. 36 showed the presence of both splice variants in human primary prostatic tissues. In primary prostatic tumor, PSM is the dominant form. In contrast, normal prostate expressed more PSM' than PSM. BPH samples showed about equal expression of both variants.

Tumor Index. The relative expression of PSM and PSM' (FIG. 36) was quantified by densitometry and expressed as a tumor index (FIG. 37). LNCaP has an index ranging from 9–11; CaP from 3–6; BPH from 0.75 to 1.6; normal prostate has values from 0.075 to 0.45.

Discussion

Sequencing data of PCR products derived from human normal prostatic mRNA with 5' and 3'end PSM oligonucleotide primers revealed a second splice variant, PSM', in addition to the previously described PSM cDNA.

PSM is a 750 a.a. protein with a calculated molecular weight of 84,330. PSM was hypothesized to be a type II integral membrane protein (5). A classic type II membrane protein is the transferrin receptor and indeed PSM has a region that has modest homology with the transferrin receptor (5). Analysis of the PSM amino acid sequence by either the methods of Rao and Argos (7) or Eisenburg et. al. (8) strongly predicted one transmembrane helix in the region from a.a.#20 to #43. Both programs found other regions that could be membrane associated but were not considered likely candidates for being transmembrane regions.

PSM' antigen, on the other hand, is a 693 a.a. protein as deduced from its mRNA sequence with a molecular weight of 78,000. PSM' antigen lacks the first 57 amino acids present in PSM antigen (FIG. 34). It is likely that PSM' antigen is cytosolic.

The function of PSM and PSM' are probably different. The cellular location of PSM antigen suggests that it may interact with either extra- or intra-cellular ligand(s) or both; while that of PSM' implies that PSM' can only react with cytosolic ligand(s). Furthermore, PSM antigen has 3 potential phosphorylation sites on its cytosolic domain. These sites are absent in PSM' antigen. On the other hand, PSM' antigen has 25 potential phosphorylation sites, 10 N-myristoylation sites and 9 N-glycosylation sites. For PSM antigen, all of these potential sites would be on the extra-cellular surface. The modifications of these sites for these homologous proteins would be different depending on their cellular locations. Consequently, the function(s) of each form would depend on how they are modified.

The relative differences in expression of PSM and PSM' by RNase protection assays was analyzed. Results of expression of PSM and PSM' in primary prostatic tissues strongly suggested a relationship between the relative expression of these variants and the status of the cell: either normal or cancerous. While it is noted here that the sample size of the study is small (FIGS. 36 and 37), the consistency of the trend is evident. The samples used were gross specimens from patients. The results may have been even more dramatic if specimens that were pure in content of CaP, BPH or normal had been used. Nevertheless, in these specimens, it is clear that there is a relative increase of PSM over PSM' mRNA in the change from normal to CaP. The Tumor Index (FIG. 37) could be useful in measuring the pathologic state of a given sample. It is also possible that the change in expression of PSM over PSM' may be a reason for tumor progression. A more differentiated tumor state may be restored by PSM' either by transfection or by the use of differentiation agents.

References of Example 6

1. Murphy, G. P. Report on the American Urologic Association/American Cancer Society Scientific Seminar on the Detection and treatment of Early-Stage Prostate Cancer. CA Cancer J. Clin. 44:91–95, 1994.

2. Israeli, R. S., Miller Jr., W. H., Su, S. L., Powell, C. T., Fair, W. R., Samadi, D. S., Huryk, R. F., DelBlasio, A., Edwards, E. T, and Heston, W. D. W. Sensitive Nested Reverse Transcription Polymerase Chain Reaction Detection of Circulating Prostatic Tumor Cells: Comparision of Prostate-specific Membrane Antigen and Prostate-specific Antigen-based Assays. Cancer Res., 54:6325–6329, 1994.

3. Horoszewicz, J. S., Kawinski, E., and Murphy, G. P. Monoclonal antibodies to a new antigenic marker in epithelial cells and serum of prostatic cancer patients. Anticancer Res., 7:927–936, 1987.

4. Horoszewicz, J. S., Leong, S. S., Kawinski, E., Karr, J. P., Rosenthal, H., Chu, T. M., Mirand, E. A. and Murphy, G. P. LNCaP model of human prostatic Carcinoma. Cancer Res., 43:1809–1818, 1983.

5. Israeli, R. S., Powell, C. T., Fair, W. R. and Heston, W. D. W. Molecular cloning of a complementary DNA encoding a prostate-specific membrane antigen. Cancer Res., 53:227–230, 1993.

6. Israeli, R. S., Powell, C. T., Corr, J. G., Fair, W. R. and Heston, W. D. W. Expression of the prostate-specific membrane antigen. Cancer Res., 54:1807–1811, 1994.

7. Melton, D. A., Krieg, P. A., Rebagliati, M. R., Maniatis, T., Zinn, K. and Green, M. R. Efficient in vitro synthesis of biologically active RNA and RNA hybridization probes from plasmids containing a bacteriophage SP6 promoter. Nucleic Acids Res., 12:7035–7056, 1984.

8. Rao, M. J. K. and Argos, P. A conformational preference parameter to predict helices in integral membrane proteins. Biochim. Biophys. Acta, 869:197–214, 1986.

9. Eisenburg, D., Schwarz, E., Komaromy, M. and Wall, R. Analysis of membrane and surface protein sequences with the hydrophbic moment plot, J. Mol. Biol. 179:125–142, 1984.

10. Troyer, J. K. and Wright Jr., G. L. Biochemical characterization and mapping of 7E-11 C-5.3. Epitope of the prostate specific membrane antigen (PSMA). American Association for Cancer Research Special Conference: Basic and Clinical Aspect of Prostate Cancer. Abstract C-38, 1994.

Example 7

Enhanced Detection of Prostatic Hematogenous Micrometasases with PSM Primers as Compared to PSA Primers Using a Sensitive Nested Reverse Transcriptase-PCR Assay 77 randomly selected samples were analyzed from patients with prostate cancer and reveals that PSM and PSA primers detected circulating prostate cells in 48 (62.3%) and 7 (9.1%) patients, respectively. In treated stage D disease patients, PSM primers detected cells in 16 of 24 (66.7%), while PSA primers detected cells in 6 of 24 patients (25%). In hormone-refractory prostate cancer (stage D3), 6 of 7 patients were positive with both PSA and PSM primers. All six of these patients died within 2–6 months of their assay, despite aggressive cytotoxic chemotherapy, in contrast to the single patient that tested negatively in this group and is alive 15 months after his assay, suggesting that PSA-PCR positivity may serve as a predictor of early mortality. In post-radical prostatectomy patients with negative serum PSA values, PSM primers detected metastases in 21 of 31 patients (67.7%), while PSA primers detected cells in only 1 of 33 (3.0%), indicating that micrometastatic spread may be a relatively early event in prostate cancer. The analysis of 40 individuals without known prostate cancer provides evidence that this assay is highly specific and suggests that PSM expression may predict the development of cancer in patients without clinically apparent prostate cancer. Using PSM primers, micrometastases were detected in 4 of 40 controls, two of whom had known BPH by prostate biopsy and were later found to have previously undetected prostate cancer following repeat prostate biopsy performed for a rising serum PSA value. These results show the clinical significance of detection of hematogenous micrometastatic prostate cells using PSM primers and potential applications of this molecular assay, as well as the assay for PSA.

Example 8

Modulation of Prostate Specific Membrane Antigen (PSM) Expression in vitro by Cytokines and Growth Factors The effectiveness of CYT-356 imaging is enhanced by manipulating expression of PSM. PSM mRNA expression is downregulated by steroids. This is consistent with the clinical observations that PSM is strongly expressed in both anaplastic and hormone refractory lesions. In contrast, PSA expression is decreased following hormone withdrawal. In hormone refractory disease, it is believed that tumor cells may produce both growth factors and receptors, thus establishing an autocrine loop that permits the cells to overcome normal growth constraints. Many prostate tumor epithelial cells express both TGFα and its receptor, epidermal growth factor receptor. Results indicate that the effects of TGFα and other selected growth factors and cytokines on the expression of PSM in-vitro, in the human prostatic carcinoma cell line LNCaP.

$2 \times 10^6$ LNCaP cells growing in androgen-depleted media were treated for 24 to 72 hours with EGF, TGFα, TNFβ or TNFα in concentrations ranging from 0.1 ng/ml to 100 ng/ml. Total RNA was extracted from the cells and PSM mRNA expression was quantitated by Northern blot analysis and laser densitometry. Both b-FGF and TGFα yielded a dose-dependent 10-fold upregulation of PSM expression, and EGF a 5-fold upregulation, compared to untreated LNCaP. In contrast, other groups have shown a marked downregulation in PSA expression induced by these growth factors in this same in-vitro model. TNFα, which is cytotoxic to LNCaP cells, and TNFβ downregulated PSM expression 8-fold in androgen depleted LNCaP cells.

TGFα is mitogenic for aggressive prostate cancer cells. There are multiple forms of PSM and only the membrane form is found in association with tumor progression. The ability to manipulate PSM expression by treatment with cytokines and growth factors may enhance the efficacy of Cytogen 356 imaging, and therapeutic targeting of prostatic metastases.

Example 9

Neoadjuvant Androgen-Deprivation Therapy (ADT) Prior to Radical Prostatectomy Results in a Significantly Decreased Incidence of Residual Micrometastatic Disease as Detected by Nested RT-PCT with Primers Radical prostatectomy for clinically localized prostate cancer is considered by many the "gold standard" treatment. Advances over the past decade have served to decrease morbidity dramatically. Improvements intended to assist clinicians in better staging patients preoperatively have been developed, however the incidence of extra-prostatic spread still exceeds 50%, as reported in numerous studies. A phase III prospective randomized clinical study designed to compare the effects of ADT for 3 months in patients undergoing radical prostatectomy with similarly matched controls receiving surgery alone was conducted. The previously completed phase II study revealed a 10% margin positive rate in the ADT group (N=69) as compared to a 33% positive rate (N=72) in the surgery alone group.

Patients who have completed the phase III study were analyzed to determine if there are any differences between the two groups with respect to residual micrometastatic disease. A positive PCR result in a post-prostatectomy patient identifies viable metastatic cells in the circulation.

Nested RT-PCR was performed with PSM primers on 12 patients from the ADT group and on 10 patients from the control group. Micrometastatic cells were detected in 9/10 patients (90%) in the control group, as compared to only 2/12 (16.7%) in the ADT group. In the ADT group, 1 of 7 patients with organ-confined disease tested positively, as compared to 3 of 3 patients in the control group. In patients with extra-prostatic disease, 1 of 5 were positive in the ADT group, as compared to 6 of 7 in the control group. These results indicate that a significantly higher number of patients may be rendered tumor-free, and potentially "cured" by the use of neoadjuvant ADT.

Example 10

Sensitive Nested RT-PCR Detection of Circulation Protstatic Tumor Cells—Comparison of PSM and PSA-based Assays Despite the improved and expanded arsenal of modalities available to clinician today, including sensitive serum PSA assays, CT scan, transrectal ultrasonography, endorectal co.I MRI, etc., many patients are still found to have metastatic disease at the time of pelvic lymph node dissection and radical prostatectomy. A highly sensitive reverse transcription PCR assay capable of detecting occult hematogenous micrometastatic prostatic cells that would otherwise go undetected by presently available staging modalities was developed. This assay is a modification of similar PCR assays performed in patients with prostate cancer and other malignancies[2,3,4,5]. The assay employs PCR primers derived from the cDNA sequences of prostate-specific antigen[6] and the prostate-specific membrane antigen recently cloned and sequenced.

Materials and Methods

Cells and Reagents. LNCaP and MCF-7 cells were obtained from the American Type Culture Collection (Rockville, Md.). Details regarding the establishment and characteristics of these cell lines have been previously published[8,9]. Cells grown in RPMI 1640 medium and supplemented with L-glutamine, nonessential amino acids, and 5% fetal calf serum (Gibco-BRL, Gaithersburg, Md.) In a 5% $CO_2$ incubator at 37° C. All cell media was obtained from the MSKCC Media Preparation Facility. Routine chemical reagents were of the highest grade possible and were obtained from Sigma Chemical Company (St. Louis, Mo.).

Patient Blood Specimens. All blood specimens used in this study were from patients seen in the outpatient offices of urologists on staff at MSKCC. Two anti-coagulated tubes per patient were obtained at the time of their regularly scheduled blood draws. Specimens were obtained with informed consent of each patient, as per a protocol approved by the MSKCC Institutional Review Board. Samples were promptly brought to the laboratory for immediate processing. Seventy-seven specimens from patients with prostate cancer were randomly selected and delivered to the laboratory "blinded" along with samples from negative controls for processing. These included 24 patients with stage D disease (3 with $D_0$, 3 with $D^1$, 11 with $D^2$, and 7 with $D^3$), 31 patients who had previously undergone radical prostatectomy and had undetectable postoperative serum PSA levels (18 with pT2 lesions, 11 with pT3, and 2 pT4), 2 patients with locally recurrent disease following radical prostatectomy, 4 patients who had received either external beam radiation therapy or interstitial $1^{125}$ implants, 10 patients with untreated clinical stage T1–T2 disease, and 6 patients with clinical stage T3 disease on anti-androgen therapy. The forty blood specimens used as negative controls were from 10 health males, 9 males with biopsy-proven BPH and elevated serum PSA levels, 7 healthy females, 4 male patients with renal cell carcinoma, 2 patients with prostatic intraepithelial neoplasia (PIN), 2 patients with transitional cell carcinoma of the bladder and a pathologically normal prostate, 1 patient with acute prostatitis, 1 patient with acute promyelocytic leukemia, 1 patient with testicular cancer, 1 female patient with renal cell carcinoma, 1 patient with lung cancer, and 1 patient with a cyst of the testicle.

Blood Sample Processing/RNA Extraction. 4 ml of whole anticoagulated venous blood was mixed with 3 ml of ice cold PBS and then carefully layered atop 8 ml of Ficoll (Pharmacia, Uppsala, Sweden) in a 14-ml polystyrene tube. Tubes were centrifuged at 200×g for 30 min. at 4° C. The buffy coat layer (approx. 1 ml.) was carefully removed and rediluted to 50 ml with ice cold PBS in a 50 ml polypropylene tube. This tube was then centrifuged at 2000×g for 30 min. at 4° C. The supernatant was carefully decanted and the pellet was allowed to drip dry. One ml of RNazol B was then added to the pellet and total RNA was isolated as per manufacturers directions (Cinna/Biotecx, Houston, Tex.) RNA concentrations and purity were determined by UV spectroscopy on a Beckman DU 640 spectrophotometer and by gel analysis.

Determination of PCR Sensitivity. RNA was isolated from LNCaP cells and from mixtures of LNCaP and MCF-7 cells at fixed ratios (i.e. 1:100, 1:1,000, etc.) using RNAzol B. Nested PCR was then performed as described below with both PSA and PSM primers in order to determine the limit of detection for the assay. LNCaP:MCF-7 (1:100,000) cDNA was diluted with distilled water to obtain concentrations of 1:1,000,000. The human breast cancer cell line MCF-7 was chosen because they had previously been tested by us and shown not to express either PSM nor PSA by both immunohistochemistry and conventional and nested PCR.

Polymerase Chain Reaction. The PSA outer primer sequences are nucleotides 494–513 (sense) in exon 4 and nucleotides 960–979 (anti-sense) in exon 5 of the PSA cDNA. These primers yield a 486 bp PCR product from PSA CDNA that can be distinguished from a product synthesized from possible contaminating genomic DNA.

PSA-494 5'-TAC CCA CTG CAT CAG GAA CA-3'
PSA-960 5'-CCT TGA AGC ACA CCA TTA CA-3'

The PSA inner upstream primer begins at nucleotide 559 and the downstream primer at nucleotide 894 to yield a 355 bp PCR product.

PSA-559 5'-ACA CAG GCC AGG TAT TTC AG-3'
PSA-894 5'-GTC CAG CGT CCA GCA CAC AG-3'

All primers were synthesized by the MSKCC Microchemistry Core Facility. 5 $\mu$g of total RNA was reverse-transcribed into cDNA using random hexamer primers (Gibco-BRL) and Superscript II reverse transcriptase (Gibco-BRL) according to the manufacturers recommendations. 1 $\mu$l of this CDNA served as the starting template for the outer primer PCR reaction. The 20 $\mu$l PCR mix included: 0.5 U Taq polymerase (Promega) Promega reaction buffer, 1.5 mM $MgCl_2$, 200 $\mu$M dNTPs, and 1.0 $\mu$M of each primer. This mix was then transferred to a Perkin Elmer 9600 DNA thermal cycler and incubated for 25 cycles. The PCR profile was as follows: 94° C.×15 sec., 60° C.×15 sec., and 72° C. for 45 sec. After 25 cycles, samples were placed on ice, and 1 $\mu$l of this reaction mix served as the template for another 25 cycles using the inner primers. The first set of tubes were returned to the thermal cycler for 25 additional cycles. The PSM outer upstream primer sequences are nucleotides 1368–1390 and the downstream primers are nucleotides 1995–2015, yielding a 67 bp PCR product.

PSM-1368 5'-CAG ATA TGT CAT TCT GGG AGG TC-3'
PSM-2015 5'-AAC ACC ATC CCT CCT CGA ACC-3'

The PSM inner upstream primer span nucleotides 1689–1713 and the downstream primer span nucleotides 1899–1923, yielding a 234 bp PCR product.

PSM-1689 5'-CCT AAC AAA AGA GCT GAA AAG CCC-3'
PSM-1923 5'-ACT GTG ATA CAG TGG ATA GCC GCT-3'

2 $\mu$l of cDNA was used as the starting DNA template in the PCR assay. The 50 $\mu$l PCR mix included: 1 U Taq polymerase (Boehringer Mannheim), 250 $\mu$M cNTPs, 10 mM $\beta$-mercaptoethanol, 2 mM $MgCl_2$, and 5 l of a 10x buffer mix containing: 166 mM $NH_4SO_4$, 670 mM Tris pH 8.8, and 2 mg/ml of acetylated BSA. PCR was carried out in a Perkin Elmer 480 DNA thermal cycler with the following parameters: 94° C.×4 minutes for 1 cycle, 94° C.×30 sec., 58° C.×1 minute, and 72° C.×1 minute for 25 cycles, followed by 72° C.×10 minutes. Samples were then iced and 2.5 $\mu$l of this reaction mix was used as the template for another 25 cycles with a new reaction mix containing the inner PSM primers. cDNA quality was verified by performing control reactions using primers derived from the $\beta$-2-microglobulin gene sequence[10] a ubiquitous housekeeping gene. These primers span exons 2–4 and generate a 620 bp PCR product. The sequences for these primers are:

$\beta$-2 (exon 2) 5'-AGC AGA GAA TGG AAA GTC AAA-3'
$\beta$-2 (exon 4) 5'-TGT TGA TGT TGG ATA AGA GAA-3'

The entire PSA mix and 7–10 $\mu$l of each PSM reaction mix were run on 1.5–2% agarose gels, stained with ethidium bromide and photographed in an Eage Eye Video Imaging System (Statagene, Torrey Pines, Calif.). Assays were repeated at least twice to verify results.

Cloning and Sequencing of PCR Products. PCR products were cloned into the pCR II plasmid vector using the TA cloning system (Invitrogen). These plasmids were transformed into competent *E. coli* cells using standard methods[11] and plasmid DNA was isolated using Magic Minipreps (Promega) and screened by restriction analysis. Double-stranded TA clones were then sequenced by the dideoxy method[12] using $^{35}$S-cCTP (NEN) and Sequenase (U.S. Biochemical). Sequencing products were then analyzed on 6% polyacrilamide/7 M urea gels, which were fixed, dried, and autoradiographed as described.

Southern Analysis. PCR products were transferred from ethidium-stained agarose gels to Nytran nylon membranes (Schletcher and Schuell) by pressure blotting with a Posi-blotter (Stratagene) according to the manufacturer's instructions. DNA was cross-linked to the membrane using a UV Stratalinker (Stratagene). Blots were pre-hybridized at 65° C. for 2 hours and subsequently hybridized with denatured $^{32}$P-labeled, random-primed[13] cDNA probes (either PSA or PSM).[6,7] Blots were washed twice in 1xSSC/0.5% SDS at 42° C. and twice in 0.1xSSC/0.1% SDS at 50° C. for 20 minutes each. Membranes were air-dried and autoradiographed for 1–3 hours at room temperature with Hyperfilm MP (Amersham).

Results

PSA and PSM Nested PCR Assays: The application of nested PCR increased the level of detection from an average of 1:10,000 using outer primers alone, to better than 1:1,000,000. Dilution curves demonstrating this added sensitivity are shown for PSA and PSM-PCR in FIGS. 1 and 2 respectively. FIG. 1 shows that the 486 bp product of the PSA outer primer set is clearly detectable with ethidium staining to 1:10,000 dilutions, whereas the PSA inner primer 355 bp product is clearly detectable in all dilutions shown. In FIG. 2 the PSM outer primer 647 bp product is also clearly detectable in dilutions to only 1:10,000 with conventional PCR, in contrast to the PSM inner nested PCR 234 bp product which is detected in dilutions as low as 1:1,000,000. Southern blotting was performed on all controls and most of the patient samples in order to confirm specificity. Southern blots of the respective dilution curves confirmed the primer specificities but did not reveal any significantly increased sensitivity.

PCR in Negative Controls: Nested PSA and PSM PCR was performed on 40 samples from patients and volunteers as described in the methods and materials section. FIG. 48 reveals results from 4 representative negative control specimens, in addition to a positive control. Each specimen in the study was also assayed with the $\beta$-2-microglobulin control, as shown in the figure, in order to verify RNA integrity. Negative results were obtained on 39 of these samples using the PSA primers, however PSM nested PCR yielded 4 positive results. Two of these "false positives" represented patients with elevated serum PSA values and an enlarged prostate who underwent a transrectal prostate biopsy revealing stromal and fibromuscular hyperplasia. In both of these patients the serum PSA level continued to rise and a repeat prostate biopsy performed at a later date revealed prostate cancer. One patient who presented to the clinic with a testicular cyst was noted to have a positive PSM nested PCR result which has been unable to explain. Unfortunately, this patient never returned for follow up, and thus have not been able to obtain another blood sample to repeat this assay. Positive result were obtained with both PSA and PSM primers in a 61 year old male patient with renal cell carcinoma. This patient has a normal serum PSA level and a normal digital rectal examination. Overall, if we exclude the two patients in whom a positive PCR, but no other clinical test, accurately predicted the presence of prostate cancer, 36/38 (94.7%) of the negative controls were negative with PSM primers, and 39/40 (97.5%) were negative using PSA primers.

Patient Samples: In a "blinded" fashion, in which the laboratory staff were unaware of the nature of each specimen, 117 samples from 77 patients mixed randomly with 40 negative controls were assayed. The patient samples represented a diverse and heterogeneous group as described earlier. Several representative patient samples are displayed in FIG. 49, corresponding to positive results from patients with both localized and disseminated disease. Patients 4 and 5, both with stage D prostate cancer exhibit positive results with both the outer and inner primer pairs, indicating a large circulating tumor cell burden, as compared to the other samples. Although the PSM and PSA primers yielded similar sensitivities in LNCaP dilution curves as previously shown, PSM primers detected micrometastases in 62.3% of the patient samples, whereas PSA primers only detected 9.1%. In patients with documented metastatic prostate cancer (stages $D_0$–$D_3$) receiving anti-androgen treatment, PSM primers detected micrometastases in 16/24 (66.7%), whereas PSA primers detected circulating cells in only 6/24 (25%). In the study 6/7 patients with hormone-refractory prostate cancer (stage $D_3$) were positive. In the study, PSA primers revealed micrometastatic cells in only 1/15 (6.7%) patients with either pT3 or pT4 (locally-advanced) prostate cancer following radical prostatectomy. PSM primers detected circulating cells in 9/15 (60%) of these patients. Interestingly, circulating cells 13/18 (72.2%) patients with pT2 (organ-confined) prostate cancer following radical prostatectomy using PSM primers was detected. None of these patient samples were positive by PSA-PCR.

Improved and more sensitive method for the detection of minimal, occult micrometastic disease have been reported for a number of malignancies by use of immunohistochemical methods (14), as well as the polymerase chain reaction (3, 4, 5). The application of PCR to detect occult hematogenous micrometastases in prostate cancer was first described by Moreno, et al. (2) using conventional PCR with PSA-derived primers.

When human prostate tumors and prostate cancer cells in-vitro were studied by immunohistochemistry and mRNA analysis, PSM appeared to be highly expressed in anaplastic cells, hormone-refractory cells, and bony metastases (22, 23, 24), in contrast to PSA. If cells capable of hematogenous micrometastasis represent the more aggressive and poorly-differentiated cells, they may express a higher level of PSM per cell as compared to PSA, enhancing their detectibility by RT-PCR.

Nested RT-PCR assays are both sensitive and specific. Results have been reliably reproduced on repeated occasions. Long term testing of both cDNA and RNA stability is presently underway. Both assays are capable of detecting one prostatic cell in at least one million non-prostatic cells of similar size. This confirms the validity of the comparison of PSM vs. PSA primers. Similar levels of PSM expression in both human prostatic cancer cells in-vivo and LNCaP cells in-vitro resulted. The specificity of the PSM-PCR assay was supported by the finding that two "negative control" patients with positive PSM-PCR results were both subsequently found to have prostate cancer. This suggests an exciting potential application for this technique for use in cancer screening. In contrast to recently published data (18), significant ability for PSA primers to accurately detect micrometastatic cells in patients with pathologically with pathologically organ-confined prostate cancer, despite the sensitivity of the assay failed to result. Rather a surprisingly high percentage of patients with localized prostate cancer that harbor occult circulating prostate cells following "curative" radical prostatectomy results which suggests that micrometastasis is an early event in prostate cancer.

The application of this powerful new modality to potentially stage and/or follow the response to therapy in patients with prostate cancer certainly merits further investigation. In comparison to molecular detection of occult tumor cells, present clinical modalities for the detection of prostate cancer spread appear inadequate.

References for Example 10

1. Boring, C. C., Squires, T. S., Tong, T., and Montgomery, S. Cancer Statistics, 1994. CA., 44:7–26, 1994.

2. Moreno, J. G., Croce, C. M., Fischer, R., Monne, M., Vihko, P., Mulholland, S. G., and Gomella, L. G., Detection of hematogenous micrometastasis in patients with prostate cancer. Cancer Res., 52:6110–6112, 1992.

3. Wu, A., Ben-Ezra, J., and Colombero, A.: Detection of micrometastasis in breast cancer by the polymerase chain reaction. Lab. Ivest., 62:109A, 1990.

4. Fey, M. F., Kulozik, A. E., and Hansen-Hagge, T. E.: The polymerase chain reactipn: A new tool for the detection of minimal residual disease in hematological malignacies. Eur. J. Cancer, 27:89–94, 1991.

5. Miller, W. H., Jr., Levine, K., DeBlasio, A., Frankel, S. R., Dmitrovsky, E., and Warrell, R. P., Jr. Detection of mininal residual disease in Acute Promyelocytic Leukemia by a reverse transcription polymerase chain reaction assay for th PML/RAR-α fusion mRNA. Blood, 82:1689–1694, 1993.

6. Lundwall, A., and Lilja, H: Molecular cloning of a human prostate specific antigen cDNA. FEBS Letters, 214:317, 1987.

7. Isaeli, R. S., Powell, C. T., Fair, W. R., and Heston, W. D. W.: Molecular cloning of a complementary DNA encoding a prostate-specific membran antigen. Cancer Res., 53:227–230, 1993.

8. Horoszewicz, J. S., Leong, S. S., Kawinski, E., Karr, J. P., Rosenthal, H., Chu, T. M., Mirand, E. A., and Murphy, G. P.: LNCaP model of human prostactic carcinoma. Cancer Res., 43:1809–1818, 1983.

9. Soule, H. D., Vazquez, J., Long, A., Albert, S., and Brennan, M.: A human cell line from a pleural effusion derived from a breast carcinoma. J. Natl. Can. Inst., 51:1409–1416, 1973.

10. Gussow, D., Rein, R., Ginjaar, I., Hochstenbach, F., Seemann, G., Kottman, A., Ploegh, H. L. The human β-2-Microglobulin gene. Primary structure and definition of the transcriptional unit. J. of Immunol. 139:3132–3138, 1987.

11. Hanahan, D.: Studies on transformation of *Escherichia coli* with plasmids. J. Mol. Biol., 166:557–580, 1983.

12. Sanger, F., Nicklen, S., and Coulson, A. R.: DNA sequncing with chain-terminating inhibitors. Proc. Natl. Acad. Sci. USA, 74:5463–5467, 1977.

13. Feinberg, A. P., and Vogelstein, B. A technique for radiolabeling DNA restriction endonuclease fragments to high specific activity. Anal. Biochem., 132:6—13, 1983.

14. Oberneder, R., Riesenberg, R., Kriegmair, M., Bitzer, U., Klammert, R., Schneede, P., Hofstetter, A., Riethmuller, G., and Pantel, K. Immunocytochemcical detection and phenytypic characterization of micrometastatic tumour cells in bone marrow of patients with prostate cancer. Urol. Res. 22:3–8, 1994.

15. Israeli, R. S., Miller, W. H., Jr., Su, S. L., Samadi, D. S., Powell, C. T., Heston, W. D. W., Wise, G. J., and Fair, W. R. Sensitive detection of prostatic hematogenous micrometastases using prostate-specific antigen (PSA) and prostate-specific membran antigen (PSM) derived primers in the polymerase chain reaction. J. Urol. 151:373A, 1994.

16. Israeli, R. S., Miller, W. H., Jr., Su, S. L, Samadi, D. S., Powell, C. T. Heston, W. D. W., Wise, G. J., and Fair, W. S. Sensitive detection of prostatic hematogenous micrometastases using PsA and PSM-derived primers in the polymerase chain reaction. In press—J. Urology.

17. Vessella, R., Stray, J., Arman, E., Ellis, W., and Lange, P. Reverse transcription polymerase chain reaction (RT-PCR) detects metastatic prostate cancer cells in lymph nodes, blood and potentially bone marrow using PSA-mRNA as template, J. Urol. 151:412A, 1994.

18. Katz, A. E., Olsson, C. A., Raffo, A. J., Cama, C., Perlman, H., Seaman, E., O'Toole, K. M., McMahon, D., Benson, M., and Buttyan, R., Molecular staging of prostate cancer with the use of an enhanced reverse transcriptase-PCR assay. Urology 43:765–775, 1994.

19. Wood, D. P., Jr., Banks, E. R., Humphries, S., McRoberts, J. W., and Rangenkar, V. M. Identification of micrometastases in paitents with prostate cancer. J. Urol. 151:303A, 1994.

20. Deguchi, T., Doi, T., Ehara, H., Ito, S., Takahashi, Y., Nishino, Y., Fujihiro, S., Kawamura, T., Komeda, H., Horie, M., Kaji, H., Shimokawa, K., Tanaka, T., and Kawada, Y. Detection of micrometastic prostate cancer cells in lymph nodes by reverse-transcriptase polymerase chain reaction. Cancer Res. 53:5350–4, 1993.

21. Ghossein, R., Scher, H., Gerald, W., Hoffman, A., Kelley, W., Curely, T., Libertz, C., and Rosai, J. Detection of cirulating tumor cells in peripheral blood of patients with advanced prostatic carcinoma. Proc. Amer. Soc. of Clin. Oncol., 13:237, 1994.

22. Israeli, R. S., Powel, C. T., Corr, J. G., Fair, W. R., and Heston, W. D. W.: Expression of the prostate-specific membrane antigen. Cancer Res., 54:1807–1811, 1994.

23. Axelrod, H. R., Gilman, S. C., D'Aleo, C. H. Petrylak, D., Reuter, V., Gulfo, J. V., Saad A., Cordon-Cardo, C., and Scher, H. I. Preclinical results and human immunohistochemical strudies with $^{90}$Y-CYT-356: a new prostatic cancer therapeutic agent. J.Urol., 147:361A, 1992.

24. Wright, G. L., Jr., Haley, C., Beckett, M. L., and Schellhammer, P. F. Expression of the prostate biomaker 7E11-C5 in primary and metastic prostate carcinoma. Proc. Amer. Ass. for Can. Res. 35:233, 1994.

25. Liotta, L. A., Kleinerman, J., and Saidel, G. M.: Quantitative relationships of intravascular tumor cells, tumors vessels, and pulmonary metastases following tumore implantation. Cancer Res., 34:997–1003, 1974.

Example 11

Chromosomal Localization of Cosmid Clones 194 and 683 by Fluouresence in-situ Hybridization PSM was initially mapped as being located on chromosome 11p11.2-p13 (FIGS. 51–54). Further information from the CDNA in-situ hybridizations experiments demonstrated as much hybridization on the q as p arms. Much larger fragments of genomic DNA was obtained as cosmids and two of these of about 60 kilobases each one going 3'and the other 5' both demonstrated binding to chromosome 11 p and q under low stringency. However under higher stringency conditions only the binding at 11q14-q21 remained. This result suggests that there is another gene on 11p that is very similar to PSM because it is so strongly binding to nearly 120 kilobases of genomic DNA (FIG. 50).

Purified DNA from cosmid clones 194 and 683 was labelled with biotin dUTP by nick translation. Labelled probes were combined with sheared human DNA and independently hybridized to normal metaphase chromosomes derived from PHA stimulated peripheral blood lymphocytes in a solution containing 50% formamide, 10% dectran sulfate, and 2XSSC. Specific hybridization signals were detected by incubating the hybridized slides in fluoresein conjugated avidin. Following signal detection the slides were counterstained with propidium iodide and analyzed. These first experiments resulted in the specific labelling of a group C chromosome on both the long and short arms. This chromosome was believed to be chromosome 11 on the basis of its size and morphology. A second set of experiments were performed in which a chromosome 11 centromere specific probe was cohybridized with the cosmid clones. These experiments were carried out in 60% formamide in an attempt to eliminate the cross reactive signal which was observed when low stringency hybridizations were done. These experiments resulted in the specific labelling of the centromere and the long arm of chromosome 11. Measurements of 10 specifically labelled chromosomes 11 demonstrated that the cosmid clones are located at a position which is 44% of the distance from the centromere to the telomere of chromosome arm 11q, an area that corresponds to band 1q. A total of 160 metaphase cells were examined with 153 cells exhibiting specific labelling.

Cloning of the 5' upstream and 3'downstream regions of the PSM genomic DNA. A bacteriophage P1 library of human fibroblast genomic DNA (Genomic Systems, St. Louis, Mich.) was screened using the PCR method of Pierce et. al. Primer pairs located at either the 5' or 3'termini of PSM cDNA were used. Positive cosmid clones were digested with restriction enzymes and confirmed by Southern analysis using probes which were constructed from either the 5' or 3'ends of PSM cDNA. Positive clone p683 contains the 5' region of PSM cDNA and about 60 kb upstream region. Clone –194 contains the 3'terminal of the PSM cDNA and about 60 kb downstream.

Example 12

Peptidase Enzymatic Activity

PSM is a type two membrane protein. Most type two membrane proteins are binding proteins, transport proteins or peptidases. PSM appears to have peptidase activity. When examining LNCaP cells with a substrate N-acetyl-aspartyl-$^{14}$C-glutamic acid, NAAG, glutamic acid was released, thus acting as a carboxypeptidase. In vitro translated PSM message also had this peptidase activity.

The result is that seminal plasma is rich in its content of glutamic acid, and are able to design inhibitors to enhance the activity of the non degraded normal substrate if its increased level will have a biologic desired activity. Also biologic activity can be measured to see how it correlates wit the level of message. Tissue may be examined for activity directly rather than indirectly using in-situ analysis or immunohistochemical probes. Because there is another gene highly similar on the other arm of chromosome 11 when isolated the expressed cloned genes can be used to determine what are the substrate differences and use those substrates for identification of PSM related activity, say in circulating cells when looking for metastases.

PSM specific substrates can be designed that could activate pro-drugs at the site of prostatic tumor cells to kill those cells.

What is claimed is:

1. An isolated nucleic acid encoding an alternatively spliced prostate-specific membrane (PSM') antigen, which antigen is a protein having an amino acid sequence consisting of the sequence set forth in SEC. ID. NO. 2 beginning with methionine at position number 58, wherein said nucleic acid is free of other nucleic acid molecules.

2. The isolated nucleic acid of claim 1, wherein said nucleic acid is a DNA molecule.

3. The isolated nucleic acid of claim 2, wherein said nucleic acid is a cDNA molecule.

4. The isolated nucleic acid of claim 1, wherein said nucleic acid is a RNA molecule.

5. The isolated nucleic acid of claim 2 operatively linked to a promoter of RNA transcription.

6. A vector which comprises the isolated nucleic acid of claim 1.

7. A host vector system for the production of polypeptide, wherein the polypeptide is the alternatively spliced prostate-specific membrane (PSM') antigen, wherein said host vector system comprises the vector of claim 6 and a suitable host cell.

8. A host vector system of claim 7, wherein the suitable host cell is a bacterial cell, insect cell, or mammalian cell.

9. A method for producing a polypeptide, wherein the polypeptide is the alternatively spliced prostate-specific membrane (PSM') antigen which comprises growing the host vector system of claim 8 under suitable conditions permitting production of the polypeptide and recovering the polypeptide so produced.

10. An isolated nucleic acid comprising a promoter sequence associated with the transcription of a gene encoding a human prostate specific membrane antigen, wherein said isolated nucleic molecule has the nucleic acid sequence as set forth from positions 1 to 2485 of SEQ ID NO: 39.

* * * * *

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
      (A) LENGTH: 2653 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens
      (F) TISSUE TYPE: Carcinoma (vii) IMMEDIATE SOURCE:
      (B) CLONE: Prostate-Specific Membrane Antigen (ix) FEATURE:
      (A) NAME/KEY: CDS
      (B) LOCATION: 262..2511

(xi) SEQUENCE DESCRIPTION: SEQ ID NO:1:

```
CTCAAAAGGG GCCGGATTTC CTTCTCCTGG AGGCAGATGT TGCCTCTCTC TCTCGCTCGG         60

ATTGGTTCAG TGCACTCTAG AAACACTGCT GTGGTGGAGA AACTGGACCC CAGGTCTGGA        120

GCGAATTCCA GCCTGCAGGG CTGATAAGCG AGGCATTAGT GAGATTGAGA GAGACTTTAC        180

CCCGCCGTGG TGGTTGGAGG GCGCGCAGTA GAGCAGCAGC ACAGGCGCGG GTCCCGGGAG        240

GCCGGCTCTG CTCGCGCCGA G ATG TGG AAT CTC CTT CAC GAA ACC GAC TCG         291
                       Met Trp Asn Leu Leu His Glu Thr Asp Ser
                         1               5                  10

GCT GTG GCC ACC GCG CGC CGC CCG CGC TGG CTG TGC GCT GGG GCG CTG         339
Ala Val Ala Thr Ala Arg Arg Pro Arg Trp Leu Cys Ala Gly Ala Leu
                 15                  20                  25

GTG CTG GCG GGT GGC TTC TTT CTC CTC GGC TTC CTC TTC GGG TGG TTT         387
Val Leu Ala Gly Gly Phe Phe Leu Leu Gly Phe Leu Phe Gly Trp Phe
             30                  35                  40

ATA AAA TCC TCC AAT GAA GCT ACT AAC ATT ACT CCA AAG CAT AAT ATG         435
Ile Lys Ser Ser Asn Glu Ala Thr Asn Ile Thr Pro Lys His Asn Met
         45                  50                  55

AAA GCA TTT TTG GAT GAA TTG AAA GCT GAG AAC ATC AAG AAG TTC TTA         483
Lys Ala Phe Leu Asp Glu Leu Lys Ala Glu Asn Ile Lys Lys Phe Leu
     60                  65                  70

TAT AAT TTT ACA CAG ATA CCA CAT TTA GCA GGA ACA GAA CAA AAC TTT         531
Tyr Asn Phe Thr Gln Ile Pro His Leu Ala Gly Thr Glu Gln Asn Phe
 75                  80                  85                  90

CAG CTT GCA AAG CAA ATT CAA TCC CAG TGG AAA GAA TTT GGC CTG GAT         579
Gln Leu Ala Lys Gln Ile Gln Ser Gln Trp Lys Glu Phe Gly Leu Asp
                 95                 100                 105

TCT GTT GAG CTA GCA CAT TAT GAT GTC CTG TTG TCC TAC CCA AAT AAG         627
Ser Val Glu Leu Ala His Tyr Asp Val Leu Leu Ser Tyr Pro Asn Lys
```

-continued

|     |     |     |     |     | 110 |     |     |     |     | 115 |     |     |     |     | 120 |     |      |
|-----|-----|-----|-----|-----|-----|-----|-----|-----|-----|-----|-----|-----|-----|-----|-----|-----|------|
| ACT | CAT | CCC | AAC | TAC | ATC | TCA | ATA | ATT | AAT | GAA | GAT | GGA | AAT | GAG | ATT |     | 675  |
| Thr | His | Pro | Asn | Tyr | Ile | Ser | Ile | Ile | Asn | Glu | Asp | Gly | Asn | Glu | Ile |     |      |
|     |     | 125 |     |     |     |     | 130 |     |     |     |     |     | 135 |     |     |     |      |

| TTC | AAC | ACA | TCA | TTA | TTT | GAA | CCA | CCT | CCT | CCA | GGA | TAT | GAA | AAT | GTT | 723 |
|-----|-----|-----|-----|-----|-----|-----|-----|-----|-----|-----|-----|-----|-----|-----|-----|-----|
| Phe | Asn | Thr | Ser | Leu | Phe | Glu | Pro | Pro | Pro | Pro | Gly | Tyr | Glu | Asn | Val |     |
|     | 140 |     |     |     |     | 145 |     |     |     |     | 150 |     |     |     |     |     |

| TCG | GAT | ATT | GTA | CCA | CCT | TTC | AGT | GCT | TTC | TCT | CCT | CAA | GGA | ATG | CCA | 771 |
|-----|-----|-----|-----|-----|-----|-----|-----|-----|-----|-----|-----|-----|-----|-----|-----|-----|
| Ser | Asp | Ile | Val | Pro | Pro | Phe | Ser | Ala | Phe | Ser | Pro | Gln | Gly | Met | Pro |     |
| 155 |     |     |     |     | 160 |     |     |     |     | 165 |     |     |     |     | 170 |     |

| GAG | GGC | GAT | CTA | GTG | TAT | GTT | AAC | TAT | GCA | CGA | ACT | GAA | GAC | TTC | TTT | 819 |
|-----|-----|-----|-----|-----|-----|-----|-----|-----|-----|-----|-----|-----|-----|-----|-----|-----|
| Glu | Gly | Asp | Leu | Val | Tyr | Val | Asn | Tyr | Ala | Arg | Thr | Glu | Asp | Phe | Phe |     |
|     |     |     |     | 175 |     |     |     |     | 180 |     |     |     |     | 185 |     |     |

| AAA | TTG | GAA | CGG | GAC | ATG | AAA | ATC | AAT | TGC | TCT | GGG | AAA | ATT | GTA | ATT | 867 |
|-----|-----|-----|-----|-----|-----|-----|-----|-----|-----|-----|-----|-----|-----|-----|-----|-----|
| Lys | Leu | Glu | Arg | Asp | Met | Lys | Ile | Asn | Cys | Ser | Gly | Lys | Ile | Val | Ile |     |
|     |     |     | 190 |     |     |     |     | 195 |     |     |     |     | 200 |     |     |     |

| GCC | AGA | TAT | GGG | AAA | GTT | TTC | AGA | GGA | AAT | AAG | GTT | AAA | AAT | GCC | CAG | 915 |
|-----|-----|-----|-----|-----|-----|-----|-----|-----|-----|-----|-----|-----|-----|-----|-----|-----|
| Ala | Arg | Tyr | Gly | Lys | Val | Phe | Arg | Gly | Asn | Lys | Val | Lys | Asn | Ala | Gln |     |
|     |     | 205 |     |     |     |     | 210 |     |     |     |     | 215 |     |     |     |     |

| CTG | GCA | GGG | GCC | AAA | GGA | GTC | ATT | CTC | TAC | TCC | GAC | CCT | GCT | GAC | TAC | 963 |
|-----|-----|-----|-----|-----|-----|-----|-----|-----|-----|-----|-----|-----|-----|-----|-----|-----|
| Leu | Ala | Gly | Ala | Lys | Gly | Val | Ile | Leu | Tyr | Ser | Asp | Pro | Ala | Asp | Tyr |     |
|     | 220 |     |     |     |     | 225 |     |     |     |     | 230 |     |     |     |     |     |

| TTT | GCT | CCT | GGG | GTG | AAG | TCC | TAT | CCA | GAT | GGT | TGG | AAT | CTT | CCT | GGA | 1011 |
|-----|-----|-----|-----|-----|-----|-----|-----|-----|-----|-----|-----|-----|-----|-----|-----|------|
| Phe | Ala | Pro | Gly | Val | Lys | Ser | Tyr | Pro | Asp | Gly | Trp | Asn | Leu | Pro | Gly |      |
| 235 |     |     |     | 240 |     |     |     |     | 245 |     |     |     |     | 250 |     |      |

| GGT | GGT | GTC | CAG | CGT | GGA | AAT | ATC | CTA | AAT | CTG | AAT | GGT | GCA | GGA | GAC | 1059 |
|-----|-----|-----|-----|-----|-----|-----|-----|-----|-----|-----|-----|-----|-----|-----|-----|------|
| Gly | Gly | Val | Gln | Arg | Gly | Asn | Ile | Leu | Asn | Leu | Asn | Gly | Ala | Gly | Asp |      |
|     |     |     | 255 |     |     |     |     | 260 |     |     |     |     | 265 |     |     |      |

| CCT | CTC | ACA | CCA | GGT | TAC | CCA | GCA | AAT | GAA | TAT | GCT | TAT | AGG | CGT | GGA | 1107 |
|-----|-----|-----|-----|-----|-----|-----|-----|-----|-----|-----|-----|-----|-----|-----|-----|------|
| Pro | Leu | Thr | Pro | Gly | Tyr | Pro | Ala | Asn | Glu | Tyr | Ala | Tyr | Arg | Arg | Gly |      |
|     |     | 270 |     |     |     |     | 275 |     |     |     |     | 280 |     |     |     |      |

| ATT | GCA | GAG | GCT | GTT | GGT | CTT | CCA | AGT | ATT | CCT | GTT | CAT | CCA | ATT | GGA | 1155 |
|-----|-----|-----|-----|-----|-----|-----|-----|-----|-----|-----|-----|-----|-----|-----|-----|------|
| Ile | Ala | Glu | Ala | Val | Gly | Leu | Pro | Ser | Ile | Pro | Val | His | Pro | Ile | Gly |      |
|     | 285 |     |     |     |     | 290 |     |     |     |     | 295 |     |     |     |     |      |

| TAC | TAT | GAT | GCA | CAG | AAG | CTC | CTA | GAA | AAA | ATG | GGT | GGC | TCA | GCA | CCA | 1203 |
|-----|-----|-----|-----|-----|-----|-----|-----|-----|-----|-----|-----|-----|-----|-----|-----|------|
| Tyr | Tyr | Asp | Ala | Gln | Lys | Leu | Leu | Glu | Lys | Met | Gly | Gly | Ser | Ala | Pro |      |
|     | 300 |     |     |     |     | 305 |     |     |     |     | 310 |     |     |     |     |      |

| CCA | GAT | AGC | AGC | TGG | AGA | GGA | AGT | CTC | AAA | GTG | CCC | TAC | AAT | GTT | GGA | 1251 |
|-----|-----|-----|-----|-----|-----|-----|-----|-----|-----|-----|-----|-----|-----|-----|-----|------|
| Pro | Asp | Ser | Ser | Trp | Arg | Gly | Ser | Leu | Lys | Val | Pro | Tyr | Asn | Val | Gly |      |
| 315 |     |     |     | 320 |     |     |     |     | 325 |     |     |     |     | 330 |     |      |

| CCT | GGC | TTT | ACT | GGA | AAC | TTT | TCT | ACA | CAA | AAA | GTC | AAG | ATG | CAC | ATC | 1299 |
|-----|-----|-----|-----|-----|-----|-----|-----|-----|-----|-----|-----|-----|-----|-----|-----|------|
| Pro | Gly | Phe | Thr | Gly | Asn | Phe | Ser | Thr | Gln | Lys | Val | Lys | Met | His | Ile |      |
|     |     |     | 335 |     |     |     |     | 340 |     |     |     |     | 345 |     |     |      |

| CAC | TCT | ACC | AAT | GAA | GTG | ACA | AGA | ATT | TAC | AAT | GTG | ATA | GGT | ACT | CTC | 1347 |
|-----|-----|-----|-----|-----|-----|-----|-----|-----|-----|-----|-----|-----|-----|-----|-----|------|
| His | Ser | Thr | Asn | Glu | Val | Thr | Arg | Ile | Tyr | Asn | Val | Ile | Gly | Thr | Leu |      |
|     |     |     | 350 |     |     |     |     | 355 |     |     |     |     | 360 |     |     |      |

| AGA | GGA | GCA | GTG | GAA | CCA | GAC | AGA | TAT | GTC | ATT | CTG | GGA | GGT | CAC | CGG | 1395 |
|-----|-----|-----|-----|-----|-----|-----|-----|-----|-----|-----|-----|-----|-----|-----|-----|------|
| Arg | Gly | Ala | Val | Glu | Pro | Asp | Arg | Tyr | Val | Ile | Leu | Gly | Gly | His | Arg |      |
|     |     |     | 365 |     |     |     |     | 370 |     |     |     |     | 375 |     |     |      |

| GAC | TCA | TGG | GTG | TTT | GGT | GGT | ATT | GAC | CCT | CAG | AGT | GGA | GCA | GCT | GTT | 1443 |
|-----|-----|-----|-----|-----|-----|-----|-----|-----|-----|-----|-----|-----|-----|-----|-----|------|
| Asp | Ser | Trp | Val | Phe | Gly | Gly | Ile | Asp | Pro | Gln | Ser | Gly | Ala | Ala | Val |      |
|     |     | 380 |     |     |     |     | 385 |     |     |     |     | 390 |     |     |     |      |

| GTT | CAT | GAA | ATT | GTG | AGG | AGC | TTT | GGA | ACA | CTG | AAA | AAG | GAA | GGG | TGG | 1491 |
|-----|-----|-----|-----|-----|-----|-----|-----|-----|-----|-----|-----|-----|-----|-----|-----|------|
| Val | His | Glu | Ile | Val | Arg | Ser | Phe | Gly | Thr | Leu | Lys | Lys | Glu | Gly | Trp |      |
| 395 |     |     |     | 400 |     |     |     |     | 405 |     |     |     |     | 410 |     |      |

| AGA | CCT | AGA | AGA | ACA | ATT | TTG | TTT | GCA | AGC | TGG | GAT | GCA | GAA | GAA | TTT | 1539 |
|-----|-----|-----|-----|-----|-----|-----|-----|-----|-----|-----|-----|-----|-----|-----|-----|------|
| Arg | Pro | Arg | Arg | Thr | Ile | Leu | Phe | Ala | Ser | Trp | Asp | Ala | Glu | Glu | Phe |      |
|     |     |     | 415 |     |     |     |     | 420 |     |     |     |     | 425 |     |     |      |

| GGT | CTT | CTT | GGT | TCT | ACT | GAG | TGG | GCA | GAG | GAG | AAT | TCA | AGA | CTC | CTT | 1587 |
|-----|-----|-----|-----|-----|-----|-----|-----|-----|-----|-----|-----|-----|-----|-----|-----|------|
| Gly | Leu | Leu | Gly | Ser | Thr | Glu | Trp | Ala | Glu | Glu | Asn | Ser | Arg | Leu | Leu |      |

-continued

```
              430                 435                 440
CAA GAG CGT GGC GTG GCT TAT ATT AAT GCT GAC TCA TCT ATA GAA GGA         1635
Gln Glu Arg Gly Val Ala Tyr Ile Asn Ala Asp Ser Ser Ile Glu Gly
            445                 450                 455

AAC TAC ACT CTG AGA GTT GAT TGT ACA CCG CTG ATG TAC AGC TTG GTA         1683
Asn Tyr Thr Leu Arg Val Asp Cys Thr Pro Leu Met Tyr Ser Leu Val
            460                 465                 470

CAC AAC CTA ACA AAA GAG CTG AAA AGC CCT GAT GAA GGC TTT GAA GGC         1731
His Asn Leu Thr Lys Glu Leu Lys Ser Pro Asp Glu Gly Phe Glu Gly
475             480                 485                 490

AAA TCT CTT TAT GAA AGT TGG ACT AAA AAA AGT CCT TCC CCA GAG TTC         1779
Lys Ser Leu Tyr Glu Ser Trp Thr Lys Lys Ser Pro Ser Pro Glu Phe
                495                 500                 505

AGT GGC ATG CCC AGG ATA AGC AAA TTG GGA TCT GGA AAT GAT TTT GAG         1827
Ser Gly Met Pro Arg Ile Ser Lys Leu Gly Ser Gly Asn Asp Phe Glu
            510                 515                 520

GTG TTC TTC CAA CGA CTT GGA ATT GCT TCA GGC AGA GCA CGG TAT ACT         1875
Val Phe Phe Gln Arg Leu Gly Ile Ala Ser Gly Arg Ala Arg Tyr Thr
            525                 530                 535

AAA AAT TGG GAA ACA AAC AAA TTC AGC GGC TAT CCA CTG TAT CAC AGT         1923
Lys Asn Trp Glu Thr Asn Lys Phe Ser Gly Tyr Pro Leu Tyr His Ser
540                 545                 550

GTC TAT GAA ACA TAT GAG TTG GTG GAA AAG TTT TAT GAT CCA ATG TTT         1971
Val Tyr Glu Thr Tyr Glu Leu Val Glu Lys Phe Tyr Asp Pro Met Phe
555                 560                 565                 570

AAA TAT CAC CTC ACT GTG GCC CAG GTT CGA GGA GGG ATG GTG TTT GAG         2019
Lys Tyr His Leu Thr Val Ala Gln Val Arg Gly Gly Met Val Phe Glu
                575                 580                 585

CTA GCC AAT TCC ATA GTG CTC CCT TTT GAT TGT CGA GAT TAT GCT GTA         2067
Leu Ala Asn Ser Ile Val Leu Pro Phe Asp Cys Arg Asp Tyr Ala Val
            590                 595                 600

GTT TTA AGA AAG TAT GCT GAC AAA ATC TAC AGT ATT TCT ATG AAA CAT         2115
Val Leu Arg Lys Tyr Ala Asp Lys Ile Tyr Ser Ile Ser Met Lys His
            605                 610                 615

CCA CAG GAA ATG AAG ACA TAC AGT GTA TCA TTT GAT TCA CTT TTT TCT         2163
Pro Gln Glu Met Lys Thr Tyr Ser Val Ser Phe Asp Ser Leu Phe Ser
            620                 625                 630

GCA GTA AAG AAT TTT ACA GAA ATT GCT TCC AAG TTC AGT GAG AGA CTC         2211
Ala Val Lys Asn Phe Thr Glu Ile Ala Ser Lys Phe Ser Glu Arg Leu
635                 640                 645                 650

CAG GAC TTT GAC AAA AGC AAC CCA ATA GTA TTA AGA ATG ATG AAT GAT         2259
Gln Asp Phe Asp Lys Ser Asn Pro Ile Val Leu Arg Met Met Asn Asp
                655                 660                 665

CAA CTC ATG TTT CTG GAA AGA GCA TTT ATT GAT CCA TTA GGG TTA CCA         2307
Gln Leu Met Phe Leu Glu Arg Ala Phe Ile Asp Pro Leu Gly Leu Pro
            670                 675                 680

GAC AGG CCT TTT TAT AGG CAT GTC ATC TAT GCT CCA AGC AGC CAC AAC         2355
Asp Arg Pro Phe Tyr Arg His Val Ile Tyr Ala Pro Ser Ser His Asn
            685                 690                 695

AAG TAT GCA GGG GAG TCA TTC CCA GGA ATT TAT GAT GCT CTG TTT GAT         2403
Lys Tyr Ala Gly Glu Ser Phe Pro Gly Ile Tyr Asp Ala Leu Phe Asp
            700                 705                 710

ATT GAA AGC AAA GTG GAC CCT TCC AAG GCC TGG GGA GAA GTG AAG AGA         2451
Ile Glu Ser Lys Val Asp Pro Ser Lys Ala Trp Gly Glu Val Lys Arg
715                 720                 725                 730

CAG ATT TAT GTT GCA GCC TTC ACA GTG CAG GCA GCT GCA GAG ACT TTG         2499
Gln Ile Tyr Val Ala Ala Phe Thr Val Gln Ala Ala Ala Glu Thr Leu
                735                 740                 745

AGT GAA GTA GCC TAAGAGGATT CTTTAGAGAA TCCGTATTGA ATTTGTGTGG             2551
Ser Glu Val Ala
```

750

TATGTCACTC AGAAAGAATC GTAATGGGTA TATTGATAAA TTTTAAAATT GGTATATTTG    2611

AAATAAAGTT GAATATTATA TATAAAAAAA AAAAAAAAAA AA                      2653

(2) INFORMATION FOR SEQ ID NO:2:

(i) SEQUENCE CHARACTERISTICS:
        (A) LENGTH: 750 amino acids
        (B) TYPE: amino acid
        (D) TOPOLOGY: linear (ii) MOLECULE TYPE: protein (xi) SEQUENCE DESCRIPTION: SEQ ID NO:2:

Met Trp Asn Leu Leu His Glu Thr Asp Ser Ala Val Ala Thr Ala Arg
 1               5                  10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

```
Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750
```

```
(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapiens
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:3:

Ser Leu Tyr Glu Ser Xaa Thr Lys
1               5

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapiens
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:4:

Xaa Tyr Pro Asp Gly Xaa Asn Leu Pro Gly Gly Xaa Val Gln Arg
1               5                   10                  15

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:5:

Phe Tyr Asp Pro Met Phe Lys
1               5
```

```
(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: double
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:6:

Ile Tyr Asn Val Ile Gly Thr Leu Lys
1               5

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:7:

Phe Leu Tyr Xaa Xaa Thr Gln Ile Pro His Leu Ala Gly Thr Glu Gln
1               5                   10                  15

Asn Phe Gln Leu Ala Lys
            20

(2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:8:
```

```
Gly Val Ile Leu Tyr Ser Asp Pro Ala Asp Tyr Phe Ala Pro Asp Val
1               5                   10                  15
Lys (2) INFORMATION FOR SEQ ID NO:9:

(i) SEQUENCE CHARACTERISTICS:
        (A) LENGTH: 17 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:9:

Pro Val Ile Leu Tyr Ser Asp Pro Ala Asp Tyr Phe Ala Pro Gly Val
1               5                   10                  15
Lys (2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:10:

Ala Phe Ile Asp Pro Leu Gly Leu Pro Asp Arg Pro Phe Tyr Arg
1               5                   10                  15

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma
```

(vii) IMMEDIATE SOURCE:
            (B) CLONE: Prostate Specific Membrane Antigen (xi) SEQUENCE DESCRIPTION: SEQ ID NO:11:

Tyr Ala Gly Glu Ser Phe Pro Gly Ile Tyr Asp Ala Leu Phe Asp Ile
1               5                  10                  15

Glu Ser Lys (2) INFORMATION FOR SEQ ID NO:12:

(i) SEQUENCE CHARACTERISTICS:
        (A) LENGTH: 22 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:12:

Thr Ile Leu Phe Ala Ser Xaa Asp Ala Glu Glu Phe Gly Xaa Xaa Xaa
1               5                  10                  15

Ser Thr Glu Glu Ala Glu
            20

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:13:

TTYTAYGAYC CNATGTT                                                17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:14:

AACATNGGRT CRTARAA                                                   17

(2) INFORMATION FOR SEQ ID NO:15:

(i) SEQUENCE CHARACTERISTICS:
             (A) LENGTH: 17 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:15:

ATHTAYAAYG TNATHGG                                                   17

(2) INFORMATION FOR SEQ ID NO:16:

(i) SEQUENCE CHARACTERISTICS:
             (A) LENGTH: 17 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:16:

CCDATNACRT TRTADAT                                                   17

(2) INFORMATION FOR SEQ ID NO:17:

(i) SEQUENCE CHARACTERISTICS:
             (A) LENGTH: 17 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:17:

CCNGCNGAYT AYTTYGC                                                     17

(2) INFORMATION FOR SEQ ID NO:18:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:18:

GCRAARTART CNGCNGG                                                     17

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien
            (F) TISSUE TYPE: Carcinoma (vii) IMMEDIATE SOURCE:
            (B) CLONE: Prostate Specific Membrane Antigen (xi) SEQUENCE DESCRIPTION: SEQ ID NO:19:

ACNGARCARA AYTTYCARCT                                                  20

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapien

```
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:20:

AGYTGRAART TYTGYTCNGT                                             20

(2) INFORMATION FOR SEQ ID NO:21:

(i) SEQUENCE CHARACTERISTICS:
         (A) LENGTH: 17 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:21:

GARCARAAYT TYCARCT                                                17

(2) INFORMATION FOR SEQ ID NO:22:

(i) SEQUENCE CHARACTERISTICS:
         (A) LENGTH: 17 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapien
         (F) TISSUE TYPE: Carcinoma (vii) IMMEDIATE SOURCE:
         (B) CLONE: Prostate Specific Membrane Antigen (xi) SEQUENCE DESCRIPTION: SEQ ID NO:22:

AGYTGRAART TYTGYTC                                                17

(2) INFORMATION FOR SEQ ID NO:23:

(i) SEQUENCE CHARACTERISTICS:
         (A) LENGTH: 20 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapien
         (F) TISSUE TYPE: Carcinoma
```

```
    (vii) IMMEDIATE SOURCE:
          (B) CLONE: Prostate Specific Membrane Antigen (xi) SEQUENCE DESCRIPTION: SEQ ID NO:23:

TGGGAYGCNG ARGARTTYGG                                              20

(2) INFORMATION FOR SEQ ID NO:24:

(i) SEQUENCE CHARACTERISTICS:
          (A) LENGTH: 20 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: Homo sapien
          (F) TISSUE TYPE: Carcinoma (vii) IMMEDIATE SOURCE:
          (B) CLONE: Prostate Specific Membrane Antigen (xi) SEQUENCE DESCRIPTION: SEQ ID NO:24:

CCRAAYTCYT CNGCRTCCCA                                              20

(2) INFORMATION FOR SEQ ID NO:25:

(i) SEQUENCE CHARACTERISTICS:
          (A) LENGTH: 17 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: Homo sapien
          (F) TISSUE TYPE: Carcinoma (vii) IMMEDIATE SOURCE:
          (B) CLONE: Prostate Specific Membrane Antigen (xi) SEQUENCE DESCRIPTION: SEQ ID NO:25:

TGGGAYGCNG ARGARTT                                                 17

(2) INFORMATION FOR SEQ ID NO:26:

(i) SEQUENCE CHARACTERISTICS:
          (A) LENGTH: 17 base pairs
          (B) TYPE: nucleic acid
          (C) STRANDEDNESS: double
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: Homo sapien
          (F) TISSUE TYPE: Carcinoma (vii) IMMEDIATE SOURCE:
          (B) CLONE: Prostate Specific Membrane Antigen
```

(xi) SEQUENCE DESCRIPTION: SEQ ID NO:26:

AAYTCYTCNG CRTCCCA 17

(2) INFORMATION FOR SEQ ID NO:27:

(i) SEQUENCE CHARACTERISTICS:
        (A) LENGTH: 780 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

```
TACACTTATC CCATTCGGAC ATGCCCACCT TGGAACTGGA GACCCTTACA CCCCAGGCTT    60
CCCTTCGTTC AACCACACCC ANNNGTTTCC ACCAGTTGAA TCTTCAGGAC TACCCCACAT   120
TGCTGTTCAG ACCATCTCTA GCAGTGCAGC AGCCAGGCTG TTCAGCAAAA TGGATGGAGA   180
CACATGCTCT GANAGNNGTT GGAAAGGTGC GATCCANNNT TCCTGTAAGG TNNGACNNAA   240
CAAAGCAGGA GANNNNGCCA GANTAATGGT GAAACTAGAT GTGAACAATT CCATGAAAGA   300
CAGGAAGATT CTGAACATCT TCGGTGCTAT CCAGGGATTT GAAGAACCTG ATCGGTATGT   360
TGTGATTGGA GCCCAGAGAG ACTCCTGGGG CCCAGGAGTG GCTAAAGCTG GCACTGGAAC   420
TGCTATATTG TTGGAACTTG CCCGTGTGAT CTCAGACATA GTGAAAAACG AGGGCTACAA   480
ACCGAGGCGA AGCATCATCT TTGCTAGCTG GAGTGCAGGA GACTACGGAG CTGTGGGTGC   540
TACTGAATGG CTGGAGGGGT ACTCTGCCAT GCTGCATGCC AAAGCTTTCA CTTACATCAN   600
NGCTTGGATG CTCCAGTCCT GGGAGCAAGC CATGTCAAGA TTTCTGCCAG CCCCTTGCTG   660
TATATGCTGC TGGGGAGTAT TATGAAGGGG GTGAAGAATC CAGCAGCAGT CTCAGAGAGC   720
NNNNCTCTAT AACAGACTTG GCCCAGACTG GGTAAAAGCA GTTGTTCCTC TTGGCCTGGA   780
```

(2) INFORMATION FOR SEQ ID NO:28:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:28:

```
TGCAGAAAAG CTATTCAAAA ACATGGAAGG AAACTGTCCT CCTAGTTGGA ATATAGATTC    60
CTCATGTAAG CTGGAACTTT CACAGAATCA AAATGTGAAG CTCACTGTGA ACAATGTACT   120
GAAAGAAACA AGAATACTTA ACATCTTTGG CGTTATTAAA GGCTATGAGG AACCAGACCG   180
CTACATTGTA GTAGGAGCCC AGAGAGACGC TTGGGGCCCT GGTNGTTGCG AAGTCCAGTG   240
TGGGAACAGG TCTTNCTGTT GAAACTTGCC CAAGTATTCT CAGATATGAT TCAAAAGAT   300
GGATTTAGAC CCAGCAGGAG TATTATCTTT GCCAGCTGGA CTGCAGGAGA CTATGGAGCT   360
GTTGGTCCGA CTGAGTGGCT GGAGGGGTAC CTTTCATCTT TGCATCTAAA GNNNGCTTTC   420
ACTTACATTA ATNCTGGATA AAGTCGTCCT GGGTACTAGC AACTTCAAGG TTTCTGCCAG   480
```

```
CCCCCTATTA TATACACTTA TGGGGAAGAT AATGCAGGAN NCGTAAAGCA TCCGANNNNN      540

NNNTTGATGG AAAATATCTA TATCGAAACA GTAATTGGAT TAGCAAAATT GAGGAACTTT      600

CCTTGGACAA TGCTGCATTC CCTTTTCTTG CATATTCAGG AATCCCAGCA GTTTCTTTCT      660
```

(2) INFORMATION FOR SEQ ID NO:29:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:29:

```
TATGGAAGGA GACTGTCCCT CTGACTGGAA AACAGACTCT ACATGTAGGA TGGTAACCTC       60

AGAAAGCAAG AATGTGAAGC TCACTGTGAG CAATGTGCTG AAAGAGATAA AAATTCTTAA      120

CATCTTTGGA GTTATTAAAG CTTTGTAGA ACCAGATCAC TATGTTGTAG TTGGGGCCCA      180

GAGAGATGCA TGGGGCCCTG GAGCTGCAAA ATCNCGGTGT AGGCACAGCT CTCCTATTGA      240

AACTTGCCCA GATGTTCTCA GATATGGTCT TAAAAGATGG GTTTCAGCCC AGCAGAAGCA      300

TTATCTTTGC CAGTTGGAGT GCTGGAGACT TTGGATCGGT TGGTGCCACT GAATGGCTAG      360

AGGGATACCT TTCGTCNCCT GCATTTAAAG GCTTTCACTT ATATTAATCT GGATAAAGCG      420

GTTCTTGGTA CCAGCAACTT CAAGGTTTCT GCCAGCCCAC TGTTGTATAC GCTTATTGAG      480

AAAACAATGC AAAATGTGAA GCATCCGGTT ACTGGGCAAT TTCTATATCA GGACAGCAAC      540
```

(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:30:

```
ACGGAGCAAA ACTTTCAGCT TGCAAAG                                          27
```

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (F) TISSUE TYPE: Carcinoma (vii) IMMEDIATE SOURCE:
             (B) CLONE: Prostate Membrane Specific Antigen (xi) SEQUENCE DESCRIPTION: SEQ ID NO:31:

Thr Glu Gln Asn Phe Gln Leu Ala Lys
1               5

(2) INFORMATION FOR SEQ ID NO:32:

(i) SEQUENCE CHARACTERISTICS:
             (A) LENGTH: 36 base pairs
             (B) TYPE: nucleic acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:32:

CTCTTCGGCA TCCCAGCTTG CAAACAAAAT TGTTCT                                    36

(2) INFORMATION FOR SEQ ID NO:33:

(i) SEQUENCE CHARACTERISTICS:
             (A) LENGTH: 36 base pairs
             (B) TYPE: nucleic acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:33:

AGAACAATTT TGTTTGCAAG CTGGGATGCC AAGGAG                                    36

(2) INFORMATION FOR SEQ ID NO:34:

(i) SEQUENCE CHARACTERISTICS:
             (A) LENGTH: 12 amino acids
             (B) TYPE: amino acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (G) CELL TYPE: Carcinoma (vii) IMMEDIATE SOURCE:
             (B) CLONE: Prostate Specific Membrane Antigen (xi) SEQUENCE DESCRIPTION: SEQ ID NO:34:

Arg Thr Ile Leu Phe Ala Ser Trp Asp Ala Glu Glu
 1               5                  10

(2) INFORMATION FOR SEQ ID NO:35:

(i) SEQUENCE CHARACTERISTICS:
             (A) LENGTH: 6 amino acids
             (B) TYPE: amino acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (G) CELL TYPE: Carcinoma (vii) IMMEDIATE SOURCE:
             (B) CLONE: Prostate Specific Membrane Antigen (xi) SEQUENCE DESCRIPTION: SEQ ID NO:35:

Asp Glu Leu Lys Ala Glu
 1               5

(2) INFORMATION FOR SEQ ID NO:36:

(i) SEQUENCE CHARACTERISTICS:
             (A) LENGTH: 6 amino acids
             (B) TYPE: amino acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (G) CELL TYPE: Carcinoma (vii) IMMEDIATE SOURCE:
             (B) CLONE: Prostate Specific Membrane Antigen (xi) SEQUENCE DESCRIPTION: SEQ ID NO:36:

Asn Glu Asp Gly Asn Glu
 1               5

(2) INFORMATION FOR SEQ ID NO:37:

(i) SEQUENCE CHARACTERISTICS:
             (A) LENGTH: 6 amino acids
             (B) TYPE: amino acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
              (A) ORGANISM: Homo Sapien
              (G) CELL TYPE: Carcinoma (vii) IMMEDIATE SOURCE:
              (B) CLONE: Prostate Specific Membrane Antigen (xi) SEQUENCE DESCRIPTION: SEQ ID NO:37:

Lys Ser Pro Asp Glu Gly
1               5

(2) INFORMATION FOR SEQ ID NO:38:

(i) SEQUENCE CHARACTERISTICS:
              (A) LENGTH: 17 amino acids
              (B) TYPE: amino acid
              (C) STRANDEDNESS: double
              (D) TOPOLOGY: linear (ii) MOLECULE TYPE: peptide (iii) HYPOTHETICAL: NO (iv) ANTI-SENSE: NO (vi) ORIGINAL SOURCE:
              (A) ORGANISM: Homo Sapien
              (G) CELL TYPE: Carcinoma (vii) IMMEDIATE SOURCE:
              (B) CLONE: Prostate Specific Membrane Antigen (xi) SEQUENCE DESCRIPTION: SEQ ID NO:38:

Ala Gly Ala Leu Val Leu Ala Gly Gly Phe Phe Leu Leu Gly Phe Leu
1               5                   10                  15

Phe (2) INFORMATION FOR SEQ ID NO:39:

(i) SEQUENCE CHARACTERISTICS:
              (A) LENGTH: 3017 base pairs
              (B) TYPE: nucleic acid
              (C) STRANDEDNESS: double
              (D) TOPOLOGY: linear (ii) MOLECULE TYPE: peptide (iii) HYPOTHETICAL: NO (iv) ANTI-SENSE: NO (vi) ORIGINAL SOURCE:
              (A) ORGANISM: Homo Sapien
              (F) TISSUE TYPE: Carcinoma (vii) IMMEDIATE SOURCE:
              (B) CLONE: Prostate Specific Membrane Antigen (xi) SEQUENCE DESCRIPTION: SEQ ID NO:39:

AAGGGTGCTC CTTAGGCTGA ATGCTTGCAG ACAGGATGCT TGGTTACAGA TGGGCTGTGA      60

CTCGAGTGGA GTTTTATAAG GGTGCTCCTT AGGCTGAATG CTTGCAGACA GGATGCTTGG     120

TTACAGATGG GCTGTGAGCT GGGTGCTTGT AAGAGGATGC TTGGGTGCTA AGTGAGCCAT     180

TTGCAGTTGA CCCTATTCTT GGAACATTCA TTCCCCTCTA CCCCTGTTTC TGTTCCTGCC     240

AGCTAAGCCC ATTTTTCATT TTTCTTTTAA CTCCTTAGCG CTCCGCAAAA CTTAATCAAT     300

TTCTTTAAAC CTCAGTTTTC TTATCTGTAA AAGGTAAATA ATAATACAGG GTGCAACAGA     360

```
AAAATCTAGT GTGGTTTACA TAATCACCTG TTAGAGATTT TAAATTATTT CAGGATAAGT      420

CATGATAATT AAATGAAATA ATGCACATAA AGCACATAGT GTGGTGTCCT CCATATAGAA      480

AATGCTCAGT ATATTGGTTA TTAACTACTT GTTGAAGGTT TATCTTCTCC ACTAAACTGT      540

AAGTTCCACA AGCCTTACAA TATGTGACAG ATATTCATTC ATTGTCTGAA TTCTTCAAAT      600

ACATCCTCTT CACCATAGCG TCTTATTAAT TGAATTATTA ATTGAATAAA TTCTATTGTT      660

CAAAAATCAC TTTTATATTT AACTGAAATT TGCTTACTTA TAATCACATC TAACCTTCAA      720

AGAAAACACA TTAACCAACT GTACTGGGTA ATGTTACTGG GTGATCCCAC GTTTTACAAA      780

TGAGAAGATA TATTCTGGTA AGTTGAATAC TTAGCACCCA GGGGTAATCA GCTTGGACAG      840

GACCAGGTCC AAAGACTGTT AAGAGTCTTC TGACTCCAAA CTCAGTGCTC CCTCCAGTGC      900

CACAAGCAAA CTCCATAAAG GTATCCTGTG CTGAATAGAG ACTGTAGAGT GGTACAAAGT      960

AAGACAGACA TTATATTAAG TCTTAGCTTT GTGACTTCGA ATGACTTACC TAATCTAGCT     1020

AAATTTCAGT TTTACCATGT GTAAATCAGG AAGAGTAATA GAACAAACCT TGAAGGGTCC     1080

CAATGGTGAT TAAATGAGGT GATGTACATA ACATGCATCA CTCATAATAA GTGCTCTTTA     1140

AATATTAGTC ACTATTATTA GCCATCTCTG ATTAGATTTG ACAATAGGAA CATTAGGAAA     1200

GATATAGTAC ATTCAGGATT TTGTTAGAAA GAGATGAAGA AATTCCCTTC CTTCCTGCCC     1260

TAGGTCATCT AGGAGTTGTC ATGGTTCATT GTTGACAAAT TAATTTTCCC AAATTTTTCA     1320

CTTTGCTCAG AAAGTCTACA TCGAAGCACC CAAGACTGTA CAATCTAGTC CATCTTTTTC     1380

CACTTAACTC ATACTGTGCT CTCCCTTTCT CAAAGCAAAC TGTTTGCTAT TCCTTGAATA     1440

CACTCTGAGT TTTCTGCCTT TGCCTACTCA GCTGGCCCAT GGCCCCTAAT GTTTCTTCTC     1500

ATCTCCACTG GGTCAAATCC TACCTGTACC TTATGGTTCT GTTAAAAGCA GTGCTTCCAT     1560

AAAGTACTCC TAGCAAATGC ACGGCCTCTC TCACGGATTA TAAGAACACA GTTTATTTTA     1620

TAAAGCATGT AGCTATTCTC TCCCTCGAAA TACGATTATT ATTATTAAGA ATTTATAGCA     1680

GGGATATAAT TTTGTATGAT GATTCTTCTG GTTAATCCAA CCAAGATTGA TTTTATATCT     1740

ATTACGTAAG ACAGTAGCCA GACATAGCCG GGATATGAAA ATAAAGTCTC TGCCTTCAAC     1800

AAGTTCCAGT ATTCTTTTCT TTCCTCCCCT CCCCTCCCCT CCCTTCCCCT CCCCTTCCTT     1860

CCCTTTCCCT TCCCTTCCTT TCTTTCTTGA GGGAGTCTCA CTCTGTCACC AGGCTCCAGT     1920

GCAGTGGCGC TATCTTGGCT GACTGCAACC TCCGCCTCCC CGGTTCAAGC GATTCTCCTG     1980

CCTCAGCCTC CTGAGTAGCT GGGACTACAG GAGCCCGCCA CCACGCCCAG CTAATTTTTG     2040

TATTTTTAGT AGAGATGGGG TTTCACCATG TTGGCCAGGA TGGTCTCGAT TTCTCGACTT     2100

CGTGATCCGC CTGTCTGGGC CTCCCAAAGT GCTGGGATTA CAGGCGTGAG CCACCACGCC     2160

CGGCTTTAAA AAATGGTTTT GTAATGTAAG TGGAGGATAA TACCCTACAT GTTTATTAAT     2220

AACAATAATA TTCTTTAGGA AAAAGGGCGC GGTGGTGATT TACACTGATG ACAAGCATTC     2280

CCGACTATGG AAAAAAAGCG CAGCTTTTTC TGCTCTGCTT TTATTCAGTA GAGTATTGTA     2340

GAGATTGTAT AGAATTTCAG AGTTGAATAA AAGTTCCTCA TAATTATAGG AGTGGAGAGA     2400

GGAGAGTCTC TTTCTTCCTT TCATTTTTAT ATTTAAGCAA GAGCTGGACA TTTTCCAAGA     2460

AAGTTTTTTT TTTTTAAGGC GCCTCTCAAA AGGGGCCGGA TTTCCTTCTC CTGGAGGCAG     2520

ATGTTGCCTC TCTCTCTCGC TCGGATTGGT TCAGTGCACT CTAGAAACAC TGCTGTGGTG     2580

GAGAAACTGG ACCCCAGGTC TGGAGCGAAT TCCAGCCTGC AGGGCTGATA AGCGAGGCAT     2640

TAGTGAGATT GAGAGAGACT TTACCCCGCC GTGGTGGTTG GAGGGCGCGC AGTAGAGCAG     2700

CAGCACAGGC GCGGGTCCCG GGAGGCCGGC TCTGCTCGCG CCGAGATGTG GAATCTCCTT     2760
```

```
CACGAAACCG ACTCGGCTGT GGCCACCGCG CGCCGCCCGC GCTGGCTGTG CGCTGGGGCG    2820

CTGGTGCTGG CGGGTGGCTT CTTTCTCCTC GGCTTCCTCT TCGGTAGGGG GGCGCCTCGC    2880

GGAGCAAACC TCGGAGTCTT CCCCGTGGTG CCGCGGTGCT GGGACTCGCG GGTCAGCTGC    2940

CGAGTGGGAT CCTGTTGCTG GTCTTCCCCA GGGGCGGCGA TTAGGGTCGG GGTAATGTGG    3000

GGTGAGCACC CCTCGAG                                                  3017
```

(2) INFORMATION FOR SEQ ID NO:40:

(i) SEQUENCE CHARACTERISTICS:
        (A) LENGTH: 776 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:40:

```
TTTGCAGACT TGACCAACTT CTAAGAAAA GCAGAACCAC ACAGGCAAGC TCAGACTCTT      60

TTATTAAATT CCAGTTTTGA CTTTGCCACT TCTTAGTGGC CTTGAACAAG TTACCGAGTC    120

CTCTCAGCGT TAGTTACCCT ATTTAATGA TGAGGATAAT ATTATCTGCC CAAATTATTG    180

GTATAGTAAA TATATAGCAT GTAAATCTCC TAGCAGAGTA CTGGGATTTC GCCACTTTAT    240

TTCTTCTTTA CCAAGATACT CCTATTGGAC TTAATACACA GGACTAGTCT AAGGTATCAC    300

CAGGTAGTCC ACTCCTGCTC GGAATCTGAC CCGGGATTAG AGTAGGGCAT GGACCAGATG    360

GGTTTAAACA AATTCAATAT CTTCCACTAG CTTCACCTTG GGGTTGTAAA AGTTTTTGAA    420

CCACACACTG TGCTCATAAC AATCTTCATC TCTTAAAAGG ATTTTATTCT TCCTGGTATC    480

CTCACTCTCA TCCCTTGTAT TCCGTGCTCA GTGGCTGACA CAGAAGAGTT CTTTATNNNN    540

NNNNNNNNNN CATCCTGTTC ATTTTTCAGA TCTCAGTTCA AGCATCTCGT CCTCAGTGTG    600

GTGTTNNCTG ATCCCTCACT CTAATCCAAG TCTTTCTGTT TTATGCACAG GTTGGAATCT    660

TATTTCCGTT TGCGNNCCAA TCNAATNGTA TTTAATATGC ATGTATATAT GTATGTGCAT    720

TTGTATGCTA NGCGATTAAG AACTAGAATA ATTAATAATT GGAAGTCTAG AAGTGG        776
```

(2) INFORMATION FOR SEQ ID NO:41:

(i) SEQUENCE CHARACTERISTICS:
        (A) LENGTH: 1310 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:

(B) CLONE: Prostate Specific Membrane Antigen (xi) SEQUENCE DESCRIPTION: SEQ ID NO:41:

TGAAAAATAC ATCAAAAATA GGCATGAGAT ACGAGCCTAT AGATAGGACT TATTTTTTAT      60

TATTGTTGTA TGTATTATTT GTAAAACACA AATTATCAAT ATTACCTCTG ACATTAGGTG     120

AGATATTCTG AATTTTAATT TCTCTTGCCT ACTTTCACTG AAAAAGAGTC ATGCAAACAG     180

ATTTTTAAGT TGCAAACCAA TTGCAAAATA TTTTTTTATC CAACTTCAAT GATAGGTATT     240

GCTGTTAATT CTAAGATATG CATTAATTGT TTCAACTAAT GGGTGTCAAA CGAGATGTTC     300

TGAAAATGAA GGCAAAAAGG AGATCCACCT TCTACTTTCA TAAAGTTTCT ATCTTCCTCT     360

GCTGACTCAA ATAAGCATTT AATACATTTT ATAACGAATT AATTATGAAT ATATTTCAAA     420

TAAATAAATT ATTTCCAAGT GTTGAAGGAA ATTCAGACTT CTAATTTGCT CTGATTCTGA     480

AACTAAAACA AATGCTCTGT GAGAGTTTGC GTTTCCAGTG AAGTAGCGTG AGAAATCCAA     540

GTCAGACAGC TACATGAAAC TACATTTACC AGCTCTCTGC CAGACACCAG TGCACGATAG     600

CGCAGAACAT GTAGCTAGAT CTCAGTCATA GCTNNNNNNN NNNNNNNNNN AGACCTTGCA     660

GTTGGCTTTT AACCTGAAGG AGATAAGGCA AGATTCCAGG GTTATTTAG AGAAATTACA     720

GGATCTGGGA ATAAAGTAGT TACAAAATTA GTCCCCAACC AGCTTTCATG GAGCTTTCAA     780

TTATTAATTA TTCTAGTTCT TAATCGCATG CATACAATGC ACATACATAT ATACATGCAT     840

ATTAAAATAC ATGATTGGAC GCAAACGGAA ATAAGATTCC ACCTGTGCAT AAAACAGAAA     900

GACTTGGTTA GAGTGAGGGA TCAGGAAACA CCACACTGAG GACGAGATGN NNNNNNNNNN     960

NTAGTGGGTG GGGGGCGGAC ATCAATAAAG AACTCTTCTG TGTCAGCCAC TGAGCACGGA    1020

ATAAAGGGAT GAGAGTGAGG GCAANTACCA GAAGAATAAA ATCCTTTTAA GAGATGAAGA    1080

TTGTTATGAG CACAGTGTGT GGNTTCAAAA ATCTTTTAAC AACCCCAAGG TGAAGCTAGT    1140

TGGAAGATAT TTGAATTTGT TTAAACCCAT CTGGTCCTAG CCCTATTCTT TGAATCCGAA    1200

GAGGTCAAGA ATTCCGAGCA GAGTGGACTA CCTGTGATAC CTTAGACTAG TCCTGTGTAT    1260

TCAAGTCCAA TGAGAGTATC TGTAAGAGAA TAAGTGCGAA ATCCAGATCT              1310

(2) INFORMATION FOR SEQ ID NO:42:

(i) SEQUENCE CHARACTERISTICS:
        (A) LENGTH: 789 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:42:

GGATTCTGTT GAGCCCTAGC TCATTATGAT GTCCTGTTGT CCTACCCAAA TAAGACTCAT      60

CCCAACTACA TCTCAATAAT TAATGAAGAT GGAAATGAGG TAAAAAATAA ATAAATAAAT     120

AAAAGAAACA TTCCCCCCCA TTTATTATTT TTTCAAATAC CTTCTATGAA ATAATGTTCT     180

ATCCCTCTCT AAATATTAAT AGAAATCAAT ATTATTGGAA CTGTGAATAC CTTTAATATC     240

```
TCATTATCCG GTGTCAACTA CTTTCCTATG ATGTTGAGTT ACTGGGTTTA GAAGTCGGGA    300

AATAATGCTG TAAANNNNNN AGTTAGTCTA CACACCAATA TCAAATATGA TATACTTGTA    360

AACCTCCAAG CATAAAAAGA GATACTTTAT AAAAGAGGTT CTTTTTTTCT TTTTTTTTTT    420

TCCAGATGGA GTTTCACTCC TGTCAGGCAG GCNGAGTGCA GTGGTGCCAT CTCGGCTCAC    480

TGCAACCTCC ACCTCCCATG TTCAAGGGAT TCTCCTTCCT CAGTCTCCTG AGTAGCTGGG    540

ATTACAGGTG TGCACCACCA CACCCAGCTA ATTTTTGTAT TTTTAATAGA GACAGGGTTT    600

CGATCGATGT TGGCCAGGCT AGTCTCGAAC TCCTGACCTC TAGGTGATCC ACCCGCTCAG    660

CTCCCAAAGT TGTAGAATTA CACGTGTGAG GCACTGCGCC TTGCCAGGAG ATACATTTTT    720

GATAGGTTTA ATTTATAAAG ACACTGCACA GATTTGAGTT GCTGGGAAAT GCACGGATTC    780

CAGTATGCA                                                            789
```

(2) INFORMATION FOR SEQ ID NO:43:

(i) SEQUENCE CHARACTERISTICS:
  (A) LENGTH: 368 base pairs
  (B) TYPE: nucleic acid
  (C) STRANDEDNESS: double
  (D) TOPOLOGY: linear (ii) MOLECULE TYPE: peptide (iii) HYPOTHETICAL: NO (iv) ANTI-SENSE: NO (vi) ORIGINAL SOURCE:
  (A) ORGANISM: Homo Sapien
  (F) TISSUE TYPE: Carcinoma (vii) IMMEDIATE SOURCE:
  (B) CLONE: Prostate Specific Membrane Antigen (xi) SEQUENCE DESCRIPTION: SEQ ID NO:43:

```
AATCAAAATA AAACAGTTAA AGTTTGATTA CTATAATCAA ACACAAAAAA AATGAATATT     60

ATCTTTTATG TCAGTAGAGG GTGAATGAAT CCTTCAGGAT TTTGATGATA GTATCAGATA    120

CCCAGCACTA TGCTAGAAGT TGTGAAGAAT TCACGAGATG AATAAATCAC AGATTCTGTC    180

CTCAAAATGG TTAGATCTAT TCAGGAAACA AAGCTAAAAA AACCCCACCA ATAACTAAAA    240

ATCAACCAAA TGAAAAACAA CAATCATAAA ATAAGTAAGT ACCTATAGAA AGAAAAGCTC    300

AGAGGAGGTA AAAAGAATCT CCTTAAAAGG AATACTATAT ACTGTAAAAC TGTGACTGAT    360

AGAAGGAA                                                             368
```

(2) INFORMATION FOR SEQ ID NO:44:

(i) SEQUENCE CHARACTERISTICS:
  (A) LENGTH: 877 base pairs
  (B) TYPE: nucleic acid
  (C) STRANDEDNESS: double
  (D) TOPOLOGY: linear (ii) MOLECULE TYPE: peptide (iii) HYPOTHETICAL: NO (iv) ANTI-SENSE: NO (vi) ORIGINAL SOURCE:
  (A) ORGANISM: Homo Sapien
  (F) TISSUE TYPE: Carcinoma (vii) IMMEDIATE SOURCE:
  (B) CLONE: Prostate Specific Membrane Antigen (xi) SEQUENCE DESCRIPTION: SEQ ID NO:44:

```
TATGGGAAAG TTTTCAGAGG AAATAAGGTA AGGGAAAAGT TATCTCTTTT TTTCTCTCCC      60

CCAATGTAAA AAGTTATAGT GGGTTTTACA TGTGTAGAAT CATTTTCTTA AAACTTTATG     120

AATACCATTA TTTTCTTGTA TTCTGTGACA TGCCACCTTA CAGAGAGGAC ACATTTACTA     180

GGTTATATCC CGGGGTTAAA TTCGAGCATT GGAATTTGGC CAGTGTAGAT GTTTAGAGTG     240

AACAGAACAA TTTTTCTGTG CTTACAGGTT ATGGCTGTGG CGTACAAGAA GCATGCACTG     300

GGTTTATTAT TAACTTTCAG TATCTTTGTT TTAAATATTT TCTACAAAAA TGTTTACTAA     360

ATTAAATTGT AGTATGAATT GTTATAAATA ATGAGGGAAA CATTTACACA TAGCAAATTT     420

AAAAATTACT GTCATTTGAT TTGTTAATAT ATTTTTCTCT TTAGTGGGAA ATTAAATTAA     480

AAAATTCCTT TCGACTGTCA GACAATAGGA TTGCTGTGGT CTACTTGCTT ATTATATTTG     540

TAGAGTCTAG AATGCAATCT CACTACACTA TAGACATCTC ANNCTAACGT AGGACAATTC     600

TGAGAAACTA TTCCAGACCT CCTTATGGGC TTAGCCAAGG NTATCCTTCA GCTGGCATTG     660

CAGGGTGACT TCTNCCTCNN AATCCAGCTC TCTNTCACAG ATGTGATCCA AGAGACACTC     720

ACAATTAATC AACTAGCATT CTAAATTTCA ATTCCAGATC TATTACCTTA ATATGGTAGC     780

TGAAGCTTTN NTCACTGTCA ATTCTGATCA GATATATGAC AATTTTAAAT TATTTGCAGT     840

GTGTAAGAAA CGCTTCAGGT AGTTTAAATT TAAGGCT                              877
```

(2) INFORMATION FOR SEQ ID NO:45:

(i) SEQUENCE CHARACTERISTICS:
        (A) LENGTH: 893 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:45:

```
CTCCTTTGGC CCCTGCCAGC TGGGCATTTT TAACCTAGTT TACACAGTGT CTTTTTTTCC      60

TTATTTTAAA TTGGTTGTTC CAGATTCGGT AATATCAATT TTTAATATTA CACTTAAATG     120

AGTACCAGAA CTTTATCTTC AACCTTTTTC TCATTAGGCC TACAACATAG GACATCTCGG     180

ATAGAATTTC CTTTTCTTTT TGCTACTATA AGCTGCTAAA ATCCTCAGAA CATCAGATTT     240

AGAAATGTTC TTATTAGTGG TAGTGAGCAT TTGCTATTTC CTACCACTAG CTTACAAATA     300

TAATAAGCAA GTAGACCCCA CAGGCCAAAT TCCTATTTGT TCTACAGTCG AAAGGGAATT     360

TTTTAAAATT TAATTTCCAC TAAAGAGAAA AATATATTAA CAATCAAATT GACAGTCGAT     420

TTTAATTGCT ATGTGTAATT GTTTTCCCTC ATTATTTATA ACAATTCATA CTACAATTTA     480

ATTTAGTAAA CATTTTTGTA GACCATATTT AAAACAAAGA TACTGAAAGT TAATATAAAC     540

CCAGTGCATG CTCTCTGTAG GCCACAGCCA TAACCTGTAA GCACAGAAAA ATTTGTTCTG     600

TTACTCTAAA CATCTACACT GGCCAAATTC CAATGCTCGA ATTTAACCCC GGGATATAAC     660

CTAGTAAATG TGTCCTCTCT GTCAAGGTGG GCATGTCACA GAATACAGAA CAATCAATGG     720
```

```
TATTCATAAA GTTTTAAGAA AATGATTCTA CACATGTAAA ACCCACTATA ACTTTTTACA      780

TTGGGGGAGA GAAAAAAAGA GATAATTTTT ACCTTACCTT ATTTCCTCTG AAAACTTTCC      840

CATATCTGGC AATTACAATT TTCCCAGAGC AATTGATTTT CATGTCCCGT TCC             893

(2) INFORMATION FOR SEQ ID NO:46:

(i) SEQUENCE CHARACTERISTICS:
        (A) LENGTH: 1105 base pairs
        (B) TYPE: nucleic acid
        (C) STRANDEDNESS: double
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo Sapien
        (F) TISSUE TYPE: Carcinoma (vii) IMMEDIATE SOURCE:
        (B) CLONE: Prostate Specific Membrane Antigen (xi) SEQUENCE DESCRIPTION: SEQ ID NO:46:

GATGCTATTT GGGCAATTTC TTATTGACAG TTTTGAAATG TTAGGCTTTT ATCTCCATTT       60

TTTAGTACTT AAATTTTCCA ACATGGGTGT TGCTTGTTAT TTTATCAGTA TAAAATAGAA      120

GAGTGGTTCT GTTCTGGAAT TTAGTATATA CATGAGTATC TAGTGTATGT CAGCCATGAA      180

AATGAACCTT TCAGATGTTT AACTTCAGGG AACCTAATTG AGTCATTGCT CCAGACATTG      240

TTGCTTTGAA CCCACTATAT TNNNNNNNCT CGGGCAATGA CTCAGTGTGG CAAGGATACT      300

ACTGCAGGCC TGTTTCTGGA AGGCACTGGA CTCCTCTGAT GCAAACTTTG GCCAGGGACT      360

CCTTGATAGC TCTTAAATAG ATGCTGCACC AACACTCTCT TTCTTTTCTC TCTTTTTCTT      420

TATTCAATAT TAGACTACAA GCAGTCTAAG GACTTCTCAG GGTTTCTAGC TCTCTCTCAT      480

TTCACACATG CTTTCCTAGT AATCTCTACT CATATATCTT ACTGCTACGC TGGGGCCAGA      540

TAACNNNNNN CTTCCATTTT GTTTTTATCT CTATTCTTCT TCCCCTTCTG CTTTCATTAT      600

TGAAACTTTC TGCTTTCATT ATTGAAACTT TCCCAGATTT GTTCTGCTTA ACCTGGCATT      660

GGAACTGTTT CCTCTTCCCT GTGCTGCTTT CTCCCATTGC CATGTCCTTT TTTTTTTTT      720

TTTTTTTTTT TGAGACAGTG TCACTCTGTT GCCCAGGCTG GAGTGCAATG GTGCAATCTT      780

GGCCACTGCA ACCCCGACTC CGGGTTCAAG TGATTCTCTA CCTGCCTCAG CCTCCTGAGT      840

AGCTGGGATT ACAGGTGCCA CCACTATGCC GGCTGATTTT GTATTTTAGT AGAGATGGGT      900

TCACATGCAG ATCAGCTGTT CCGACTCTGA CCAGNNNNNN NNNNNNNNNN ATCAAAGTCA      960

GCCAAAGTGC TAGGCTTAGA GTAATTGTGT AATTTCCACA CAAGTGCAAC CTAGTGTAAT     1020

GCCTCAAGAA TGTNNNTATG AATGTCTCGA ACGTTAGTAA CTAATAACAA GTAGTTAGTT     1080

TATAGATGTA TCCTAGTATG TAGCA                                          1105

(2) INFORMATION FOR SEQ ID NO:47:

(i) SEQUENCE CHARACTERISTICS:
        (A) LENGTH: 930 base pairs
        (B) TYPE: nucleic acid
        (C) STRANDEDNESS: double
        (D) TOPOLOGY: linear (ii) MOLECULE TYPE: peptide (iii) HYPOTHETICAL: NO
```

(iv) ANTI-SENSE: NO (vi) ORIGINAL SOURCE:
             (A) ORGANISM: Homo Sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:47:

```
CACAAAAAAA GATTATTAGC CACAAAAAAA CCTTGAAGTA ACGCATTAAA ATGTTAATGG      60

ATTCACTTTA TTGAGCATCT GCTCATAATA CTTTAATGAG TGCAAAGTGC TTTGAATATA     120

ATACGTCATT TAAACCTTAC CATAATTCTG AGGAATTGCT ACCTCCACTT CACAGATGGG     180

GCACAGGAGG CTTAGATAAC ATGCCCAAAG TCATGCTTCT AGTAAATGGA TATAATTAAG     240

ATTCAAATTA TTGATAAGAA TTTGATCTGC CTTACCAGTA TCTAGTAGTA AATCTAAAAG     300

CGCTTTCCAG AGCATGTGCT GTTGATAGAG CTTGATGTCT AACTCTCTGA AATTTTCCAT     360

TCTTATTTGT CTCACTGGTA TATAGTTATT TTTTACTACT TTCATACACC TACTAAGAAG     420

ACAGGAGGAT CAAAGATAGG ATTTCATTTA GAATGCCTAA AGCTTCACGT ATTTTAATTC     480

AGAATAAGAT TCAGGCAGAC CACCAGTATA TGCCATGGTC CCTGGTTATC TTTCAGCAGG     540

TGACCGAGAA AGAAAACATG GTAATGTTTA TGAAATGGTG GGTTCTTGTA GTTTCACTTC     600

AACATATCTG CCTTTACTGT ATTAAGATGA TGGATTAACT TATTCTTGAT ATGGGCATGT     660

AAAACAATAT ACTTTTACTA AACAGCTACA GAGAGACAAA TGTGTTTCCA GACAAACTTA     720

AGAGACTGAG TGTTCAAACT GAATAATCTC GACCTTAATT GTAACTATAT TTTATGAAAT     780

CCAGCTGTAA GGCAAAACAG ACTCTTGGCT ACACGGCATT TGTCTGTTAA TGATACTCAA     840

CCTTAACCGT CACTTAATAA TGCTGAATAA TGTCATTAAT CTGAGATGTT AGTATGATCA     900

ATGGGAATCA CTGCTGAGCT CTCGAAGCCC                                     930
```

(2) INFORMATION FOR SEQ ID NO:48:

(i) SEQUENCE CHARACTERISTICS:
             (A) LENGTH: 2957 base pairs
             (B) TYPE: nucleic acid
             (C) STRANDEDNESS: double
             (D) TOPOLOGY: linear (ii) MOLECULE TYPE: peptide (iii) HYPOTHETICAL: NO (iv) ANTI-SENSE: NO (vi) ORIGINAL SOURCE:
             (A) ORGANISM: Homo Sapien
             (F) TISSUE TYPE: Carcinoma (vii) IMMEDIATE SOURCE:
             (B) CLONE: Prostate Specific Membrane Antigen (xi) SEQUENCE DESCRIPTION: SEQ ID NO:48:

```
CTCGAGGGGT GCTCACCCCA CATTACCCCG ACCCTAATCG CCGCCCCTGG GGAAGACCAG      60

CAACAGGATC CCACTCGGCA GCTGACCCGC GAGTCCCAGC ACCGCGGCAC CACGGGGAAG     120

ACTCCGAGGT TTGCTCCGCG AGGCGCCCCC CTACCGAAGA GGAAGCCGAG GAGAAAGAAG     180

CCACCCGCCA GCACCAGCGC CCCAGCGCAC AGCCAGCGCG GCGGCGCGC GGTGGCCACA      240

GCCGAGTCGG TTTCGTGAAG GAGATTCCAC ATCTCGGCGC GAGCAGAGCC GGCCTCCCGG     300

GACCCGCGCC TGTGCTGCTG CTCTACTGCG CGCCCTCCAA CCACCACGGC GGGGTAAAGT     360
```

```
CTCTCTCAAT CTCACTAATG CCTCGCTTAT CAGCCCTGCA GGCTGGAATT CGCTCCAGAC    420

CTGGGGTCCA GTTTCTCCAC CACAGCAGTG TTTCTAGAGT GCACTGAACC AATCCGAGCG    480

AGAGAGAGAG GCAACATCTG CCTCCAGGAG AAGGAAATCC GGCCCCTTTT GAGAGGCGCC    540

TTAAAAAAAA AAAACTTTCT TGGAAAATGT CCAGCTCTTG CTTAAATATA AAATGAAAG    600

GAAGAAAGAG ACTCTCCTCT CTCCACTCCT ATAATTATGA GGAACTTTTA TTCAACTCTG    660

AAATTCTATA CAATCTCTAC AATACTCTAC TGAATAAAAG CAGAGCAGAA AAAGCTGCGC    720

TTTTTTTCCA TAGTCGGGAA TGCTTGTCAT CAGTGTAAAT CACCACCGCG CCCTTTTTCC    780

TAAAGAATAT TATTGTTATT AATAAACATG TAGGGTATTA TCCTCCACTT ACATTACAAA    840

ACCATTTTTT AAAGCCGGGC GTGGTGGCTC ACGCCTGTAA TCCCAGCACT TTGGGAGGCC    900

CAGACAGGCG GATCACGAAG TCGAGAAATC GAGACCATCC TGGCCAACAT GGTGAAACCC    960

CATCTCTACT AAAAATACAA AAATTAGCTG GGCGTGGTGG CGGGCTCCTG TAGTCCCAGC   1020

TACTCAGGAG GCTGAGGCAG GAGAATCGCT TGAACCGGGG AGGCGGAGGT TGCAGTCAGC   1080

CAAGATAGCG CCACTGCACT GGAGCCTGGT GACAGAGTGA GACTCCCTCA AGAAAGAAAG   1140

GAAGGGAAGG GAAAGGGAAG GAAGGGGAGG GGAAGGGAGG GGAGGGGAGG GGAGGAAAGA   1200

AAAGAATACT GGAACTTGTT GAAGGCAGAG ACTTTATTTT CATATCCCGG CTATGTCTGG   1260

CTACTGTCTT ACGTAATAGA TATAAAATCA ATCTTGGTTG GATTAACCAG AAGAATCATC   1320

ATACAAAATT ATATCCCTGC TATAAATTCT TAATAATAAT AATCGTATTT CGAGGGAGAG   1380

AATAGCTACA TGCTTTATAA AATAAACTGT GTTCTTATAA TCCGTGAGAG AGGCCGTGCA   1440

TTTGCTAGGA GTACTTTATG GAAGCACTGC TTTTAACAGA ACCATAAGGT ACAGGTAGGA   1500

TTTGACCCAG TGGAGATGAG AAGAAACATT AGGGGCCATG GGCCAGCTGA GTAGGCAAAG   1560

GCAGAAAACT CAGAGTGTAT TCAAGGAATA GCAAACAGTT TGCTTTGAGA AAGGGAGAGC   1620

ACAGTATGAG TTAAGTGGAA AAAGATGGAC TAGATTGTAC AGTCTTGGGT GCTTCGATGT   1680

AGACTTTCTG AGCAAAGTGA AAAATTTGGG AAAATTAATT TGTCAACAAT GAACCATGAC   1740

AACTCCTAGA TGACCTAGGG CAGGAAGGAA GGGAATTTCT TCATCTCTTT CTAACAAAAT   1800

CCTGAATGTA CTATATCTTT CCTAATGTTC CTATTGTCAA ATCTAATCAG AGATGGCTAA   1860

TAATAGTGAC TAATATTTAA AGAGCACTTA TTATGAGTGA TGCATGTTAT GTACATCACC   1920

TCATTTAATC ACCATTGGGA CCCTTCAAGG TTTGTTCTAT TACTCTTCCT GATTTACACA   1980

TGGTAAAACT GAAATTTAGC TAGATTAGGT AAGTCATTCG AAGTCACAAA GCTAAGACTT   2040

AATATAATGT CTGTCTTACT TTGTACCACT CTACAGTCTC TATTCAGCAC AGGATACCTT   2100

TATGGAGTTT GCTTGTGGCA CTGGAGGGAG CACTGAGTTT GGAGTCAGAA GACTCTTAAC   2160

AGTCTTTGGA CCTGGTCCTG TCCAAGCTGA TTACCCCTGG GTGCTAAGTA TTCAACTTAC   2220

CAGAATATAT CTTCTCATTT GTAAAACGTG GGATCACCCA GTAACATTAC CCAGTACAGT   2280

TGGTTAATGT GTTTTCTTTG AAGGTTAGAT GTGATTATAA GTAAGCAAAT TTCAGTTAAA   2340

TATAAAAGTG ATTTTTGAAC AATAGAATTT ATTCAATTAA TAATTCAATT AATAAGACGC   2400

TATGGTGAAG AGGATGTATT TGAAGAATTC AGACAATGAA TGAATATCTG TCACATATTG   2460

TAAGGCTTGT GGAACTTACA GTTTAGTGGA GAAGATAAAC CTTCAACAAG TAGTTAATAA   2520

CCAATATACT GAGCATTTTC TATATGGAGG ACACCACACT ATGTGCTTTA TGTGCATTAT   2580

TTCATTTAAT TATCATGACT TATCCTGAAA TAATTTAAAA TCTCTAACAG GTGATTATGT   2640

AAACCACACT AGATTTTTCT GTTGCACCCT GTATTATTAT TTACCTTTTA CAGATAAGAA   2700

AACTGAGGTT TAAAGAAATT GATTAAGTTT TGCGGAGCGC TAAGGAGTTA AAAGAAAAAT   2760
```

-continued

| | | | | | |
|---|---|---|---|---|---|
| GAAAAATGGG | CTTAGCTGGC | AGGAACAGAA | ACAGGGGTAG | AGGGGAATGA | ATGTTCCAAG | 2820 |
| AATAGGGTCA | ACTGCAAATG | GCTCACTTAG | CACCCAAGCA | TCCTCTTACA | AGCACCCAGC | 2880 |
| TCACAGCCCA | TCTGTAACCA | AGCATCCTGT | CTGCAAGCAT | TCAGCCTAAG | GAGCACCCTT | 2940 |
| ATAAAACTCC | ACTCGAG | | | | | 2957 |